United States Patent
Wang et al.

(10) Patent No.: US 9,932,606 B2
(45) Date of Patent: Apr. 3, 2018

(54) SUBGROUP B RECOMBINANT HUMAN ADENOVIRUS VECTOR, AND METHODS FOR CONSTRUCTING AND FOR USING THE SAME

(71) Applicant: Beijing Bio-Targeting Therapeutics Technology Inc., Beijing (CN)

(72) Inventors: Yaohe Wang, Zhengzhou (CN); Guozhong Jiang, Zhengzhou (CN); Hanshi Wong, Zhengzhou (CN); Fengyu Cao, Zhengzhou (CN); Nick Lemoine, London (GB)

(73) Assignee: BEIJING BIO-TARGETING THERAPEUTICS TECHNOLOGY INC., Beijing (CN)

( * ) Notice: Subject to any disclaimer, the term of this patent is extended or adjusted under 35 U.S.C. 154(b) by 55 days.

(21) Appl. No.: 15/098,342

(22) Filed: Apr. 14, 2016

(65) Prior Publication Data

US 2016/0222413 A1    Aug. 4, 2016

Related U.S. Application Data

(60) Division of application No. 14/093,078, filed on Nov. 29, 2013, now Pat. No. 9,315,827, which is a continuation-in-part of application No. PCT/CN2012/071757, filed on Feb. 29, 2012.

(30) Foreign Application Priority Data

May 31, 2011 (CN) .......................... 2011 1 0143385

(51) Int. Cl.
| | |
|---|---|
| *C12N 15/64* | (2006.01) |
| *C12N 15/86* | (2006.01) |
| *A61K 48/00* | (2006.01) |
| *A61P 35/00* | (2006.01) |
| *A61K 35/761* | (2015.01) |
| *C12N 7/00* | (2006.01) |

(52) U.S. Cl.
CPC ............ *C12N 15/86* (2013.01); *A61K 35/761* (2013.01); *C12N 7/00* (2013.01); *C12N 2710/10321* (2013.01); *C12N 2710/10332* (2013.01); *C12N 2710/10343* (2013.01)

(58) Field of Classification Search
CPC ........ A61K 35/761; C12N 2710/10332; C12N 15/86; C12N 2710/10343
USPC ...... 435/6.1, 6.11, 91.1, 91.31, 91.41, 320.1, 435/455; 514/44; 536/23.1, 24.5
See application file for complete search history.

*Primary Examiner* — Jane J Zara
(74) *Attorney, Agent, or Firm* — Matthias Scholl, PC; Matthias Scholl

(57) ABSTRACT

A method for reconstructing a replication-selective oncolytic adenovirus using a subgroup B recombinant human adenovirus vector Ad11-5EP. The method includes: 1) deleting E1A CR2 gene and/or anti-apoptotic gene E1B 21K that is necessary for viability of an adenovirus in normal cells but not necessary in tumor cells; 2) inserting a tumor-specific promoter to drive the expression of E1A gene; 3) redirecting a cellular tropism of Ad11-5EP according to receptors on a tumor cell surface; or 4) allowing adenovirus to selectively replicate in tumor cells.

5 Claims, 9 Drawing Sheets

SUBGROUP B RECOMBINANT HUMAN ADENOVIRUS VECTOR, AND METHODS FOR CONSTRUCTING AND FOR USING THE SAME

CROSS-REFERENCE TO RELATED APPLICATIONS

This application is a divisional of U.S. application Ser. No. 14/093,078, filed on Nov. 29, 2013, now pending, which is a continuation-in-part of International Patent Application No. PCT/CN2012/071757 with an international filing date of Feb. 29, 2012, designating the United States, now pending, and further claims priority benefits to Chinese Patent Application No. 201110143385.3 filed May 31, 2011. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND OF THE INVENTION

Field of the Invention

The invention relates to a subgroup B recombinant human adenovirus vectors Ad11-5EP and Ad11-5ETel-GFP and methods for constructing and for using the same.

Description of the Related Art

Adenovirus 11 (Ad11) is a serotype of the subgroup B human adenovirus and is obviously superior to Ad 5 in oncolytic virotherapy. Ad11 is able to combine other cell surface receptor X besides the CD46 receptor. Tuve has reported that Ad11 is the only virus in the B subgroup adenovirus that is able to combine CD46 as well as the surface receptor X, which indicated that Ad11 is capable of infecting a much wider spectrum of tumor cells, thereby solving the problem of low infection rate in the application of Ad5 due to downregulation of virus acceptor. Ad11 is also superior to Ad5 in that the content of neutralizing antibodies of Ad11 is relatively low, being 10-31%, compared with 45-90% of that of Ad5, and the neutralizing antibodies of Ad11 have no cross-reactivity. When Ad11 is intravenously injected to transgenic mice expressing CD46, no obvious intrahepatic transduction or hepatotoxicity occurs. Furthermore, Ad11 is able to effectively transduce dendritic cells, allows tumor-specific antigens to express, and enhances the immune response to benefit the cancer therapy.

Studies on other adenovirus serotypes except Ad5 used as a vaccine or gene conversion vector have been reported, but the use of the adenovirus serotype used as an oncolytic virus has been rarely conducted. In vitro and in vivo studies from Sandberg indicated that transduction, replication, and lysis of Ad11 effectively undergo in prostate cancer cell line PC-3, but the comparison between Ad5 was not conducted by Sandberg. Shashakova et al. have compared oncolytic efficacy among Ad5, Ad6, Ad11, and Ad35 based on in vitro studies on human tumor cell lines and in vivo studies on human prostate cancer cell lines DC145, and found that Ad5, Ad6, and Ad11 have similar antitumoral efficacy whereas Ad35 has no antitumoral efficacy. The most important is that only Ad5 has hepatotoxicity. After that, chimeric oncolytic Ad5 (by substituting cilium of Ad5 by that of the B subgroup adenovirus) was constructed for allowing the chimeric oncolytic Ad5 to combine with membrane receptor CD46 to improve the antitumoral efficacy. However, compared with a whole B subgroup adenovirus, this method is not able to overcome the neutralizing ability of hexon antigen of Ad5.

The number of circulating tumor cells (CTCs) is in relation to the clinical stage, treatment effect, and short survival rate. CTCs level in peripheral blood in tumor patient is taken as the basis for monitoring, adjusting the treatment, and anticipating the results. Thus, a specific and sensitive method for detecting these cells is necessitated. In recent years, immune cells counting analysis and quantitative PCR have been applied by which a small amount of CTCs were detected, however, the application of these methods were restricted because of a high testing cost and the lack of specific biological markers.

Replication-selective oncolytic adenovirus is a new kind of medicine for treating tumors. To be noted, it has been reported recently that the replication-selective oncolytic adenovirus expressing GFP has been used to detect CTCs among more than hundred million of peripheral blood cells. However, genetic variation of tumor cells is a very important factor affecting the infection ability of adenovirus. A low expression of CAR in tumor cells significantly decreases the infection ability of Ad5, which further influences the positive rate of tumor cells. Besides the known influence mechanism of the low expression of CAR, it has also been found that other tumor related genes like CEACAM6 influences Ad5 from entering the nuclear, thereby decreasing the infection ability of Ad5 on tumor cells. These data indicate that methods for testing CTCs using Ad5 have a low sensitivity in some tumor cells.

SUMMARY OF THE INVENTION

In view of the above-described problems, it is one objective of the invention to provide an adenovirus vector Ad11-5EP that is more effective in cancer therapy, and to provide a subgroup B recombinant human adenovirus vector Ad11-5ETel-GFP for treating tumor or detecting tumor cells in circulating blood.

Inventors have first compared the anti-tumor potencies of Ad11 and Ad5 in human cancer cell lines in vitro, and found that only 9 among 25 cell lines being tested are Ad11-sensitive, in which, PC-3 is insensitive to Ad5 and sensitive to Ad11. Compared with Ad5, Ad11 obviously inhibits the growth of subcutaneous tumors of PC-3 cells in vivo, and further improves the survival of tumor-bearing animals. When the above experiment is conducted on Ad5-sensitive and Ad11-insensitive MIAPaCa-2 cell line, the antitumoral efficacy of Ad11 is obviously reduced.

Although Ad11 receptors are often highly expressed within human tumor cells, the wild-type Ad11 is not able to effectively kill the tumor cells. The inventors have conducted extensive studies and proved that more Ad11 than Ad5 are attached to the membrane of tumor cells by using two different methods. The attached Ad11 virus particles are capable of entering the nucleus, which means a relatively high level of Ad11 exists in the nucleus in early stage of the virus infection compared with Ad5. The inventors have studied expressions of two viruses in early stage of tumor cells infection, and levels of mRNA of E1A are tested by using specific primers for quantitative PCR. After 2 hours of virus infection in all cell lines, it was found that in cell lines that had a high level of Ad11, E1AmRNA was highly expressed. Expression of E1AmRNA of Ad11 in Ad11-insensitive cell lines (MIAPaCa-2 and LNCaP) after 2 hours of the infection is obviously decreased. Ad11-sensitive Capan-2 and PC-3 cells have a high level of Ad11E1 AmRNA. Ad11E1 AmRNA directly influences the replication of virus, so that the decrease of the level of Ad11E1AmRNA in MIAPaCa-2 and LNCaP cell lines will decrease the replication level of the virus, and correspondingly decrease the synthesis of hexon protein. Such result is in accordance with the production of low level of Ad11 virus particles and the cytotoxicity from the initial observation. These results indicate that the replication and cell killing of Ad11 have no relationship with its infectivity, but are associated with the activity of the enhancer and the promoter of early gene E1A.

To solve the above problem, one objective of the invention is to construct a tumor targeting adenoviral vector (Ad11-5EP) where the original enhancer and promoter of Ad11 E1A gene was replaced by the counterpart of Ad5. Experiments indicate that Ad11-5EP is a very useful backbone vector capable of developing replication-selective oncolytic adenovirus for treating a wider spectrum of human cancers.

To explore the application of the new adenovirus vector and improve the sensitivity to detect circulating tumor cells in the blood using replication-selective adenovirus, the Ad5 promoter of Ad11-5EP is substituted by a promoter of human telomerase gene, a reporter gene GFP was inserted into E3gp18.5 K of Ad11, and a replication-selective adenovirus (Ad11-5ETel-GFP) capable of expressing reporter genes was created by homologous recombination. As telomerase is highly expressed in 95% of human tumor cells, Ad11-5ETel-GFP selectively replicates and expresses GFP in tumor cells but has no activity in normal epithelial cells.

To achieve the above objective, in accordance with one embodiment of the invention, there is provided a method for constructing a subgroup B recombinant human adenovirus vector Ad11-5EP (SEQ ID NO: 1), comprises substituting a 365 bp fragment comprising an enhancer and a promoter of an upstream coding sequence of Ad5 E1A (SEQ ID NO: 2) for a corresponding region of a serotype Ad11 (SEQ ID NO: 3) of the subgroup B human adenovirus vector by homologous recombination to construct the subgroup B recombinant human adenovirus vector Ad11-5EP.

In a class of this embodiment, the homologous recombination comprises: amplifying a 329 bp fragment in the front of the Ad11 genome as a left arm sequence, providing a fragment formed by ligating a 195-559 bp fragment of Ad5 E1A comprising the enhancer and the promoter and a 568-1125 bp fragment of Ad11 E1A (SEQ ID NO: 4) as a right arm sequence, and ligating the left arm sequence and the right arm sequence to multi-cloning sites arranged on two sides of pSS-ChI (SEQ ID NO: 12), respectively, to construct a shuttle vector pSS-A1A7 (SEQ ID NO: 5); digesting and purifying the pSS-A1A7 by PmeI while performing homologous recombination between a PmeI digested segment and pAd11 (SEQ ID NO: 6) plasmid within BJ5183 cells, and screening positive clones using agar plates comprising ampicillin and chloramphenicol; and digesting the positive clones by SwaI, and deleting a chloramphenicol-resistance gene expression cassette to yield pAd11-Ad5EP (SEQ ID NO: 7), digesting and linearizing the pAd11-Ad5EP by NotI, and transfecting 293 cells to yield the adenovirus vector Ad11-5EP.

In a class of this embodiment, the concentrations of ampicillin and chloramphenicol are 100 mg/mL and 25 mg/mL, respectively.

A method for reconstructing replication-selective oncolytic adenovirus using the subgroup B recombinant human adenovirus vector Ad11-5EP, the method comprises one of the following steps:

1) deleting E1A CR2 gene (SEQ ID NO: 8) and/or anti-apoptotic gene E1B 21K (SEQ ID NO: 9) that are necessary for viability of the adenovirus in normal cells but not necessary in tumor cells;
2) inserting a tumor-specific promoter to drive the expression of E1A gene;
3) re-directing a cellular tropism of Ad11-5EP according to receptors on a tumor cell surface; or
4) allowing adenovirus to selectively replicate in tumor cells combining with MicroRNA technology.

A method for constructing a subgroup B recombinant human adenovirus vector Ad11-5ETel-GFP (SEQ ID NO: 10), the method comprises:

1) constructing vectors pSS-ChI and pSS-kna (SEQ ID NO: 13) by using two different antibiotics-resistance cassettes, introducing SwaI restriction sites to two flanks of a chloramphenicol-resistance gene sequence cassette, and introducing sbfI restriction sites to two flanks of a kanamycin-resistance gene sequence cassette;
2) cloning an initiation sequence for replication of pBR322 (SEQ ID NO: 14) by pUC18 (SEQ ID NO: 15), ligating a first synthetic nucleotide sequence comprising multi-cloning sites to the chloramphenicol-resistance gene sequence cassette to yield pSS-ChI, homologously recombining an upstream of a left arm sequence and a downstream of a right arm sequence of the chloramphenicol-resistance gene sequence cassette, and inserting the upstream of the left arm sequence of the chloramphenicol-resistance gene sequence cassette and the downstream of the right arm sequence of the chloramphenicol-resistance gene sequence cassette into the multi-cloning sites on two sides of pSS-ChI by blunt end insertion or cohesive end insertion, respectively, to construct a shuttle vector pSSENTel (SEQ ID NO: 16) for recombination;
3) cloning an initiation sequence for replication of pBR322 by pUC18, ligating a second synthetic nucleotide sequence comprising multi-cloning sites to the kanamycin-resistance gene sequence cassette to yield pSS-kna, homologously recombining an upstream of a left arm sequence and a downstream of a right arm sequence of the kanamycin-resistance gene sequence cassette, and inserting the upstream of the left arm sequence of the kanamycin-resistance gene sequence cassette and the downstream of the right arm sequence of the kanamycin-resistance gene sequence cassette into the multi-cloning sites on two sides of pSS-kna by blunt end insertion or cohesive end insertion, respectively, to construct a shuttle vector pSSGFP (SEQ ID NO: 17) for recombination;
4) constructing pSSENTe comprising: amplifying a 329 bp in the front of Ad11 genome as a left arm sequence, providing a fragment formed by ligating 195-378 bp of Ad5 E1A enhancer, −714-0 bp of human TERT promoter, and 568-1125 bp of Ad11 E1A in order as a right arm sequence, introducing two restriction enzyme sites XbaI and NcoI to two sides of the human TERT promoter, and inserting the left arm sequence and the right arm sequence into SnabI and EcoRV arranged on two sides of pSS-ChI, respectively, by blunt end insertion, to yield pSSENTel;
5) constructing pSSGFP comprising: providing a left arm being a product by ligating 27301-27837 bp of DNA segment of Ad11 genome with EGFP gene via NcoI, and introducing a SnaBI site to 3' terminal of EGFP; providing a right arm being 28337-28920 bp of DNA segment of Ad11 genome; and inserting the left arm and the right arm into SnabI and EcoRV sites arranged on two sides of pSS-kna by blunt end insertion, to yield pSSGFP; and 6) digesting and purifying the pSSENTel and pSSGFP by PmeI, to yield two PmeI digested segments, performing homogenous recombination synchronously between the two PmeI digested segments and pAd11 plasmid, respectively, in BJ5183 cells; screening positive clones using agar plates comprising ampicillin, kanamycin, and chloramphenicol; digesting the positive clones by SwaI and SbfI, and deleting chloramphenicol-resistance gene expression cassette and kanamycin-resistance gene expression cassette to yield pAd11-5ETel-GFP (SEQ ID NO: 11); and digesting and linearizing the pAd11-5ETel-GFP by NotI, and transfecting 293 cells to produce adenovirs vector Ad11-5ETel-GFP.

In a class of this embodiment, the concentrations of ampicillin, kanamycin, and chloramphenicol are 100 mg/mL, 50 μg/mL, and 25 mg/mL, respectively.

In a class of this embodiment, Tel sequence of pSSENTel is substitutable by promoters of other tumor specific genes to yield a tumor-specific oncolytic adenovirus; and GFP sequence of pSSGFP is substitutable by a signal gene or therapeutic gene.

In a class of this embodiment, Ad11 18.5 K gene promoter of pSSGFP is substitutable by a tumor-specific promoter.

A method for treatment of tumor comprises applying a subgroup B recombinant human adenovirus vector Ad11-5EP.

A method for treatment of tumor or detection of tumor cells in circulating blood comprises applying a subgroup B adenovirus vector Ad11-5ETel-GFP.

Advantages of the invention are as follows:

1) The tumor targeting adenovirus vector Ad11-5EP is acquired by substituting the enhancer and the promoter of E1A by the enhancer and the promoter of Ad5E1A based on the wild type Ad11. Such a vector has stronger oncolytic efficacy than the wild type Ad11, thereby enhancing the potency on the tumor cells.

2) The tumor targeting adenovirus vector Ad11-5EP has tumor targeting and antitumoral efficacy. Experiments from oncolytic potency have indicated that Ad11-5EP has stronger potency on tumor cells than Ad5 and stronger cell toxicity than Ad11. Measurements of tumor growth and tumor clearance indicate that Ad11-5EP significantly reduces the tumor growth, and the non-tumor ratio of the tumor-bearing mice is significantly better than Ad11.

3) The tumor targeting adenovirus vector Ad11-5EP can be used as a tumor-targeting genetic engineering drug for treating cancer, thereby producing social and economic benefits.

4) The method for constructing subgroup B human recombinant adenovirus vector Ad11-5ETel-GFP of the invention features that homogeneous recombination is performed synchronously between Ad11-5EP genome and shutter vectors of pSSENTel and pSSGFP to produce recombinant virus vector Ad11-5ETel-GFP. Ad11-5ETel-GFP can be used in cancer therapy or detection of cancer cells in circulating blood. Expression tests of GFP of Ad11-5ETel-GFP in human normal epithelial cells and cancer cells and CTCs tests demonstrated that Ad11-5ETel-GFP is very sensitive to cancer cells and is capable of infecting a wide spectrum of cancer cells, thereby being specific, sensitive, and economic to apply in cancer cells detection in circulating blood.

BRIEF DESCRIPTION OF THE DRAWINGS

in FIGS. 2 and 3, white columns represent Ad5, black columns represents Ad11, grid columns represent Ad11-5EP;

in FIGS. 4-5, 1 represents PBS, 2 represents Ad11, 3 represents Ad11-5EP, and 4 represents Ad5;

DETAILED DESCRIPTION OF THE EMBODIMENTS

The invention is further described by the following embodiments but not to limit the protection scope of the invention. It will be obvious to those skilled in the art that changes and modifications may be made without departing from the invention in its broader aspects, and therefore, the aim in the appended claims is to cover all such changes and modifications as fall within the true spirit and scope of the invention.

Example 1

Method for Constructing a Subgroup B Recombinant Human Adenovirus Vector Ad11-5EP A 365 bp fragment comprising an enhancer and a promoter of an upstream coding sequence of Ad5 E1A was substituted for a corresponding region of a serotype Ad11 of the subgroup B human adenovirus vector by homologous recombination to construct the subgroup B recombinant human adenovirus vector Ad11-5EP.

Figure 1:
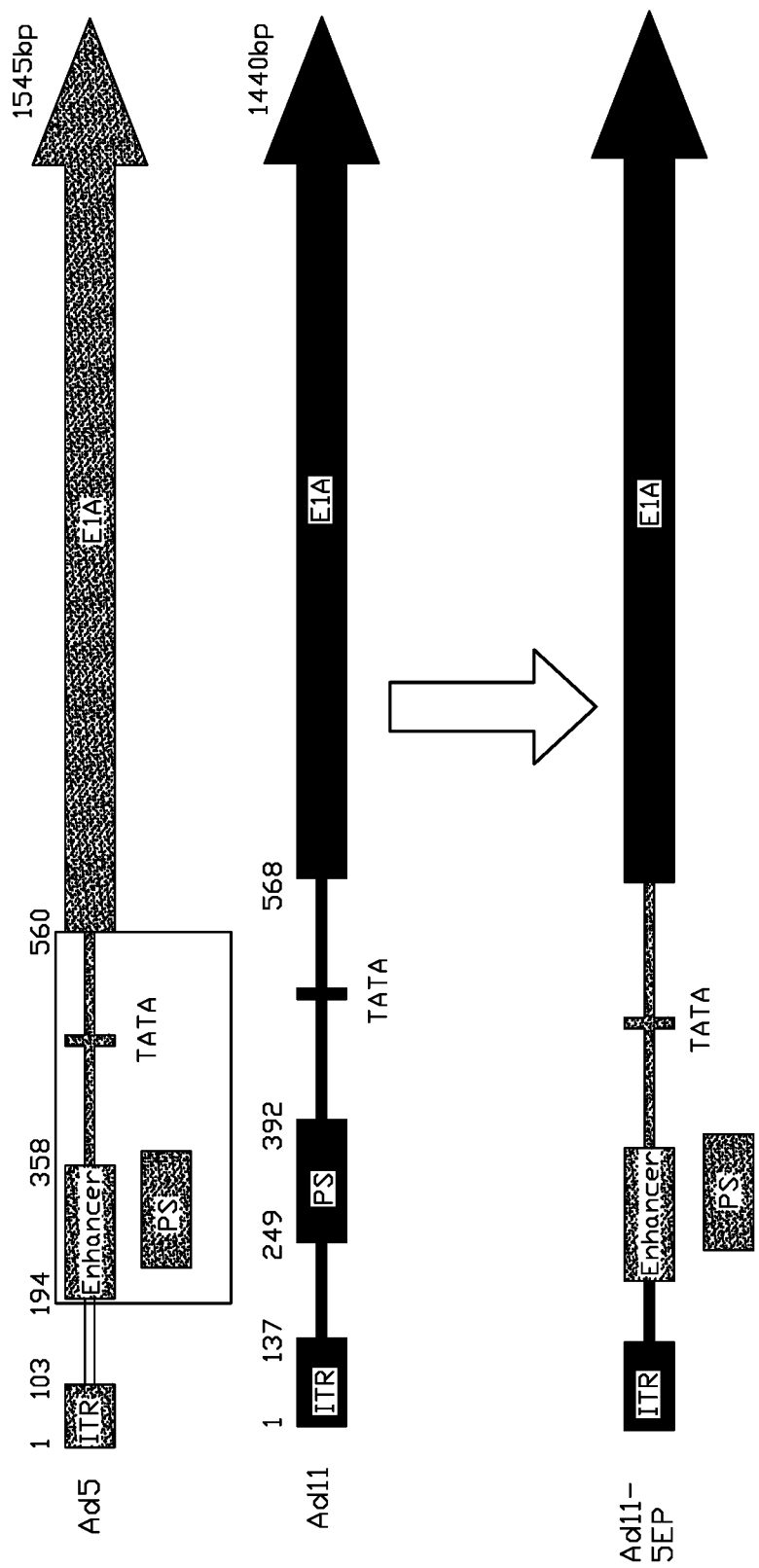
FIG. 1 is a diagram showing a method of construction of a subgroup B recombinant human adenovirus vector Ad11-5EP.

A 329 bp fragment in the front of the Ad11 genome was provided as a left arm sequence, and a fragment formed by ligating a 195-559 bp fragment of Ad5 E1A comprising the enhancer and the promoter and a 568-1125 bp fragment of Ad11 E1A was provided as a right arm sequence. The left arm sequence and the right arm sequence were connected to multi-cloning sites arranged on two sides of pSS-ChI, respectively, to construct a shuttle vector pSS-A1A7. The pSS-A1A7 was digested and purified by PmeI while performing homologous recombination between a PmeI digested segment and pAd11 plasmid within BJ5183 cells. Positive clones were screened using agar plates comprising ampicillin and chloramphenicol. The positive clones were digested by SwaI, and a chloramphenicol-resistance gene expression cassette was deleted to yield pAd11-Ad5EP. The pAd11-Ad5EP was and linearized by NotI, and 293 cells were transfected to yield the adenovirus vector Ad11-5EP (as shown in FIG. 1).

Example 2

Oncolytic Potencies of Ad5, Ad11, and Ad11-5EP in Ad11-Sensitive and -Insensitive Human Cancer Cell Lines Oncolytic potencies of Ad5, Ad11, and Ad11-5EP were tested on Ad11-sensitive human tumor cell lines Capan-2, PaTu8988s, PC-3m MCF7, HT-29 and Ad11-insensitive human tumor cell lines MIAPaCa-2, MDA-MB-231, HCT116, LNCaP, and A549 in vitro. 2% of fetal bovine serum (FBS) medium was employed to prepare cell suspensions of the above 10 cell lines, respectively, and were inoculated to a 96-well plate. After 14-18 h, virus was diluted by a serious dilution. An original concentration was $1 \times 10^4$ pt/cell, and the viral solution was then diluted by a ten-fold series dilution. The diluted solution was added to different cell lines of the 96-well plate at an addition of 10 μl/hole, and the oncolytic potencies of Ad5, Ad11, and Ad11-5EP were tested by MTS on a $6^{th}$ day after the infection.

Figure 2:
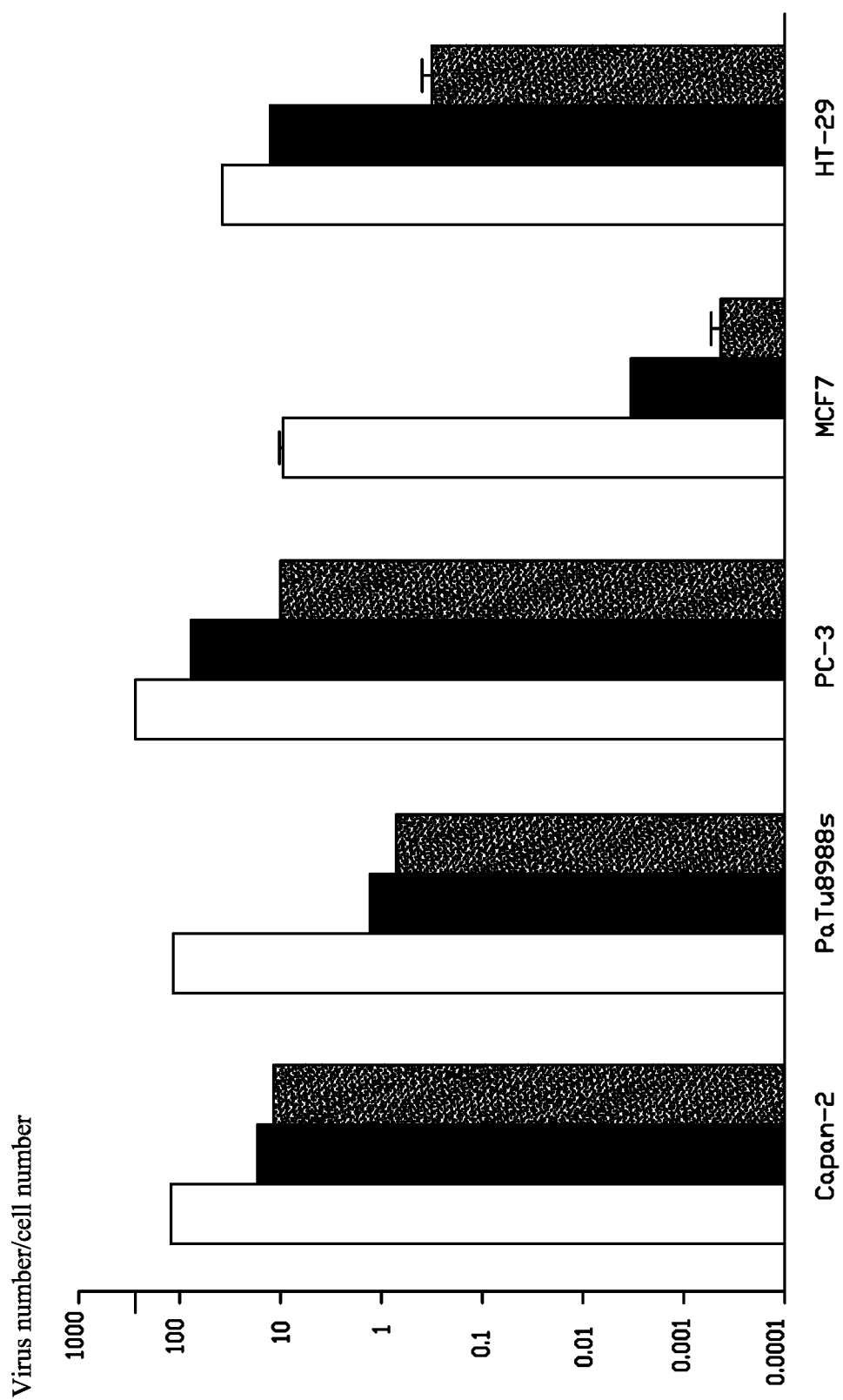
FIG. 2 is a diagram showing oncolytic potency of Ad5, Ad11 and Ad11-5EP in human cancer cells sensitive to Ad11.
Figure 3:
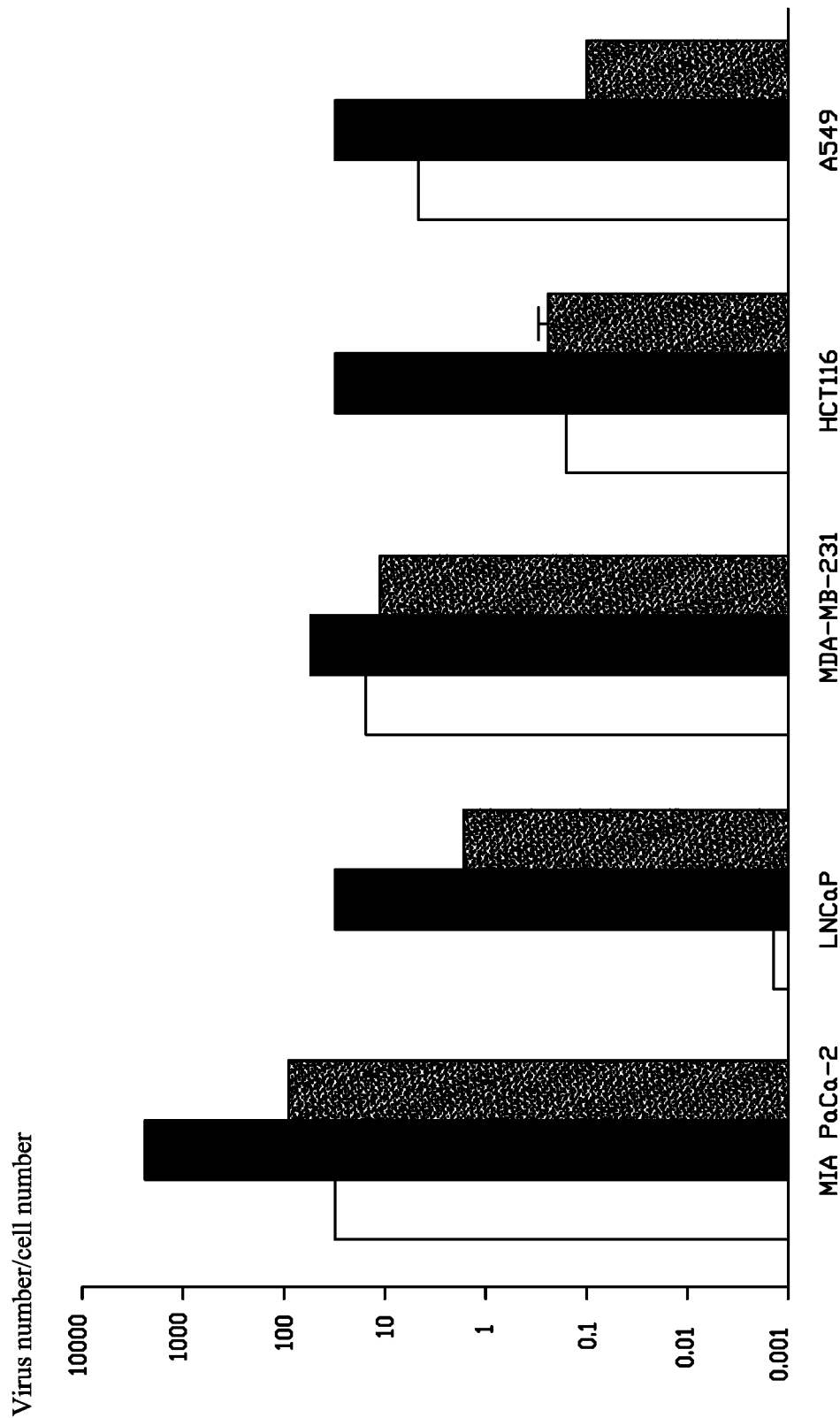
FIG. 3 is a diagram showing oncolytic potency of Ad5, Ad11 and Ad11-5EP in human cancer cells less sensitive to Ad11.

Results showed that: in all Ad11-sensitive cell lines, Ad11-5EP has better oncolytic potency than Ad5, and Ad11 produced stronger cytotoxicity (as shown in FIG. 2) whereas in Ad11-insensitive cell lines, performance of Ad11-5EP was significantly improved (as shown in FIG. 3). Ad11-5EP showed a high sensitivity in 90% ($9/10$) cell lines, which indicated that Ad5 and Ad11 has better cancer killing efficacy, and Ad11-5EP was capable of killing a wide spectrum of cancer cells.

Example 3

Figure 4:
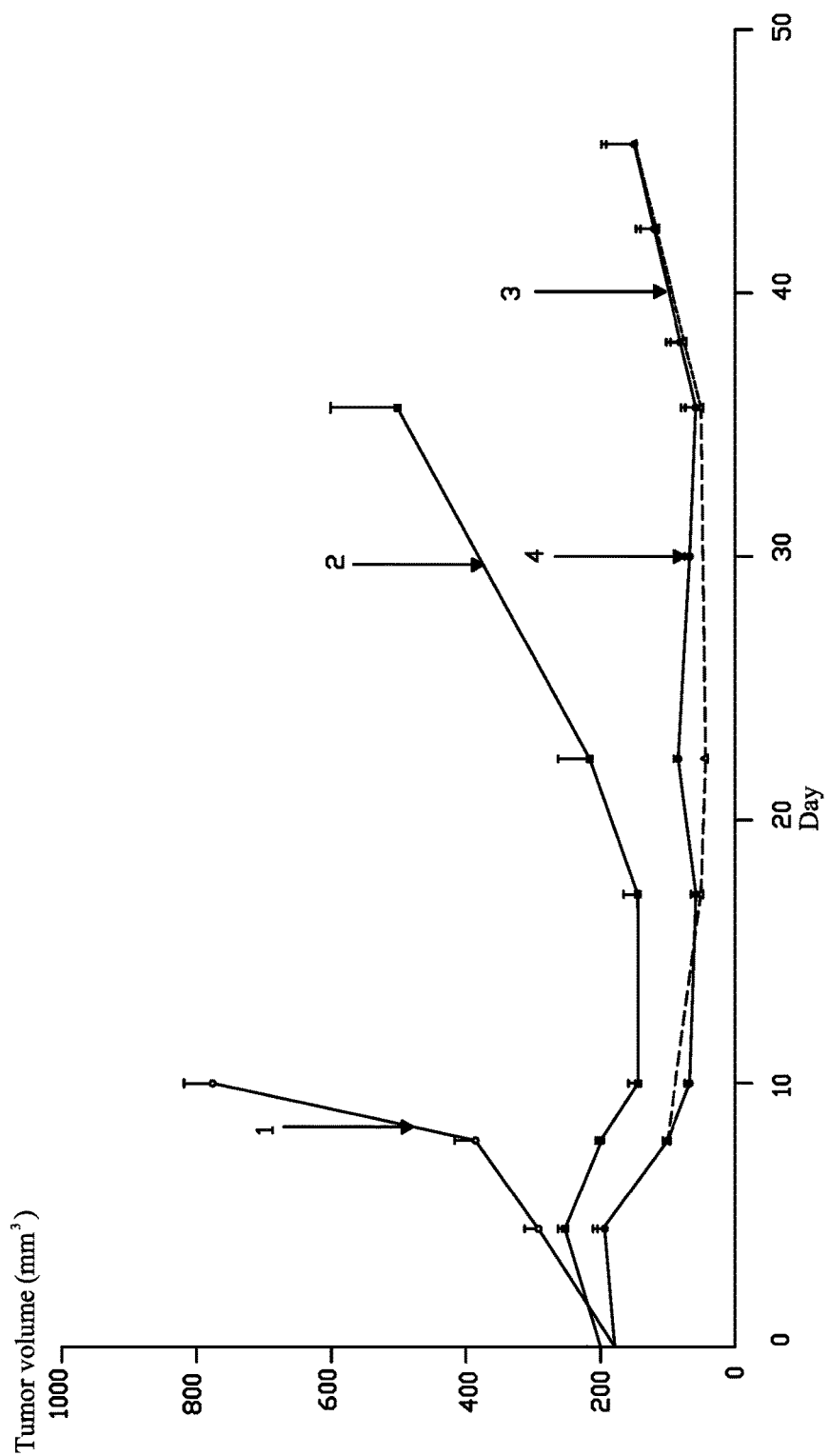
FIG. 4 is a curve chart showing mean tumor volume after treatment of Ad5, Ad11, and Ad11-5EP in MIAPaCa-2 subcutaneous xenograft model.
Figure 5:
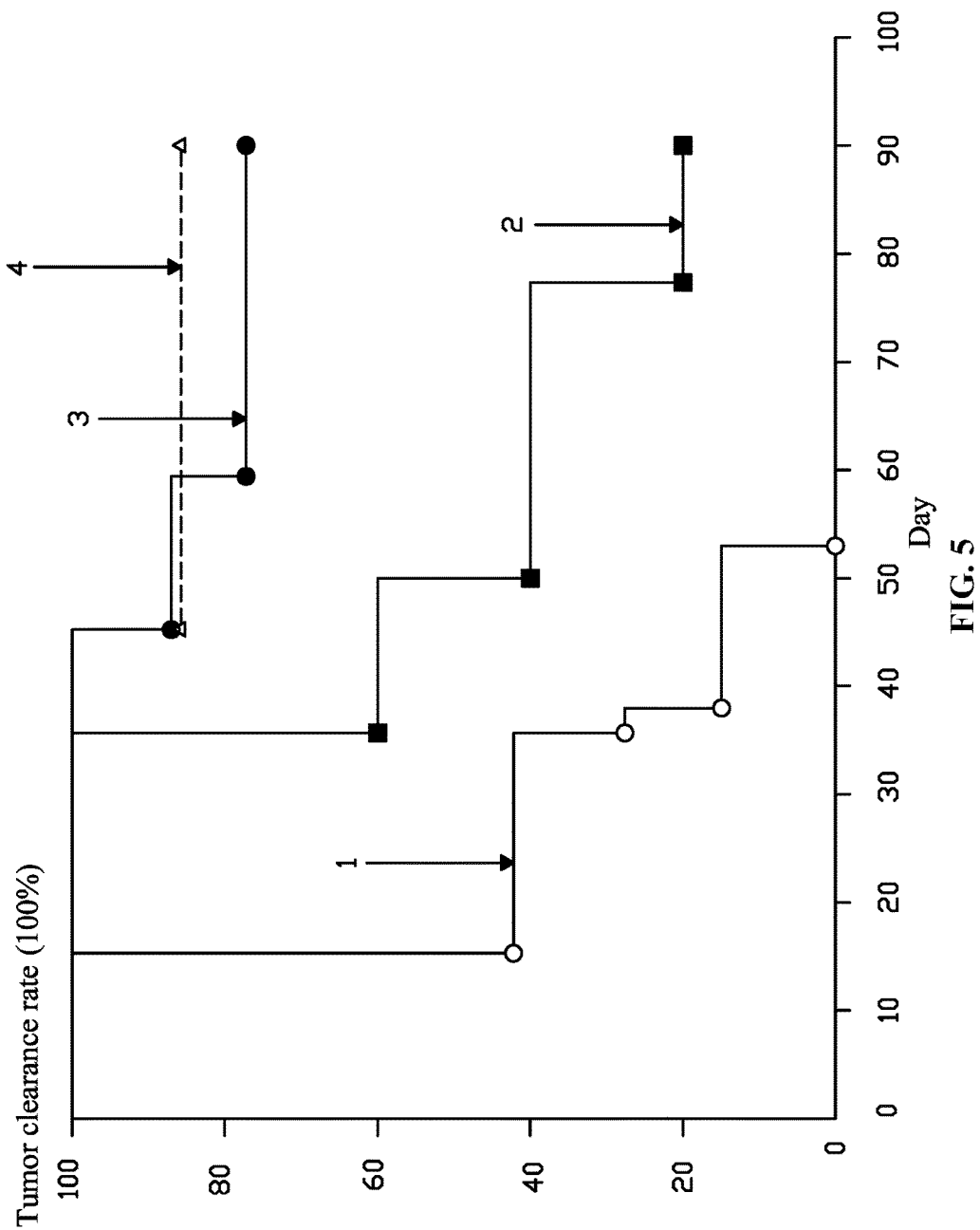
FIG. 5 is a chart showing percentage of progression-free mice after treatment with Ad5, Ad11, and Ad11-5EP in MIAPaCa-2 subcutaneous xenograft model.

Antitumoral Efficacy of Ad5, Ad11, and Ad11-5EP in a MIAPaCa-2 Subcutaneous Xenograft Model MIAPaCa-2 cells (as MIAPaCa-2 is Ad11-insensitve and Ad5-sensitive) were subcutaneously grafted to right backs of BALA/c nude mice (n=8/group), respectively, to construct subcutaneous xenograft models. When a volume of the tumor reached 180 mm$^3$, PBS or viruses (Ad5, Ad11, and Ad11-5EP, $1 \times 10^{10}$ viral particles/injection) were injected at a $1^{st}$, $3^{rd}$, and $5^{th}$ days, tumor growth and tumor clearance rate were observed. Results showed that Ad11-5EP was as effective as Ad5 in reducing tumor growth (as shown in FIG. 4), and non-tumor ratio of tumor-bearing mice was significantly better than Ad11-treated group (as shown in FIG. 5).

Example 4

Method for Constructing a Subgroup B Recombinant Human Adenovirus Vector Ad11-5ETel-GFP 1) Vectors pSS-ChI and pSS-kna were constructed by using two different antibiotics-resistance cassettes, SwaI restriction sites were introduced to two flanks of a chloramphenicol-resistance gene sequence cassette, and sbfI restriction sites were introduced to two flanks of a kanamycin-resistance gene sequence cassette.

2) An initiation sequence for replication of pBR32 was cloned by pUC18, and a first synthetic nucleotide sequence comprising multi-cloning sites was connected to the chloramphenicol-resistance gene sequence cassette to yield pSS-ChI. Homologously recombination between an upstream of a left arm sequence and a downstream of a right arm sequence of the chloramphenicol-resistance gene sequence cassette was performed, and the upstream of the left arm sequence of the chloramphenicol-resistance gene sequence cassette and the downstream of the right arm sequence of the chloramphenicol-resistance gene sequence cassette were inserted into the multi-cloning sites on two sides of pSS-ChI by blunt end insertion or cohesive end insertion, respectively, to construct a shuttle vector pSSEN-Tel for recombination.

3) An initiation sequence for replication of pBR32 was cloned by pUC18, and a second synthetic nucleotide sequence comprising multi-cloning sites was connected to the kanamycin-resistance gene sequence cassette to yield pSS-kna. Homologously recombination was performed between an upstream of a left arm sequence and a downstream of a right arm sequence of the kanamycin-resistance gene sequence cassette, and the upstream of the left arm sequence of the kanamycin-resistance gene sequence cassette and the downstream of the right arm sequence of the kanamycin-resistance gene sequence cassette were inserted into the multi-cloning sites on two sides of pSS-kna by blunt end insertion or cohesive end insertion, respectively, to construct a shuttle vector pSSGFP for recombination.

4) pSSENTe was constructed, and the construction of pSSENTe comprised: amplifying a 329 bp in the front of Ad11 genome as a left arm sequence, providing a fragment formed by ligating 195-378 bp of Ad5 E1A enhancer, −714-0 bp of human TERT promoter, and 568-1125 bp of Ad11 E1A in order as a right arm sequence, introducing two restriction enzyme sites XbaI and NcoI to two sides of the human TERT promoter, and inserting the left arm sequence and the right arm sequence into SnabI and EcoRV arranged on two sides of pSS-ChI, respectively, by blunt end insertion, to yield pSSENTel.

5) pSSGFP was constructed and the construction of pSSGFP comprised: providing a left arm being a product by ligating 27301-27837 bp of DNA segment of Ad11 genome with EGFP gene via NcoI, and introducing a SnaBI site to 3' terminal of EGFP; providing a right arm being 28337-28920 bp of DNA segment of Ad11 genome; and inserting the left arm and the right arm into SnabI and EcoRV sites arranged on two sides of pSS-kna by blunt end insertion, to yield pSSGFP.

Figure 6:
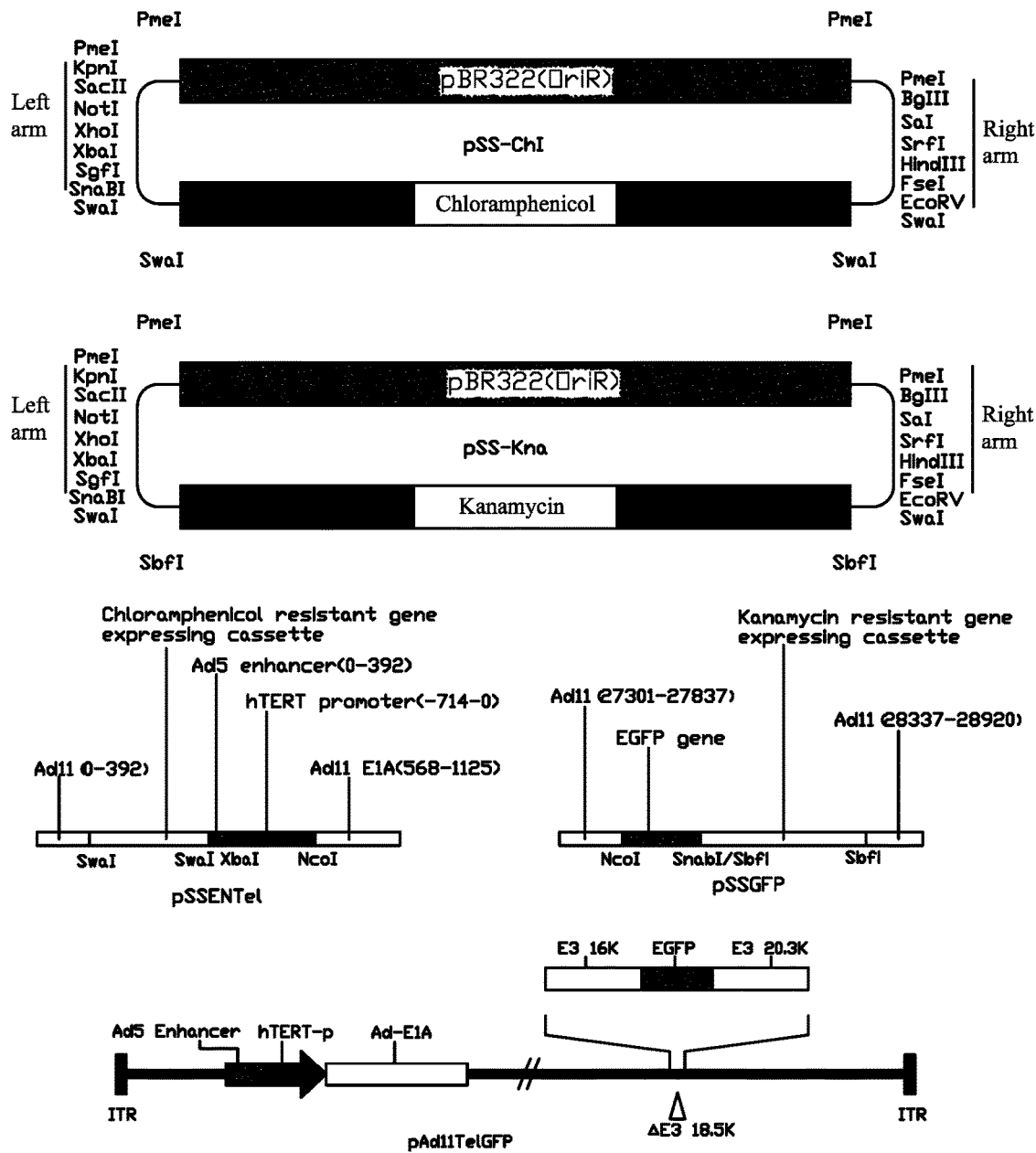
FIG. 6 is a procedure diagram of construction of shutter vectors pSSENTel and pSSGFP and replication-selective oncolytic adenovirus plasmid pAd11-5ETel-GFP.

6) pSSENTel and pSSGFP were digested and purified by PmeI to yield two PmeI digested segments, homogenous recombination was synchronously performed between the two PmeI digested segments and pAd11 plasmid, respectively, in BJ5183 cells. Positive clones were screened using agar plates comprising ampicillin, kanamycin, and chloramphenicol. The positive clones were digested by SwaI and SbfI, and chloramphenicol-resistance gene expression cassette and kanamycin-resistance gene expression cassette were deleted to yield pAd11-5ETel-GFP (as shown in FIG. 6).

The pAd11-5ETel-GFP was and linearized by NotI, and 293 cells were transfected to produce adenovirus vector Ad11-5ETel-GFP.

Example 5

Figure 7:
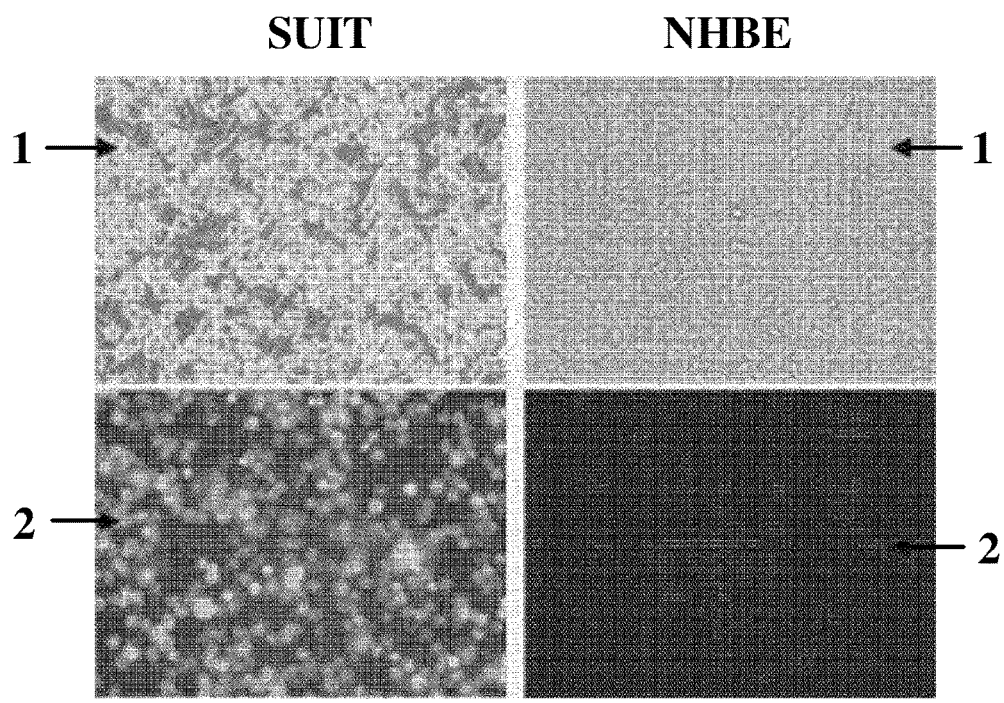
FIG. 7 is a comparison chart of GFP expression after Ad11-5ETel-GFP infection in human normal epithelial cells and cancer cells.

Expression of GFP of Ad11-5ETel-GFP in Human Normal Epithelial Cells and Cancer Cells Ad11-5ETel-GFP was used to infect human pancreatic cancer cell line SUIT-2 and human normal bronchial epithelial cell line NHBE (an infection concentration of 100 pfu/cell), expression of GFP was observed under immunofluorescence microscope after 24 h. It has been found that GFP had a high expression in cancer cell line SUIT-2, and relatively low expression in normal cells NHBE (as shown in FIG. 7), which indicated that the cancer cell line SUIT-2 is Ad11-5ETel-GFP-sensitive.

Example 6

Figure 8:
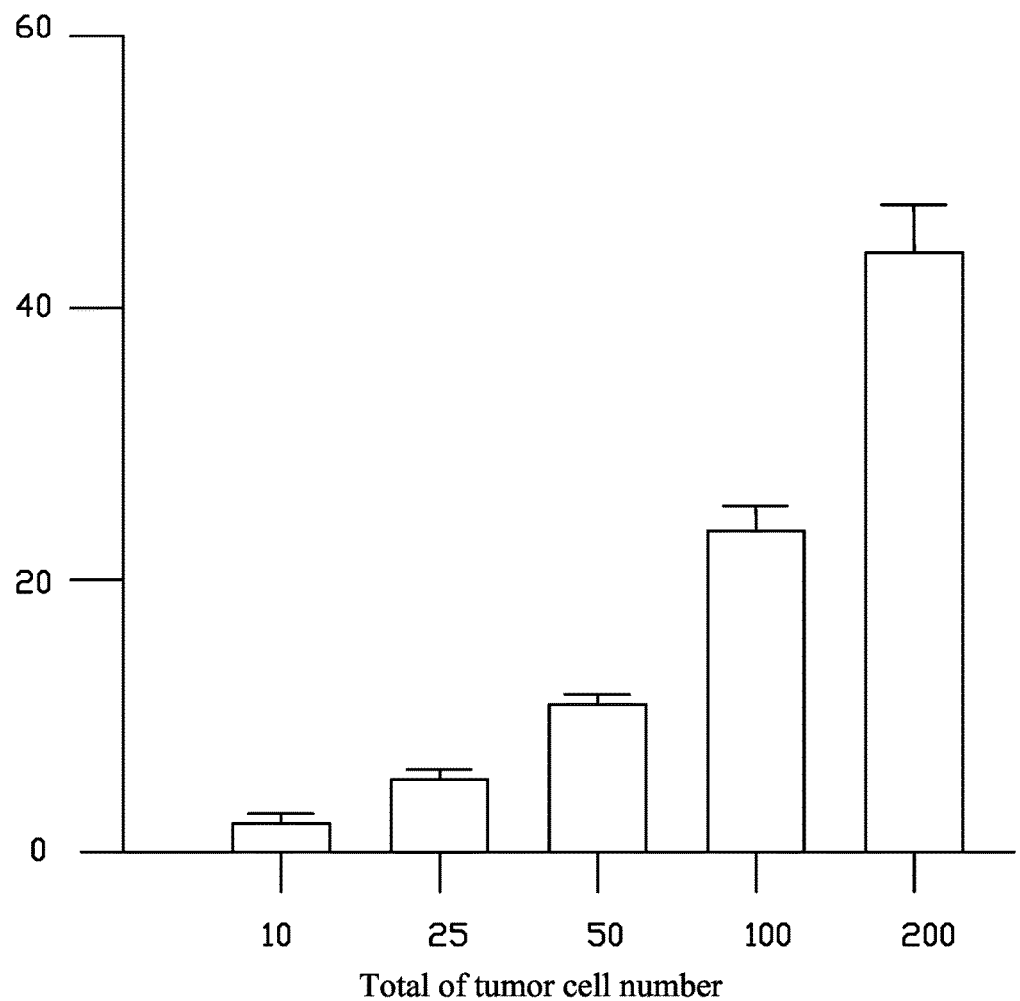
FIG. 8 is a histogram of detected tumor cells in blood by Ad11-5ETel-GFP in number.
Figure 9:
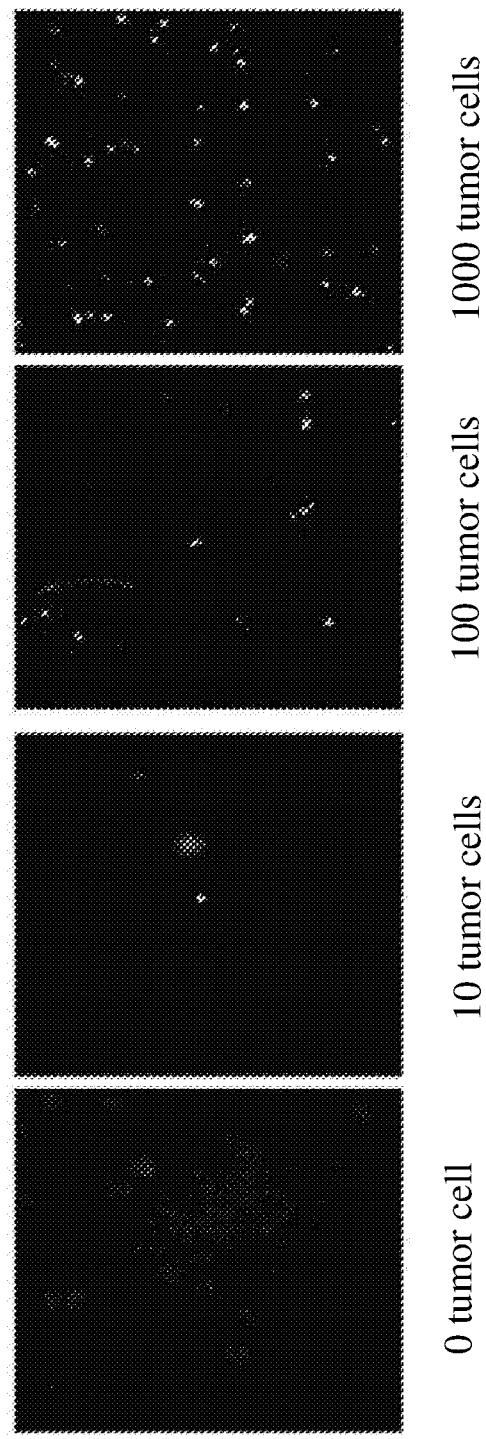
FIG. 9 is a fluorescent image showing detected tumor cells in blood by Ad11-5ETel-GFP in fluorescent image.

Circulation Tumor Cells (CTCs) Detection Using Ad11-5ETel-GFP 10, 25, 50, 100, and 200 human pancreatic cancer cell line SUIT-2 were respectively mixed with 3 mL of blood, nucleated cells were collected by centrifugation after red blood cells were lysised. Thereafter, the nucleated cells were resuspended in 900 μL of DMEM medium, added with 1×104 pfu of Ad11-5ETel-GFP, and cultured for 24 h. GFP positive cells were counted under an immunofluorescence microscope (as shown in FIG. 8). Peripheral blood cells were mixed with 0, 10, 100, and 1000 human pancreatic cancer cell line SUIT-2, respectively (an infection concentration of 100 pfu/cell). The samples were processed as described above. GFP positive cells were observed under the immunofluorescence microscope after 24 h of culturing and it demonstrated that the cancer cell line SUIT-2 is Ad11-5ETel-GFP-sensitive. The GFP-positive cells were correlated to the number of tumor cells mixed with the blood cells.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method for constructing a subgroup B recombinant human adenovirus vector Ad11-5ETel-GFP (SEQ ID NO: 10), the method comprising:
   1) constructing vectors pSS-ChI (SEQ ID NO: 12) and pSS-kna (SEQ ID NO: 13) by using two different antibiotics-resistance cassettes, introducing SwaI restriction sites to two flanks of a chloramphenicol-resistance gene sequence cassette, and introducing sbfI restriction sites to two flanks of a kanamycin-resistance gene sequence cassette;
   2) cloning an initiation sequence for replication of pBR322 (SEQ ID NO: 14) by pUC18 (SEQ ID NO: 15), ligating a first synthetic nucleotide sequence comprising multi-cloning sites to the chloramphenicol-resistance gene sequence cassette to yield pSS-ChI (SEQ ID NO: 12), homologously recombining an upstream of a left arm sequence and a downstream of a right arm sequence of the chloramphenicol-resistance gene sequence cassette, and inserting the upstream of the left arm sequence of the chloramphenicol-resistance gene sequence cassette and the downstream of the right arm sequence of the chloramphenicol-resistance gene sequence cassette into the multi-cloning sites on two sides of pSS-ChI (SEQ ID NO: 12) by blunt end insertion or cohesive end insertion, respectively, to construct a shuttle vector pSSENTel (SEQ ID NO: 16) for recombination;
   3) cloning an initiation sequence for replication of pBR322 (SEQ ID NO: 14) by pUC18 (SEQ ID NO: 15), ligating a second synthetic nucleotide sequence comprising multi-cloning sites to the kanamycin-resistance gene sequence cassette to yield pSS-kna (SEQ ID NO: 13), homologously recombining an upstream of a left arm sequence and a downstream of a right arm sequence of the kanamycin-resistance gene sequence cassette, and inserting the upstream of the left arm sequence of the kanamycin-resistance gene sequence cassette and the downstream of the right arm sequence of the kanamycin-resistance gene sequence cassette into the multi-cloning sites on two sides of pSS-kna (SEQ ID NO: 13) by blunt end insertion or cohesive end insertion, respectively, to construct a shuttle vector pSSGFP (SEQ ID NO: 17) for recombination;
   4) constructing pSSENTel (SEQ ID NO: 16), comprising: amplifying a 329 bp in the front of Ad11 (SEQ ID NO: 3) genome as a left arm sequence, providing a fragment formed by ligating 195-378 bp of Ad5 E1A (SEQ ID NO: 2) enhancer, −714-0 bp of human TERT promoter, and 568-1125 bp of Ad11 E1A (SEQ ID NO: 4) in order as a right arm sequence, introducing two restriction enzyme sites XbaI and NcoI to two sides of the human TERT promoter, and inserting the left arm sequence and the right arm sequence into SnabI and EcoRV arranged on two sides of pSS-ChI (SEQ ID NO: 12), respectively, by blunt end insertion, to yield pSSENTel (SEQ ID NO: 16);
   5) constructing pSSGFP (SEQ ID NO: 17), comprising: providing a left arm being a product by ligating 27301-27837 bp of DNA segment of Ad11 (SEQ ID NO: 3) genome with EGFP gene via NcoI, and introducing a SnaBI site to 3' terminal of EGFP; providing a right arm being 28337-28920 bp of DNA segment of Ad11 (SEQ ID NO: 3) genome; and inserting the left arm and the right arm into SnabI and EcoRV sites arranged on two sides of pSS-kna (SEQ ID NO: 13) by blunt end insertion, to yield pSSGFP (SEQ ID NO: 17); and 6) digesting and purifying the pSSENTel (SEQ ID NO: 16) and pSSGFP (SEQ ID NO: 17) by PmeI, to yield two PmeI digested segments, performing homogenous recombination synchronously between the two PmeI digested segments and pAd11 (SEQ ID NO: 6) plasmid, respectively, in BJ5183 cells; screening positive clones using agar plates comprising ampicillin, kanamycin, and chloramphenicol; digesting the positive clones by SwaI and SbfI, and deleting chloramphenicol-resistance gene expression cassette and kanamycin-resistance gene expression cassette to yield pAd11-5ETel-GFP (SEQ ID NO: 11); and digesting and linearizing the pAd11-5ETel-GFP (SEQ ID NO: 11) by NotI, and transfecting 293 cells to produce adenovirs vector Ad11-5ETel-GFP (SEQ ID NO: 10).

2. The method of claim 1, wherein concentrations of the ampicillin, kanamycin, and chloramphenicol are 100 mg/mL, 50 ug/mL, and 25 mg/mL, respectively.

3. The method of claim 1, wherein Tel sequence of pSSENTel (SEQ ID NO: 16) is substitutable by promoters of other tumor specific genes to yield a tumor-specific oncolytic adenovirus; and GFP sequence of pSSGFP (SEQ ID NO: 17) is substitutable by a signal gene or therapeutic gene.

4. The method of claim 1, wherein Ad11 18.5 K gene promoter of pSSGFP (SEQ ID NO: 17) is substitutable by a tumor-specific promoter.

5. A method for treatment of tumor or detection of tumor cells in circulating blood, the method comprising applying a subgroup B adenovirus vector Ad11-5ETel-GFP (SEQ ID NO: 10) constructed according to a method of claim 1.

* * * * *

SEQUENCE LISTING

<160> NUMBER OF SEQ ID NOS: 17

<210> SEQ ID NO 1
<211> LENGTH: 34801
<212> TYPE: DNA
<213> ORGANISM: Artificial Sequence
<220> FEATURE:
<223> OTHER INFORMATION: Fully synthetic

<400> SEQUENCE: 1

```
catcatcaat aatatacctt atagatggaa tggtgccaat atgtaaatga ggtgatttta        60
aaaagtgtgg atcgtgtggt gattggctgt ggggttaacg gctaaaaggg gcggtgcgac       120
cgtgggaaaa tgacgttttg tgggggtgga gttttttttgc aagttgtcgc gggaaatgtg       180
acgcataaaa aggctacaca ggaagtgaca attttcgcgc ggttttaggc ggatgttgta       240
gtaaatttgg gcgtaaccga gtaagatttg gccattttcg cgggaaaact gaataagagg       300
aagtgaaatc tgaataattt tgtgttactc atagcgcgta atatttgtct agggccgcgg       360
ggactttgac cgtttacgtg gagactcgcc caggtgtttt tctcaggtgt tttccgcgtt       420
cgggtcaaag ttggcgtttt attattatag tcagctgacg tgtagtgtat ttatacccgg       480
tgagttcctc aagaggccac tcttgagtgc cagcgagtag agttttctcc tccgagccgc       540
tccgacaccg ggactgaaaa atgagagatt tgcgatttct gcctcaggaa ataatctctg       600
ctgagactgg aaatgaaata ttggagcttg tggtgcacgc cctgatggga gacgatccgg       660
agccacctgt gcagcttttt gagcctccta cgcttcagga actgtatgat ttagaggtag       720
agggatcgga ggattctaat gaggaagctg taaatgcctt ttttaccgat tctatgcttt       780
tagctgctaa tgaagggtta gaattagatc cgcctttgga cacttttgat actccagggg       840
taattgtgga aagcggtaca ggtgtaagaa aattacctga tttgagttcc gtggactgtg       900
atttgcactg ctatgaagac gggtttcctc cgagtgatga ggaggaccat gaaaaggagc       960
agtccatgca gactgcagcg ggtgagggag tgaaggctgc caatgttggt tttcagttgg      1020
attgcccgga gcttcctgga catggctgta agtcttgtga atttcacagg aaaaatactg      1080
gagtaaagga actgttatgt tcgctttgtt atatgagaac gcactgccac tttatttaca      1140
gtaagtgtgt ttaagttaaa atttaaagga atatgctgtt tttcacatgt atattgagtg      1200
tgagttttgt gcttcttatt ataggtcctg tgtctgatgc tgatgaatca ccatctcctg      1260
```

-continued

```
attctactac ctcacctcct gagattcaag cacctgttcc tgtggacgtg cgcaagccca  1320
ttcctgtgaa gcttaagcct gggaaacgtc cagcagtgga aaaacttgag gacttgttac  1380
agggtgggga cggacctttg gacttgagta cacggaaacg tccaagacaa taagtgttcc  1440
atatccgtgt ttacttaagg tgacgtcaat atttgtgtga cagtgcaatg taataaaaat  1500
atgttaactg ttcactggtt tttattgctt tttgggcggg gactcaggta tataagtaga  1560
agcagacctg tgtggttagc tcataggagc tggctttcat ccatggaggt ttgggccatt  1620
ttggaagacc ttaggaagac taggcaactg ttagagaacg cttcggacgg agtctccggt  1680
ttttggagat tctggttcgc tagtgaatta gctagggtag ttttttaggat aaaacaggac  1740
tataaacaag aatttgaaaa gttgttggta gattgcccag gactttttga agctcttaat  1800
ttgggccatc aggttcactt taaagaaaaa gttttatcag ttttagactt ttcaacccca  1860
ggtagaactg ctgctgctgt ggcttttctt acttttatat tagataaatg gatcccgcag  1920
actcatttca gcaggggata cgttttggat ttcatagcca cagcattgtg gagaacatgg  1980
aaggttcgca agatgaggac aatcttaggt tactggccag tgcagccttt gggtgtagcg  2040
ggaatcctga ggcatccacc ggtcatgcca gcggttctgg aggaggaaca gcaagaggac  2100
aacccgagag ccggcctgga ccctccagtg gaggaggcgg agtagctgac ttgtctcctg  2160
aactgcaacg ggtgcttact ggatctacgt ccactggacg ggatagggc gttaagaggg  2220
agagggcatc tagtggtact gatgctagat ctgagttggc tttaagttta atgagtcgca  2280
gacgtcctga aaccatttgg tggcatgagg ttcagaaaga gggaagggat gaagtttctg  2340
tattgcagga gaaatattca ctggaacagg tgaaaacatg ttggttggag cctgaggatg  2400
attgggaggt ggccattaaa aattatgcca agatagcttt gaggcctgat aaacagtata  2460
agattactag acgattaat atccggaatg cttgttacat atctggaaat ggggctgagg  2520
tggtaataga tactcaagac aaggcagtta ttagatgctg catgatggat atgtggcctg  2580
gggtagtcgg tatggaagca gtaacttttg taaatgttaa gtttagggga gatggttata  2640
atggaatagt gtttatggcc aataccaaac ttatattgca tggttgtagc ttttttggtt  2700
tcaacaatac ctgtgtagat gcctggggac aggttagtgt acggggatgt agtttctatg  2760
cgtgttggat tgccacagct ggcagaacca agagtcaatt gtctctgaag aaatgcatat  2820
ttcaaagatg taacctgggc attctgaatg aaggcgaagc aagggtccgc cactgcgctt  2880
ctacagatac tggatgtttt attttgatta agggaaatgc cagcgtaaag cataacatga  2940
tttgcggtgc ttccgatgag aggccttatc aaatgctcac ttgtgctggt gggcattgta  3000
atatgctggc tactgtgcat attgtttccc atcaacgcaa aaaatggcct gtttttgatc  3060
acaatgtgat gacgaagtgt accatgcatg caggtgggcg tagaggaatg tttatgcctt  3120
accagtgtaa catgaatcat gtgaaagtgt tgttggaacc agatgccttt tccagaatga  3180
gcctaacagg aattttttgac atgaacatgc aaatctggaa gatcctgagg tatgatgata  3240
cgagatcgag ggtacgcgca tgcgaatgcg gaggcaagca tgccaggttc cagccggtgt  3300
gtgtagatgt gactgaagat ctcagaccgg atcatttggt tattgcccgc actggagcag  3360
agttcggatc cagtggagaa gaaactgact aaggtagta ttgggaaaac tttggggtgg  3420
gattttcaga tggacagatt gagtaaaaat ttgttttttc tgtcttgcag ctgtcatgag  3480
tggaaacgct tctttttaagg ggggagtctt cagcccttat ctgacagggc gtctcccatc  3540
ctgggcagga gttcgtcaga atgttatggg atctactgtg gatggaagac ccgtccaacc  3600
cgccaattct tcaacgctga cctatgctac tttaagttct tcacctttgg acgcagctgc  3660
```

-continued

```
agctgccgcc gccgcttctg ttgccgctaa cactgtgctt ggaatgggtt actatggaag    3720
catcatggct aattccactt cctctaataa cccttctacc ctgactcagg acaagttact    3780
tgtccttttg gcccagctgg aggctttgac ccaacgtctg ggtgaacttt ctcagcaggt    3840
ggtcgagttg cgagtacaaa ctgagtctgc tgtcggcacg gcaaagtcta aataaaaaaa    3900
tcccagaatc aatgaataaa taaacaagct tgttgttgat ttaaaatcaa gtgtttttat    3960 ttcattttc gcgcacggta tgccctagac caccgatctc tatcattgag aactcggtgg     4020
attttttcca ggatcctata gaggtgggat tgaatgttta gatacatggg cattaggccg    4080
tctttggggt ggagatagct ccattgaagg gattcatgct ccggggtagt gttgtaaatc    4140
acccagtcat aacaaggtcg cagtgcatgg tgttgcacaa tatcttttag aagtaggctg    4200
attgccacag ataagccctt ggtgtaggtg tttacaaacc ggttgagctg ggatgggtgc    4260
attcggggtg aaattatgtg cattttggat tggattttta agttggcaat attgccgcca    4320
agatcccgtc ttgggttcat gttatgaagg accaccaaga cggtgtatcc ggtacattta    4380
ggaaatttat cgtgcagctt ggatggaaaa gcgtggaaaa atttggagac cccttgtgt    4440 cctccaagat tttccatgca ctcatccatg ataatagcaa tggggccgtg ggcagcggcg    4500
cgggcaaaca cgttccgtgg gtctgacaca tcatagttat gttcctgagt aaatcatca    4560 taagccattt taatgaattt ggggcggaga gtaccagatt ggggtatgaa tgttccttcg    4620
ggccccggag catagttccc ctcacagatt tgcatttccc aagctttcag ttccgagggt    4680
ggaatcatgt ccacctgggg ggctatgaaa aacaccgttt ctgggcggg ggtgattaat     4740 tgtgatgata gcaaatttct gagcaattga gatttgccac atccggtggg gccataaatg    4800
attccgatta cgggttgcag gtggtagttt agggaacggc aactgccgtc ttctcgaagc    4860 aaggggggcca cctcgttcat catttccctt acatgcatat tttcccgcac caaatccatt    4920
aggaggcgct ctcctcctag tgatagaagt tcttgtagtg aggaaaagtt tttcagcggt    4980
ttcagaccgt cagccatggg cattttggag agagtttgct gcaaaagttc tagtctgttc    5040
cacagttcag tgatgtgttc tatggcatct cgatccagca gacctcctcg tttcgcgggt    5100
ttggacggct cctggaatag ggtatgagac gatgggcgtc cagcgctgcc agggttcggt    5160
ccttccaggg tctcagtgtt cgagtcaggg ttgtttccgt cacagtgaag gggtgtgcgc    5220
ctgcttgggc gcttgccagg gtgcgcttca gactcatcct gctggtcgaa aacttctgtc    5280
gcttggcgcc ctgtatgtcg gccaagtagc agtttaccat gagttcgtag ttgagcgcct    5340
cggctgcgtg gcctttggcg cggagcttac ctttggaagt tttcttgcat accgggcagt    5400
ataggcattt cagcgcatac aacttgggcg caaggaaaac ggattctggg gagtatgcat    5460
ctgcgccgca ggaggcgcaa acagtttcac attccaccag ccaggttaaa tccggttcat    5520
tggggtcaaa aacaagtttt ccgccatatt ttttgatgcg tttcttacct ttggtctcca    5580
tgagttcgtg tcctcgttga gtgacaaaca ggctgtccgt gtcccgtag actgattta     5640 caggcctctt ctccagtgga gtgcctcggt cttcttcgta caggaactct gaccactctg    5700
atacaaaggc gcgcgtccag gccagcacaa aggaggctat gtgggagggg tagcgatcgt    5760
tgtcaaccag ggggtccacc ttttccaaag tatgcaaaca catgtcaccc tcttcaacat    5820
ccaggaatgt gattggcttg taggtgtatt tcacgtgacc tggggtcccc gctgggggg    5880 tataaaaggg ggcggttctt tgctcttcct cactgtcttc cggatcgctg tccaggaacg    5940
tcagctgttg gggtaggtat tccctctcga aggcgggcat gacctctgca ctcaggttgt    6000
```

```
cagtttctaa gaacgaggag gatttgatat tgacagtgcc ggttgagatg cctttcatga   6060
ggttttcgtc catttggtca gaaaacacaa ttttttttatt gtcaagtttg gtggcaaatg   6120
atccatacag ggcgttggat aaaagtttgg caatggatcg catggtttgg ttcttttcct   6180
tgtccgcgcg ctctttggcg gcgatgttga gttggacata ctcgcgtgcc aggcacttcc   6240
attcggggaa gatagttgtt aattcatctg gcacgattct cacttgccac cctcgattat   6300
gcaaggtaat taaatccaca ctggtggcca cctcgcctcg aagggggttca ttggtccaac   6360 agagcctacc tcctttccta gaacagaaag ggggaagtgg gtctagcata agttcatcgg   6420
gagggtctgc atccatggta aagattcccg gaagtaaatc cttatcaaaa tagctgatgg   6480 gagtgggtc atctaaggcc atttgccatt ctcgagctgc cagtgcgcgc tcatatgggt   6540 taagggact gccccatggc atgggatggg tgagtgcaga ggcatacatg ccacagatgt   6600
catagacgta gatgggatcc tcaaagatgc ctatgtaggt tggatagcat cgccccctc   6660 tgatacttgc tcgcacatag tcatatagtt catgtgatgg cgctagcagc cccggaccca   6720
agttggtgcg attgggtttt tctgttctgt agacgatctg gcgaaagatg gcgtgagaat   6780
tggaagagat ggtgggtctt tgaaaaatgt tgaaatgggc atgaggtaga cctacagagt   6840
ctctgacaaa gtgggcataa gattcttgaa gcttggttac cagttcggcg gtgacaagta   6900
cgtctagggc gcagtagtca agtgtttctt gaatgatgtc ataacctggt tggttttct   6960 tttcccacag ttcgcggttg agaaggtatt cttcgcgatc cttccagtac tcttctagcg   7020
gaaacccgtc tttgtctgca cggtaagatc ctagcatgta gaactgatta actgccttgt   7080
aagggcagca gcccttctct acgggtagag agtatgcttg agcagctttt cgtagcgaag   7140
cgtgagtaag ggcaaaggtg tctctgacca tgactttgag aaattggtat ttgaagtcga   7200
tgtcgtcaca ggctccctgt tcccagagtt ggaagtctac ccgtttcttg taggcggggt   7260
tgggcaaagc gaaagtaaca tcattgaaga gaatcttacc ggctctgggc ataaaattgc   7320
gagtgatgcg aaaaggctgt ggtacttccg ctcgattgtt gatcacctgg gcagctagga   7380
cgatctcgtc gaaaccgttg atgttgtgtc ctacgatgta taattctatg aaacgcggcg   7440
tgcctctgac gtgaggtagc ttactgagct catcaaaggt taggtctgtg ggtcagata   7500 aggcgtagtg ttcgagagcc cattcgtgca ggtgaggatt tgcatgtagg aatgatgacc   7560
aaagatctac cgccagtgct gtttgtaact ggtcccgata ctgacgaaaa tgccggccaa   7620
ttgccatttt ttctggagtg acacagtaga aggttctggg gtcttgttgc catcgatccc   7680
acttgagttt aatggctaga tcgtgggcca tgttgacgag acgctcttct cctgagagtt   7740
tcatgaccag catgaaagga actagttgtt tgccaaagga tcccatccag gtgtaagttt   7800
ccacatcgta ggtcaggaag agtctttctg tgcgaggatg agagccgatc gggaagaact   7860
ggatttcctg ccaccagttg gaggattggc tgttgatgtg atggaagtag aagtttctgc   7920
ggcgcgccga gcattcgtgt ttgtgcttgt acagacggcc gcagtagtcg cagcgttgca   7980
cgggttgtat ctcgtgaatg agttgtacct ggcttccctt gacgagaaat ttcagtggga   8040
agccgaggcc tggcgattgt atctcgtgct cttctatatt cgctgtatcg gcctgttcat   8100
cttctgtttc gatggtggtc atgctgacga gcccccgcgg gaggcaagtc cagacctcgg   8160
cgcgggaggg gcggagctga aggacgagag cgcgcaggct ggagctgtcc agagtcctga   8220
gacgctgcgg actcaggtta gtaggtaggg acagaagatt aacttgcatg atcttttcca   8280
gggcgtgcgg gaggttcaga tggtacttga tttccacagg ttcgtttgta gagacgtcaa   8340
tggcttgcag ggttccgtgt ccttggggcg ccactaccgt acctttgttt ttcttttga   8400
```

-continued

```
tcggtggtgg ctctcttgct tcttgcatgc tcagaagcgg tgacggggac gcgcgccggg    8460
cggcagcggt tgttccggac ccgagggcat ggctggtagt ggcacgtcgg cgccgcgcac    8520
gggcaggttc tggtactgcg ctctgagaag acttgcgtgc gccaccacgc gtcgattgac    8580
gtcttgtatc tgacgtctct gggtgaaagc taccggcccc gtgagcttga acctgaaaga    8640
gagttcaaca gaatcaattt cggtatcgtt aacggcagct tgtctcagta tttcttgtac    8700
gtcaccagag ttgtcctggt aggcgatctc cgccatgaac tgctcgattt cttcctcctg    8760
aagatctccg cgacccgctc tttcgacggt ggccgcgagg tcattggaga tacggcccat    8820
gagttgggag aatgcattca tgcccgcctc gttccagacg cggctgtaaa ccacggcccc    8880
ctcggagtct cttgcgcgca tcaccacctg agcgaggtta agctccacgt gtctggtgaa    8940
gaccgcatag ttgcataggc gctgaaaaag gtagttgagt gtggtggcaa tgtgttcggc    9000
gacgaagaaa tacatgatcc atcgtctcag cggcatttcg ctaacatcgc ccagagcttc    9060
caagcgctcc atggcctcgt agaagtccac ggcaaaatta aaaaactggg agtttcgcgc    9120
ggacacggtc aattcctcct cgagaagacg gatgagttcg gctatggtgg cccgtacttc    9180
gcgttcgaag gctcccggga tctcttcttc ctcttctatc tcttcttcca ctaacatctc    9240
ttcttcgtct tcaggcgggg gcggaggggg cacgcggcga cgtcgacggc gcacgggcaa    9300 acgtcgatg aatcgttcaa tgacctctcc gcggcggcgg cgcatggttt cagtgacggc    9360
gcggccgttc tcgcgcggtc gcagagtaaa acaccgccg cgcatctcct taaagtggtg    9420
actgggaggt tctccgtttg ggagggagag ggcgctgatt atacatttta ttaattggcc    9480
cgtagggact gcacgcagag atctgatcgt gtcaagatcc acgggatctg aaaacctttc    9540
gacgaaagcg tctaaccagt cacagtcaca aggtaggctg agtacggctt cttgtgggcg    9600
ggggtggtta tgtgttcggt ctgggtcttc tgtttcttct tcatctcggg aaggtgagac    9660
gatgctgctg gtgatgaaat taaagtaggc agttctaaga cggcggatgg tggcgaggag    9720
caccaggtct ttgggtccgg cttgctggat acgcaggcga ttggccattc cccaagcatt    9780
atcctgacat ctagcaagat cttttgtagta gtcttgcatg agccgttcta cgggcacttc    9840
ttcctcaccc gttctgccat gcatacgtgt gagtccaaat ccgcgcattg gttgtaccag    9900
tgccaagtca gctacgactc tttcggcgag gatggcttgc tgtacttggg taagggtggc    9960
ttgaaagtca tcaaaatcca caagcggtg gtaagctcct gtattaatgg tgtaagcaca   10020
gttggccatg actgaccagt taactgtctg gtgaccaggg cgcacgagct cggtgtattt   10080
aaggcgcgaa taggcgcggg tgtcaaagat gtaatcgttg caggtgcgca ccagatactg   10140
gtaccctata agaaaatgcg gcggtggttg gcggtagaga ggccatcgtt ctgtagctgg   10200
agcgccaggg gcgaggtctt ccaacataag gcggtgatag ccgtagatgt acctggacat   10260
ccaggtgatt cctgcggcgg tagtagaagc ccgaggaaac tcgcgtacgc ggttccaaat   10320
gttgcgtagc ggcatgaagt agttcattgt aggcacggtt tgaccagtga ggcgcgcgca   10380
gtcattgatg ctctatagac acgagaaaa tgaaagcgtt cagcgactcg actccgtagc   10440
ctggaggaac gtgaacgggt tgggtcgcgg tgtaccccgg ttcgagactt gtactcgagc   10500
cggccggagc cgcggctaac gtggtattgg cactcccgtc tcgacccagc ctacaaaaat   10560
ccaggatacg gaatcgagtc gttttgctgg tttccgaatg gcaggaagt gagtcctatt   10620 tttttttttt tgccgctcag atgcatcccg tgctgcgaca gatgcgcccc caacaacagc   10680
ccccctcgca gcagcagcag cagcaatcac aaaaggctgt ccctgcaact actgcaactg   10740
```

```
ccgccgtgag cggtgcggga cagcccgcct atgatctgga cttggaagag ggcgaaggac   10800
tggcacgtct aggtgcgcct tcacccgagc ggcatccgcg agttcaactg aaaaaagatt   10860
ctcgcgaggc gtatgtgccc aacagaacc tatttagaga cagaagcggc gaggagccgg    10920
aggagatgcg agcttcccgc tttaacgcgg gtcgtgagct gcgtcacggt ttggaccgaa   10980
gacgagtgtt gcgggacgag gatttcgaag ttgatgaaat gacagggatc agtcctgcca   11040
gggcacacgt ggctgcagcc aaccttgtat cggcttacga gcagacagta aaggaagagc   11100
gtaacttcca aaagtctttt aataatcatg tgcgaaccct gattgccgc gaagaagtta    11160 cccttggttt gatgcatttg tgggatttga tggaagctat cattcagaac cctactagca   11220
aacctctgac cgcccagctg tttctggtgg tgcaacacag cagagacaat gaggctttca   11280
gagaggcgct gctgaacatc accgaacccg aggggagatg gttgtatgat cttatcaaca   11340
ttctacagag tatcatagtg caggagcgga gcctgggcct ggccgagaag gtggctgcca   11400
tcaattactc ggttttgagc ttgggaaaat attacgctcg caaaatctac aagactccat   11460
acgttcccat agacaaggag gtgaagatag atgggttcta catgcgcatg acgctcaagg   11520
tcttgaccct gagcgatgat cttggggtgt atcgcaatga cagaatgcat cgcgcggtta   11580
gcgccagcag gaggcgcgag ttaagcgaca gggaactgat gcacagtttg caaagagctc   11640
tgactggagc tggaaccgag ggtgagaatt acttcgacat gggagctgac ttgcagtggc   11700
agcctagtcg cagggctctg agcgccgcga cggcaggatg tgagcttcct tacatagaag   11760
aggcggatga aggcgaggag gaagagggcg agtacttgga agactgatgg cacaacccgt   11820 gtttttgct agatggaaca gcaagcaccg gatcccgcaa tgcgggcggc gctgcagagc    11880
cagccgtccg gcattaactc ctcggacgat tggacccagg ccatgcaacg tatcatggcg   11940
ttgacgactc gcaaccccga agcctttaga cagcaacccc aggccaaccg tctatcggcc   12000
atcatggaag ctgtagtgcc ttcccgctct aatcccactc atgagaaggt cctggccatc   12060
gtgaacgcgt tggtggagaa caaagctatt cgtccagatg aggccggact ggtatacaac   12120
gctctcttag aacgcgtggc tcgctacaac agtagcaatg tgcaaaccaa tttggaccgt   12180
atgataacag atgtacgcga agccgtgtct cagcgcgaaa ggttccagcg tgatgccaac   12240
ctgggttcgc tggtggcgtt aaatgctttc ttgagtactc agcctgctaa tgtgccgcgt   12300
ggtcaacagg attatactaa ctttttaagt gctttgagac tgatggtatc agaagtacct   12360
cagagcgaag tgtatcagtc cggtcctgat tacttctttc agactagcag acagggcttg   12420
cagacggtaa atctgagcca agcttttaaa aaccttaaag gtttgtgggg agtgcatgcc   12480
ccggtaggag aaagagcaac cgtgtctagc ttgttaactc cgaactcccg cctattatta   12540
ctgttggtag ctccttttcac cgacagcggt agcatcgacc gtaattccta tttgggttac   12600
ctactaaacc tgtatcgcga agccataggg caaagtcagg tggacgagca gacctatcaa   12660
gaaattaccc aagtcagtcg cgcttttggga caggaagaca ctggcagttt ggaagccact   12720
ctgaacttct tgcttaccaa tcggtctcaa aagatccctc ctcaatatgc tcttactgcg   12780
gaggaggaga ggatccttag atatgtgcag cagagcgtgg gattgtttct gatgcaagag   12840
ggggcaactc cgactgcagc actggacatg acagcgcgaa atatggagcc cagcatgtat   12900
gccagtaacc gacctttcat taacaaactg ctggactact tgcacagagc tgccgctatg   12960
aactctgatt atttcaccaa tgccatctta aacccgcact ggctgccccc acctggtttc   13020
tacacgggcg aatatgacat gcccgaccct aatgacggat ttctgtggga cgacgtggac   13080
agcgatgttt tttcacctct ttctgatcat cgcacgtgga aaaaggaagg cggcgataga   13140
```

```
atgcattctt ctgcatcgct gtccggggtc atgggtgcta ccgcggctga gcccgagtct   13200
gcaagtcctt ttcctagtct acccttttct ctacacagtg tacgtagcag cgaagtgggt   13260
agaataagtc gcccgagttt aatgggcgaa gaggagtatc taaacgattc cttgctcaga   13320
ccggcaagag aaaaaaattt cccaaacaat ggaatagaaa gtttggtgga taaaatgagt   13380
agatggaaga cttatgctca ggatcacaga gacgagcctg ggatcatggg gattacaagt   13440
agagcgagcc gtagacgcca gcgccatgac agacagaggg gtcttgtgtg ggacgatgag   13500
gattcggccg atgatagcag cgtgctggac ttgggtggga gaggaagggg caacccgttt   13560
gctcatttgc gccctcgctt gggtggtatg ttgtaaaaaa aaataaaaaa aaaactcacc   13620
aaggccatgg cgacgagcgt acgttcgttc ttctttatta tctgtgtcta gtataatgag   13680
gcgagtcgtg ctaggcggag cggtggtgta tccggagggt cctcctcctt cgtacgagag   13740
cgtgatgcag cagcagcagg cgacggcggt gatgcaatcc ccactggagg ctccctttgt   13800
gcctccgcga tacctggcac ctacggaggg cagaaacagc attcgttatt cggaactggc   13860
acctcagtac gataccacca ggttgtatct ggtggacaac aagtcggcgg acattgcttc   13920
tctgaactat cagaatgacc acagcaactt cttgaccacg gtggtgcaaa acaatgactt   13980 taccccctacg gaagccagca cccagaccat taactttgat gaacgatcgc ggtggggcgg   14040
tcagctaaag accatcatgc atactaacat gccaaacgtg aacgagtata tgtttagtaa   14100
caagttcaaa gcgcgtgtga tggtgtccag aaaacctccc gacggtgctg cagttgggga   14160
tacttatgat cacaagcagg atattttgaa atatgagtgg ttcgagttta ctttgccaga   14220
aggcaacttt tcagttacta tgactattga tttgatgaac aatgccatca tagataatta   14280
cttgaaagtg ggtagacaga atggagtgct tgaaagtgac attggtgtta agttcgacac   14340
caggaacttc aagctgggat gggatcccga aaccaagttg atcatgcctg gagtgtatac   14400
gtatgaagcc ttccatcctg acattgtctt actgcctggc tgcggagtgg attttaccga   14460
gagtcgtttg agcaaccttc ttggtatcag aaaaaaacag ccatttcaag agggttttaa   14520
gattttgtat gaagatttag aaggtggtaa tattccggcc ctcttggatg tagatgccta   14580
tgagaacagt aagaaagaac aaaaagccaa aatagaagct gctacagctg ctgcagaagc   14640
taaggcaaac atagttgcca gcgactctac aagggttgct aacgctggag aggtcagagg   14700
agacaatttt gcgccaacac ctgttccgac tgcagaatca ttattggccg atgtgtctga   14760
aggaacggac gtgaaactca ctattcaacc tgtagaaaaa gatagtaaga atagaagcta   14820
taatgtgttg gaagacaaaa tcaacacagc ctatcgcagt tggtatcttt cgtacaatta   14880
tggcgatccc gaaaaaggag tgcgttcctg gacattgctc accacctcag atgtcacctg   14940
cggagcagag caggtctact ggtcgcttcc agacatgatg aaggatcctg tcactttccg   15000
ctccactaga caagtcagta actaccctgt ggtgggtgca gagcttatgc ccgtcttctc   15060
aaagagcttc tacaacgaac aagctgtgta ctcccagcag ctccgccagt ccacctcgct   15120
tacgcacgtc ttcaaccgct ttcctgagaa ccagatttta atccgtccgc cggcgcccac   15180
cattaccacc gtcagtgaaa acgttcctgc tctcacagat cacgggaccc tgccgttgcg   15240
cagcagtatc cggggagtcc aacgtgtgac cgttactgac gccagacgcc gcacctgtcc   15300
ctacgtgtac aaggcactgg gcatagtcgc accgcgcgtc ctttcaagcc gcactttcta   15360
aaaaaaaaaa aaatgtccat tcttatctcg cccagtaata acaccggttg gggtctgcgc   15420
gctccaagca agatgtacgg aggcgcacgc aaacgttcta cccaacatcc tgtccgtgtt   15480
```

```
cgcggacatt ttcgcgctcc atggggcgcc ctcaagggcc gcactcgcgt tcgaaccacc    15540
gtcgatgatg taatcgatca ggtggttgcc gacgcccgta attatactcc tactgcgcct    15600
acatctactg tggatgcagt tattgacagt gtagtggctg acgctcgcaa ctatgctcga    15660
cgtaagagcc ggcgaaggcg cattgccaga cgccaccgag ctaccactgc catgcgagcc    15720
gcaagagctc tgctacgaag agctagacgc gtggggcgaa gagccatgct tagggcggcc    15780
agacgtgcag cttcgggcgc cagcgccggc aggtcccgca ggcaagcagc cgctttcgca    15840
gcggcgacta ttgccgacat ggcccaatcg cgaagaggca atgtatactg ggtgcgtgac    15900
gctgccaccg gtcaacgtgt acccgtgcgc acccgtcccc ctcgcactta aagatactg    15960 agcagtctcc gatgttgtgt cccagcggcg aggatgtcca agcgcaaata caaggaagaa    16020
atgctgcagg ttatcgcacc tgaagtctac ggccaaccgt tgaaggatga aaaaaaaccc    16080
cgcaaaatca agcgggttaa aaaggacaaa aaagaagagg aagatggcga tgatgggctg    16140
gcggagtttg tgcgcgagtt tgccccacgg cgacgcgtgc aatggcgtgg gcgcaaagtt    16200
cgacatgtgt tgagacctgg aacttcggtg gtctttacac ccggcgagcg ttcaagcgct    16260
acttttaagc gttcctatga tgaggtgtac ggggatgatg atattcttga gcaggcggct    16320
gaccgattag gcgagtttgc ttatggcaag cgtagtagaa taacttccaa ggatgagaca    16380
gtgtcgatac ccttggatca tggaaatccc acccctagtc ttaaaccggt cactttgcag    16440
caagtgttac ccgtaactcc gcgaacaggt gttaaacgcg aaggtgaaga tttgtatccc    16500
actatgcaac tgatggtacc caaacgccag aagttggagg acgttttgga gaaagtaaaa    16560
gtggatccag atattcaacc tgaggttaaa gtgagaccca ttaagcaggt agcgcctggt    16620 ctggggtac aaactgtaga cattaagatt cccactgaaa gtatggaagt gcaaactgaa    16680
cccgcaaagc ctactgccac ctccactgaa gtgcaaacgg atccatggat gcccatgcct    16740
attacaactg acgccgccgg tcccactcga agatcccgac gaaagtacgg tccagcaagt    16800
ctgttgatgc ccaattatgt tgtacaccca tctattattc ctactcctgg ttaccgaggc    16860
actcgctact atcgcagccg aaacagtacc tcccgccgtc gccgcaagac acctgcaaat    16920
cgcagtcgtc gccgtagacg cacaagcaaa ccgactcccg cgccctggt gcggcaagtg    16980 taccgcaatg gtagtgcgga acctttgaca ctgccgcgtg cgcgttacca tccgagtatc    17040
atcacttaat caatgttgcc gctgcctcct tgcagatatg gccctcactt gtcgccttcg    17100
cgttcccatc actggttacc gaggaagaaa ctcgcgccgt agaagaggga tgttgggacg    17160
cggaatgcga cgctacaggc gacggcgtgc tatccgcaag caattgcggg gtggttttt    17220 accagcctta attccaatta tcgctgctgc aattggcgcg ataccaggca tagcttccgt    17280
ggcggttcag gcctcgcaac gacattgaca ttggaaaaaa acgtataaat aaaaaaaaaa    17340
aaatacaatg gactctgaca ctcctggtcc tgtgactatg ttttcttaga gatggaagac    17400 atcaatttttt catccttggc tccgcgacac ggcacgaagc cgtacatggg cacctggagc    17460
gacatcggca cgagccaact gaacgggggc gccttcaatt ggagcagtat ctggagcggg    17520
cttaaaaatt ttggctcaac cataaaaaca tacgggaaca aagcttggaa cagcagtaca    17580
ggacaggcgc ttagaaataa acttaaagac cagaacttcc aacaaaaagt agtcgatggg    17640
atagcttccg gcatcaatgg agtggtagat ttggctaacc aggctgtgca gaaaaagata    17700
aacagtcgtt tggaccccgcc gccagcaacc ccaggtgaaa tgcaagtgga ggaagaaatt    17760
cctccgccag aaaaacgagg cgacaagcgt ccgcgtcccg atttggaaga gacgctggtg    17820
acgcgcgtag atgaaccgcc ttcttatgag gaagcaacga agcttggaat gcccaccact    17880
```

```
agaccgatag ccccaatggc caccggggtg atgaaacctt ctcagttgca tcgacccgtc    17940
accttggatt tgcccctcc ccctgctgct actgctgtac ccgcttctaa gcctgtcgct    18000
gccccgaaac cagtcgccgt agccaggtca cgtcccgggg gcgctcctcg tccaaatgcg    18060
cactggcaaa atactctgaa cagcatcgtg ggtctaggcg tgcaaagtgt aaaacgccgt    18120
cgctgctttt aattaaatat ggagtagcgc ttaacttgcc tatctgtgta tatgtgtcat    18180
tacacgccgt cacagcagca gaggaaaaaa ggaagaggtc gtgcgtcgac gctgagttac    18240
tttcaagatg gccaccccat cgatgctgcc ccaatgggca tacatgcaca tcgccggaca    18300
ggatgcttcg gagtacctga gtccgggtct ggtgcagttc gcccgcgcca cagacaccta    18360
cttcaatctg ggaaataagt ttagaaatcc caccgtagcg ccgacccacg atgtgaccac    18420
cgaccgtagc cagcggctca tgttgcgctt cgtgcccgtt gaccgggagg acaatacata    18480
ctcttacaaa gtgcggtaca ccctggccgt gggcgacaac agagtgctgg atatggccag    18540
cacgttcttt gacattaggg gtgtgttgga cagaggtccc agtttcaaac cctattctgg    18600
tacggcttac aactccctgg ctcctaaagg cgctccaaat acatctcagt ggattgcaga    18660
aggtgtaaaa aatacaactg gtgaggaaca cgtaacagaa gaggaaacca atactactac    18720
ttacactttt ggcaatgctc ctgtaaaagc tgaagctgaa attacaaaag aaggactccc    18780
agtaggtttg gaagtttcag atgaagaaag taaaccgatt tatgctgata aaacatatca    18840
gccagaacct cagctgggag atgaaacttg gactgacctt gatggaaaaa ccgaaaagta    18900
tggaggcagg gctctcaaac ccgatactaa gatgaaacca tgctacgggt cctttgccaa    18960
acctactaat gtgaaaggcg gtcaggcaaa acaaaaaaca acggagcagc caaatcagaa    19020
agtcgaatat gatatcgaca tggagttttt tgatgcggca tcgcagaaaa caaacttaag    19080
tcctaaaatt gtcatgtatg cagaaaatgt aaatttggaa actccagaca ctcatgtagt    19140
gtacaaacct ggaacagaag acacaagttc cgaagctaat ttgggacaac aatctatgcc    19200
caacagaccc aactacattg gcttcagaga taactttatt ggacttatgt actataacag    19260
tactggtaac atgggggtgc tggctggtca agcgtctcag ttaaatgcag tggttgactt    19320
gcaggacaga aacacagaac tttcttacca actcttgctt gactctctgg gcgacagaac    19380
cagatacttt agcatgtgga atcaggctgt ggacagttat gatcctgatg tacgtgttat    19440
tgaaaatcat ggtgtggaag atgaacttcc caactactgt tttccactgg acggcatagg    19500
tgttccaaca accagttaca aatcaatagt tccaaatgga gacaatgcgc ctaattggaa    19560
ggaacctgaa gtaaatggaa caagtgagat cggacagggt aatttgtttg ccatggaaat    19620
taaccttcaa gccaatctat ggcgaagttt cctttattcc aatgtggctc tatatctccc    19680
agactcgtac aaatacaccc cgtccaatgt cactcttcca gaaaacaaaa acacctacga    19740
ctacatgaac gggcgggtgg tgccgccatc tctagtagac acctatgtga acattggtgc    19800
caggtggtct ctggatgcca tggacaatgt caacccattc aaccaccacc gtaacgctgg    19860
cttgcgttac cgatccatgc ttctgggtaa cggacgttat gtgccttcc acatacaagt    19920 gcctcaaaaa ttcttcgctg ttaaaaacct gctgcttctc ccaggctcct acacttatga    19980
gtggaacttt aggaaggatg tgaacatggt tctacagagt ccctcggta acgacctgcg    20040 ggtagatggc gccagcatca gtttcacgag catcaacctc tatgctactt ttttcccat    20100 ggctcacaac accgcttcca cccttgaagc catgctgcgg aatgacacca atgatcagtc    20160
attcaacgac tacctatctg cagctaacat gctctacccc attcctgcca atgcaaccaa    20220
```

```
tattcccatt tccattcctt ctcgcaactg ggcggctttc agaggctggt catttaccag    20280
actgaaaacc aaagaaactc cctctttggg gtctggattt gacccctact ttgtctattc    20340
tggttctatt ccctacctgg atggtacctt ctacctgaac cacactttta agaaggtttc    20400
catcatgttt gactcttcag tgagctggcc tggaaatgac aggttactat ctcctaacga    20460
atttgaaata aagcgcactg tggatggcga aggctacaac gtagcccaat gcaacatgac    20520
caaagactgg ttcttggtac agatgctcgc caactacaac atcggctatc agggcttcta    20580
cattccagaa ggatacaaag atcgcatgta ttcattttc agaaacttcc agcccatgag    20640
caggcaggtg gttgatgagg tcaattacaa agacttcaag gccgtcgcca taccctacca    20700
acacaacaac tctggctttg tgggttacat ggctccgacc atgcgccaag gtcaaccta    20760
tcccgctaac tatccctatc cactcattgg aacaactgcc gtaaatagtg ttacgcagaa    20820
aaagttcttg tgtgacagaa ccatgtggcg cataccgttc tcgagcaact tcatgtctat    20880
gggggccctt acagacttgg gacagaatat gctctatgcc aactcagctc atgctctgga    20940
catgaccttt gaggtggatc ccatggatga gcccacccctg ctttatcttc tcttcgaagt    21000
tttcgacgtg gtcagagtgc atcagccaca ccgcggcatc atcgaggcag tctacctgcg    21060
tacaccgttc tcggccggta acgctaccac gtaagaagct tcttgcttct tgcaaatagc    21120
agctgcaacc atggcctgcg gatcccaaaa cggctccagc gagcaagagc tcagagccat    21180
tgtccaagac ctgggttgcg gaccctatt tttgggaacc tacgataagc gcttcccggg    21240
gttcatggcc cccgataagc tcgcctgtgc cattgtaaat acggccggac gtgagacggg    21300
gggagagcac tggttggctt tcggttggaa cccacgttct aacacctgct acctttttga    21360
tccttttgga ttctcggatg atcgtctcaa acagatttac cagtttgaat atgagggtct    21420
cctgcgccgc agcgctcttg ctaccaagga ccgctgtatt acgctggaaa aatctaccca    21480
gaccgtgcag ggtccccgtt ctgccgcctg cggactttt tgctgcatgt tccttcacgc    21540
ctttgtgcac tggcctgacc gtcccatgga cggaaacccc ccatgaaaat tgctaactgg    21600
agtgccaaac aacatgcttc attctcctaa agtccagccc accctgtgtg acaatcaaaa    21660
agcactctac cattttctta ataccccatc gccttatttt cgctcccatc gtacacacat    21720
cgaaagggcc actgcgttcg accgtatgga tgttcaataa tgactcatgt aaacaacgtg    21780
ttcaataaac atcactttat ttttttacat gtatcaaggc tctgcattac ttatttattt    21840
acaagtcgaa tgggttctga cgagaatcag aatgacccgc aggcagtgat acgttgcgga    21900
actgatactt gggttgccac ttgaattcgg gaatcaccaa cttgggaacc ggtatatcgg    21960
gcaggatgtc actccacagc tttctggtca gctgcaaagc tccaagcagg tcaggagccg    22020
aaatcttgaa atcacaatta ggaccagtgc tttgagcgcg agagttgcgg tacaccggat    22080
tgcagcactg aaacaccatc agcgacggat gtctcacgct tgccagcacg gtgggatctg    22140
caatcatgcc cacatccaga tcttcagcat tggcaatgct gaacgggtc atcttgcagg    22200
tctgcctacc catggcgggc acccaattag gcttgtggtt gcaatcgcag tgcaggggga    22260
tcagtatcat cttggcctga tcctgtctga ttcctggata cacggctctc atgaaagcat    22320
catattgctt gaaagcctgc tgggctttac taccctcggt ataaaacatc ccgcaggacc    22380
tgctcgaaaa ctggttagct gcacagccgg catcattcac acagcagcgg gcgtcattgt    22440
tagctatttg caccacactt ctgccccagc ggttttgggt gattttggtt cgctcgggat    22500
tctccttttaa ggctcgttgt ccgttctcgc tggcccacatc catctcgata atctgctcct    22560
tctgaatcat aatattgcca tgcaggcact tcagcttgcc ctcataatca ttgcagccat    22620
```

```
gaggccacaa cgcacagcct gtacattccc aattatggtg ggcgatctga gaaaaagaat    22680
gtatcattcc ctgcagaaat cttcccatca tcgtgctcag tgtcttgtga ctagtgaaag    22740
ttaactggat gcctcggtgc tcctcgttta cgtactggtg acagatgcgc ttgtattgtt    22800
cgtgttgctc aggcattagt ttaaaagagg ttctaagttc gttatccagc ctgtacttct    22860
ccatcagcag acacatcact tccatgcctt tctcccaagc agacaccagg ggcaagctaa    22920
tcggattctt aacagtgcag gcagcagctc ctttagccag agggtcatct ttagcgatct    22980
tctcaatgct tcttttgcca tccttctcaa cgatgcgcac gggcgggtag ctgaaaccca    23040
ctgctacaag ttgcgcctct tctctttctt cttcgctgtc ttgactgatg tcttgcatgg    23100
ggatatgttt ggtcttcctt ggcttctttt tgggggtat cggaggagga ggactgtcgc     23160
tccgttccgg agacagggag gattgtgacg tttcgctcac cattaccaac tgactgtcgg    23220
tagaagaacc tgaccccaca cggcgacagg tgtttctctt cggggcaga ggtggaggcg     23280 attgcgaagg gctgcggtcc gacctggaag gcggatgact ggcagaaccc cttccgcgtt    23340
cgggggtgtg ctccctgtgg cggtcgctta actgatttcc ttcgcggctg gccattgtgt    23400
tctcctaggc agagaaacaa cagacatgga aactcagcca ttgctgtcaa catcgccacg    23460
agtgccatca catctcgtcc tcagcgacga ggaaaaggag cagagcttaa gcattccacc    23520
gcccagtcct gccaccacct ctaccctaga agataaggag gtcgacgcat ctcatgacat    23580
gcagaataaa aaagcgaaag agtctgagac agacatcgag caagacccgg gctatgtgac    23640
accggtggaa cacgaggaag agttgaaacg ctttctagag agagaggatg aaaactgccc    23700
aaaacaacga gcagataact atcaccaaga tgctggaaat agggatcaga acaccgacta    23760
cctcataggg cttgacgggg aagacgcgct ccttaaacat ctagcaagac agtcgctcat    23820
agtcaaggat gcattattgg acagaactga agtgcccatc agtgtggaag agctcagccg    23880
cgcctacgag cttaacctct tttcacctcg tactccccc aaacgtcagc caaacggcac     23940
ctgcgagcca aatcctcgct taaacttta tccagctttt gctgtgccag aagtactggc     24000
tacctatcac atcttttta aaaatcaaaa aattccagtc tcctgccgcg ctaatcgcac     24060
ccgcgccgat gccctactca atctgggacc tggttcacgc ttacctgata tagcttcctt    24120
ggaagaggtt ccaaagatct tcgagggtct gggcaataat gagactcggg ccgcaaatgc    24180
tctgcaaaag ggagaaaatg gcatggatga gcatcacagc gttctggtgg aattggaagg    24240
cgataatgcc agactcgcag tactcaagcg aagcatcgag gtcacacact tcgcatatcc    24300
cgctgtcaac ctgcccccta aagtcatgac ggcggtcatg gaccagttac tcattaagcg    24360
cgcaagtccc ctttcagaag acatgcatga cccagatgcc tgtgatgagg gtaaaccagt    24420
ggtcagtgat gagcagctaa cccgatggct gggcaccgac tctcccaggg atttggaaga    24480
gcgtcgcaag cttatgatgg ccgtggtgct ggttaccgta gaactagagt gtctccgacg    24540
tttctttacc gattcagaaa ccttgcgcaa actcgaagag aatctgcact acactttag    24600 acacggcttt gtgcggcagg catgcaagat atctaacgtg gaactcacca acctggtttc    24660 ctacatggt attctgcatg agaatcgcct aggacaaagc gtgctgcaca gcaccctgaa    24720
gggggaagcc cgccgtgatt acatccgcga ttgtgtctat ctgtacctgt gccaaacgtg    24780
gcaaaccggc atgggtgtat ggcagcaatg tttagaagaa cagaacttga aagagcttga    24840
caagctctta cagaaatctc ttaaggttct gtggacaggg ttcgacgagc gcaccgtcgc    24900
ttccgacctg gcagacctca tcttcccaga gcgtctcagg gttactttgc gaaacggatt    24960
```

```
gcctgacttt atgagccaga gcatgcttaa caattttcgc tctttcatcc tggaacgctc    25020
cggtatcctg cccgccacct gctgcgcact gccctccgac tttgtgcctc tcacctaccg    25080
cgagtgcccc ccgccgctat ggagtcactg ctacctgttc cgtctggcca actatctctc    25140
ctaccactcg gatgtgatcg aggatgtgag cggagacggc ttgctggagt gtcactgccg    25200
ctgcaatctg tgcacgcccc accggtccct agcttgcaac ccccagttga tgagcgaaac    25260
ccagataata ggcacctttg aattgcaagg ccccagcagc caaggcgatg ggtcttctcc    25320
tgggcaaagt ttaaaactga ccccgggact gtggacctcc gcctacttgc gcaagtttgc    25380
tccggaagat taccacccct atgaaatcaa gttctatgag gaccaatcac agcctccaaa    25440
ggccgaactt tcggcctgcg tcatcaccca gggggcaatt ctggcccaat gcaagccat    25500 ccaaaaatcc cgccaagaat ttctactgaa aaagggtaag ggggtctacc ttgacccca    25560 gaccggcgag gaactcaaca caaggttccc tcaggatgtc ccaacgacga gaaaacaaga    25620
agttgaaggt gcagccgccg cccccagaag atatggagga agattgggac agtcaggcag    25680
aggaggcgga ggaggacagt ctggaggaca gtctggagga agacagtttg gaggaggaaa    25740
acgaggaggc agaggaggtg gaagaagtaa ccgccgacaa acagttatcc tcggctgcgg    25800
agacaagcaa cagcgctacc atctccgctc cgagtcgagg aacccggcgg cgtcccagca    25860
gtagatggga cgagaccgga cgcttcccga acccaaccag cgcttccaag accggtaaga    25920
aggatcggca gggatacaag tcctggcggg ggcataagaa tgccatcatc tcctgcttgc    25980
atgagtgcgg gggcaacata tccttcacgc ggcgctactt gctattccac catggggtga    26040
actttccgcg caatgttttg cattactacc gtcacctcca cagcccctac tatagccagc    26100
aaatcccggc agtctcgaca gataaagaca gcggcggcga cctccaacag aaaaccagca    26160
gcggcagtta gaaaatacac aacaagtgca gcaacaggag gattaaagat tacagccaac    26220
gagccagcgc aaacccgaga gttaagaaat cggatctttc caaccctgta tgccatcttc    26280
cagcagagtc ggggtcaaga gcaggaactg aaaataaaaa accgatctct gcgttcgctc    26340
accagaagtt gtttgtatca caagagcgaa gatcaacttc agcgcactct cgaggacgcc    26400
gaggctctct tcaacaagta ctgcgcgctg actcttaaag agtaggcagc gaccgcgctt    26460
attcaaaaaa ggcgggaatt acatcatcct cgacatgagt aaagaaattc ccacgcctta    26520
catgtggagt tatcaacccc aaatgggatt ggcggcaggc gcctcccagg actactccac    26580
ccgcatgaat tggctcagcg ccgggccttc tatgatttct cgagttaatg atatacgcgc    26640
ctaccgaaac caaatacttt tggaacagtc agctcttacc accacgcccc gccaacacct    26700
taatcccaga aattggcccg ccgccctagt gtaccaggaa agtcccgctc ccaccactgt    26760
attacttcct cgagacgccc aggccgaagt ccaaatgact aatgcaggtg cgcagttagc    26820
tggcggctcc accctatgtc gtcacaggcc tcggcataat ataaaacgcc tgatgatcag    26880
aggccgaggt atccagctca cgacgcagtc ggtgagctct ccgcttggtc tacgaccaga    26940 cggaatctttt cagattgccg gctgcgggag atcttccttc acccctcgtc aggctgttct    27000
gactttggaa agttcgtctt cgcaaccccg ctcgggcgga atcgggaccg ttcaatttgt    27060
ggaggagttt actccctctg tctacttcaa ccccttctcc ggatctcctg gcattaccc    27120 ggacgagttc ataccgaact tcgacgcgat tagcgagtca gtggacggct acgattgatg    27180
tctggtgacg cggctgagct atctcggctg cgacatctag accactgccg ccgcttccgc    27240
tgctttgccc gggaactcat tgagttcatc tacttcgaac tccccaagga tcaccctcaa    27300
ggtccggccc acggagtgcg gatttctatc gaaggcaaaa tagactctcg cctgcaacga    27360
```

```
attttctccc agcggcccgt gctgatcgag cgagaccagg gaaacaccac ggtttccatc    27420
tactgcattt gtaatcaccc cggattgcat gaaagccttt gctgtcttat gtgtactgag    27480
tttaataaaa actgaattaa gactctccta cggactgccg cttcttcaac ccggatttta    27540
caaccagaag aacgaaactt ttcctgtcgt ccaggactct gttaacttca cctttcctac    27600
tcacaaacta gaagctcaac gactacaccg cttttccaga agcattttcc ctactaatac    27660
tactttcaaa accggaggtg agctccaagg tcttcctaca gaaaacccct gggtggaagc    27720
gggccttgta gtgctaggaa ttcttgcggg tgggcttgtg attattcttt gctacctata    27780
cacaccttgc ttcactttct tagtggtgtt gtggtattgg tttaaaaaat ggggcccata    27840
ctagtcttgc ttgttttact ttcgcttttg aaccgggtt ctgccaatta cgatccatgt     27900
ctagacttcg acccagaaaa ctgcacactt acttttgcac ccgacacaag ccgcatctgt    27960
ggagttctta ttaagtgcgg atgggaatgc aggtccgttg aaattacaca caataacaaa    28020
acctggaaca ataccttatc caccacatgg gagccaggag ttcccgagtg gtacactgtc    28080
tctgtccgag gtcctgacgg ttccatccgc attagtaaca acactttcat ttttctgaa     28140 atgtgcgatc tggccatgtt catgagcaaa cagtattctc tatggcctcc tagcaaggac    28200
aacatcgtaa cgttctccat tgcttattgc ttgtgcgctt gccttcttac tgctttactg    28260
tgcgtatgca tacacctgct tgtaaccact cgcatcaaaa acgccaataa caaagaaaaa    28320
atgccttaac ctctttctgt ttacctcttt ctgtttacag acatggcttc tcttacatct    28380
ctcatatttg tcagcattgt cactgccgct catggacaaa cagtcgtctc tatccctcta    28440
ggacataatt acactctcat aggaccccca atcacttcag aggtcatctg gccaaactg     28500 ggaagcgttg attactttga tataatctgc aacaaaacaa accaataat agtaacttgc     28560 aacatacaaa atcttacatt gattaatgtt agcaaagttt acagcggtta ctattatggt    28620
tatgacagat acagtagtca atatagaaat tacttggttc gtgttaccca gttgaaaacc    28680
acgaaaatgc caaatatggc aaagattcga tccgatgaca attctctaga aacttttaca    28740
tctcccacca cacccgacga aaaaaacatc ccagattcaa tgattgcaat tgttgcagcg    28800
gtggcagtgg tgatggcact aataataata tgcatgcttt tatatgcttg tcgctacaaa    28860
aagtttcatc ctaaaaaaca agatctccta ctaaggctta acatttaatt tcttttttata    28920 cagccatggt ttccactacc acattcctta tgcttactag tctcgcaact ctgacttctg    28980
ctcgctcaca cctcactgta actataggct caaactgcac actaaaagga cctcaaggtg    29040
gtcatgtctt ttggtggaga atatatgaca atggatggtt tacaaaacca tgtgaccaac    29100
ctggtagatt tttctgcaac ggcagagacc taaccattat caacgtgaca gcaaatgaca    29160
aaggcttcta ttatggaacc gactataaaa gtagtttaga ttataacatt attgtactgc    29220
catctaccac tccagcaccc cgcacaacta cttttctag cagcagtgtc gctaacaata     29280
caatttccaa tccaaccttt gccgcgcttt aaaacgcac tgtgaataat tctacaactt     29340
cacatacaac aatttccact tcaacaatca gcattatcgc tgcagtgaca attggaatat    29400
ctattcttgt ttttaccata acctactacg cctgctgcta tagaaaagac aaacataaag    29460
gtgatccatt acttagattt gatatttaat ttgttctttt tttttttatt tacagtatgg    29520
tgaacaccaa tcatggtacc tagaaatttc ttcttcacca tactcatttg tgcatttaat    29580
gtttgcgcta ctttcacagc agtagccaca gcaaccccag actgtatagg agcatttgct    29640
tcctatgcac tttttgcttt tgttacttgc atctgcgtat gtagcatagt ctgcctggtt    29700
```

```
attaattttt tccaacttat agactggatc cttgtgcgaa ttgcctacct gcgccaccat   29760
cccgaatacc gcaaccaaaa tatcgcggca cttcttagac tcatctaaaa ccatgcaggc   29820
tatactacca atattttgc ttctattgct tccctacgct gtctcaaccc cagctgccta    29880
tagtactcca ccagaacacc ttagaaaatg caaattccaa caaccgtggt catttcttgc   29940
ttgctatcga gaaaaatcag aaattccccc aaatttaata atgattgctg gaataattaa   30000
tataatctgt tgcaccataa tttcattttt gatatacccc ctatttgatt ttggctggaa   30060
tgctcccaat gcacatgatc atccacaaga cccagaggaa cacattcccc tacaaaacat   30120
gcaacatcca atagcgctaa tagattacga aagtgaacca caaccccccac tactccctgc   30180 tattagttac ttcaacctaa ccggcggaga tgactgaaac actcaccacc tccaattccg   30240
ccgaggatct gctcgatatg gacggccgcg tctcagaaca gcgactcgcc caactacgca   30300
tccgccagca gcaggaacgc gcggccaaag agctcagaga tgtcatccaa attcaccaat   30360
gcaaaaaagg catattctgt ttggtaaaac aagccaagat atcctacgag atcaccgcta   30420
ctgaccatcg cctctcttac gaacttggcc cccaacgaca aaaatttacc tgcatggtgg   30480
gaatcaaccc catagttatc acccagcaaa gtggagatac taagggttgc attcactgct   30540
cctgcgattc catcgagtgc acctacaccc tgctgaagac cctatgcggc ctaagagacc   30600
tgctaccaat gaattaaaaa atgattaata aaaatcact tacttgaaat cagcaataag    30660
gtctctgttg aaattttctc ccagcagcac ctcacttccc tcttcccaac tctggtattc   30720
taaaccccgt tcagcggcat actttctcca tactttaaag gggatgtcaa attttagctc   30780
ctctcctgta cccacaatct tcatgtcttt cttcccagat gaccaagaga gtccggctca   30840
gtgactcctt caaccctgtc taccctatg aagatgaaag cacctcccaa cacccttta    30900 taaacccagg gtttatttcc ccaaatggct tcacacaaag cccaaacgga gttcttactt   30960
taaaatgttt aaccccacta caaccacag gcggatctct acagctaaaa gtgggagggg   31020
gacttacagt ggatgacacc aacgttttt tgaaagaaaa cataagtgcc accacaccac   31080
tcgttaagac tggtcactct ataggtttac cactaggagc cggattggga acgaatgaaa   31140
ataaactttg tatcaaatta ggacaaggac ttacattcaa ttcaaacaac atttgcattg   31200
atgacaatat taacaccttt tggacaggag tcaaccccac cgaagccaac tgtcaaatca   31260
tgaactccag tgaatctaat gattgcaaat taattctaac actagttaaa actgagcac   31320 tagtcactgc atttgtttat gttataggag tatctaacaa ttttaatatg ctaactacac   31380
acagaaatat aaattttact gcagagctgt ttttcgattc tactggtaat ttactaacta   31440
gactctcatc cctcaaaact ccacttaatc ataaatcagg acaaaacatg gctactggtg   31500
ccattactaa tgctaaaggt ttcatgccca gcacgactgc ctatcctttc aatgataatt   31560
ctagagaaaa agaaaactac atttacggaa cttgttacta cacagctagt gatcgcactg   31620
cttttcccat tgcatatct gtcatgctta accgaagagc aataaatgac gagacatcat    31680
attgtattcg tataacttgg tcctggaaca caggagatgc cccagaggtg caaacctctg   31740
ctacaaccct agtcacctcc ccatttacct tttactacat cagagaagac gactgacaaa   31800
taaagtttaa cttgtttatt tgaaaatcaa ttcacaaaat ccgagtagtt attttgcctc   31860 cccccttccca tttaacagaa tacaccaatc tctccccacg cacagcttta aacatttgga   31920
taccattaga tatagacatg gttttagatt ccacattcca aacagtttca gagcgagcca   31980
atctggggtc agtgatagat aaaaatccat cgggatagtc ttttaaagcg ctttcacagt   32040
ccaactgctg cggatggact ccggagtctg gatcacggtc atctggaaga agaacgatgg   32100
```

-continued

```
gaatcataat ccgaaaacgg tatcggacga ttgtgtctca tcaaacccac aagcagccgc    32160
tgtctgcgtc gctccgtgcg actgctgttt atgggatcag ggtccacagt gtcctgaagc    32220
atgattttaa tagcccttaa catcaacttt ctggtgcgat gcgcgcagca acgcattctg    32280
atttcactca aatctttgca gtaggtacaa cacattatta caatattgtt taataaacca    32340
taattaaaag cgctccagcc aaaactcata tctgatataa tcgcccctgc atgaccatca    32400
taccaaagtt aatataaat taatgacgt tccctcaaaa acacactacc cacatacatg      32460
atctcttttg gcatgtgcat attaacaatc tgtctgtacc atggacaacg ttggttaatc    32520
atgcaaccca atataacctt ccggaaccac actgccaaca ccgctccccc agccatgcat    32580
tgaagtgaac cctgctgatt acaatgacaa tgaagaaccc aattctctcg accgtgaatc    32640
acttgagaat gaaaaatatc tatagtggca aacatagac ataaatgcat gcatcttctc     32700 ataatttta actcctcagg atttagaaac atatcccagg gaataggaag ctcttgcaga     32760
acagtaaagc tggcagaaca aggaagacca cgaacacaac ttacactatg catagtcata   32820
gtatcacaat ctggcaacag cgggtggtct tcagtcatag aagctcgggt ttcatttcc    32880 tcacaacgtg gtaactgggc tctggtgtaa gggtgatgtc tggcgcatga tgtcgagcgt   32940
gcgcgcaacc ttgtcataat ggagttgctt cctgacattc tcgtattttg tatagcaaaa   33000
cgcggccctg gcagaacaca ctcttcttcg ccttctatcc tgccgcttag cgtgttccgt   33060
gtgatagttc aagtacaacc acactcttaa gttggtcaaa agaatgctgg cttcagttgt    33120
aatcaaaact ccatcgcatc taatcgttct gaggaaatca tccacggtag catatgcaaa   33180
tcccaaccaa gcaatgcaac tggattgtgt ttcaagcagg agaggagagg gaagagacgg   33240
aagaaccatg ttaattttta ttccaaacga tctcgcagta cttcaaattg tagatcgcgc    33300
agatggcatc tctcgccccc actgtgttgg tgaaaaagca cagctagatc aaaagaaatg   33360
cgattttcaa ggtgctcaac ggtggcttcc agcaaagcct ccacgcgcac atccaagaac   33420
aaaagaatac caaagaagg agcatttct aactcctcaa tcatcatatt acattcctgc      33480
accattccca gataattttc agcttttccag ccttgaatta ttcgtgtcag ttcttgtggt   33540
aaatccaatc cacacattac aaacaggtcc cggagggcgc cctccaccac cattcttaaa    33600
cacaccctca taatgacaaa atatcttgct cctgtgtcac ctgtagcgaa ttgagaatgg   33660
caacatcaat tgacatgccc ttggctctaa gttcttcttt aagttctagt tgtaaaaact   33720
ctctcatatt atcaccaaac tgcttagcca gaagcccccc gggaacaaga gcagggacg     33780 ctacagtgca gtacaagcgc agacctcccc aattggctcc agcaaaaaca agattggaat    33840
aagcatattg ggaaccgcca gtaatatcat cgaagttgct ggaaatataa tcaggcagag    33900
tttcttgtaa aaattgaata aagaaaaat ttgccaaaaa aacattcaaa acctctggga    33960
tgcaaatgca ataggttacc gcgctgcgct ccaacattgt tagttttgaa ttagtctgca   34020
aaaataaaaa aaaaacaag cgtcatatca tagtagcctg acgaacagat ggataaatca     34080
gtctttccat cacaagacaa gccacagggt ctccagctcg accctcgtaa aacctgtcat    34140
catgattaaa caacagcacc gaaagttcct cgcggtgacc agcatgaata attcttgatg   34200
aagcatacaa tccagacatg ttagcatcag ttaacgagaa aaaacagcca acatagcctt    34260
tgggtataat tatgcttaat cgtaagtata gcaaagccac ccctcgcgga tacaaagtaa   34320
aaggcacagg agaataaaaa atataattat ttctctgctg ctgttcaggc aacgtcgccc   34380
ccggtccctc taaatacaca tacaaagcct catcagccat ggcttaccag acaaagtaca   34440
```

```
gcgggcacac aaagcacaag ctctaaagtg actctccaac ctctccacaa tatatatata    34500
cacaagccct aaactgacgt aatgggagta aagtgtaaaa aatcccgcca aacccaacac    34560
acaccccgaa actgcgtcac cagggaaaag tacagtttca cttccgcaat cccaacaggc    34620
gtaacttcct ctttctcacg gtacgtgata tcccactaac ttgcaacgtc attttcccac    34680
ggtcgcaccg cccctttag ccgttaaccc cacagccaat caccacacga tccacacttt    34740
ttaaaatcac ctcatttaca tattggcacc attccatcta aaggtatat tattgatgat    34800 g                                                                    34801
```

<210> SEQ ID NO 2
<211> LENGTH: 1545
<212> TYPE: DNA
<213> ORGANISM: Artificial Sequence
<220> FEATURE:
<223> OTHER INFORMATION: Fully synthetic

<400> SEQUENCE: 2

```
catcatcaat aatataccct attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgttttg      180 gtgtgcgccg gtgtacacag gaagtgacaa ttttcgcgcg gttttaggcg gatgttgtag     240
taaatttggg cgtaaccgag taagatttgg ccatttttcgc gggaaaactg aataagagga    300
agtgaaatct gaataatttt gtgttactca tagcgcgtaa tatttgtcta gggccgcggg     360
gactttgacc gtttacgtgg agactcgccc aggtgttttt ctcaggtgtt ttccgcgttc     420
cgggtcaaag ttggcgtttt attattatag tcagctgacg tgtagtgtat ttatacccgg     480
tgagttcctc aagaggccac tcttgagtgc cagcgagtag agttttctcc tccgagccgc     540
tccgacaccg ggactgaaaa tgagacatat tatctgccac ggaggtgtta ttaccgaaga     600 aatgccgcc agtctttttgg accagctgat cgaagaggta ctggctgata atcttccacc     660
tcctagccat tttgaaccac ctacccttca cgaactgtat gatttagacg tgacggcccc     720
cgaagatccc aacgaggagg cggtttcgca gattttcccc gactctgtaa tgttggcggt     780
gcaggaaggg attgacttac tcactttttcc gccggcgccc ggttctccgg agccgcctca    840
cctttccggg cagcccgagc agccggagca gagagcttg ggtccggttt ctatgccaaa     900
ccttgtaccg gaggtgatcg atcttacctg ccacgaggct ggctttccac ccagtgacga    960
cgaggatgaa gagggtgagg agtttgtgtt agattatgtg gagcaccccg ggcacggttg    1020
caggtcttgt cattatcacc ggaggaatac gggggaccca gatattatgt gttcgctttg    1080
ctatatgagg acctgtggca tgtttgtcta cagtaagtga aaattatggg cagtgggtga    1140
tagagtggtg ggtttggtgt ggtaatttt tttttaattt ttacagtttt gtggtttaaa     1200
gaattttgta ttgtgatttt tttaaaaggt cctgtgtctg aacctgagcc tgagcccgag    1260
ccagaaccgg agcctgcaag acctacccgc cgtcctaaaa tggcgcctgc tatcctgaga    1320
cgcccgacat cacctgtgtc tagagaatgc aatagtagta cggatagctg tgactccggt    1380
ccttctaaca cacctcctga gatacacccg gtggtcccgc tgtgccccat taaaccagtt    1440
gccgtgagag ttggtgggcg tcgccaggct gtggaatgta tcgaggactt gcttaacgag    1500
cctgggcaac ctttggactt gagctgtaaa cgccccaggc cataa                    1545
```

<210> SEQ ID NO 3
<211> LENGTH: 34793

<212> TYPE: DNA
<213> ORGANISM: Artificial Sequence
<220> FEATURE:
<223> OTHER INFORMATION: Fully synthetic

<400> SEQUENCE: 3

| | | | | | |
|---|---|---|---|---|---|
| catcatcaat | aatatacctt | atagatggaa | tggtgccaat | atgtaaatga | ggtgattta | 60 |
| aaaagtgtgg | atcgtgtggt | gattggctgt | ggggttaacg | gctaaaaggg | gcggtgcgac | 120 |
| cgtgggaaaa | tgacgttttg | tgggggtgga | gttttttgc | aagttgtcgc | gggaaatgtg | 180 |
| acgcataaaa | aggcttttt | ctcacggaac | tacttagttt | tcccacggta | tttaacagga | 240 |
| aatgaggtag | ttttgaccgg | atgcaagtga | aaattgttga | ttttcgcgcg | aaaactgaat | 300 |
| gaggaagtgt | ttttctgaat | aatgtggtat | ttatggcagg | gtggagtatt | tgttcagggc | 360 |
| caggtagact | ttgacccatt | acgtggaggt | ttcgattacc | gtgtttttta | cctgaatttc | 420 |
| cgcgtaccgt | gtcaaagtct | tctgttttta | cgtaggtgtc | agctgatcgc | tagggtattt | 480 |
| atacctcagg | gtttgtgtca | agaggccact | cttgagtgcc | agcgagaaga | gttttctcct | 540 |
| ctgcgccggc | agtttaataa | taaaaaaatg | agagatttgc | gatttctgcc | tcaggaaata | 600 |
| atctctgctg | agactggaaa | tgaaatattg | gagcttgtgg | tgcacgccct | gatgggagac | 660 |
| gatccggagc | cacctgtgca | gctttttgag | cctcctacgc | ttcaggaact | gtatgattta | 720 |
| gaggtagagg | gatcggagga | ttctaatgag | gaagctgtaa | atggcttttt | taccgattct | 780 |
| atgcttttag | ctgctaatga | agggttagaa | ttagatccgc | ctttggacac | ttttgatact | 840 |
| ccaggggtaa | ttgtggaaag | cggtacaggt | gtaagaaaat | tacctgattt | gagttccgtg | 900 |
| gactgtgatt | tgcactgcta | tgaagacggg | tttcctccga | gtgatgagga | ggaccatgaa | 960 |
| aaggagcagt | ccatgcagac | tgcagcgggt | gagggagtga | aggctgccaa | tgttggtttt | 1020 |
| cagttggatt | gcccggagct | tcctggacat | ggctgtaagt | cttgtgaatt | tcacaggaaa | 1080 |
| aatactggag | taaaggaact | gttatgttcg | ctttgttata | tgagaacgca | ctgccacttt | 1140 |
| atttacagta | agtgtgttta | agttaaaatt | taaaggaata | tgctgttttt | cacatgtata | 1200 |
| ttgagtgtga | gttttgtgct | tcttattata | ggtcctgtgt | ctgatgctga | tgaatcacca | 1260 |
| tctcctgatt | ctactacctc | acctcctgag | attcaagcac | ctgttcctgt | ggacgtgcgc | 1320 |
| aagcccattc | ctgtgaagct | taagcctggg | aaacgtccag | cagtggaaaa | acttgaggac | 1380 |
| ttgttacagg | gtggggacgg | acctttggac | ttgagtacac | ggaaacgtcc | aagacaataa | 1440 |
| gtgttccata | tccgtgttta | cttaaggtga | cgtcaatatt | tgtgtgacag | tgcaatgtaa | 1500 |
| taaaaatatg | ttaactgttc | actggttttt | attgcttttt | gggcggggac | tcaggtatat | 1560 |
| aagtagaagc | agacctgtgt | ggttagctca | taggagctgg | ctttcatcca | tggaggtttg | 1620 |
| ggccattttg | gaagacctta | ggaagactag | gcaactgtta | gagaacgctt | cggacggagt | 1680 |
| ctccggtttt | tggagattct | ggttcgctag | tgaattagct | agggtagttt | ttaggataaa | 1740 |
| acaggactat | aaacaagaat | ttgaaaagtt | gttggtagat | tgcccaggac | tttttgaagc | 1800 |
| tcttaatttg | ggccatcagg | ttcactttaa | agaaaaagtt | ttatcagttt | tagacttttc | 1860 |
| aaccccaggt | agaactgctg | ctgctgtggc | ttttcttact | tttatattag | ataaatggat | 1920 |
| cccgcagact | catttcagca | ggggatacgt | tttggatttc | atagccacag | cattgtggag | 1980 |
| aacatggaag | gttcgcaaga | tgaggacaat | cttaggttac | tggccagtgc | agcctttggg | 2040 |
| tgtagcggga | atcctgaggc | atccaccggt | catgccagcg | gttctggagg | aggaacagca | 2100 |
| agaggacaac | ccgagagccg | gcctggaccc | tccagtggag | gaggcggagt | agctgacttg | 2160 |

```
tctcctgaac tgcaacgggt gcttactgga tctacgtcca ctggacggga tagggcgtt    2220 aagagggaga gggcatctag tggtactgat gctagatctg agttggcttt aagtttaatg    2280
agtcgcagac gtcctgaaac catttggtgg catgaggttc agaaagaggg aagggatgaa    2340
gtttctgtat tgcaggagaa atattcactg gaacaggtga aaacatgttg gttggagcct    2400
gaggatgatt gggaggtggc cattaaaaat tatgccaaga tagctttgag gcctgataaa    2460
cagtataaga ttactagacg gattaatatc cggaatgctt gttacatatc tggaaatggg    2520
gctgaggtgg taatagatac tcaagacaag gcagttatta gatgctgcat gatggatatg    2580
tggcctgggg tagtcggtat ggaagcagta acttttgtaa atgttaagtt taggggagat    2640
ggttataatg aatagtgtt tatggccaat accaaactta tattgcatgg ttgtagcttt    2700
tttggtttca acaatacctg tgtagatgcc tggggacagg ttagtgtacg gggatgtagt    2760
ttctatgcgt gttggattgc cacagctggc agaaccaaga gtcaattgtc tctgaagaaa    2820
tgcatatttc aaagatgtaa cctgggcatt ctgaatgaag gcgaagcaag ggtccgccac    2880
tgcgcttcta cagatactgg atgttttatt ttgattaagg gaaatgccag cgtaaagcat    2940
aacatgattt gcggtgcttc cgatgagagg ccttatcaaa tgctcacttg tgctggtggg    3000
cattgtaata tgctggctac tgtgcatatt gtttcccatc aacgcaaaaa atggcctgtt    3060
tttgatcaca atgtgatgac gaagtgtacc atgcatgcag gtgggcgtag aggaatgttt    3120
atgccttacc agtgtaacat gaatcatgtg aaagtgttgt tggaaccaga tgccttttcc    3180
agaatgagcc taacaggaat ttttgacatg aacatgcaaa tctggaagat cctgaggtat    3240
gatgatacga gatcgagggt acgcgcatgc gaatgcggag gcaagcatgc caggttccag    3300
ccggtgtgtg tagatgtgac tgaagatctc agaccggatc atttggttat tgcccgcact    3360
ggagcagagt tcggatccag tggagaagaa actgactaag gtgagtattg ggaaaacttt    3420
ggggtgggat tttcagatgg acagattgag taaaaatttg ttttttctgt cttgcagctg    3480
tcatgagtgg aaaacgcttct tttaagggg gagtcttcag cccttatctg acagggcgtc    3540
tcccatcctg ggcaggagtt cgtcagaatg ttatgggatc tactgtggat ggaagacccg    3600
tccaacccgc caattcttca acgctgacct atgctacttt aagttcttca cctttggacg    3660
cagctgcagc tgccgccgcc gcttctgttg ccgctaacac tgtgcttgga atgggttact    3720
atggaagcat catggctaat tccacttcct ctaataaccc ttctaccctg actcaggaca    3780
agttacttgt cctttttggcc cagctggagg ctttgaccca acgtctgggt gaactttctc    3840
agcaggtggt cgagttgcga gtacaaactg agtctgctgt cggcacggca aagtctaaat    3900
aaaaaaatcc cagaatcaat gaataaataa acaagcttgt tgttgattta aaatcaagtg    3960 ttttatttc atttttcgcg cacggtatgc cctagaccac cgatctctat cattgagaac    4020
tcggtggatt ttttccagga tcctatagag gtgggattga atgtttagat acatgggcat    4080
taggccgtct ttggggtgga gatagctcca ttgaagggat tcatgctccg ggtagtgtt    4140 gtaaatcacc cagtcataac aaggtcgcag tgcatggtgt tgcacaatat cttttagaag    4200
taggctgatt gccacagata agcccttggt gtaggtgttt acaaaccggt tgagctggga    4260
tgggtgcatt cggggtgaaa ttatgtgcat ttttggattgg attttaagt tggcaatatt    4320 gccgccaaga tcccgtcttg ggttcatgtt atgaaggacc accaagacgg tgtatccggt    4380
acatttagga aatttatcgt gcagcttgga tggaaaagcg tggaaaaatt tggagacacc    4440
cttgtgtcct ccaagatttt ccatgcactc atccatgata atagcaatgg ggccgtgggc    4500
agcggcgcgg gcaaacacgt tccgtgggtc tgacacatca tagttatgtt cctgagttaa    4560
```

```
atcatcataa gccatttttaa tgaatttggg gcggagagta ccagattggg gtatgaatgt    4620
tccttcgggc cccggagcat agttcccctc acagatttgc atttcccaag ctttcagttc    4680
cgagggtgga atcatgtcca cctgggggc tatgaaaaac accgtttctg ggcggggt       4740 gattaattgt gatgatagca aatttctgag caattgagat ttgccacatc cggtggggcc    4800
ataaatgatt ccgattacgg gttgcaggtg gtagtttagg gaacggcaac tgccgtcttc    4860
tcgaagcaag ggggccacct cgttcatcat ttcccttaca tgcatatttt cccgcaccaa    4920
atccattagg aggcgctctc ctcctagtga tagaagttct tgtagtgagg aaaagttttt    4980
cagcggtttc agaccgtcag ccatgggcat tttggagaga gtttgctgca aaagttctag    5040
tctgttccac agttcagtga tgtgttctat ggcatctcga tccagcagac ctcctcgttt    5100
cgcgggtttg dacggctcct ggaataggt atgagacgat gggcgtccag cgctgccagg     5160
gttcggtcct tccagggtct cagtgttcga gtcagggttg tttccgtcac agtgaagggg    5220 tgtgcgcct cttgggcgct tgccagggtg cgcttcagac tcatcctgct ggtcgaaaac     5280
ttctgtcgct tggcgccctg tatgtcggcc aagtagcagt ttaccatgag ttcgtagttg    5340
agcgcctcgg ctgcgtggcc tttgcgcgg agcttacctt tggaagtttt cttgcatacc     5400
gggcagtata ggcatttcag cgcatacaac ttgggcgcaa ggaaaacgga ttctggggag    5460
tatgcatctg cgccgcagga ggcgcaaaca gtttcacatt ccaccagcca ggttaaatcc    5520
ggttcattgg ggtcaaaaac aagttttccg ccatattttt tgatgcgttt cttacctttg    5580
gtctccatga gttcgtgtcc tcgttgagtg acaaacaggc tgtccgtgtc cccgtagact    5640
gattttacag gcctcttctc cagtggagtg cctcggtctt cttcgtacag gaactctgac    5700
cactctgata caaaggcgcg cgtccaggcc agcacaaagg aggctatgtg ggaggggtag    5760
cgatcgttgt caaccagggg gtccacctttt tccaaagtat gcaaacacat gtcaccctct    5820
tcaacatcca ggaatgtgat tggcttgtag gtgtatttca cgtgacctgg ggtccccgct    5880
gggggggtat aaaagggggc ggttctttgc tcttcctcac tgtcttccgg atcgctgtcc    5940
aggaacgtca gctgttgggg taggtattcc ctctcgaagg cgggcatgac ctctgcactc    6000
aggttgtcag tttctaagaa cgaggaggat ttgatattga cagtgccggt tgagatgcct    6060
ttcatgaggt tttcgtccat ttggtcagaa aacacaattt tttattgtc aagtttggtg      6120 gcaaatgatc catacagggc gttggataaa agtttgcaa tggatcgcat ggtttggttc     6180 tttccttgt ccgcgcgctc tttggcggcg atgttgagtt ggacatactc gcgtgccagg     6240
cacttccatt cggggaagat agttgttaat tcatctggca cgattctcac ttgccaccct    6300
cgattatgca aggtaattaa atccacactg gtggccacct cgcctcgaag gggttcattg    6360
gtccaacaga gcctacctcc tttcctagaa cagaaagggg gaagtgggtc tagcataagt    6420
tcatcgggag ggtctgcatc catggtaaag attcccggaa gtaaatcctt atcaaaatag    6480
ctgatgggag tggggtcatc taaggccatt tgccattctc gagctgccag tgcgcgctca    6540
tatgggttaa ggggactgcc ccatggcatg ggatgggtga gtgcagaggc atacatgcca    6600
cagatgtcat agacgtagat gggatcctca aagatgccta tgtaggttgg atagcatcgc    6660 cccctctga tacttgctcg cacatagtca tatagttcat gtgatggcgc tagcagcccc     6720
ggacccaagt tggtgcgatt gggttttttct gttctgtaga cgatctggcg aaagatggcg    6780
tgagaattgg aagagatggt gggtctttga aaaatgttga atgggcatg aggtagacct     6840 acagagtctc tgacaaagtg ggcataagat tcttgaagct tggttaccag ttcggcggtg    6900
```

```
acaagtacgt ctagggcgca gtagtcaagt gtttcttgaa tgatgtcata acctggttgg    6960
ttttcttttt cccacagttc gcggttgaga aggtattctt cgcgatcctt ccagtactct    7020
tctagcggaa acccgtcttt gtctgcacgg taagatccta gcatgtagaa ctgattaact    7080
gccttgtaag ggcagcagcc cttctctacg ggtagagagt atgcttgagc agcttttcgt    7140
agcgaagcgt gagtaagggc aaaggtgtct ctgaccatga ctttgagaaa ttggtatttg    7200
aagtcgatgt cgtcacaggc tccctgttcc cagagttgga agtctacccg tttcttgtag    7260
gcggggttgg gcaaagcgaa agtaacatca ttgaagagaa tcttaccggc tctgggcata    7320
aaattgcgag tgatgcgaaa aggctgtggt acttccgctc gattgttgat cacctgggca    7380
gctaggacga tctcgtcgaa accgttgatg ttgtgtccta cgatgtataa ttctatgaaa    7440
cgcggcgtgc ctctgacgtg aggtagctta ctgagctcat caaaggttag gtctgtgggg    7500
tcagataagg cgtagtgttc gagagcccat tcgtgcaggt gaggatttgc atgtaggaat    7560
gatgaccaaa gatctaccgc cagtgctgtt tgtaactggt cccgatactg acgaaaatgc    7620
cggccaattg ccattttttc tggagtgaca cagtagaagg ttctggggtc ttgttgccat    7680
cgatcccact tgagtttaat ggctagatcg tgggccatgt tgacgagacg ctcttctcct    7740
gagagtttca tgaccagcat gaaaggaact agttgtttgc caaaggatcc catccaggtg    7800 taagttttcca catcgtaggt caggaagagt cttctgtgc gaggatgaga gccgatcggg    7860
aagaactgga tttcctgcca ccagttggag gattggctgt tgatgtgatg gaagtagaag    7920
tttctgcggc gcgccgagca ttcgtgtttg tgcttgtaca gacggccgca gtagtcgcag    7980
cgttgcacgg gttgtatctc gtgaatgagt tgtacctggc ttcccttgac gagaaatttc    8040
agtgggaagc cgaggcctgg cgattgtatc tcgtgctctt ctatattcgc tgtatcggcc    8100
tgttcatctt ctgtttcgat ggtggtcatg ctgacgagcc cccgcgggag gcaagtccag    8160
acctcggcgc gggaggggcg gagctgaagg acgagagcgc gcaggctgga gctgtccaga    8220
gtcctgagac gctgcggact caggttagta ggtaggaca aagattaac ttgcatgatc     8280 ttttccaggg cgtgcgggag gttcagatgg tacttgattt ccacaggttc gtttgtagag    8340
acgtcaatgg cttgcagggt tccgtgtcct ttgggcgcca ctaccgtacc tttgttttttt    8400 cttttgatcg gtggtggctc tcttgcttct tgcatgctca gaagcggtga cggggacgcg    8460
cgccgggcgg cagcggttgt tccggacccg agggcatggc tggtagtggc acgtcggcgc    8520
cgcgcacggg caggttctgg tactgcgctc tgagaagact tgcgtgcgcc accacgcgtc    8580
gattgacgtc ttgtatctga cgtctctggg tgaaagctac cggccccgtg agcttgaacc    8640
tgaaagagag ttcaacagaa tcaatttcgg tatcgttaac ggcagcttgt ctcagtattt    8700
cttgtacgtc accagagttg tcctggtagg cgatctccgc catgaactgc tcgatttctt    8760
cctcctgaag atctccgcga cccgctcttt cgacggtggc cgcgaggtca ttggagatac    8820
ggcccatgag ttgggagaat gcattcatgc ccgcctcgtt ccagacgcgg ctgtaaacca    8880 cggcccctc ggagtctctt gcgcgcatca ccacctgagc gaggttaagc tccacgtgtc     8940
tggtgaagac cgcatagttg cataggcgct gaaaaggta gttgagtgtg gtggcaatgt    9000
gttcggcgac gaagaaatac atgatccatc gtctcagcgg catttcgcta acatcgccca    9060
gagcttccaa gcgctccatg gcctcgtaga agtccacggc aaaattaaaa aactgggagt    9120
ttcgcgcgga cacggtcaat tcctcctcga agacggat gagttcggct atggtggccc      9180
gtacttcgcg ttcgaaggct cccgggatct cttcttcctc ttctatctct tcttccacta    9240
acatctcttc ttcgtcttca ggcggggggcg gaggggcac gcggcgacgt cgacggcgca    9300
```

-continued

```
cgggcaaacg gtcgatgaat cgttcaatga cctctccgcg gcggcggcgc atggtttcag    9360
tgacggcgcg gccgttctcg cgcggtcgca gagtaaaaac accgccgcgc atctccttaa    9420
agtggtgact gggaggttct ccgtttggga gggagagggc gctgattata cattttatta    9480
attggcccgt agggactgca cgcagagatc tgatcgtgtc aagatccacg ggatctgaaa    9540
acctttcgac gaaagcgtct aaccagtcac agtcacaagg taggctgagt acggcttctt    9600
gtgggcgggt gtggttatgt gttcggtctg ggtcttctgt ttcttcttca tctcgggaag    9660
gtgagacgat gctgctggtg atgaaattaa agtaggcagt tctaagacgg cggatggtgg    9720
cgaggagcac caggtctttg ggtccggctt gctggatacg caggcgattg gccattcccc    9780
aagcattatc ctgacatcta gcaagatctt tgtagtagtc ttgcatgagc cgttctacgg    9840
gcacttcttc ctcacccgtt ctgccatgca tacgtgtgag tccaaatccg cgcattggtt    9900
gtaccagtgc caagtcagct acgactcttt cggcgaggat ggcttgctgt acttgggtaa    9960
gggtggcttg aaagtcatca aaatccacaa agcggtggta agctcctgta ttaatggtgt   10020
aagcacagtt ggccatgact gaccagttaa ctgtctggtg accagggcgc acgagctcgg   10080
tgtatttaag gcgcgaatag gcgcgggtgt caaagatgta atcgttgcag gtgcgcacca   10140
gatactggta ccctataaga aaatgcggcg gtggttggcg gtagagaggc catcgttctg   10200
tagctggagc gccaggggcg aggtcttcca acataaggcg gtgatagccg tagatgtacc   10260
tggacatcca ggtgattcct gcggcggtag tagaagcccg aggaaactcg cgtacgcggt   10320
tccaaatgtt gcgtagcggc atgaagtagt tcattgtagg cacggtttga ccagtgaggc   10380
gcgcgcagtc attgatgctc tatagacacg gagaaaatga aagcgttcag cgactcgact   10440
ccgtagcctg gaggaacgtg aacgggttgg gtcgcggtgt accccggttc gagacttgta   10500
ctcgagccgg ccggagccgc ggctaacgtg gtattggcac tcccgtctcg acccagccta   10560
caaaaatcca ggatacggaa tcgagtcgtt ttgctggttt ccgaatggca gggaagtgag   10620
tcctattttt ttttttttgc cgctcagatg catcccgtgc tgcgacagat gcgcccccaa   10680
caacagcccc cctcgcagca gcagcagcag caatcacaaa aggctgtccc tgcaactact   10740
gcaactgccg ccgtgagcgg tgcgggacag cccgcctatg atctggactt ggaagagggc   10800
gaaggactgg cacgtctagg tgcgccttca cccgagcggc atccgcgagt tcaactgaaa   10860
aaagattctc gcgaggcgta tgtgcccccaa cagaacctat ttagagacag aagcggcgag   10920
gagccggagg agatgcgagc ttcccgcttt aacgcgggtc gtgagctgcg tcacggtttg   10980
gaccgaagac gagtgttgcg ggacgaggat ttcgaagttg atgaaatgac agggatcagt   11040
cctgccaggg cacacgtggc tgcagccaac cttgtatcgg cttacgagca gacagtaaag   11100
gaagagcgta acttccaaaa gtcttttaat aatcatgtgc gaaccctgat tgcccgcgaa   11160
gaagttaccc ttggtttgat gcatttgtgg gatttgatgg aagctatcat tcagaaccct   11220
actagcaaac ctctgaccgc ccagctgttt ctggtggtgc aacacagcag agacaatgag   11280
gctttcagag aggcgctgct gaacatcacc gaacccgagg ggagatggtt gtatgatctt   11340
atcaacattc tacagagtat catagtgcag gagcggagcc tgggcctggc cgagaaggtg   11400
gctgccatca attactcggt tttgagcttg ggaaaatatt acgctcgcaa aatctacaag   11460
actccatacg ttcccataga caaggaggtg aagatagatg ggttctacat gcgcatgacg   11520
ctcaaggtct tgacccctgag cgatgatctt ggggtgtatc gcaatgacag aatgcatcgc   11580
gcggttagcg ccagcaggag gcgcgagtta agcgacaggg aactgatgca cagtttgcaa   11640
```

```
agagctctga ctggagctgg aaccgagggt gagaattact tcgacatggg agctgacttg   11700
cagtggcagc ctagtcgcag ggctctgagc gccgcgacgg caggatgtga gcttccttac   11760
atagaagagg cggatgaagg cgaggaggaa gagggcgagt acttggaaga ctgatggcac   11820
aacccgtgtt ttttgctaga tggaacagca agcaccggat cccgcaatgc gggcggcgct   11880
gcagagccag ccgtccggca ttaactcctc ggacgattgg acccaggcca tgcaacgtat   11940
catggcgttg acgactcgca accccgaagc ctttagacag caaccccagg ccaaccgtct   12000
atcggccatc atggaagctg tagtgccttc ccgctctaat cccactcatg agaaggtcct   12060
ggccatcgtg aacgcgttgg tggagaacaa agctattcgt ccagatgagg ccggactggt   12120
atacaacgct ctcttagaac gcgtggctcg ctacaacagt agcaatgtgc aaaccaattt   12180
ggaccgtatg ataacagatg tacgcgaagc cgtgtctcag cgcgaaaggt tccagcgtga   12240
tgccaacctg ggttcgctgg tggcgttaaa tgctttcttg agtactcagc ctgctaatgt   12300
gccgcgtggt caacaggatt atactaactt tttaagtgct ttgagactga tggtatcaga   12360
agtacctcag agcgaagtgt atcagtccgg tcctgattac ttctttcaga ctagcagaca   12420
gggcttgcag acggtaaatc tgagccaagc ttttaaaaac cttaaaggtt tgtggggagt   12480
gcatgccccg gtaggagaaa gagcaaccgt gtctagcttg ttaactccga actcccgcct   12540
attattactg ttggtagctc cttttcaccga cagcggtagc atcgaccgta attcctattt   12600
gggttaccta ctaaacctgt atcgcgaagc catagggcaa agtcaggtgg acgagcagac   12660
ctatcaagaa attacccaag tcagtcgcgc tttgggacag gaagacactg gcagtttgga   12720
agccactctg aacttcttgc ttaccaatcg gtctcaaaag atccctcctc aatatgctct   12780
tactgcggag gaggagagga tccttagata tgtgcagcag agcgtgggat tgtttctgat   12840
gcaagagggg gcaactccga ctgcagcact ggacatgaca gcgcgaaata tggagcccag   12900
catgtatgcc agtaaccgac ctttcattaa caaactgctg gactacttgc acagagctgc   12960
cgctatgaac tctgattatt tcaccaatgc catcttaaac ccgcactggc tgcccccacc   13020
tggtttctac acgggcgaat atgacatgcc cgaccctaat gacggatttc tgtgggacga   13080
cgtggacagc gatgtttttt cacctctttc tgatcatcgc acgtggaaaa aggaaggcgg   13140
cgatagaatg cattcttctg catcgctgtc cggggtcatg ggtgctaccg cggctgagcc   13200
cgagtctgca gtcctttttc ctagtctacc cttttctcta cacagtgtac gtagcagcga   13260
agtgggtaga ataagtcgcc cgagtttaat gggcgaagag gagtatctaa acgattcctt   13320
gctcagaccg gcaagagaaa aaaatttccc aaacaatgga atagaaagtt tggtggataa   13380
aatgagtaga tggaagactt atgctcagga tcacagagac gagcctggga tcatggggat   13440
tacaagtaga gcgagccgta gacgccagcg ccatgacaga cagaggggtc ttgtgtggga   13500
cgatgaggat tcggccgatg atagcagcgt gctggacttg ggtgggagag gaaggggcaa   13560
cccgtttgct catttgcgcc ctcgcttggg tggtatgttg taaaaaaaaa taaaaaaaaa   13620
actcaccaag gccatggcga cgagcgtacg ttcgttcttc tttattatct gtgtctagta   13680
taatgaggcg agtcgtgcta ggcggagcgg tggtgtatcc ggagggtcct cctccttcgt   13740
acgagagcgt gatgcagcag cagcaggcga cggcggtgat gcaatcccca ctggaggctc   13800
ccttttgtgcc tccgcgatac ctggcaccta cggagggcag aaacagcatt cgttattcgg   13860
aactggcacc tcagtacgat accaccaggt tgtatctggt ggacaacaag tcggcggaca   13920
ttgcttctct gaactatcag aatgaccaca gcaacttctt gaccacgtg gtgcaaaaca   13980
atgactttac ccctacggaa gccagcaccc agaccattaa ctttgatgaa cgatcgcggt   14040
```

```
ggggcggtca gctaaagacc atcatgcata ctaacatgcc aaacgtgaac gagtatatgt    14100
ttagtaacaa gttcaaagcg cgtgtgatgg tgtccagaaa acctcccgac ggtgctgcag    14160
ttggggatac ttatgatcac aagcaggata ttttgaaata tgagtggttc gagtttactt    14220
tgccagaagg caacttttca gttactatga ctattgattt gatgaacaat gccatcatag    14280
ataattactt gaaagtgggt agacagaatg gagtgcttga aagtgacatt ggtgttaagt    14340
tcgacaccag gaacttcaag ctgggatggg atcccgaaac caagttgatc atgcctggag    14400
tgtatacgta tgaagccttc catcctgaca ttgtcttact gcctggctgc ggagtggatt    14460
ttaccgagag tcgtttgagc aaccttcttg gtatcagaaa aaaacagcca tttcaagagg    14520
gttttaagat tttgtatgaa gatttagaag gtggtaatat tccggccctc ttggatgtag    14580
atgcctatga gaacagtaag aaagaacaaa aagccaaaat agaagctgct acagctgctg    14640
cagaagctaa ggcaaacata gttgccagcg actctacaag ggttgctaac gctggagagg    14700
tcagaggaga caattttgcg ccaacacctg ttccgactgc agaatcatta ttggccgatg    14760
tgtctgaagg aacggacgtg aaactcacta ttcaacctgt agaaaagat agtaagaata    14820 gaagctataa tgtgttggaa gacaaaaatca acacagccta tcgcagttgg tatctttcgt    14880
acaattatgg cgatcccgaa aaaggagtgc gttcctggac attgctcacc acctcagatg    14940
tcacctgcgg agcagagcag gtctactggt cgcttccaga catgatgaag gatcctgtca    15000
ctttccgctc cactagacaa gtcagtaact accctgtggt gggtgcagag cttatgcccg    15060
tcttctcaaa gagcttctac aacgaacaag ctgtgtactc ccagcagctc cgccagtcca    15120
cctcgcttac gcacgtcttc aaccgctttc ctgagaacca gattttaatc cgtccgccgg    15180
cgcccaccat taccaccgtc agtgaaaacg ttcctgctct cacagatcac gggaccctgc    15240
cgttgcgcag cagtatccgg ggagtccaac gtgtgaccgt tactgacgcc agacgccgca    15300
cctgtcccta cgtgtacaag gcactgggca tagtcgcacc gcgcgtcctt tcaagccgca    15360 cttctaaaa aaaaaaaaaa tgtccattct tatctcgccc agtaataaca ccggttgggg    15420
tctgcgcgct ccaagcaaga tgtacggagg cgcacgcaaa cgttctaccc aacatcctgt    15480
ccgtgttcgc ggacattttc gcgctccatg gggcgccctc aagggccgca ctcgcgttcg    15540
aaccaccgtc gatgatgtaa tcgatcaggt ggttgccgac gcccgtaatt atactcctac    15600
tgcgcctaca tctactgtgg atgcagttat tgacagtgta gtggctgacg ctcgcaacta    15660
tgctcgacgt aagagccggc gaaggcgcat tgccagacgc caccgagcta ccactgccat    15720
gcgagccgca agagctctgc tacgaagagc tagacgcgtg gggcgaagag ccatgcttag    15780
ggcggccaga cgtgcagctt cgggcgccag cgccggcagg tcccgcaggc aagcagccgc    15840
tttcgcagcg gcgactattg ccgacatggc caatcgcga agaggcaatg tatactgggt    15900
gcgtgacgct gccaccggtc aacgtgtacc cgtgcgcacc cgtcccccctc gcacttagaa    15960 gatactgagc agtctccgat gttgtgtccc agcggcgagg atgtccaagc gcaaatacaa    16020
ggaagaaatg ctgcaggtta tcgcacctga agtctacggc caaccgttga aggatgaaaa    16080
aaaaccccgc aaaatcaagc gggttaaaaa ggacaaaaaa gaagaggaag atggcgatga    16140
tgggctggcg gagtttgtgc gcgagtttgc cccacgcgca cgcgtgcaat ggcgtgggcg    16200
caaagttcga catgtgttga gacctggaac ttcggtggtc tttacacccg gcgagcgttc    16260
aagcgctact tttaagcgtt cctatgatga ggtgtacggg gatgatgata ttcttgagca    16320
ggcggctgac cgattaggcg agtttgctta tggcaagcgt agtagaataa cttccaagga    16380
```

```
tgagacagtg tcgatacccct tggatcatgg aaatcccacc cctagtctta aaccggtcac    16440
tttgcagcaa gtgttacccg taactccgcg aacaggtgtt aaacgcgaag gtgaagattt    16500
gtatcccact atgcaactga tggtacccaa acgccagaag ttggaggacg ttttggagaa    16560
agtaaaagtg gatccagata ttcaacctga ggttaaagtg agacccatta agcaggtagc    16620
gcctggtctg ggggtacaaa ctgtagacat taagattccc actgaaagta tggaagtgca    16680
aactgaaccc gcaaagccta ctgccacctc cactgaagtg caaacggatc catggatgcc    16740
catgcctatt acaactgacg ccgccggtcc cactcgaaga tcccgacgaa agtacggtcc    16800
agcaagtctg ttgatgccca attatgttgt acacccatct attattccta ctcctggtta    16860
ccgaggcact cgctactatc gcagccgaaa cagtacctcc cgccgtcgcc gcaagacacc    16920
tgcaaatcgc agtcgtcgcc gtagacgcac aagcaaaccg actcccggcg ccctggtgcg    16980
gcaagtgtac cgcaatggta gtgcggaacc tttgacactg ccgcgtgcgc gttaccatcc    17040
gagtatcatc acttaatcaa tgttccgct gcctccttgc agatatggcc ctcacttgtc    17100
gccttcgcgt tcccatcact ggttaccgag gaagaaactc gcgccgtaga agagggatgt    17160
tgggacgcgg aatgcgacgc tacaggcgac ggcgtgctat ccgcaagcaa ttgcggggtg    17220
gttttttacc agccttaatt ccaattatcg ctgctgcaat tggcgcgata ccaggcatag    17280
cttccgtggc ggttcaggcc tcgcaacgac attgacattg aaaaaaacg tataaataaa    17340 aaaaaaaaa tacaatggac tctgacactc ctggtcctgt gactatgttt tcttagagat    17400
ggaagacatc aattttcat ccttggctcc gcgacacggc acgaagccgt acatgggcac    17460
ctggagcgac atcggcacga gccaactgaa cgggggcgcc ttcaattgga gcagtatctg    17520
gagcgggctt aaaaattttg gctcaaccat aaaaacatac gggaacaaag cttggaacag    17580
cagtacagga caggcgctta gaaataaact taaagaccag aacttccaac aaaaagtagt    17640
cgatgggata gcttccggca tcaatggagt ggtagatttg gctaaccagg ctgtgcagaa    17700
aaagataaac agtcgtttgg accccgccgcc agcaaccca ggtgaaatgc aagtgggaga    17760
agaaattcct ccgccagaaa aacgaggcga caagcgtccg cgtcccgatt tggaagagac    17820
gctggtgacg cgcgtagatg aaccgccttc ttatgaggaa gcaacgaagc ttggaatgcc    17880
caccactaga ccgatagccc caatggccac cggggtgatg aaaccttctc agttgcatcg    17940
acccgtcacc ttggatttgc cccctccccc tgctgctact gctgtacccg cttctaagcc    18000
tgtcgctgcc ccgaaaccag tcgccgtagc caggtcacgt cccggggggcg ctcctcgtcc    18060 aaatgcgcac tggcaaaata ctctgaacag catcgtgggt ctaggcgtgc aaagtgtaaa    18120
acgccgtcgc tgcttttaat taaatatgga gtagcgctta acttgccat ctgtgtatat    18180 gtgtcattac acgccgtcac agcagcagag gaaaaaagga agaggtcgtg cgtcgacgct    18240
gagttacttt caagatggcc accccatcga tgctgcccca atgggcatac atgcacatcg    18300
ccggacagga tgcttcggag tacctgagtc cgggtctggt gcagttcgcc cgcgccacag    18360
acacctactt caatctggga aataagttta gaaatcccac cgtagcgccg acccacgatg    18420
tgaccaccga ccgtagccag cggctcatgt tgcgcttcgt gcccgttgac cgggaggaca    18480
atacatactc ttacaaagtg cggtacaccc tggccgtggg cgacaacaga gtgctggata    18540
tggccagcac gttctttgac attaggggtg tgttggacag aggtcccagt ttcaaacccct   18600 attctggtac ggcttacaac tccctggctc ctaaaggcgc tccaaataca tctcagtgga    18660
ttgcagaagg tgtaaaaaat acaactggtg aggaacacgt aacagaagag gaaaccaata    18720
ctactactta cactttggc aatgctcctg taaaagctga agctgaaatt acaaaagaag    18780
```

```
gactcccagt aggtttggaa gtttcagatg aagaaagtaa accgatttat gctgataaaa   18840
catatcagcc agaacctcag ctgggagatg aaacttggac tgaccttgat ggaaaaaccg   18900
aaaagtatgg aggcagggct ctcaaacccg atactaagat gaaaccatgc tacgggtcct   18960
ttgccaaacc tactaatgtg aaaggcggtc aggcaaaaca aaaaacaacg gagcagccaa   19020
atcagaaagt cgaatatgat atcgacatgg agttttttga tgcggcatcg cagaaaacaa   19080
acttaagtcc taaaattgtc atgtatgcag aaaatgtaaa tttggaaact ccagacactc   19140
atgtagtgta caaacctgga acagaagaca caagttccga agctaatttg ggacaacaat   19200
ctatgcccaa cagacccaac tacattggct tcagagataa cttatattgga cttatgtact   19260 ataacagtac tggtaacatg ggggtgctgg ctggtcaagc gtctcagtta aatgcagtgg   19320
ttgacttgca ggacagaaac acagaacttt cttaccaact cttgcttgac tctctgggcg   19380
acagaaccag atactttagc atgtggaatc aggctgtgga cagttatgat cctgatgtac   19440
gtgttattga aaatcatggt gtggaagatg aacttcccaa ctactgtttt ccactggacg   19500
gcataggtgt tccaacaacc agttacaaat caatagttcc aaatggagac aatgcgccta   19560
attggaagga acctgaagta aatgaacaa gtgagatcgg acagggtaat ttgtttgcca   19620
tggaaattaa ccttcaagcc aatctatggc gaagtttcct ttattccaat gtggctctat   19680
atctcccaga ctcgtacaaa tacaccccgt ccaatgtcac tcttccagaa aacaaaaaca   19740
cctacgacta catgaacggg cgggtggtgc cgccatctct agtagacacc tatgtgaaca   19800
ttggtgccag gtggtctctg gatgccatgg acaatgtcaa cccattcaac caccaccgta   19860
acgctggctt gcgttaccga tccatgcttc tgggtaacgg acgttatgtg cctttccaca   19920
tacaagtgcc tcaaaaattc ttcgctgtta aaaacctgct gcttctccca ggctcctaca   19980
cttatgagtg gactttagg aaggatgtga acatggttct acagagttcc ctcggtaacg   20040
acctgcgggt agatggcgcc agcatcagtt tcacgagcat caacctctat gctacttttt   20100
tccccatggc tcacaacacc gcttccaccc ttgaagccat gctgcggaat gacaccaatg   20160
atcagtcatt caacgactac ctatctgcag ctaacatgct ctaccccatt cctgccaatg   20220
caaccaatat tcccattcc attccttctc gcaactgggc ggcttcaga ggctggtcat   20280 ttaccagact gaaaaccaaa gaaactccct ctttggggtc tggatttgac ccctactttg   20340
tctattctgg ttctattccc tacctggatg gtaccttcta cctgaaccac acttttaaga   20400
aggtttccat catgtttgac tcttcagtga gctggcctgg aaatgacagg ttactatctc   20460
ctaacgaatt tgaaataaag cgcactgtgg atggcgaagg ctacaacgta gcccaatgca   20520
acatgaccaa agactggttc ttggtacaga tgctcgccaa ctacaacatc ggctatcagg   20580
gcttctacat tccagaagga tacaaagatc gcatgtattc attttttcaga aacttccagc   20640 ccatgagcag gcaggtggtt gatgaggtca attacaaaga cttcaaggcc gtcgccatac   20700
cctaccaaca caacaactct ggcttttgtg gttacatggc tccgaccatg cgccaaggtc   20760
aaccctatcc cgctaactat ccctatccac tcattggaac aactgccgta aatagtgtta   20820
cgcagaaaaa gttcttgtgt gacagaacca tgtggcgcat accgttctcg agcaacttca   20880
tgtctatggg ggcccttaca gacttgggac agaaatatgct ctatgccaac tcagctcatg   20940
ctctggacat gaccttttgag gtggatccca tggatgagcc caccctgctt tatcttctct   21000
tcgaagtttt cgacgtggtc agagtgcatc agccacaccg cggcatcatc gaggcagtct   21060
acctgcgtac accgttctcg gccggtaacg ctaccacgta agaagcttct tgcttcttgc   21120
```

```
aaatagcagc tgcaaccatg gcctgcggat cccaaaacgg ctccagcgag caagagctca    21180
gagccattgt ccaagacctg ggttgcggac cctattttt  gggaacctac gataagcgct    21240
tcccggggtt catggccccc gataagctcg cctgtgccat tgtaaatacg gccggacgtg    21300
agacgggggg agagcactgg ttggctttcg gttggaaccc acgttctaac acctgctacc    21360
tttttgatcc ttttggattc tcggatgatc gtctcaaaca gatttaccag tttgaatatg    21420
agggtctcct gcgccgcagc gctcttgcta ccaaggaccg ctgtattacg ctggaaaaat    21480
ctacccagac cgtgcagggt ccccgttctg ccgcctgcgg acttttctgc tgcatgttcc    21540
ttcacgcctt tgtgcactgg cctgaccgtc ccatggacgg aaaccccacc atgaaattgc    21600
taactggagt gccaaacaac atgcttcatt ctcctaaagt ccagcccacc ctgtgtgaca    21660
atcaaaaagc actctaccat tttcttaata cccattcgcc ttattttcgc tcccatcgta    21720
cacacatcga aagggccact cgcttcgacc gtatggatgt tcaataatga ctcatgtaaa    21780
caacgtgttc aataaacatc actttatttt tttacatgta tcaaggctct gcattactta    21840
tttatttaca agtcgaatgg gttctgacga gaatcagaat gacccgcagg cagtgatacg    21900
ttgcggaact gatacttggg ttgccacttg aattcgggaa tcaccaactt gggaaccggt    21960
atatcgggca ggatgtcact ccacagcttt ctggtcagct gcaaagctcc aagcaggtca    22020
ggagccgaaa tcttgaaatc acaattagga ccagtgcttt gagcgcgaga gttgcggtac    22080
accggattgc agcactgaaa caccatcagc gacggatgtc tcacgcttgc cagcacggtg    22140
ggatctgcaa tcatgcccac atccagatct tcagcattgg caatgctgaa cggggtcatc    22200
ttgcaggtct gcctacccat ggcgggcacc caattaggct tgtggttgca atcgcagtgc    22260 aggggatca  gtatcatctt ggcctgatcc tgtctgattc ctggatacac ggctctcatg    22320
aaagcatcat attgcttgaa agcctgctgg gctttactac cctcggtata aacatcccg     22380 caggacctgc tcgaaaactg gttagctgca cagccggcat cattcacaca gcagcgggcg    22440
tcattgttag ctatttgcac cacacttctg ccccagcggt tttgggtgat tttggttcgc    22500
tcgggattct cctttaaggc tcgttgtccg ttctcgctgg ccacatccat ctcgataatc    22560
tgctccttct gaatcataat attgccatgc aggcacttca gcttgccctc ataatcattg    22620
cagccatgag gccacaacgc acagcctgta cattcccaat tatggtgggc gatctgagaa    22680
aaagaatgta tcattccctg cagaaatctt cccatcatcg tgctcagtgt cttgtgacta    22740
gtgaaagtta actggatgcc tcggtgctcc tcgtttacgt actggtgaca gatgcgcttg    22800
tattgttcgt gttgctcagg cattagttta aaagaggttc taagttcgtt atccagcctg    22860
tacttctcca tcagcagaca catcacttcc atgcctttct cccaagcaga caccagggggc    22920 aagctaatcg gattcttaac agtgcaggca gcagctcctt tagccagagg gtcatcttta    22980
gcgatcttct caatgcttct tttgccatcc ttctcaacga tgcgcacggg cgggtagctg    23040
aaacccactg ctacaagttg cgcctcttct ctttcttctt cgctgtcttg actgatgtct    23100
tgcatgggga tatgtttggt cttccttggc ttctttttgg ggggtatcgg aggaggagga    23160
ctgtcgctcc gttccggaga cagggaggat tgtgacgttt cgctcaccat taccaactga    23220
ctgtcggtag aagaacctga ccccacacgc cgacaggtgt ttctcttcgg gggcagaggt    23280
ggaggcgatt gcgaagggct gcggtccgac ctggaaggcg gatgactggc agaaccccctt   23340 ccgcgttcgg gggtgtgctc cctgtggcgg tcgcttaact gatttccttc gcggctggcc    23400
attgtgttct cctaggcaga gaaacaacag acatggaaac tcagccattg ctgtcaacat    23460
cgccacgagt gccatcacat ctcgtcctca gcgacgagga aaaggagcag agcttaagca    23520
```

```
ttccaccgcc cagtcctgcc accacctcta ccctagaaga taaggaggtc gacgcatctc   23580
atgacatgca gaataaaaaa gcgaaagagt ctgagacaga catcgagcaa gacccgggct   23640
atgtgacacc ggtggaacac gaggaagagt tgaaacgctt tctagagaga gaggatgaaa   23700
actgcccaaa acaacgagca gataactatc accaagatgc tggaaatagg gatcagaaca   23760
ccgactacct catagggctt gacggggaag acgcgctcct taaacatcta gcaagacagt   23820
cgctcatagt caaggatgca ttattggaca gaactgaagt gcccatcagt gtggaagagc   23880
tcagccgcgc ctacgagctt aacctctttt cacctcgtac tcccccccaaa cgtcagccaa   23940 acggcacctg cgagccaaat cctcgcttaa acttttatcc agcttttgct gtgccagaag   24000
tactggctac ctatcacatc ttttttaaaa atcaaaaaat tccagtctcc tgccgcgcta   24060
atcgcacccg cgccgatgcc ctactcaatc tgggacctgg ttcacgctta cctgatatag   24120
cttccttgga agaggttcca aagatcttcg agggtctggg caataatgag actcgggccg   24180
caaatgctct gcaaaaggga gaaaatggca tggatgagca tcacagcgtt ctggtggaat   24240
tggaaggcga taatgccaga ctcgcagtac tcaagcgaag catcgaggtc acacacttcg   24300
catatcccgc tgtcaacctg ccccctaaag tcatgacggc ggtcatggac cagttactca   24360
ttaagcgcgc aagtccccctt tcagaagaca tgcatgaccc agatgcctgt gatgagggta   24420
aaccagtggt cagtgatgag cagctaaccc gatggctggg caccgactct cccagggatt   24480
tggaagagcg tcgcaagctt atgatggccg tggtgctggt taccgtagaa ctagagtgtc   24540
tccgacgttt ctttaccgat tcagaaacct tgcgcaaact cgaagagaat ctgcactaca   24600
cttttagaca cggctttgtg cggcaggcat gcaagatatc taacgtggaa ctcaccaacc   24660
tggtttccta catgggtatt ctgcatgaga atcgcctagg acaaagcgtg ctgcacagca   24720
ccctgaaggg ggaagcccgc cgtgattaca tccgcgattg tgtctatctg tacctgtgcc   24780
aaacgtggca accggcatg ggtgtatggc agcaatgttt agaagaacag aacttgaaag   24840
agcttgacaa gctcttacag aaatctctta aggttctgtg gacagggttc gacgagcgca   24900
ccgtcgcttc cgacctggca gacctcatct cccagagcg tctcagggtt actttgcgaa   24960
acggattgcc tgactttatg agccagagca tgcttaacaa ttttcgctct ttcatcctgg   25020
aacgctccgg tatcctgccc gccacctgct gcgcactgcc ctccgacttt gtgcctctca   25080
cctaccgcga gtgccccccg ccgctatgga gtcactgcta cctgttccgt ctggccaact   25140
atctctccta ccactcggat gtgatcgagg atgtgagcgg agacggcttg ctggagtgtc   25200
actgccgctg caatctgtgc acgccccacc ggtccctagc ttgcaacccc cagttgatga   25260
gcgaaaccca gataataggc acctttgaat tgcaaggccc cagcagccaa ggcgatgggt   25320
cttctcctgg gcaaagttta aaactgaccc cgggactgtg gacctccgcc tacttgcgca   25380
agtttgctcc ggaagattac caccctatg aaatcaagtt ctatgaggac caatcacagc   25440
ctccaaaggc cgaactttcg gcctgcgtca tcacccaggg ggcaattctg cccaattgc   25500 aagccatcca aaaatcccgc caagaatttc tactgaaaaa gggtaagggg gtctaccttg   25560
acccccagac cggcgaggaa ctcaacacaa ggttccctca ggatgtccca acgacgagaa   25620
aacaagaagt tgaaggtgca gccgccgccc ccagaagata tggaggaaga ttgggacagt   25680
caggcagagg aggcggagga ggacagtctg aggacagtc tggaggaaga cagtttggag   25740
gaggaaaacg aggaggcaga ggaggtggaa gaagtaaccg ccgacaaaca gttatcctcg   25800
gctgcggaga caagcaacag cgctaccatc tccgctccga gtcgaggaac ccggcggcgt   25860
```

```
cccagcagta gatgggacga gaccggacgc ttcccgaacc caaccagcgc ttccaagacc   25920
ggtaagaagg atcggcaggg atacaagtcc tggcgggggc ataagaatgc catcatctcc   25980
tgcttgcatg agtgcggggg caacatatcc ttcacgcggc gctacttgct attccaccat   26040
ggggtgaact ttccgcgcaa tgttttgcat tactaccgtc acctccacag cccctactat   26100
agccagcaaa tcccggcagt ctcgacagat aaagacagcg gcggcgacct ccaacagaaa   26160
accagcagcg gcagttagaa aatacacaac aagtgcagca acaggaggat taaagattac   26220
agccaacgag ccagcgcaaa cccgagagtt aagaaatcgg atctttccaa ccctgtatgc   26280
catcttccag cagagtcggg gtcaagagca ggaactgaaa ataaaaaacc gatctctgcg   26340
ttcgctcacc agaagttgtt tgtatcacaa gagcgaagat caacttcagc gcactctcga   26400
ggacgccgag gctctcttca acaagtactg cgcgctgact cttaaagagt aggcagcgac   26460
cgcgcttatt caaaaaggc gggaattaca tcatcctcga catgagtaaa gaaattccca   26520
cgccttacat gtggagttat caaccccaaa tgggattggc ggcaggcgcc tcccaggact   26580
actccacccg catgaattgg ctcagcgccg ggccttctat gatttctcga gttaatgata   26640
tacgcgccta ccgaaaccaa atacttttgg aacagtcagc tcttaccacc acgccccgcc   26700
aacaccttaa tcccagaaat tggcccgccg ccctagtgta ccaggaaagt cccgctccca   26760
ccactgtatt acttcctcga gacgcccagg ccgaagtcca aatgactaat gcaggtgcgc   26820
gttagctggc ggctccaccc tatgtcgtca caggcctcgg cataatataa aacgcctgat   26880
gatcagaggc cgaggtatcc agctcaacga cgagtcggtg agctctccgc ttggtctacg   26940
accagacgga atctttcaga ttgccggctg cgggagatct tccttcaccc ctcgtcaggc   27000
tgttctgact ttggaaagtt cgtcttcgca accccgctcg ggcggaatcg ggaccgttca   27060
atttgtggag gagtttactc cctctgtcta cttcaacccc ttctccggat ctcctgggca   27120
ttacccggac gagttcatac cgaacttcga cgcgattagc gagtcagtgg acggctacga   27180
ttgatgtctg gtgacgcggc tgagctatct cggctgcgac atctagacca ctgccgccgc   27240
tttcgctgct ttgcccggga actcattgag ttcatctact tcgaactccc caaggatcac   27300
cctcaaggtc cggcccacgg agtgcggatt tctatcgaag gcaaaataga ctctcgcctg   27360
caacgaattt tctcccagcg gcccgtgctg atcgagcgag accagggaaa caccacggtt   27420
tccatctact gcatttgtaa tcaccccgga ttgcatgaaa gcctttgctg tcttatgtgt   27480
actgagttta ataaaaactg aattaagact ctcctacgga ctgccgcttc ttcaacccgg   27540
attttacaac cagaagaacg aaacttttcc tgtcgtccag gactctgtta acttcacctt   27600
tcctactcac aaactagaag ctcaacgact acaccgcttt tccagaagca ttttccctac   27660
taatactact ttcaaaaccg gaggtgagct ccaaggtctt cctacagaaa acccttgggt   27720
ggaagcgggc cttgtagtgc taggaattct tgcgggtggg cttgtgatta ttcttttgcta   27780 cctatacaca ccttgcttca cttttcttagt ggtgttgtgg tattggttta aaaaatgggg   27840
cccatactag tcttgcttgt tttactttcg cttttggaac cgggttctgc caattacgat   27900
ccatgtctag acttcgaccc agaaaactgc acacttactt ttgcacccga cacaagccgc   27960
atctgtggag ttcttattaa gtgcggatgg gaatgcaggt ccgttgaaat tacacacaat   28020
aacaaaacct ggaacaatac cttatccacc acatgggagc caggagttcc cgagtggtac   28080
actgtctctg tccgaggtcc tgacggttcc atccgcatta gtaacaacac tttcattttt   28140
tctgaaatgt gcgatctggc catgttcatg agcaaacagt attctctatg gcctcctagc   28200
aaggacaaca tcgtaacgtt ctccattgct tattgcttgt gcgcttgcct tcttactgct   28260
```

```
ttactgtgcg tatgcataca cctgcttgta accactcgca tcaaaaacgc caataacaaa    28320
gaaaaaatgc cttaacctct ttctgtttac agacatggct tctcttacat ctctcatatt    28380
tgtcagcatt gtcactgccg ctcatggaca aacagtcgtc tctatccctc taggacataa    28440
ttacactctc ataggacccc caatcacttc agaggtcatc tgggccaaac tgggaagcgt    28500
tgattacttt gatataatct gcaacaaaac aaaaccaata atagtaactt gcaacataca    28560
aaatcttaca ttgattaatg ttagcaaagt ttacagcggt tactattatg gttatgacag    28620
atacagtagt caatatagaa attacttggt tcgtgttacc cagttgaaaa ccacgaaaat    28680
gccaaatatg gcaaagattc gatccgatga caattctcta gaaactttta catctcccac    28740
cacacccgac gaaaaaaaca tcccagattc aatgattgca attgttgcag cggtggcagt    28800
ggtgatggca ctaataataa tatgcatgct tttatatgct tgtcgctaca aaagtttca    28860 tcctaaaaaa caagatctcc tactaaggct taacatttaa tttctttta tacagccatg    28920 gtttccacta ccacattcct tatgcttact agtctcgcaa ctctgacttc tgctcgctca    28980
cacctcactg taactatagg ctcaaactgc acactaaaag gacctcaagg tggtcatgtc    29040
ttttggtgga gaatatatga caatggatgg tttacaaaac catgtgacca acctggtaga    29100
tttttctgca acggcagaga cctaaccatt atcaacgtga cagcaaatga caaggcttc    29160 tattatggaa ccgactataa aagtagttta gattataaca ttattgtact gccatctacc    29220
actccagcac cccgcacaac tactttctct agcagcagtg tcgctaacaa tacaatttcc    29280
aatccaacct ttgccgcgct tttaaaacgc actgtgaata attctacaac ttcacataca    29340
acaatttcca cttcaacaat cagcattatc gctgcagtga caattggaat atctattctt    29400
gtttttacca taacctacta cgcctgctgc tatagaaaag acaaacataa aggtgatcca    29460
ttacttagat ttgatattta atttgttctt tttttttta tttacagtat ggtgaacacc    29520
aatcatggta cctagaaatt tcttcttcac catactcatt tgtgcattta atgtttgcgc    29580
tactttcaca gcagtagcca cagcaacccc agactgtata ggagcatttg cttcctatgc    29640
acttttgtct tttgttactt gcatctgcgt atgtagcata gtctgcctgg ttattaattt    29700
tttccaactt atagactgga tccttgtgcg aattgcctac ctgcgccacc atcccgaata    29760
ccgcaaccaa aatatcgcgg cacttcttag actcatctaa aaccatgcag gctatactac    29820
caatattttt gcttctattg cttccctacg ctgtctcaac cccagctgcc tatagtactc    29880
caccagaaca ccttagaaaa tgcaaattcc aacaaccgtg gtcatttctt gcttgctatc    29940
gagaaaaatc agaaattccc ccaaatttaa taatgattgc tggaataatt aatataatct    30000
gttgcaccat aatttcattt ttgatatacc ccctatttga ttttggctgg aatgctccca    30060
atgcacatga tcatccacaa gacccagagg aacacattcc cctacaaaac atgcaacatc    30120
caatagcgct aatagattac gaaagtgaac cacaaccccc actactccct gctattagtt    30180
acttcaacct aaccgcggga gatgactgaa acactcacca cctccaattc cgccgaggat    30240
ctgctcgata tggacggccg cgtctcagaa cagcgactcg cccaactacg catccgccag    30300
cagcaggaac gcgcggccaa agagctcaga gatgtcatcc aaattcacca atgcaaaaaa    30360
ggcatattct gtttggtaaa acaagccaag atatcctacg agatcaccgc tactgaccat    30420
cgcctctctt acgaacttgg cccccaacga caaaaattta cctgcatggt gggaatcaac    30480
cccatagtta tcacccagca aagtggagat actaagggtt gcattcactg ctcctgcgat    30540
tccatcgagt gcacctacac cctgctgaag accctatgcg gcctaagaga cctgctacca    30600
```

```
atgaattaaa aaatgattaa taaaaaatca cttacttgaa atcagcaata aggtctctgt   30660
tgaaattttc tcccagcagc acctcacttc cctcttccca actctggtat tctaaacccc   30720
gttcagcggc atactttctc catactttaa aggggatgtc aaattttagc tcctctcctg   30780
tacccacaat cttcatgtct ttcttcccag atgaccaaga gagtccggct cagtgactcc   30840
ttcaaccctg tctacccta tgaagatgaa agcacctccc aacacccctt tataaaccca   30900
gggtttattt ccccaaatgg cttcacacaa agcccaaacg gagttcttac tttaaaatgt   30960
ttaaccccac taacaaccac aggcggatct ctacagctaa aagtgggagg gggacttaca   31020
gtggatgaca ccaacggttt tttgaaagaa aacataagtg ccaccacacc actcgttaag   31080
actggtcact ctataggttt accactagga gccggattgg gaacgaatga aaataaactt   31140
tgtatcaaat taggacaagg acttacattc aattcaaaca acatttgcat tgatgacaat   31200
attaacacct tatggacagg agtcaacccc accgaagcca actgtcaaat catgaactcc   31260
agtgaatcta atgattgcaa attaattcta acactagtta aaactggagc actagtcact   31320
gcatttgttt atgttatagg agtatctaac aattttaata tgctaactac acacagaaat   31380
ataaattta ctgcagagct gttttttcgat tctactggta atttactaac tagactctca   31440
tccctcaaaa ctccacttaa tcataaatca ggacaaaaca tggctactgg tgccattact   31500
aatgctaaag gtttcatgcc cagcacgact gcctatcctt tcaatgataa ttctagagaa   31560
aaagaaaact acatttacgg aacttgttac tacacagcta gtgatcgcac tgcttttccc   31620
attgacatat ctgtcatgct taaccgaaga gcaataaatg acgagacatc atattgtatt   31680
cgtataactt ggtcctggaa cacaggagat gccccagagg tgcaaacctc tgctacaacc   31740
ctagtcacct ccccattac ctttactac atcagagaag acgactgaca aataaagttt   31800
aacttgttta tttgaaaatc aattcacaaa atccgagtag ttattttgcc tccccttcc   31860
cattaacag aatacaccaa tctctcccca cgcacagctt aaacatttg ataccatta   31920
gatatagaca tggttttaga ttccacattc caaacagttt cagagcgagc caatctgggg   31980
tcagtgatag ataaaaatcc atcgggatag tcttttaaag cgctttcaca gtccaactgc   32040
tgcggatgga ctccggagtc tggatcacgg tcatctggaa gaagaacgat gggaatcata   32100
atccgaaaac ggtatcggac gattgtgtct catcaaaccc acaagcagcc gctgtctgcg   32160
tcgctccgtg cgactgctgt ttatgggatc agggtccaca gtgtcctgaa gcatgatttt   32220
aatagccctt aacatcaact ttctggtgcg atgcgcgcag caacgcattc tgatttcact   32280
caaatctttg cagtaggtac aacacattat tacaatattg tttaataaac cataattaaa   32340
agcgctccag ccaaaactca tatctgatat aatcgcccct gcatgaccat cataccaaag   32400
tttaatataa attaaatgac gttccctcaa aaacacacta cccacataca tgatctcttt   32460
tggcatgtgc atattaacaa tctgtctgta ccatggacaa cgttggttaa tcatgcaacc   32520
caatataacc ttccggaacc acactgccaa caccgctccc ccagccatgc attgaagtga   32580
accctgctga ttacaatgac aatgaagaac ccaattctct cgaccgtgaa tcacttgaga   32640
atgaaaaata tctatagtgg cacaacatag acataaatgc atgcatcttc tcataatttt   32700
taactcctca ggatttagaa acatatccca gggaatagga agctcttgca gaacagtaaa   32760
gctggcagaa caaggaagac cacgaacaca acttacacta tgcatagtca tagtatcaca   32820
atctggcaac agcgggtggt cttcagtcat agaagctcgg gtttcatttt cctcacaacg   32880
tggtaactgg gctctggtgt aagggtgatg tctggcgcat gatgtcgagc gtgcgcgcaa   32940
cctttgtcata atggagttgc ttcctgacat tctcgtattt tgtatagcaa aacgcggccc   33000
```

```
tggcagaaca cactcttctt cgccttctat cctgccgctt agcgtgttcc gtgtgatagt    33060
tcaagtacaa ccacactctt aagttggtca aagaatgct  ggcttcagtt gtaatcaaaa    33120
ctccatcgca tctaatcgtt ctgaggaaat catccacggt agcatatgca aatcccaacc    33180
aagcaatgca actggattgt gtttcaagca ggagaggaga gggaagagac ggaagaacca    33240
tgttaatttt tattccaaac gatctcgcag tacttcaaat tgtagatcgc gcagatggca    33300
tctctcgccc ccactgtgtt ggtgaaaaag cacagctaga tcaaaagaaa tgcgattttc    33360
aaggtgctca acggtggctt ccagcaaagc ctccacgcgc acatccaaga acaaagaat     33420 accaaaagaa ggagcatttt ctaactcctc aatcatcata ttacattcct gcaccattcc    33480
cagataattt tcagctttcc agccttgaat tattcgtgtc agttcttgtg gtaaatccaa    33540
tccacacatt acaaacaggt cccggagggc gccctccacc accattctta aacacaccct    33600
cataatgaca aaatatcttg ctcctgtgtc acctgtagcg aattgagaat ggcaacatca    33660
attgacatgc ccttggctct aagttcttct ttaagttcta gttgtaaaaa ctctctcata    33720
ttatcaccaa actgcttagc cagaagcccc ccgggaacaa gagcagggga cgctacagtg    33780
cagtacaagc gcagacctcc ccaattggct ccagcaaaaa caagattgga ataagcatat    33840
tgggaaccgc cagtaatatc atcgaagttg ctggaaatat aatcaggcag agtttcttgt    33900
aaaaattgaa taaagaaaa  atttgccaaa aaacattca aaacctctgg gatgcaaatg     33960
caataggtta ccgcgctgcg ctccaacatt gttagttttg aattagtctg caaaaataaa    34020
aaaaaaaaca agcgtcatat catagtagcc tgacgaacag atggataaat cagtctttcc    34080
atcacaagac aagccacagg gtctccagct cgaccctcgt aaaacctgtc atcatgatta    34140
aacaacagca ccgaaagttc ctcgcggtga ccagcatgaa taattcttga tgaagcatac    34200
aatccagaca tgttagcatc agttaacgag aaaaaacagc caacatagcc tttgggtata    34260
attatgctta atcgtaagta tagcaaagcc acccctcgcg gatacaaagt aaaaggcaca    34320
ggagaataaa aaatataatt atttctctgc tgctgttcag gcaacgtcgc ccccggtccc    34380
tctaaataca catacaaagc ctcatcagcc atggcttacc agacaaagta cagcgggcac    34440
acaaagcaca agctctaaag tgactctcca acctctccac aatatatata tacacaagcc    34500
ctaaactgac gtaatgggag taaagtgtaa aaaatcccgc caaacccaac acacaccccg    34560
aaactgcgtc accagggaaa agtacagttt cacttccgca atcccaacag gcgtaacttc    34620
ctctttctca cggtacgtga tatcccacta acttgcaacg tcattttccc acggtcgcac    34680 cgccccttt  agccgttaac cccacagcca atcaccacac gatccacact ttttaaaatc    34740
acctcattta catattggca ccattccatc tataaggtat attattgatg atg           34793
```

<210> SEQ ID NO 4
<211> LENGTH: 1440
<212> TYPE: DNA
<213> ORGANISM: Artificial Sequence
<220> FEATURE:
<223> OTHER INFORMATION: Fully synthetic

<400> SEQUENCE: 4

```
catcatcaat aatataccct atagatggaa tggtgccaat atgtaaatga ggtgatttta      60
aaaagtgtgg atcgtgtggt gattggctgt ggggttaacg gctaaaaggg gcggtgcgac     120
cgtgggaaaa tgacgttttg tggggtgga  gttttttgc  aagttgtcgc gggaaatgtg    180
acgcataaaa aggcttttttt ctcacggaac tacttagttt tcccacgta  tttaacagga    240
```

```
aatgaggtag ttttgaccgg atgcaagtga aaattgttga ttttcgcgcg aaaactgaat    300
gaggaagtgt ttttctgaat aatgtggtat ttatggcagg gtggagtatt tgttcagggc    360
caggtagact ttgacccatt acgtggaggt ttcgattacc gtgttttta cctgaatttc      420
cgcgtaccgt gtcaaagtct tctgttttta cgtaggtgtc agctgatcgc tagggtattt    480
atacctcagg gtttgtgtca agaggccact cttgagtgcc agcgagaaga gttttctcct    540
ctgcgccggc agtttaataa taaaaaaatg agagatttgc gatttctgcc tcaggaaata    600
atctctgctg agactggaaa tgaaatattg gagcttgtgg tgcacgccct gatgggagac    660
gatccggagc cacctgtgca gcttttgag cctcctacgc ttcaggaact gtatgattta      720
gaggtagagg gatcggagga ttctaatgag gaagctgtaa atggctttt taccgattct      780
atgcttttag ctgctaatga agggttagaa ttagatccgc cttggacac ttttgatact      840
ccaggggtaa ttgtggaaag cggtacaggt gtaagaaaat tacctgattt gagttccgtg    900
gactgtgatt tgcactgcta tgaagacggg tttcctccga gtgatgagga ggaccatgaa    960
aaggagcagt ccatgcagac tgcagcgggt gagggagtga aggctgccaa tgttggtttt    1020
cagttggatt gcccggagct tcctggacat ggctgtaagt cttgtgaatt tcacaggaaa    1080
aatactggag taaggaact gttatgttcg ctttgttata tgagaacgca ctgccacttt      1140
atttacagta agtgtgttta agttaaaatt taaaggaata tgctgttttt cacatgtata    1200
ttgagtgtga gttttgtgct tcttattata ggtcctgtgt ctgatgctga tgaatcacca    1260
tctcctgatt ctactacctc acctcctgag attcaagcac ctgttcctgt ggacgtgcgc    1320
aagcccattc ctgtgaagct taagcctggg aaacgtccag cagtgaaaaa acttgaggac    1380
ttgttacagg gtggggacgg acctttggac ttgagtacac ggaaacgtcc aagacaataa    1440

<210> SEQ ID NO 5
<211> LENGTH: 3153
<212> TYPE: DNA
<213> ORGANISM: Artificial Sequence
<220> FEATURE:
<223> OTHER INFORMATION: Fully synthetic

<400> SEQUENCE: 5
atacctgtga cggaagatca cttcgcagaa taaataaatc ctggtgtccc tgttgatacc     60
gggaagccct gggccaactt ttggcgaaaa tgagacgttg atcggcacgt aagaggttcc    120
aactttcacc ataatgaaat aagatcacta ccgggcgtat tttttgagtt atcgagattt    180
tcaggagcta aggaagctaa aatggagaaa aaatcactg gatataccac cgttgatata    240
tcccaatggc atcgtaaaga acatttgag gcatttcagt cagttgctca atgtacctat    300
aaccagaccg ttcagctgga tattacggcc ttttaaaga ccgtaaagaa aaataagcac    360
aagtttatc cggcctttat tcacattctt gcccgcctga tgaatgctca tccggaattc      420
cgtatggcaa tgaaagacgg tgagctggtg atatgggata tgttcaccc ttgttacacc    480
gttttccatg agcaaactga aacgttttca tcgctctgga gtgaatacca cgacgatttc    540
cggcagtttc tacacatata ttcgcaagat gtggcgtgtt acggtgaaaa cctggcctat    600
ttccctaaag ggtttattga gaatatgttt ttcgtctcag ccaatccctg ggtgagtttc    660
accagttttg atttaaacgt ggccaatatg gacaacttct tcgccccgt tttcaccatg      720
ggcaaatatt atacgcaagg cgacaaggtg ctgatgccgc tggcgattca ggttcatcat    780
gccgtctgtg atggcttcca tgtcggcaga atgcttaatg aattacaaca gtactgcgat    840
gagtggcagg gcggggcgta atttttttaa ggcagttatt ggtggcctta aacgcctatt    900
```

```
taaattacgt cattttccca cggtcgcacc gcccctttta gccgttaacc ccacagccaa    960
tcaccacacg atccacactt tttaaaatca cctcatttac atattggcac cattccatct   1020
ataaggtata ttattgatga tgcatcatca ataatatacc ttatagatgg aatggtgcca   1080
atatgtaaat gaggtgattt taaaaagtgt ggatcgtgtg gtgattggct gtggggttaa   1140
cggctaaaag gggcggtgcg accgtgggaa aatgacgttt tgtggggtg gagtttttt    1200
gcaagttgtc gcgggaaatg tgacgcataa aaaggctgta gcgatcgctt agactcgagc   1260
ggccgcggtc cgtttaaact gtcagaccaa gtttactcat atatacttta gattgattta   1320
aaacttcatt tttaatttaa aaggatctag gtgaagatcc tttttgataa tctcatgacc   1380
aaaatccctt aacgtgagtt ttcgttccac tgagcgtcag accccgtaga aaagaccaaa   1440
ggatcttctt gagatccttt ttttctgcgc gtaatctgct gcttgcaaac aaaaaaacca   1500
ccgctaccag cggtggtttg tttgccggat caagagctac caactctttt tccgaaggta   1560
actggcttca gcagagcgca gataccaaat actgtccttc tagtgtagcc gtagttgggc   1620
caccacttca agaactctgt agcaccgcct acatacctcg ctctgctaat cctgttacca   1680
gtggctgctg ccagtggcga taagtcgtgt cttaccgggt tggactcaag acgatagtta   1740
ccggataagg cgcagcggtc gggctgaacg gggggttcgt gcacacagcc cagcttggag   1800
cgaacgacct acaccgaact gagatacta cagcgtgagc tatgagaaag cgccacgctt   1860
cccgaaggga gaaaggcgga caggtatccg gtaagcggca gggtcggaac aggagagcgc   1920
acgaaggagc ttccagggg aaacgcctgg tatctttata gtcctgtcgg gtttcgccac   1980
ctctgacttg agcgtcgatt tttgtgatgc tcgtcagggg ggcggagcct atggaaaaac   2040
gccagcaacg cggccttttt acggttcctg gccttttgct ggccttttgc tcacatgttc   2100
cttcctgcgt tatcccctga ttctgtggat aaccgtatta ccgcctttga gtgagctgat   2160
accgctcgcc gcaggtttaa acagatcgt cgacgcccgg gcaagctggc cggccgatac   2220
acaggaagtg acaatttcg cgcggtttta ggcggatgtt gtagtaaatt tgggcgtaac   2280
cgagtaagat ttggccattt tcgcgggaaa actgaataag aggaagtgaa atctgaataa   2340
ttttgtgtta ctcatagcgc gtaatatttg tctagggccg cggggacttt gaccgtttac   2400
gtggagactc gcccaggtgt ttttctcagg tgttttccgc gttccgggtc aaagttggcg   2460
ttttattatt atagtcagct gacgtgtagt gtatttatac ccggtgagtt cctcaagagg   2520
ccactcttga gtgccagcga gtagagtttt ctcctccgag ccgctccgac accgggactg   2580
aaaaatgaga gatttgcgat ttctgcctca ggaaataatc tctgctgaga ctggaaatga   2640
aatattggag cttgtggtgc acgccctgat gggagacgat ccggagccac ctgtgcagct   2700
ttttgagcct cctacgcttc aggaactgta tgatttagag gtagagggat cggaggattc   2760
taatgaggaa gctgtaaatg cttttttac cgattctatg cttttagctg ctaatgaagg   2820
gttagaatta gatccgccctt tggacacttt tgatactcca ggggtaattg tggaaagcgg   2880
tacaggtgta agaaaattac ctgatttgag ttccgtggac tgtgatttgc actgctatga   2940
agacgggttt cctccgagtg atgaggagga ccatgaaaag gagcagtcca tgcagactgc   3000
agcgggtgag ggagtgaagg ctgccaatgt tggttttcag ttggattgcc ggagcttcc   3060
tggacatggc tgtaagtctt gtgaatttca caggaaaaat actggagtaa aggaactgtt   3120
atgttcgctt tgttatatga gaatcattta aat                                3153
```

<210> SEQ ID NO 6

<211> LENGTH: 34793
<212> TYPE: DNA
<213> ORGANISM: Artificial Sequence
<220> FEATURE:
<223> OTHER INFORMATION: Fully synthetic

<400> SEQUENCE: 6

| | |
|---|---:|
| catcatcaat aatatacctt atagatggaa tggtgccaat atgtaaatga ggtgatttta | 60 |
| aaaagtgtgg atcgtgtggt gattggctgt ggggttaacg gctaaaaggg gcggtgcgac | 120 |
| cgtgggaaaa tgacgttttg tggggtgga gttttttttgc aagttgtcgc gggaaatgtg | 180 |
| acgcataaaa aggctttttt ctcacggaac tacttagttt tcccacggta tttaacagga | 240 |
| aatgaggtag ttttgaccgg atgcaagtga aaattgttga ttttcgcgcg aaaactgaat | 300 |
| gaggaagtgt ttttctgaat aatgtggtat ttatggcagg gtggagtatt tgttcagggc | 360 |
| caggtagact ttgacccatt acgtggaggt ttcgattacc gtgttttttta cctgaatttc | 420 |
| cgcgtaccgt gtcaaagtct tctgttttta cgtaggtgtc agctgatcgc tagggtattt | 480 |
| atacctcagg gtttgtgtca agaggccact cttgagtgcc agcgagaaga gttttctcct | 540 |
| ctgcgccggc agtttaataa taaaaaaatg agagatttgc gatttctgcc tcaggaaata | 600 |
| atctctgctg agactggaaa tgaaatattg gagcttgtgg tgcacgccct gatgggagac | 660 |
| gatccggagc cacctgtgca gcttttttgag cctcctacgc ttcaggaact gtatgattta | 720 |
| gaggtagagg atcggagga ttctaatgag gaagctgtaa atggcttttt taccgattct | 780 |
| atgcttttag ctgctaatga agggttagaa ttagatccgc cttttggacac ttttgatact | 840 |
| ccaggggtaa ttgtggaaag cggtacaggt gtaagaaaat tacctgatttt gagttccgtg | 900 |
| gactgtgatt tgcactgcta tgaagacggg tttcctccga gtgatgagga ggaccatgaa | 960 |
| aaggagcagt ccatgcagac tgcagcgggt gaggagtga aggctgccaa tgttggtttt | 1020 |
| cagttggatt gcccggagct tcctggacat ggctgtaagt cttgtgaatt tcacaggaaa | 1080 |
| aatactggag taaggaact gttatgttcg ctttgttata tgagaacgca ctgccacttt | 1140 |
| atttacagta agtgtgttta agttaaaatt taaaggaata tgctgttttt cacatgtata | 1200 |
| ttgagtgtga gttttgtgct tcttattata ggtcctgtgt ctgatgctga tgaatcacca | 1260 |
| tctcctgatt ctactacctc acctcctgag attcaagcac ctgttcctgt ggacgtgcgc | 1320 |
| aagcccattc ctgtgaagct taagcctggg aaacgtccag cagtgaaaaa acttgaggac | 1380 |
| ttgttacagg gtgggacgg acctttggac ttgagtacac ggaaacgtcc aagacaataa | 1440 |
| gtgttccata tccgtgttta cttaaggtga cgtcaatatt tgtgtgacag tgcaatgtaa | 1500 |
| taaaaatatg ttaactgttc actggttttt attgcttttt gggcggggac tcaggtatat | 1560 |
| aagtagaagc agacctgtgt ggttagctca taggagctgg cttttcatcca tggaggtttg | 1620 |
| ggccattttg gaagaccta ggaagactag gcaactgtta gagaacgctt cggacggagt | 1680 |
| ctccggtttt tggagattct ggttcgctag tgaattagct agggtagttt ttaggataaa | 1740 |
| acaggactat aaacaagaat ttgaaaagtt gttggtagat tgcccaggac tttttgaagc | 1800 |
| tcttaatttg ggccatcagg ttcactttaa agaaaaagtt ttatcagttt tagacttttc | 1860 |
| aaccccaggt agaactgctg ctgctgtggc ttttcttact tttatattag ataaatggat | 1920 |
| cccgcagact catttcagca ggggatacgt tttggatttc atagccacag cattgtggag | 1980 |
| aacatggaag gttcgcaaga tgaggacaat cttaggttac tggccagtgc agcctttggg | 2040 |
| tgtagcggga atcctgaggc atccaccggt catgccagcg gttctggagg aggaacagca | 2100 |
| agaggacaac ccgagagccg gcctggaccc tccagtggag gaggcggagt agctgacttg | 2160 |

```
tctcctgaac tgcaacgggt gcttactgga tctacgtcca ctggacggga taggggcgtt    2220
aagagggaga gggcatctag tggtactgat gctagatctg agttggcttt aagtttaatg    2280
agtcgcagac gtcctgaaac catttggtgg catgaggttc agaaagaggg aagggatgaa    2340
gtttctgtat tgcaggagaa atattcactg gaacaggtga aaacatgttg gttggagcct    2400
gaggatgatt gggaggtggc cattaaaaat tatgccaaga tagctttgag gcctgataaa    2460
cagtataaga ttactagacg gattaatatc cggaatgctt gttacatatc tggaaatggg    2520
gctgaggtgg taatagatac tcaagacaag gcagttatta gatgctgcat gatggatatg    2580
tggcctgggg tagtcggtat ggaagcagta acttttgtaa atgttaagtt taggggagat    2640
ggttataatg gaatagtgtt tatggccaat accaaactta tattgcatgg ttgtagcttt    2700
tttggtttca acaatacctg tgtagatgcc tggggacagg ttagtgtacg ggatgtagt    2760 ttctatgcgt gttggattgc cacagctggc agaaccaaga gtcaattgtc tctgaagaaa    2820
tgcatatttc aaagatgtaa cctgggcatt ctgaatgaag gcgaagcaag ggtccgccac    2880
tgcgcttcta cagatactgg atgttttatt ttgattaagg gaaatgccag cgtaaagcat    2940
aacatgattt gcggtgcttc cgatgagagg cctatcaaa tgctcacttg tgctggtggg    3000
cattgtaata tgctggctac tgtgcatatt gtttcccatc aacgcaaaaa atggcctgtt    3060
tttgatcaca atgtgatgac gaagtgtacc atgcatgcag gtgggcgtag aggaatgttt    3120
atgccttacc agtgtaacat gaatcatgtg aaagtgttgt tggaaccaga tgccttttcc    3180
agaatgagcc taacaggaat ttttgacatg aacatgcaaa tctggaagat cctgaggtat    3240
gatgatacga gatcgagggt acgcgcatgc gaatgcggag gcaagcatgc caggttccag    3300
ccggtgtgtg tagatgtgac tgaagatctc agaccggatc atttggttat tgcccgcact    3360
ggagcagagt tcggatccag tggagaagaa actgactaag gtgagtattg ggaaaacttt    3420
ggggtgggat tttcagatgg acagattgag taaaaatttg ttttttctgt cttgcagctg    3480
tcatgagtgg aaacgcttct tttaaggggg gagtcttcag cccttatctg acagggcgtc    3540
tcccatcctg ggcaggagtt cgtcagaatg ttatgggatc tactgtggat ggaagacccg    3600
tccaacccgc caattcttca acgctgacct atgctacttt aagttcttca cctttggacg    3660
cagctgcagc tgccgccgcc gcttctgttg ccgctaacac tgtgcttgga atgggttact    3720
atggaagcat catggctaat tccacttcct ctaataaccc ttctaccctg actcaggaca    3780
agttacttgt ccttttggcc cagctggagg ctttgaccca acgtctgggt gaactttctc    3840
agcaggtggt cgagttgcga gtacaaactg agtctgctgt cggcacggca aagtctaaat    3900
aaaaaaatcc cagaatcaat gaataaataa acaagcttgt tgttgattta aaatcaagtg    3960
tttttatttc attttttcgcg cacggtatgc cctagaccac cgatctctat cattgagaac    4020
tcggtggatt ttttccagga tcctatagag gtgggattga atgtttagat acatgggcat    4080
taggccgtct ttggggtgga gatagctcca ttgaagggat tcatgctccg ggtagtgtt    4140 gtaaatcacc cagtcataac aaggtcgcag tgcatggtgt tgcacaatat cttttagaag    4200
taggctgatt gccacagata agcccttggt gtaggtgttt acaaaccggt tgagctggga    4260
tgggtgcatt cggggtgaaa ttatgtgcat tttggattgg atttttaagt tggcaatatt    4320
gccgccaaga tcccgtcttg ggttcatgtt atgaaggacc accaagacgg tgtatccggt    4380
acatttagga aatttatcgt gcagcttgga tggaaaagcg tggaaaaatt tggagacacc    4440
cttgtgtcct ccaagatttt ccatgcactc atccatgata atagcaatgg ggccgtgggc    4500
```

```
agcggcgcgg gcaaacacgt tccgtgggtc tgacacatca tagttatgtt cctgagttaa    4560
atcatcataa gccattttaa tgaatttggg gcggagagta ccagattggg gtatgaatgt    4620
tccttcgggc cccggagcat agttcccctc acagatttgc atttcccaag ctttcagttc    4680
cgagggtgga atcatgtcca cctgggggc tatgaaaaac accgtttctg ggcgggggt      4740 gattaattgt gatgatagca aatttctgag caattgagat ttgccacatc cggtggggcc    4800
ataaatgatt ccgattacgg gttgcaggtg gtagtttagg gaacggcaac tgccgtcttc    4860
tcgaagcaag ggggccacct cgttcatcat ttcccttaca tgcatatttt cccgcaccaa    4920
atccattagg aggcgctctc ctcctagtga tagaagttct tgtagtgagg aaaagttttt    4980
cagcggtttc agaccgtcag ccatgggcat tttggagaga gtttgctgca aaagttctag    5040
tctgttccac agttcagtga tgtgttctat ggcatctcga tccagcagac ctcctcgttt    5100
cgcgggtttg gacggctcct ggaatagggt atgagacgat gggcgtccag cgctgccagg    5160
gttcggtcct tccagggtct cagtgttcga gtcagggttg tttccgtcac agtgaagggg    5220
tgtgcgcctc cttgggcgct tgccagggtg cgcttcagac tcatcctgct ggtcgaaaac    5280
ttctgtcgct tggcgccctg tatgtcggcc aagtagcagt ttaccatgag ttcgtagttg    5340
agcgcctcgg ctgcgtggcc tttggcgcgg agcttacctt tggaagtttt cttgcatacc    5400
gggcagtata ggcatttcag cgcatacaac ttgggcgcaa ggaaaacgga ttctggggag    5460
tatgcatctg cgccgcagga ggcgcaaaca gtttcacatt ccaccagcca ggttaaatcc    5520
ggttcattgg ggtcaaaaac aagttttccg ccatattttt tgatgcgttt cttacctttg    5580
gtctccatga gttcgtgtcc tcgttgagtg acaaacaggc tgtccgtgtc cccgtagact    5640
gattttacag gcctcttctc cagtggagtg cctcggtctt cttcgtacag gaactctgac    5700
cactctgata caaggcgcg cgtccaggcc agcacaaagg aggctatgtg ggaggggtag     5760
cgatcgttgt caaccagggg gtccaccttt tccaaagtat gcaaacacat gtcaccctct    5820
tcaacatcca ggaatgtgat tggccttgtag gtgtatttca cgtgacctgg ggtccccgct    5880 ggggggggtat aaaaggggc ggttctttgc tcttcctcac tgtcttccgg atcgctgtcc     5940
aggaacgtca gctgttgggg taggtattcc ctctcgaagg cgggcatgac ctctgcactc    6000
aggttgtcag tttctaagaa cgaggaggat ttgatattga cagtgccggt tgagatgcct    6060
ttcatgaggt tttcgtccat ttggtcagaa aacacaattt ttttattgtc aagtttggtg    6120
gcaaatgatc catacagggc gttggataaa agtttggcaa tggatcgcat ggtttggttc    6180
ttttccttgt ccgcgcgctc tttggcgcg atgttgagtt ggacatactc gcgtgccagg      6240
cacttccatt cggggaagat agttgttaat tcatctggca cgattctcac ttgccaccct    6300
cgattatgca aggtaattaa atccacactg gtggccacct cgcctcgaag gggttcattg    6360
gtccaacaga gcctacctcc tttcctagaa cagaaagggg gaagtgggtc tagcataagt    6420
tcatcgggag ggtctgcatc catggtaaag attcccggaa gtaaatcctt atcaaaatag    6480
ctgatgggag tggggtcatc taaggccatt tgccattctc gagctgccag tgcgcgctca    6540
tatgggttaa ggggactgcc ccatggcatg ggatgggtga gtgcagaggc atacatgcca    6600
cagatgtcat agacgtagat gggatcctca aagatgccta tgtaggttgg atagcatcgc    6660
ccccctctga tacttgctcg cacatagtca tatagttcat gtgatggcgc tagcagcccc    6720
ggacccaagt tggtgcgatt gggtttttct gttctgtaga cgatctggcg aaagatggcg    6780
tgagaattgg aagagatggt gggtcttgaa aaaatgttga aatgggcatg aggtagacct    6840
acagagtctc tgacaaagtg ggcataagat tcttgaagct tggttaccag ttcggcggtg    6900
```

```
acaagtacgt ctagggcgca gtagtcaagt gtttcttgaa tgatgtcata acctggttgg    6960
ttttcttttt cccacagttc gcggttgaga aggtattctt cgcgatcctt ccagtactct    7020
tctagcggaa acccgtcttt gtctgcacgg taagatccta gcatgtagaa ctgattaact    7080
gccttgtaag ggcagcagcc cttctctacg ggtagagagt atgcttgagc agcttttcgt    7140
agcgaagcgt gagtaagggc aaaggtgtct ctgaccatga ctttgagaaa ttggtatttg    7200
aagtcgatgt cgtcacaggc tccctgttcc cagagttgga agtctacccg tttcttgtag    7260
gcggggttgg gcaaagcgaa agtaacatca ttgaagagaa tcttaccggc tctgggcata    7320
aaattgcgag tgatgcgaaa aggctgtggt acttccgctc gattgttgat cacctgggca    7380
gctaggacga tctcgtcgaa accgttgatg ttgtgtccta cgatgtataa ttctatgaaa    7440
cgcggcgtgc ctctgacgtg aggtagctta ctgagctcat caaaggttag gtctgtgggg    7500
tcagataagg cgtagtgttc gagagcccat tcgtgcaggt gaggatttgc atgtaggaat    7560
gatgaccaaa gatctaccgc cagtgctgtt tgtaactggt cccgatactg acgaaaatgc    7620
cggccaattg ccattttttc tggagtgaca cagtagaagg ttctggggtc ttgttgccat    7680
cgatcccact tgagtttaat ggctagatcg tgggccatgt tgacgagacg ctcttctcct    7740
gagagtttca tgaccagcat gaaaggaact agttgtttgc caaggatcc catccaggtg    7800 taagtttcca catcgtaggt caggaagagt ctttctgtgc gaggatgaga gccgatcggg    7860
aagaactgga tttcctgcca ccagttggag gattggctgt tgatgtgatg aagtagaag    7920 tttctgcggc cgccgagca ttcgtgtttg tgcttgtaca gacggccgca gtagtcgcag    7980
cgttgcacgg gttgtatctc gtgaatgagt tgtacctggc ttcccttgac gagaaatttc    8040
agtgggaagc cgaggcctgg cgattgtatc tcgtgctctt ctatattcgc tgtatcggcc    8100
tgttcatctt ctgtttcgat ggtggtcatg ctgacgagcc ccgcgggag gcaagtccag    8160 acctcggcgc gggaggggcg gagctgaagg acgagagcgc gcaggctgga gctgtccaga    8220
gtcctgagac gctgcggact caggttagta ggtagggaca gaagattaac ttgcatgatc    8280
ttttccaggg cgtgcgggag gttcagatgg tacttgattt ccacaggttc gtttgtagag    8340
acgtcaatgg cttgcagggt tccgtgtcct ttgggcgcca ctaccgtacc tttgttttt    8400 cttttgatcg gtggtggctc tcttgcttct tgcatgctca gaagcggtga cggggacgcg    8460
cgccgggcgg cagcggttgt tccggacccg agggcatggc tggtagtggc acgtcggcgc    8520
cgcgcacggg caggttctgg tactgcgctc tgagaagact tgcgtgcgcc accacgcgtc    8580
gattgacgtc ttgtatctga cgtctctggg tgaaagctac cggccccgtg agcttgaacc    8640
tgaaagagag ttcaacagaa tcaatttcgg tatcgttaac ggcagcttgt ctcagtattt    8700
cttgtacgtc accagagttg tcctggtagg cgatctccgc catgaactgc tcgatttctt    8760
cctcctgaag atctccgcga cccgctcttt cgacggtggc cgcgaggtca ttggagatac    8820
ggcccatgag ttgggagaat gcattcatgc ccgcctcgtt ccagacgcgg ctgtaaacca    8880 cggcccctc ggagtctctt gcgcgcatca ccacctgagc gaggttaagc tccacgtgtc    8940
tggtgaagac cgcatagttg cataggcgct gaaaaggta gttgagtgtg gtggcaatgt    9000
gttcggcgac gaagaaatac atgatccatc gtctcagcgg catttcgcta acatcgccca    9060
gagcttccaa gcgctccatg gcctcgtaga agtccacggc aaaattaaaa aactgggagt    9120
ttcgcgcgga cacggtcaat tcctcctcga gaagacggat gagttcggct atggtggccc    9180
gtacttcgcg ttcgaaggct cccgggatct cttcttcctc ttctatctct tcttccacta    9240
```

| | |
|---|---|
| acatctcttc ttcgtcttca ggcggggcg aggggggcac gcggcgacgt cgacggcgca | 9300 |
| cgggcaaacg gtcgatgaat cgttcaatga cctctccgcg gcggcggcgc atggtttcag | 9360 |
| tgacggcgcg gccgttctcg cgcggtcgca gagtaaaaac accgccgcgc atctccttaa | 9420 |
| agtggtgact gggaggttct ccgtttggga gggagagggc gctgattata cattttatta | 9480 |
| attggcccgt agggactgca cgcagagatc tgatcgtgtc aagatccacg ggatctgaaa | 9540 |
| acctttcgac gaaagcgtct aaccagtcac agtcacaagg taggctgagt acggcttctt | 9600 |
| gtgggcgggg gtggttatgt gttcggtctg ggtcttctgt ttcttcttca tctcgggaag | 9660 |
| gtgagacgat gctgctggtg atgaaattaa agtaggcagt tctaagacgg cggatggtgg | 9720 |
| cgaggagcac caggtctttg ggtccggctt gctggatacg caggcgattg gccattcccc | 9780 |
| aagcattatc ctgacatcta gcaagatctt tgtagtagtc ttgcatgagc cgttctacgg | 9840 |
| gcacttcttc ctcacccgtt ctgccatgca tacgtgtgag tccaaatccg cgcattggtt | 9900 |
| gtaccagtgc caagtcagct acgactcttt cggcgaggat ggcttgctgt acttgggtaa | 9960 |
| gggtggcttg aaagtcatca aaatccacaa agcggtggta agctcctgta ttaatggtgt | 10020 |
| aagcacagtt ggccatgact gaccagttaa ctgtctggtg accagggcgc acgagctcgg | 10080 |
| tgtatttaag gcgcgaatag gcgcgggtgt caaagatgta atcgttgcag gtgcgcacca | 10140 |
| gatactggta ccctataaga aaatgcggcg gtggttggcg gtagagaggc catcgttctg | 10200 |
| tagctggagc gccaggggcg aggtcttcca acataaggcg gtgatagccg tagatgtacc | 10260 |
| tggacatcca ggtgattcct gcggcggtag tagaagcccg aggaaactcg cgtacgcggt | 10320 |
| tccaaatgtt gcgtagcggc atgaagtagt tcattgtagg cacggtttga ccagtgaggc | 10380 |
| gcgcgcagtc attgatgctc tatagacacg gagaaaatga aagcgttcag cgactcgact | 10440 |
| ccgtagcctg gaggaacgtg aacgggttgg gtcgcggtgt accccggttc gagacttgta | 10500 |
| ctcgagccgg ccggagccgc ggctaacgtg gtattggcac tcccgtctcg acccagccta | 10560 |
| caaaaatcca ggtacggaa tcgagtcgtt ttgctggttt ccgaatggca gggaagtgag | 10620 |
| tcctattttt ttttttttgc cgctcagatg catcccgtgc tgcgacagat gcgcccccaa | 10680 |
| caacagcccc cctcgcagca gcagcagcag caatcacaaa aggctgtccc tgcaactact | 10740 |
| gcaactgccg ccgtgagcgg tgcgggacag cccgcctatg atctggactt ggaagagggc | 10800 |
| gaaggactgg cacgtctagg tgcgccttca cccgagcggc atccgcgagt tcaactgaaa | 10860 |
| aaagattctc gcgaggcgta tgtgccccaa cagaacctat ttagagacag aagcggcgag | 10920 |
| gagccggagg agatgcgagc ttcccgcttt aacgcgggtc gtgagctgcg tcacggtttg | 10980 |
| gaccgaagac gagtgttgcg ggacgaggat ttcgaagttg atgaaatgac agggatcagt | 11040 |
| cctgccaggg cacacgtggc tgcagccaac cttgtatcgg cttacgagca gacagtaaag | 11100 |
| gaagagcgta acttccaaaa gtcttttaat aatcatgtgc gaaccctgat tgcccgcgaa | 11160 |
| gaagttaccc ttggtttgat gcatttgtgg gatttgatgg aagctatcat tcagaaccct | 11220 |
| actagcaaac ctctgaccgc ccagctgttt ctggtggtgc aacacagcag agacaatgag | 11280 |
| gctttcagag aggcgctgct gaacatcacc gaacccgagg ggagatggtt gtatgatctt | 11340 |
| atcaacattc tacagagtat catagtgcag gagcggagcc tgggcctggc cgagaaggtg | 11400 |
| gctgccatca attactcggt tttgagcttg ggaaaatatt acgctcgcaa aatctacaag | 11460 |
| actccatacg ttcccataga caaggaggtg aagatagatg ggttctacat gcgcatgacg | 11520 |
| ctcaaggtct tgaccctgag cgatgatctt ggggtgtatc gcaatgacag aatgcatcgc | 11580 |
| gcggttagcg ccagcaggag gcgcgagtta agcgacaggg aactgatgca cagtttgcaa | 11640 |

```
agagctctga ctggagctgg aaccgagggt gagaattact tcgacatggg agctgacttg   11700
cagtggcagc ctagtcgcag ggctctgagc gccgcgacgg caggatgtga gcttccttac   11760
atagaagagg cggatgaagg cgaggaggaa gagggcgagt acttggaaga ctgatggcac   11820
aacccgtgtt ttttgctaga tggaacagca agcaccggat cccgcaatgc gggcggcgct   11880
gcagagccag ccgtccggca ttaactcctc ggacgattgg acccaggcca tgcaacgtat   11940 catgcgttg acgactcgca accccgaagc ctttagacag caaccccagg ccaaccgtct   12000
atcggccatc atggaagctg tagtgccttc ccgctctaat cccactcatg agaaggtcct   12060
ggccatcgtg aacgcgttgg tggagaacaa agctattcgt ccagatgagg ccggactggt   12120
atacaacgct ctcttagaac gcgtggctcg ctacaacagt agcaatgtgc aaaccaattt   12180
ggaccgtatg ataacagatg tacgcgaagc cgtgtctcag cgcgaaaggt tccagcgtga   12240
tgccaacctg ggttcgctgg tggcgttaaa tgctttcttg agtactcagc ctgctaatgt   12300
gccgcgtggt caacaggatt atactaactt tttaagtgct ttgagactga tggtatcaga   12360
agtacctcag agcgaagtgt atcagtccgg tcctgattac ttctttcaga ctagcagaca   12420
gggcttgcag acggtaaatc tgagccaagc ttttaaaaac cttaaaggtt tgtgggagt   12480 gcatgccccg gtaggagaaa gagcaaccgt gtctagcttg ttaactccga actcccgcct   12540
attattactg ttggtagctc cttcaccga cagcggtagc atcgaccgta attcctattt   12600
gggttaccta ctaaacctgt atcgcgaagc catagggcaa agtcaggtgg acgagcagac   12660
ctatcaagaa attacccaag tcagtcgcgc tttgggacag gaagacactg gcagtttgga   12720
agccactctg aacttcttgc ttaccaatcg gtctcaaaag atccctcctc aatatgctct   12780
tactgcggag gaggagagga tccttagata tgtgcagcag agcgtgggat tgtttctgat   12840
gcaagagggg gcaactccga ctgcagcact ggacatgaca gcgcgaaata tggagcccag   12900
catgtatgcc agtaaccgac ctttcattaa caaactgctg gactacttgc acagagctgc   12960
cgctatgaac tctgattatt tcaccaatgc catcttaaac ccgcactggc tgcccccacc   13020
tggtttctac acgggcgaat atgacatgcc cgaccctaat gacggatttc tgtgggacga   13080
cgtggacagc gatgtttttt cacctctttc tgatcatcgc acgtggaaaa aggaaggcgg   13140
cgatagaatg cattcttctg catcgctgtc cggggtcatg ggtgctaccg cggctgagcc   13200
cgagtctgca gtcctttc ctagtctacc ttttctcta cacagtgtac gtagcagcga   13260
agtgggtaga ataagtcgcc cgagtttaat gggcgaagag gagtatctaa acgattcctt   13320
gctcagaccg gcaagagaaa aaaatttccc aaacaatgga atagaaagtt tggtggataa   13380
aatgagtaga tggaagactt atgctcagga tcacagagac gagcctggga tcatggggat   13440
tacaagtaga gcgagccgta gacgccgcg ccatgacaga cagaggggtc ttgtgtggga   13500
cgatgaggat tcggccgatg atagcagcgt gctggacttg ggtgggagag aagggcaa   13560 cccgtttgct catttgcgcc ctcgcttggg tggtatgttg taaaaaaaaa taaaaaaaaa   13620
actcaccaag gccatggcga cgagcgtacg ttcgttcttc tttattatct gtgtctagta   13680
taatgaggcg agtcgtgcta ggcggagcgg tggtgtatcc ggagggtcct cctccttcgt   13740
acgagagcgt gatgcagcag cagcaggcga cggcggtgat gcaatcccca ctggaggctc   13800 ccttttgtgcc tccgcgatac ctggcaccta cggagggcag aaacagcatt cgttattcgg   13860
aactggcacc tcagtacgat accaccaggt tgtatctggt ggacaacaag tcggcggaca   13920
ttgcttctct gaactatcag aatgaccaca gcaacttctt gaccacggtg gtgcaaaaca   13980
```

```
atgactttac ccctacggaa gccagcaccc agaccattaa ctttgatgaa cgatcgcggt    14040
ggggcggtca gctaaagacc atcatgcata ctaacatgcc aaacgtgaac gagtatatgt    14100
ttagtaacaa gttcaaagcg cgtgtgatgg tgtccagaaa acctcccgac ggtgctgcag    14160
ttggggatac ttatgatcac aagcaggata ttttgaaata tgagtggttc gagtttactt    14220
tgccagaagg caacttttca gttactatga ctattgattt tgatgaacaa tgccatcatag    14280 ataattactt gaaagtgggt agacagaatg gagtgcttga aagtgacatt ggtgttaagt    14340
tcgacaccag gaacttcaag ctgggatggg atcccgaaac caagttgatc atgcctggag    14400
tgtatacgta tgaagccttc catcctgaca ttgtcttact gcctggctgc ggagtggatt    14460
ttaccgagag tcgtttgagc aaccttcttg gtatcagaaa aaaacagcca tttcaagagg    14520
gttttaagat tttgtatgaa gatttagaag gtggtaatat tccggccctc ttggatgtag    14580
atgcctatga gaacagtaag aaagaacaaa aagccaaaat agaagctgct acagctgctg    14640
cagaagctaa ggcaaacata gttgccagcg actctacaag ggttgctaac gctggagagg    14700
tcagaggaga caattttgcg ccaacacctg ttccgactgc agaatcatta ttggccgatg    14760
tgtctgaagg aacggacgtg aaactcacta ttcaacctgt agaaaaagat agtaagaata    14820
gaagctataa tgtgttggaa gacaaaatca acacagccta tcgcagttgg tatctttcgt    14880
acaattatgg cgatcccgaa aaaggagtgc gttcctggac attgctcacc acctcagatg    14940
tcacctgcgg agcagagcag gtctactggt cgcttccaga catgatgaag gatcctgtca    15000
ctttccgctc cactagacaa gtcagtaact accctgtggt gggtgcagag cttatgcccg    15060
tcttctcaaa gagcttctac aacgaacaag ctgtgtactc ccagcagctc cgccagtcca    15120
cctcgcttac gcacgtcttc aaccgctttc ctgagaacca gattttaatc cgtccgccgg    15180
cgcccaccat taccaccgtc agtgaaaacg ttcctgctct cacagatcac gggaccctgc    15240
cgttgcgcag cagtatccgg ggagtccaac gtgtgaccgt tactgacgcc agacgccgca    15300
cctgtcccta cgtgtacaag gcactgggca tagtcgcacc cgcgcgtcctt tcaagccgca    15360 ctttctaaaa aaaaaaaaaa tgtccattct tatctcgccc agtaataaca ccggttgggg    15420
tctgcgcgct ccaagcaaga tgtacggagg cgcacgcaaa cgttctaccc aacatcctgt    15480
ccgtgttcgc ggacattttc gcgctccatg gggcgccctc aagggccgca ctcgcgttcg    15540
aaccaccgtc gatgatgtaa tcgatcaggt ggttgccgac gcccgtaatt atactcctac    15600
tgcgcctaca tctactgtgg atgcagttat tgacagtgta gtggctgacg ctcgcaacta    15660
tgctcgacgt aagagccggc gaaggcgcat tgccagacgc caccgagcta ccactgccat    15720
gcgagccgca agagctctgc tacgaagagc tagacgcgtg gggcgaagag ccatgcttag    15780
ggcggccaga cgtgcagctt cgggcgccag cgccggcagg tcccgcaggc aagcagccgc    15840
tttcgcagcg gcgactattg ccgacatggc ccaatcgcga agaggcaatg tatactgggt    15900
gcgtgacgct gccaccggtc aacgtgtacc cgtgcgcacc cgtcccccte gcacttagaa    15960 gatactgagc agtctccgat gttgtgtccc agcggcgagg atgtccaagc gcaaatacaa    16020
ggaagaaatg ctgcaggtta tcgcacctga agtctacggc caaccgttga aggatgaaaa    16080
aaaaccccgc aaaatcaagc gggttaaaaa ggacaaaaaa gaagaggaag atggcgatga    16140
tgggctggcg gagtttgtgc gcgagtttgc cccacggcga cgcgtgcaat ggcgtgggcg    16200
caaagttcga catgtgttga gacctggaac ttcggtggtc tttacacccg gcgagcgttc    16260
aagcgctact tttaagcgtt cctatgatga ggtgtacggg gatgatgata ttcttgagca    16320
ggcggctgac cgattaggcg agtttgctta tggcaagcgt agtagaataa cttccaagga    16380
```

```
tgagacagtg tcgataccct tggatcatgg aaatcccacc cctagtctta aaccggtcac   16440
tttgcagcaa gtgttacccg taactccgcg aacaggtgtt aaacgcgaag gtgaagattt   16500
gtatcccact atgcaactga tggtacccaa acgccagaag ttggaggacg ttttggagaa   16560
agtaaaagtg gatccagata ttcaacctga ggttaaagtg agacccatta agcaggtagc   16620
gcctggtctg ggggtacaaa ctgtagacat taagattccc actgaaagta tggaagtgca   16680
aactgaaccc gcaaagccta ctgccacctc cactgaagtg caaacggatc catggatgcc   16740
catgcctatt acaactgacg ccgccggtcc cactcgaaga tcccgacgaa agtacggtcc   16800
agcaagtctg ttgatgccca attatgttgt acacccatct attattccta ctcctggtta   16860
ccgaggcact cgctactatc gcagccgaaa cagtacctcc cgccgtcgcc gcaagacacc   16920
tgcaaatcgc agtcgtcgcc gtagacgcac aagcaaaccg actcccggcg ccctggtgcg   16980
gcaagtgtac cgcaatggta gtgcggaacc tttgacactg ccgcgtgcgc gttaccatcc   17040
gagtatcatc acttaatcaa tgttgccgct gcctccttgc agatatggcc ctcacttgtc   17100
gccttcgcgt tcccatcact ggttaccgag gaagaaactc gcgccgtaga agagggatgt   17160
tgggacgcgg aatgcgacgc tacaggcgac ggcgtgctat ccgcaagcaa ttgcggggtg   17220
gttttttacc agccttaatt ccaattatcg ctgctgcaat tggcgcgata ccaggcatag   17280
cttccgtggc ggttcaggcc tcgcaacgac attgacattg gaaaaaaacg tataaataaa   17340 aaaaaaaaa tacaatggac tctgacactc ctggtcctgt gactatgttt tcttagagat   17400
ggaagacatc aattttttcat ccttggctcc gcgacacggc acgaagccgt acatgggcac   17460
ctggagcgac atcggcacga gccaactgaa cgggggcgcc ttcaattgga gcagtatctg   17520
gagcgggctt aaaaattttg gctcaaccat aaaaacatac gggaacaaag cttggaacag   17580
cagtacagga caggcgctta gaaataaact taaagaccag aacttccaac aaaaagtagt   17640
cgatgggata gcttccggca tcaatggagt ggtagatttg gctaaccagg ctgtgcagaa   17700
aaagataaac agtcgtttgg acccgccgcc agcaacccca ggtgaaatgc aagtggagga   17760
agaaattcct ccgccagaaa aacgaggcga caagcgtccg cgtcccgatt tggaagagac   17820
gctggtgacg cgcgtagatg aaccgccttc ttatgaggaa gcaacgaagc ttggaatgcc   17880
caccactaga ccgatagccc caatggccac cggggtgatg aaaccttctc agttgcatcg   17940
acccgtcacc ttgatttgc cccctccccc tgctgctact gctgtacccg cttctaagcc   18000
tgtcgctgcc ccgaaaccag tcgccgtagc caggtcacgt cccggggggcg ctcctcgtcc   18060 aaatgcgcac tggcaaaata ctctgaacag catcgtgggt ctaggcgtgc aaagtgtaaa   18120
acgccgtcgc tgcttttaat taaatatgga gtagcgctta acttgcctat ctgtgtatat   18180
gtgtcattac acgccgtcac agcagcagag gaaaaaagga agaggtcgtg cgtcgacgct   18240
gagttacttt caagatggcc acccccatcga tgctgcccca atgggcatac atgcacatcg   18300
ccggacagga tgcttcggag tacctgagtc cgggtctggt gcagttcgcc cgcgccacag   18360
acacctactt caatctggga aataagttta gaaatcccac cgtagcgccg acccacgatg   18420
tgaccaccga ccgtagccag cggctcatgt tgcgcttcgt gcccgttgac cgggaggaca   18480
atacatactc ttacaaagtg cggtacaccc tggccgtggg cgacaacaga gtgctggata   18540
tggccagcac gttctttgac attaggggtg tgttggacag aggtcccagt ttcaaaccct   18600
attctggtac ggcttacaac tccctggctc ctaaaggcgc tccaaataca tctcagtgga   18660
ttgcagaagg tgtaaaaaat acaactggtg aggaacacgt aacagaagag gaaaccaata   18720
```

```
ctactactta cacttttggc aatgctcctg taaaagctga agctgaaatt acaaaagaag  18780
gactcccagt aggtttggaa gtttcagatg aagaaagtaa accgatttat gctgataaaa  18840
catatcagcc agaacctcag ctgggagatg aaacttggac tgaccttgat ggaaaaaccg  18900
aaaagtatgg aggcagggct ctcaaacccg atactaagat gaaaccatgc tacgggtcct  18960
ttgccaaacc tactaatgtg aaaggcggtc aggcaaaaca aaaacaacg gagcagccaa   19020
atcagaaagt cgaatatgat atcgacatgg agttttttga tgcggcatcg cagaaaacaa  19080
acttaagtcc taaaattgtc atgtatgcag aaaatgtaaa tttggaaact ccagacactc  19140
atgtagtgta caaacctgga acagaagaca caagttccga agctaatttg ggacaacaat  19200
ctatgcccaa cagacccaac tacattggct tcagagataa cttttattgga cttatgtact  19260
ataacagtac tggtaacatg ggggtgctgg ctggtcaagc gtctcagtta aatgcagtgg  19320
ttgacttgca ggacagaaac acagaacttt cttaccaact cttgcttgac tctctgggcg  19380
acagaaccag atactttagc atgtggaatc aggctgtgga cagttatgat cctgatgtac  19440
gtgttattga aaatcatggt gtggaagatg aacttcccaa ctactgtttt ccactggacg  19500
gcataggtgt tccaacaacc agttacaaat caatagttcc aaatggagac aatgcgccta  19560
attggaagga acctgaagta aatgaacaa gtgagatcgg acagggtaat ttgtttgcca  19620
tggaaattaa ccttcaagcc aatctatggc gaagtttcct ttattccaat gtggctctat  19680
atctcccaga ctcgtacaaa tacacccgt ccaatgtcac tcttccagaa aacaaaaaca  19740
cctacgacta catgaacggg cgggtggtgc cgccatctct agtagacacc tatgtgaaca  19800
ttggtgccag gtggtctctg gatgccatgg acaatgtcaa cccattcaac caccaccgta  19860
acgctggctt gcgttaccga tccatgcttc tgggtaacgg acgttatgtg cctttccaca  19920
tacaagtgcc tcaaaaattc ttcgctgtta aaaacctgct gcttctccca ggctcctaca  19980
cttatgagtg aactttagg aaggatgtga acatggttct acagagttcc ctcggtaacg  20040
acctgcgggt agatggcgcc agcatcagtt tcacgagcat caacctctat gctactttt   20100
tccccatggc tcacaacacc gcttccaccc ttgaagccat gctgcggaat gacaccaatg  20160
atcagtcatt caacgactac ctatctgcag ctaacatgct ctaccccatt cctgccaatg  20220
caaccaatat tcccatttcc attccttctc gcaactgggc ggctttcaga ggctggtcat  20280
ttaccagact gaaaaccaaa gaaactccct ctttggggtc tggatttgac ccctactttg  20340
tctattctgg ttctattccc tacctggatg gtaccttcta cctgaaccac acttttaaga  20400
aggtttccat catgtttgac tcttcagtga gctggcctgg aaatgacagg ttactatctc  20460
ctaacgaatt tgaaataaag cgcactgtgg atggcgaagg ctacaacgta gcccaatgca  20520
acatgaccaa agactggttc ttggtacaga tgctcgccaa ctacaacatc ggctatcagg  20580
gcttctacat tccagaagga tacaaagatc gcatgtattc atttttcaga aacttccagc  20640
ccatgagcag gcaggtggtt gatgaggtca attacaaaga cttcaaggcc gtcgccatac  20700
cctaccaaca caacaactct ggctttgtgg gttacatggc tccgaccatg cgccaaggtc  20760
aaccctatcc cgctaactat ccctatccac tcattggaac aactgccgta aatagtgtta  20820
cgcagaaaaa gttcttgtgt gacagaacca tgtggcgcat accgtctccg agcaacttca  20880
tgtctatggg ggcccttaca gacttgggac agaatatgct ctatgccaac tcagctcatg  20940
ctctggacat gacctttgag gtggatccca tggatgagcc cacctgctt tatcttctct  21000
tcgaagtttt cgacgtggtc agagtgcatc agccacaccg cggcatcatc gaggcagtct  21060
acctgcgtac accgttctcg gccggtaacg ctaccacgta agaagcttct tgcttcttgc  21120
```

```
aaatagcagc tgcaaccatg gcctgcggat cccaaaacgg ctccagcgag caagagctca   21180
gagccattgt ccaagacctg ggttgcggac cctatttttt gggaacctac gataagcgct   21240
tcccggggtt catggccccc gataagctcg cctgtgccat tgtaaatacg gccggacgtg   21300
agacgggggg agagcactgg ttggcttccg gttggaaccc acgttctaac acctgctacc   21360
ttttttgatcc ttttggattc tcggatgatc gtctcaaaca gatttaccag tttgaatatg   21420
agggtctcct gcgccgcagc gctcttgcta ccaaggaccg ctgtattacg ctggaaaaat   21480
ctacccagac cgtgcagggt ccccgttctg ccgcctgcgg acttttctgc tgcatgttcc   21540
ttcacgcctt tgtgcactgg cctgaccgtc catggacggg aaaccccacc atgaaattgc   21600
taactggagt gccaaacaac atgcttcatt ctcctaaagt ccagcccacc ctgtgtgaca   21660
atcaaaaagc actctaccat tttcttaata cccattcgcc ttattttcgc tcccatcgta   21720
cacacatcga aagggccact gcgttcgacc gtatggatgt tcaataatga ctcatgtaaa   21780
caacgtgttc aataaacatc actttatttt tttacatgta tcaaggctct gcattactta   21840
tttatttaca agtcgaatgg gttctgacga gaatcagaat gacccgcagg cagtgatacg   21900
ttgcggaact gatacttggg ttgccacttg aattcgggaa tcaccaactt gggaaccggt   21960
atatcgggca ggatgtcact ccacagcttt ctggtcagct gcaaagctcc aagcaggtca   22020
ggagccgaaa tcttgaaatc acaattagga ccagtgcttt gagcgcgaga gttgcggtac   22080
accggattgc agcactgaaa caccatcagc gacggatgtc tcacgcttgc cagcacggtg   22140
ggatctgcaa tcatgcccac atccagatct tcagcattgg caatgctgaa cggggtcatc   22200
ttgcaggtct gcctacccat ggcgggcacc caattaggct tgtggttgca atcgcagtgc   22260
aggggggatca gtatcatctt ggcctgatcc tgtctgattc ctggatacac ggctctcatg   22320
aaagcatcat attgcttgaa agcctgctgg gctttactac cctcggtata aaacatcccg   22380
caggacctgc tcgaaaactg gttagctgca cagccggcat cattcacaca gcagcgggcg   22440
tcattgttag ctatttgcac cacacttctg ccccagcggt tttgggtgat tttggttcgc   22500
tcggattct cctttaaggc tcgttgtccg ttctcgctgg ccacatccat ctcgataatc   22560
tgctccttct gaatcataat attgccatgc aggcacttca gcttgccctc ataatcattg   22620
cagccatgag gccacaacgc acagcctgta cattcccaat tatggtgggc gatctgagaa   22680
aaagaatgta tcattccctg cagaaatctt cccatcatcg tgctcagtgt cttgtgacta   22740
gtgaaagtta actggatgcc tcggtgctcc tcgtttacgt actggtgaca gatgcgcttg   22800
tattgttcgt gttgctcagg cattagttta aaagaggttc taagttcgtt atccagcctg   22860
tacttctcca tcagcagaca catcacttcc atgcctttct cccaagcaga caccaggggc   22920
aagctaatcg gattcttaac agtgcaggca gcagctcctt tagccagagg gtcatcttta   22980
gcgatcttct caatgcttct tttgccatcc ttctcaacga tgcgcacggg cgggtagctg   23040
aaacccactg ctacaagttg cgcctcttct ctttcttctt cgctgtcttg actgatgtct   23100
tgcatgggga tatgtttggt cttccttggc ttcttttttgg ggggtatcgg aggaggagga   23160
ctgtcgctcc gttccggaga cagggaggat tgtgacgttt cgctcaccat taccaactga   23220
ctgtcggtag aagaacctga ccccacacgg cgacaggtgt ttctcttcgg gggcagaggt   23280
ggaggcgatt gcgaagggct gcggtccgac ctggaaggcg gatgactggc agaaccccctt   23340
ccgcgttcgg gggtgtgctc cctgtggcgg tcgcttaact gatttccttc gcggctggcc   23400
attgtgttct cctaggcaga gaaacaacag acatggaaac tcagccattg ctgtcaacat   23460
```

```
cgccacgagt gccatcacat ctcgtcctca gcgacgagga aaaggagcag agcttaagca    23520
ttccaccgcc cagtcctgcc accacctcta ccctagaaga taaggaggtc gacgcatctc    23580
atgacatgca gaataaaaaa gcgaaagagt ctgagacaga catcgagcaa gacccgggct    23640
atgtgacacc ggtggaacac gaggaagagt tgaaacgctt tctagagaga gaggatgaaa    23700
actgcccaaa acaacgagca gataactatc accaagatgc tggaaatagg gatcagaaca    23760
ccgactacct catagggctt gacggggaag acgcgctcct taaacatcta gcaagacagt    23820
cgctcatagt caaggatgca ttattggaca gaactgaagt gcccatcagt gtggaagagc    23880
tcagccgcgc ctacgagctt aacctctttt cacctcgtac tcccccaaa cgtcagccaa     23940 acggcacctg cgagccaaat cctcgcttaa acttttatcc agcttttgct gtgccagaag    24000
tactggctac ctatcacatc tttttttaaaa atcaaaaaat tccagtctcc tgccgcgcta   24060
atcgcacccg cgccgatgcc ctactcaatc tgggacctgg ttcacgctta cctgatatag    24120
cttccttgga agaggttcca aagatcttcg agggtctggg caataatgag actcgggccg    24180
caaatgctct gcaaaaggga gaaaatggca tggatgagca tcacagcgtt ctggtggaat    24240
tggaaggcga taatgccaga ctcgcagtac tcaagcgaag catcgaggtc acacacttcg    24300
catatcccgc tgtcaacctg cccccctaaag tcatgacggc ggtcatggac cagttactca   24360
ttaagcgcgc aagtcccctt tcagaagaca tgcatgaccc agatgcctgt gatgagggta    24420
aaccagtggt cagtgatgag cagctaaccc gatggctggg caccgactct cccagggatt    24480
tggaagagcg tcgcaagctt atgatggccg tggtgctggt taccgtagaa ctagagtgtc    24540
tccgacgttt ctttaccgat tcagaaacct tgcgcaaact cgaagagaat ctgcactaca    24600
cttttagaca cggctttgtg cggcaggcat gcaagatatc taacgtggaa ctcaccaacc    24660
tggtttccta catgggtatt ctgcatgaga atcgcctagg acaaagcgtg ctgcacagca    24720
ccctgaaggg ggaagcccgc cgtgattaca tccgcgattg tgtctatctg tacctgtgcc    24780
aaacgtggca aaccggcatg ggtgtatggc agcaatgttt agaagaacag aacttgaaag    24840
agcttgacaa gctcttacag aaatctctta aggttctgtg gacagggttc gacgagcgca    24900
ccgtcgcttc cgacctggca gacctcatct tcccagagcg tctcagggtt actttgcgaa    24960
acggattgcc tgactttatg agccagagca tgcttaacaa ttttcgctct ttcatcctgg    25020
aacgctccgg tatcctgccc gccacctgct gcgcactgcc ctccgacttt gtgcctctca    25080
cctaccgcga gtgcccccccg ccgctatgga gtcactgcta cctgttccgt ctggccaact   25140
atctctccta ccactcggat gtgatcgagg atgtgagcgg agacggcttg ctggagtgtc    25200
actgccgctg caatctgtgc acgccccacc ggtccctagc ttgcaacccc cagttgatga    25260
gcgaaaccca gataataggc acctttgaat tgcaaggccc cagcagccaa ggcgatgggt    25320
cttctcctgg gcaaagttta aaactgaccc cgggactgtg gacctccgcc tacttgcgca    25380
agtttgctcc ggaagattac caccccctatg aaatcaagtt ctatgaggac caatcacagc   25440
ctccaaaggc cgaactttcg gcctgcgtca tcacccaggg ggcaattctg gcccaattgc    25500
aagccatcca aaaatcccgc caagaatttc tactgaaaaa gggtaagggg gtctaccttg    25560
acccccagac cggcgaggaa ctcaacacaa ggttccctca ggatgtccca acgacgagaa    25620
aacaagaagt tgaaggtgca gccgccgccc ccagaagata tggaggaaga ttgggacagt    25680
caggcagagg aggcggagga ggacagtctg gaggacagtc tggaggaaga cagtttggag    25740
gaggaaaacg aggaggcaga ggaggtggaa gaagtaaccg ccgacaaaca gttatcctcg    25800
gctgcggaga caagcaacag cgctaccatc tccgctccga gtcgaggaac ccggcggcgt    25860
```

```
cccagcagta gatgggacga gaccggacgc ttcccgaacc caaccagcgc ttccaagacc    25920
ggtaagaagg atcggcaggg atacaagtcc tggcggggc ataagaatgc catcatctcc     25980
tgcttgcatg agtgcggggg caacatatcc ttcacgcggc gctacttgct attccaccat    26040
ggggtgaact ttccgcgcaa tgttttgcat tactaccgtc acctccacag ccctactat     26100 agccagcaaa tcccggcagt ctcgacagat aaagacagcg gcggcgacct ccaacagaaa    26160
accagcagcg gcagttagaa aatacacaac aagtgcagca acaggaggat taaagattac    26220
agccaacgag ccagcgcaaa cccgagagtt aagaaatcgg atctttccaa ccctgtatgc    26280
catcttccag cagagtcggg gtcaagagca ggaactgaaa ataaaaaacc gatctctgcg    26340
ttcgctcacc agaagttgtt tgtatcacaa gagcgaagat caacttcagc gcactctcga    26400
ggacgccgag gctctcttca acaagtactg cgcgctgact cttaaagagt aggcagcgac    26460
cgcgcttatt caaaaaggc gggaattaca tcatcctcga catgagtaaa gaaattccca     26520
cgccttacat gtggagttat caaccccaaa tgggattggc ggcaggcgcc tcccaggact    26580
actccacccg catgaattgg ctcagcgccg ggccttctat gatttctcga gttaatgata    26640
tacgcgccta ccgaaaccaa atacttttgg aacagtcagc tcttaccacc acgccccgcc    26700
aacaccttaa tcccagaaat tggcccgccg ccctagtgta ccaggaaagt cccgctccca    26760
ccactgtatt acttcctcga gacgcccagg ccgaagtcca aatgactaat gcaggtgcgc    26820
gttagctggc ggctccaccc tatgtcgtca caggcctcgg cataatataa aacgcctgat    26880
gatcagaggc cgaggtatcc agctcaacga cgagtcggtg agctctccgc ttggtctacg    26940
accagacgga atctttcaga ttgccggctg cgggagatct tccttcaccc ctcgtcaggc    27000
tgttctgact ttggaaagtt cgtcttcgca accccgctcg ggcggaatcg ggaccgttca    27060
atttgtggag gagtttactc cctctgtcta cttcaacccc ttctccggat ctcctgggca    27120
ttacccggac gagttcatac cgaacttcga cgcgattagc gagtcagtgg acggctacga    27180
ttgatgtctg gtgacgcggc tgagctatct cggctgcgac atctagacca ctgccgccgc    27240
tttcgctgct ttgcccggga actcattgag ttcatctact tcgaactccc caaggatcac    27300
cctcaaggtc cggcccacgg agtgcggatt tctatcgaag gcaaaataga ctctcgcctg    27360
caacgaattt tctcccagcg gcccgtgctg atcgagcgag accagggaaa caccacggtt    27420
tccatctact gcatttgtaa tcaccccgga ttgcatgaaa gcctttgctg tcttatgtgt    27480
actgagttta ataaaaactg aattaagact ctcctacgga ctgccgcttc ttcaacccgg    27540
attttacaac cagaagaacg aaacttttcc tgtcgtccag gactctgtta acttcacctt    27600
tcctactcac aaactagaag ctcaacgact acaccgcttt tccagaagca ttttccctac    27660
taatactact ttcaaaaccg gaggtgagct ccaaggtctt cctacagaaa acccttgggt    27720
ggaagcgggc cttgtagtgc taggaattct tgcgggtggg cttgtgatta ttctttgcta    27780
cctatacaca ccttgcttca ctttcttagt ggtgttgtgg tattggttta aaaaatgggg    27840
cccatactag tcttgcttgt tttactttcg cttttggaac cgggttctgc caattacgat    27900
ccatgtctag acttcgaccc agaaaactgc acacttactt ttgcacccga cacaagccgc    27960
atctgtggag ttcttattaa gtgcggatgg gaatgcaggt ccgttgaaat tacacacaat    28020
aacaaaacct ggaacaatac cttatccacc acatgggagc caggagttcc cgagtggtac    28080
actgtctctg tccgaggtcc tgacggtcc atccgcatta gtaacaacac tttcattttt     28140
tctgaaatgt gcgatctggc catgttcatg agcaaacagt attctctatg gcctcctagc    28200
```

```
aaggacaaca tcgtaacgtt ctccattgct tattgcttgt gcgcttgcct tcttactgct    28260
ttactgtgcg tatgcataca cctgcttgta accactcgca tcaaaaacgc caataacaaa    28320
gaaaaaatgc cttaacctct ttctgtttac agacatggct tctcttacat ctctcatatt    28380
tgtcagcatt gtcactgccg ctcatggaca acagtcgtc tctatccctc taggacataa     28440
ttacactctc ataggacccc caatcacttc agaggtcatc tgggccaaac tgggaagcgt    28500
tgattacttt gatataatct gcaacaaaac aaaaccaata atagtaactt gcaacataca    28560
aaatcttaca ttgattaatg ttagcaaagt ttacagcggt tactattatg gttatgacag    28620
atacagtagt caatatagaa attacttggt tcgtgttacc cagttgaaaa ccacgaaaat    28680
gccaaatatg gcaaagattc gatccgatga caattctcta gaaacttta catctcccac     28740 cacacccgac gaaaaaaaca tcccagattc aatgattgca attgttgcag cggtggcagt    28800
ggtgatggca ctaataataa tatgcatgct tttatatgct tgtcgctaca aaagtttca    28860 tcctaaaaaa caagatctcc tactaaggct taacatttaa tttctttta tacagccatg     28920 gtttccacta ccacattcct tatgcttact agtctcgcaa ctctgacttc tgctcgctca    28980
cacctcactg taactatagg ctcaaactgc acactaaaag gacctcaagg tggtcatgtc    29040
ttttggtgga gaatatatga caatggatgg tttacaaaac catgtgacca acctggtaga    29100
tttttctgca acggcagaga cctaaccatt atcaacgtga cagcaaatga caaaggcttc    29160
tattatggaa ccgactataa aagtagttta gattataaca ttattgtact gccatctacc    29220
actccagcac cccgcacaac tactttctct agcagcagtg tcgctaacaa tacaatttcc    29280
aatccaacct ttgccgcgct tttaaaacgc actgtgaata attctacaac ttcacataca    29340
acaatttcca cttcaacaat cagcattatc gctgcagtga caattggaat atcattctt    29400 gtttttacca taacctacta cgcctgctgc tatagaaaag acaaacataa aggtgatcca    29460
ttacttagat ttgatattta atttgttctt ttttttttta tttacagtat ggtgaacacc    29520
aatcatggta cctagaaatt tcttcttcac catactcatt tgtgcattta atgtttgcgc    29580
tactttcaca gcagtagcca cagcaacccc agactgtata ggagcatttg cttcctatgc    29640 acttttgct tttgttactt gcatctgcgt atgtagcata gtctgcctgg ttattaattt     29700
tttccaactt atagactgga tccttgtgcg aattgcctac ctgcgccacc atcccgaata    29760
ccgcaaccaa aatatcgcgg cacttcttag actcatctaa aaccatgcag gctatactac    29820
caatattttt gcttctattg cttccctacg ctgtctcaac cccagctgcc tatagtactc    29880
caccagaaca ccttagaaaa tgcaaattcc aacaaccgtg gtcatttctt gcttgctatc    29940
gagaaaaatc agaaattccc ccaaatttaa taatgattgc tggaataatt aatataatct    30000
gttgcaccat aatttcattt ttgatatacc ccctatttga ttttggctgg aatgctccca    30060
atgcacatga tcatccacaa gacccagagg aacacattcc cctacaaaac atgcaacatc    30120
caatagcgct aatagattac gaaagtgaac cacaaccccc actactccct gctattagtt    30180
acttcaacct aaccggcgga gatgactgaa acactcacca cctccaattc cgccgaggat    30240
ctgctcgata tggacggccg cgtctcagaa cagcgactcg cccaactacg catccgccag    30300
cagcaggaac gcgcggccaa agagctcaga gatgtcatcc aaattcacca atgcaaaaaa    30360
ggcatattct gtttggtaaa acaagccaag atatcctacg agatcaccgc tactgaccat    30420
cgcctctctt acgaacttgg ccccaacga caaaaatta cctgcatggt gggaatcaac     30480
cccatagtta tcacccagca aagtggagat actaagggtt gcattcactg ctcctgcgat    30540
tccatcgagt gcacctacac cctgctgaag accctatgcg gcctaagaga cctgctacca    30600
```

```
atgaattaaa aaatgattaa taaaaaatca cttacttgaa atcagcaata aggtctctgt   30660
tgaaattttc tcccagcagc acctcacttc cctcttccca actctggtat tctaaacccc   30720
gttcagcggc atactttctc catactttaa aggggatgtc aaattttagc tcctctcctg   30780
tacccacaat cttcatgtct ttcttcccag atgaccaaga gagtccggct cagtgactcc   30840
ttcaaccctg tctaccccta tgaagatgaa agcacctccc aacaccccct tataaaccca   30900
gggtttattt cccaaatgg cttcacacaa agcccaaacg gagttcttac tttaaaatgt   30960
ttaaccccac taacaaccac aggcggatct ctacagctaa aagtgggagg gggacttaca   31020
gtggatgaca ccaacggttt tttgaaagaa aacataagtg ccaccacacc actcgttaag   31080
actggtcact ctataggttt accactagga gccggattgg gaacgaatga aaataaactt   31140
tgtatcaaat taggacaagg acttacattc aattcaaaca acatttgcat tgatgacaat   31200
attaacacct tatggacagg agtcaacccc accgaagcca actgtcaaat catgaactcc   31260
agtgaatcta atgattgcaa attaattcta acactagtta aaactggagc actagtcact   31320
gcatttgttt atgttatagg agtatctaac aattttaata tgctaactac acacagaaat   31380
ataaatttta ctgcagagct gtttttcgat tctactggta atttactaac tagactctca   31440
tccctcaaaa ctccacttaa tcataaatca ggacaaaaca tggctactgg tgccattact   31500
aatgctaaag gtttcatgcc cagcacgact gcctatcctt tcaatgataa ttctagagaa   31560
aaagaaaact acatttacgg aacttgttac tacacagcta gtgatcgcac tgcttttccc   31620
attgacatat ctgtcatgct taaccgaaga gcaataaatg acgagacatc atattgtatt   31680
cgtataactt ggtcctggaa cacaggagat gccccagagg tgcaaacctc tgctacaacc   31740
ctagtcacct ccccatttac cttttactac atcagagaag acgactgaca aataaagttt   31800
aacttgttta tttgaaaatc aattcacaaa atccgagtag ttattttgcc tcccccttcc   31860
catttaacag aatacaccaa tctctcccca cgcacagctt taaacatttg gataccatta   31920
gatatagaca tggtttaga ttccacattc aaaacagttt cagagcgagc caatctgggg   31980
tcagtgatag ataaaaatcc atcgggatag tcttttaaag cgctttcaca gtccaactgc   32040
tgcggatgga ctccggagtc tggatcacgg tcatctggaa gaagaacgat gggaatcata   32100
atccgaaaac ggtatcggac gattgtgtct catcaaaccc acaagcagcc gctgtctgcg   32160
tcgctccgtg cgactgctgt ttatgggatc agggtccaca gtgtcctgaa gcatgatttt   32220
aatagccctt aacatcaact ttctggtgcg atgcgcgcag caacgcattc tgatttcact   32280
caaatctttg cagtaggtac aacacattat tacaatattg tttaataaac cataattaaa   32340
agcgctccag ccaaaactca tatctgatat aatcgcccct gcatgaccat cataccaaag   32400
tttaatataa attaaatgac gttccctcaa aaacacacta cccacataca tgatctcttt   32460
tggcatgtgc atattaacaa tctgtctgta ccatggacaa cgttggttaa tcatgcaacc   32520
caatataacc ttccggaacc acactgccaa caccgctccc ccagccatgc attgaagtga   32580
accctgctga ttacaatgac aatgaagaac ccaattctct cgaccgtgaa tcacttgaga   32640
atgaaaaata tctatagtgg cacaacatag acataaatgc atgcatcttc tcataatttt   32700
taactcctca ggatttagaa acatatccca gggaatagga agctcttgca gaacagtaaa   32760
gctggcagaa caaggaagac cacgaacaca acttacacta tgcatagtca tagtatcaca   32820
atctggcaac agcgggtggt cttcagtcat agaagctcgg gtttcatttt cctcacaacg   32880
tggtaactgg gctctggtgt aagggtgatg tctggcgcat gatgtcgagc gtgcgcgcaa   32940
```

```
ccttgtcata atggagttgc ttcctgacat tctcgtattt tgtatagcaa aacgcggccc   33000
tggcagaaca cactcttctt cgccttctat cctgccgctt agcgtgttcc gtgtgatagt   33060
tcaagtacaa ccacactctt aagttggtca aaagaatgct ggcttcagtt gtaatcaaaa   33120
ctccatcgca tctaatcgtt ctgaggaaat catccacggt agcatatgca aatcccaacc   33180
aagcaatgca actggattgt gtttcaagca ggagaggaga gggaagagac ggaagaacca   33240
tgttaatttt tattccaaac gatctcgcag tacttcaaat tgtagatcgc gcagatggca   33300
tctctcgccc ccactgtgtt ggtgaaaaag cacagctaga tcaaagaaa tgcgattttc    33360
aaggtgctca acggtggctt ccagcaaagc ctccacgcgc acatccaaga acaaaagaat   33420
accaaaagaa ggagcatttt ctaactcctc aatcatcata ttacattcct gcaccattcc   33480
cagataattt tcagctttcc agccttgaat tattcgtgtc agttcttgtg gtaaatccaa   33540
tccacacatt acaaacaggt cccggagggc gccctccacc accattctta aacacaccct   33600
cataatgaca aaatatcttg ctcctgtgtc acctgtagcg aattgagaat ggcaacatca   33660
attgacatgc ccttggctct aagttcttct ttaagttcta gttgtaaaaa ctctctcata   33720
ttatcaccaa actgcttagc cagaagcccc ccgggaacaa gagcagggga cgctacagtg   33780
cagtacaagc gcagacctcc ccaattggct ccagcaaaaa caagattgga ataagcatat   33840
tgggaaccgc cagtaatatc atcgaagttg ctggaaatat aatcaggcag agtttcttgt   33900
aaaaattgaa taaagaaaa atttgccaaa aaacattca aaacctctgg gatgcaaatg     33960
caataggtta ccgcgctgcg ctccaacatt gttagttttg aattagtctg caaaaataaa   34020
aaaaaaaaca agcgtcatat catagtagcc tgacgaacag atggataaat cagtcttttcc  34080
atcacaagac aagccacagg gtctccagct cgaccctcgt aaaacctgtc atcatgatta   34140
aacaacagca ccgaaagttc ctcgcggtga ccagcatgaa taattcttga tgaagcatac   34200
aatccagaca tgttagcatc agttaacgag aaaaaacagc caacatagcc tttgggtata   34260
attatgctta atcgtaagta tagcaaagcc acccctcgcg gatacaaagt aaaaggcaca   34320
ggagaataaa aaatataatt atttctctgc tgctgttcag gcaacgtcgc ccccggtccc   34380
tctaaataca catacaaagc ctcatcagcc atggcttacc agacaaagta cagcgggcac   34440
acaaagcaca agctctaaag tgactctcca acctctccac aatatatata tacacaagcc   34500
ctaaactgac gtaatgggag taaagtgtaa aaaatcccgc caaacccaac acacacccccg  34560
aaactgcgtc accagggaaa agtacagttt cacttccgca atcccaacag gcgtaacttc   34620
ctctttctca cggtacgtga tatcccacta acttgcaacg tcattttccc acggtcgcac   34680
cgcccctttt agccgttaac cccacagcca atcaccacac gatccacact tttaaaatc    34740
acctcattta catattggca ccattccatc tataaggtat attattgatg atg          34793
```

<210> SEQ ID NO 7
<211> LENGTH: 34801
<212> TYPE: DNA
<213> ORGANISM: Artificial Sequence
<220> FEATURE:
<223> OTHER INFORMATION: Fully synthetic

<400> SEQUENCE: 7

```
catcatcaat aatataccct atagatggaa tggtgccaat atgtaaatga ggtgatttta      60
aaaagtgtgg atcgtgtggt gattggctgt ggggttaacg gctaaagggg gcggtgcgac     120
cgtgggaaaa tgacgttttg tggggtgga gttttttttgc aagttgtcgc gggaaatgtg     180
acgcataaaa aggctacaca ggaagtgaca attttcgcgc ggttttaggc ggatgttgta     240
```

```
gtaaatttgg gcgtaaccga gtaagatttg gccattttcg cgggaaaact gaataagagg    300
aagtgaaatc tgaataattt tgtgttactc atagcgcgta atatttgtct agggccgcgg    360
ggactttgac cgtttacgtg gagactcgcc caggtgtttt tctcaggtgt tttccgcgtt    420
cgggtcaaag ttggcgtttt attattatag tcagctgacg tgtagtgtat ttatacccgg    480
tgagttcctc aagaggccac tcttgagtgc cagcgagtag agttttctcc tccgagccgc    540
tccgacaccg ggactgaaaa atgagagatt tgcgatttct gcctcaggaa ataatctctg    600
ctgagactgg aaatgaaata ttggagcttg tggtgcacgc cctgatggga gacgatccgg    660
agccacctgt gcagctttt gagcctccta cgcttcagga actgtatgat ttagaggtag    720
agggatcgga ggattctaat gaggaagctg taaatggctt ttttaccgat tctatgcttt    780
tagctgctaa tgaagggtta gaattagatc cgcctttgga cacttttgat actccagggg    840
taattgtgga aagcggtaca ggtgtaagaa aattacctga tttgagttcc gtggactgtg    900
atttgcactg ctatgaagac gggtttcctc cgagtgatga ggaggaccat gaaaaggagc    960
agtccatgca gactgcagcg ggtgagggag tgaaggctgc caatgttggt tttcagttgg   1020
attgcccgga gcttcctgga catggctgta agtcttgtga atttcacagg aaaaatactg   1080
gagtaaagga actgttatgt tcgctttgtt atatgagaac gcactgccac tttatttaca   1140
gtaagtgtgt ttaagttaaa atttaaagga atatgctgtt tttcacatgt atattgagtg   1200
tgagttttgt gcttcttatt ataggtcctg tgtctgatgc tgatgaatca ccatctcctg   1260
attctactac ctcacctcct gagattcaag cacctgttcc tgtggacgtg cgcaagccca   1320
ttcctgtgaa gcttaagcct gggaaacgtc cagcagtgga aaaacttgag gacttgttac   1380
agggtgggga cggacctttg gacttgagta cacggaaacg tccaagacaa taagtgttcc   1440
atatccgtgt ttacttaagg tgacgtcaat atttgtgtga cagtgcaatg taataaaaat   1500
atgttaactg ttcactggtt tttattgctt tttgggcggg gactcaggta tataagtaga   1560
agcagacctg tgtggttagc tcataggagc tggctttcat ccatggaggt ttgggccatt   1620
ttggaagacc ttaggaagac taggcaactg ttagagaacg cttcggacgg agtctccggt   1680
ttttggagat tctggttcgc tagtgaatta gctagggtag tttttaggat aaaacaggac   1740
tataaacaag aatttgaaaa gttgttggta gattgcccag gacttttta agctcttaat   1800
ttgggccatc aggttcactt taaagaaaaa gttttatcag ttttagactt ttcaaccca    1860
ggtagaactg ctgctgctgt ggcttttctt actttatat tagataaatg gatcccgcag    1920
actcatttca gcaggggata cgttttggat ttcatagcca cagcattgtg gagaacatgg    1980
aaggttcgca agatgaggac aatcttaggt tactggccag tgcagccttt gggtgtagcg    2040
ggaatcctga ggcatccacc ggtcatgcca gcggttctgg aggaggaaca gcaagaggac    2100
aacccgagag ccggcctgga ccctccagtg gaggaggcgg agtagctgac ttgtctcctg    2160
aactgcaacg ggtgcttact ggatctacgt ccactgacg ggataggggc gttaagaggg    2220
agagggcatc tagtggtact gatgctagat ctgagttggc tttaagttta atgagtcgca    2280
gacgtcctga aaccatttgg tggcatgagg ttcagaaaga gggaagggat gaagtttctg    2340
tattgcagga gaaatattca ctggaacagg tgaaaacatg ttggttggag cctgaggatg    2400
attgggaggt ggccattaaa aattatgcca agatagcttt gaggcctgat aaacagtata    2460
agattactag acggattaat atccggaatg cttgttacat atctggaaat ggggctgagg    2520
tggtaataga tactcaagac aaggcagtta ttagatgctg catgatggat atgtggcctg    2580
```

```
gggtagtcgg tatggaagca gtaacttttg taaatgttaa gtttagggga gatggttata    2640
atggaatagt gtttatggcc aataccaaac ttatattgca tggttgtagc ttttttggtt    2700
tcaacaatac ctgtgtagat gcctggggac aggttagtgt acggggatgt agtttctatg    2760
cgtgttggat tgccacagct ggcagaacca agagtcaatt gtctctgaag aaatgcatat    2820
ttcaaagatg taacctgggc attctgaatg aaggcgaagc aagggtccgc cactgcgctt    2880
ctacagatac tggatgtttt attttgatta agggaaatgc cagcgtaaag cataacatga    2940
tttgcggtgc ttccgatgag aggccttatc aaatgctcac ttgtgctggt gggcattgta    3000
atatgctggc tactgtgcat attgtttccc atcaacgcaa aaaatggcct gtttttgatc    3060
acaatgtgat gacgaagtgt accatgcatg caggtgggcg tagaggaatg tttatgcctt    3120
accagtgtaa catgaatcat gtgaaagtgt tgttggaacc agatgccttt tccagaatga    3180
gcctaacagg aattttttgac atgaacatgc aaatctggaa gatcctgagg tatgatgata    3240
cgagatcgag ggtacgcgca tgcgaatgcg gaggcaagca tgccaggttc cagccggtgt    3300
gtgtagatgt gactgaagat ctcagaccgg atcatttggt tattgcccgc actggagcag    3360
agttcggatc cagtggagaa gaaactgact aaggtgagta ttgggaaaac tttggggtgg    3420
gattttcaga tggacagatt gagtaaaaat ttgttttttc tgtcttgcag ctgtcatgag    3480
tggaaacgct tcttttaagg ggggagtctt cagcccttat ctgacagggc gtctcccatc    3540
ctgggcagga gttcgtcaga atgttatggg atctactgtg gatggaagac ccgtccaacc    3600
cgccaattct tcaacgctga cctatgctac tttaagttct tcacctttgg acgcagctgc    3660
agctgccgcc gccgcttctg ttgccgctaa cactgtgctt ggaatgggtt actatggaag    3720
catcatggct aattccactt cctctaataa ccccttctacc ctgactcagg acaagttact    3780
tgtccttttg gcccagctgg aggctttgac ccaacgtctg ggtgaacttt ctcagcaggt    3840
ggtcgagttg cgagtacaaa ctgagtctgc tgtcggcacg gcaaagtcta aataaaaaaa    3900
tcccagaatc aatgaataaa taaacaagct tgttgttgat ttaaaatcaa gtgttttat     3960 ttcattttc gcgcacggta tgccctagac caccgatctc tatcattgag aactcggtgg     4020
attttttcca ggatcctata gaggtgggat tgaatgttta gatacatggg cattaggccg    4080
tctttggggt ggagatagct ccattgaagg gattcatgct ccggggtagt gttgtaaatc    4140
acccagtcat aacaaggtcg cagtgcatgg tgttgcacaa tatctttag aagtaggctg     4200 attgccacag ataagcccctt ggtgtaggtg tttacaaacc ggttgagctg ggatgggtgc   4260
attcggggtg aaaattatgtg cattttggat tggattttta agttggcaat attgccgcca   4320
agatcccgtc ttgggttcat gttatgaagg accaccaaga cggtgtatcc ggtacattta    4380
ggaaatttat cgtgcagctt ggatggaaaa gcgtggaaaa atttggagac acccttgtgt    4440
cctccaagat tttccatgca ctcatccatg ataatagcaa tggggccgtg ggcagcggcg    4500
cgggcaaaca cgttccgtgg gtctgacaca tcatagttat gttcctgagt taaatcatca    4560
taagccattt taatgaattt ggggcggaga gtaccagatt ggggtatgaa tgttccttcg    4620
ggccccggag catagttccc ctcacagatt tgcatttccc aagctttcag ttccgagggt    4680
ggaatcatgt ccacctgggg ggctatgaaa acaccgtttt ctggggcggg ggtgattaat    4740
tgtgatgata gcaaatttct gagcaattga gatttgccac atccggtggg gccataaatg    4800
attccgatta cgggttgcag gtggtagttt agggaacggc aactgccgtc ttctcgaagc    4860
aagggggcca cctcgttcat catttccctt acatgcatat tttcccgcac caaatccatt    4920
aggaggcgct ctcctcctag tgatagaagt tcttgtagtg aggaaaagtt tttcagcggt    4980
```

```
ttcagaccgt cagccatggg cattttggag agagtttgct gcaaaagttc tagtctgttc    5040
cacagttcag tgatgtgttc tatggcatct cgatccagca gacctcctcg tttcgcgggt    5100
ttggacggct cctggaatag ggtatgagac gatgggcgtc cagcgctgcc agggttcggt    5160
ccttccaggg tctcagtgtt cgagtcaggg ttgtttccgt cacagtgaag gggtgtgcgc    5220
ctgcttgggc gcttgccagg gtgcgcttca gactcatcct gctggtcgaa aacttctgtc    5280
gcttggcgcc ctgtatgtcg gccaagtagc agtttaccat gagttcgtag ttgagcgcct    5340
cggctgcgtg gcctttggcg cggagcttac ctttggaagt tttcttgcat accgggcagt    5400
ataggcattt cagcgcatac aacttgggcg caaggaaaac ggattctggg gagtatgcat    5460
ctgcgccgca ggaggcgcaa acagtttcac attccaccag ccaggttaaa tccggttcat    5520
tggggtcaaa aacaagtttt ccgccatatt ttttgatgcg tttcttacct ttggtctcca    5580
tgagttcgtg tcctcgttga gtgacaaaca ggctgtccgt gtccccgtag actgatttta    5640
caggcctctt ctccagtgga gtgcctcggt cttcttcgta caggaactct gaccactctg    5700
atacaaaggc gcgcgtccag gccagcacaa aggaggctat gtgggagggg tagcgatcgt    5760
tgtcaaccag ggggtccacc ttttccaaag tatgcaaaca catgtcaccc tcttcaacat    5820
ccaggaatgt gattggcttg taggtgtatt tcacgtgacc tggggtcccc gctggggggg    5880
tataaaaggg ggcggttctt tgctcttcct cactgtcttc cggatcgctg tccaggaacg    5940
tcagctgttg gggtaggtat tccctctcga aggcgggcat gacctctgca ctcaggttgt    6000
cagtttctaa gaacgaggag gatttgatat tgacagtgcc ggttgagatg cctttcatga    6060
ggttttcgtc catttggtca gaaaacacaa ttttttttatt gtcaagtttg gtggcaaatg    6120
atccatacag ggcgttggat aaaagtttgg caatggatcg catggtttgg ttctttttcct    6180 tgtccgcgcg ctctttggcg gcgatgttga gttggacata ctcgcgtgcc aggcacttcc    6240
attcggggaa gatagttgtt aattcatctg gcacgattct cacttgccac cctcgattat    6300
gcaaggtaat taaatccaca ctggtggcca cctcgcctcg aaggggttca ttggtccaac    6360
agagcctacc tccttcccta gaacagaaag ggggaagtgg gtctagcata agttcatcgg    6420
gagggtctgc atccatggta aagattcccg gaagtaaatc cttatcaaaa tagctgatgg    6480 gagtgggtc atctaaggcc atttgccatt ctcgagctgc cagtgcgcgc tcatatgggt    6540 taagggact gccccatggc atgggatggg tgagtgcaga ggcatacatg ccacagatgt    6600
catagacgta gatgggatcc tcaaagatgc ctatgtaggt tggatagcat cgcccccctc    6660
tgatacttgc tcgcacatag tcatatagtt catgtgatgg cgctagcagc cccggaccca    6720
agttggtgcg attgggtttt tctgttctgt agacgatctg gcgaaagatg gcgtgagaat    6780
tggaagagat ggtgggtctt tgaaaaatgt tgaaatgggc atgaggtaga cctacagagt    6840
ctctgacaaa gtgggcataa gattcttgaa gcttggttac cagttcggcg gtgacaagta    6900
cgtctagggc gcagtagtca agtgtttctt gaatgatgtc ataacctggt tggttttttct    6960 tttcccacag ttcgcggttg agaaggtatt cttcgcgatc cttccagtac tcttctagcg    7020
gaaacccgtc tttgtctgca cggtaagatc ctagcatgta gaactgatta actgccttgt    7080
aagggcagca gcccttctct acgggtagag agtatgcttg agcagttttt cgtagcgaag    7140
cgtgagtaag ggcaaaggtg tctctgacca tgactttgag aaattggtat ttgaagtcga    7200
tgtcgtcaca ggctccctgt tcccagagtt ggaagtctac ccgtttcttg taggcggggt    7260
tgggcaaagc gaaagtaaca tcattgaaga gaatcttacc ggctctgggc ataaaattgc    7320
```

```
gagtgatgcg aaaaggctgt ggtacttccg ctcgattgtt gatcacctgg gcagctagga    7380
cgatctcgtc gaaaccgttg atgttgtgtc ctacgatgta taattctatg aaacgcggcg    7440
tgcctctgac gtgaggtagc ttactgagct catcaaaggt taggtctgtg gggtcagata    7500
aggcgtagtg ttcgagagcc cattcgtgca ggtgaggatt tgcatgtagg aatgatgacc    7560
aaagatctac cgccagtgct gtttgtaact ggtcccgata ctgacgaaaa tgccggccaa    7620
ttgccatttt ttctggagtg acacagtaga aggttctggg gtcttgttgc catcgatccc    7680
acttgagttt aatggctaga tcgtgggcca tgttgacgag acgctcttct cctgagagtt    7740
tcatgaccag catgaaagga actagttgtt tgccaaagga tcccatccag gtgtaagttt    7800
ccacatcgta ggtcaggaag agtctttctg tgcgaggatg agagccgatc gggaagaact    7860
ggatttcctg ccaccagttg gaggattggc tgttgatgtg atggaagtag aagtttctgc    7920
ggcgcgccga gcattcgtgt tgtgcttgt acagacggcc gcagtagtcg cagcgttgca    7980
cgggttgtat ctcgtgaatg agttgtacct ggcttcccct gacgagaaat tcagtgggaa    8040
agccgaggcc tggcgattgt atctcgtgct cttctatatt cgctgtatcg gcctgttcat    8100
cttctgtttc gatggtggtc atgctgacga gccccgcgg gaggcaagtc cagacctcgg    8160
cgcgggaggg gcggagctga aggacagag gcgcaggct ggagctgtcc agagtcctga    8220
gacgctgcgg actcaggtta gtaggtaggg acagaagatt aacttgcatg atcttttcca    8280
gggcgtgcgg gaggttcaga tggtacttga tttccacagg ttcgtttgta gagacgtcaa    8340
tggcttgcag ggttccgtgt cctttgggcg ccactaccgt acctttgttt tttctttga    8400 tcggtggtgg ctctcttgct tcttgcatgc tcagaagcgg tgacggggac gcgcgccggg    8460
cggcagcggt tgttccggac ccgagggcat ggctggtagt ggcacgtcgg cgccgcgcac    8520
gggcaggttc tggtactgcg ctctgagaag acttgcgtgc gccaccacgc gtcgattgac    8580
gtcttgtatc tgacgtctct gggtgaaagc taccggcccc gtgagcttga acctgaaaga    8640
gagttcaaca gaatcaattt cggtatcgtt aacggcagct tgtctcagta tttcttgtac    8700
gtcaccagag ttgtcctggt aggcgatctc cgccatgaac tgctcgattt cttcctcctg    8760
aagatctccg cgaccgctc tttcgacggt ggccgcgagg tcattggaga tacgcccat    8820 gagttgggag aatgcattca tgcccgcctc gttccagacg cggctgtaaa ccacggcccc    8880
ctcggagtct cttgcgcgca tcaccacctg agcgaggtta agctccacgt gtctggtgaa    8940
gaccgcatag ttgcataggc gctgaaaaag gtagttgagt gtggtggcaa tgtgttcggc    9000
gacgaagaaa tacatgatcc atcgtctcag cggcatttcg ctaacatcgc ccagagcttc    9060
caagcgctcc atggcctcgt agaagtccac ggcaaaatta aaaaactggg agtttcgcgc    9120
ggacacggtc aattcctcct cgagaagacg atgagttcg gctatggtgg cccgtacttc    9180
gcgttcgaag gctcccggga tctcttcttc ctcttctatc tcttcttcca ctaacatctc    9240
ttcttcgtct tcaggcgggg gcggaggggg cacgcggcga cgtcgacggc gcacgggcaa    9300
acggtcgatg aatcgttcaa tgacctctcc gcggcggcgg cgcatggttt cagtgacggc    9360
gcggccgttc tcgcgcggtc gcagagtaaa acaccgccg cgcatctcct taaagtggtg    9420
actgggaggt tctccgtttg ggagggagag ggcgctgatt atacatttta ttaattggcc    9480
cgtagggact gcacgcagag atctgatcgt gtcaagatcc acgggatctg aaaacctttc    9540
gacgaaagcg tctaaccagt cacagtcaca aggtaggctg agtacggctt cttgtgggcg    9600
ggggtggtta tgtgttcggt ctgggtcttc tgtttcttct tcatctcggg aaggtgagac    9660
gatgctgctg gtgatgaaat taaagtaggc agttctaaga cggcggatgg tggcgaggag    9720
```

```
caccaggtct ttgggtccgg cttgctggat acgcaggcga ttggccattc cccaagcatt   9780
atcctgacat ctagcaagat ctttgtagta gtcttgcatg agccgttcta cgggcacttc   9840
ttcctcaccc gttctgccat gcatacgtgt gagtccaaat ccgcgcattg gttgtaccag   9900
tgccaagtca gctacgactc tttcggcgag gatggcttgc tgtacttggg taagggtggc   9960
ttgaaagtca tcaaaatcca caaagcggtg gtaagctcct gtattaatgg tgtaagcaca  10020
gttggccatg actgaccagt taactgtctg gtgaccaggg cgcacgagct cggtgtattt  10080
aaggcgcgaa taggcgcggg tgtcaaagat gtaatcgttg caggtgcgca ccagatactg  10140
gtaccctata agaaaatgcg gcggtggttg gcggtagaga ggccatcgtt ctgtagctgg  10200
agcgccaggg gcgaggtctt ccaacataag gcggtgatag ccgtagatgt acctggacat  10260
ccaggtgatt cctgcggcgg tagtagaagc ccgaggaaac tcgcgtacgc ggttccaaat  10320
gttgcgtagc ggcatgaagt agttcattgt aggcacggtt tgaccagtga ggcgcgcgca  10380
gtcattgatc tctatagac acggagaaaa tgaaagcgtt cagcgactcg actccgtagc  10440
ctggaggaac gtgaacgggt tgggtcgcgg tgtaccccgg ttcgagactt gtactcgagc  10500
cggccggagc cgcggctaac gtggtattgg cactcccgtc tcgacccagc ctacaaaaat  10560
ccaggatacg gaatcgagtc gttttgctgg tttccgaatg gcagggaagt gagtcctatt  10620
ttttttttt tgccgctcag atgcatcccg tgctgcgaca gatgcgcccc caacaacagc  10680
ccccctcgca gcagcagcag cagcaatcac aaaaggctgt ccctgcaact actgcaactg  10740
ccgccgtgag cggtgcggga cagcccgcct atgatctgga cttggaagag ggcgaaggac  10800
tggcacgtct aggtgcgcct tcacccgagc ggcatccgcg agttcaactg aaaaaagatt  10860
ctcgcgaggc gtatgtgccc caacagaacc tatttagaga cagaagcggc gaggagccgg  10920
aggagatgcg agcttcccgc tttaacgcgg gtcgtgagct gcgtcacggt ttggaccgaa  10980
gacgagtgtt gcgggacgag gatttcgaag ttgatgaaat gacagggatc agtcctgcca  11040
gggcacacgt ggctgcagcc aaccttgtat cggcttacga gcagacagta aaggaagagc  11100
gtaacttcca aaagtctttt aataatcatg tgcgaaccct gattgccgc gaagaagtta  11160
cccttggttt gatgcatttg tgggatttga tggaagctat cattcagaac cctactagca  11220
aacctctgac cgcccagctg tttctggtgg tgcaacacag cagagacaat gaggctttca  11280
gagaggcgct gctgaacatc accgaacccg aggggagatg gttgtatgat cttatcaaca  11340
ttctacagag tatcatagtg caggagcgga gcctgggcct ggccgagaag gtggctgcca  11400
tcaattactc ggttttgagc ttgggaaaat attacgctcg caaaatctac aagactccat  11460
acgttcccat agacaaggag gtgaagatag atgggttcta catgcgcatg acgctcaagg  11520
tcttgacccct gagcgatgat cttggggtgt atcgcaatga cagaatgcat cgcgcggtta  11580
gcgccagcag gaggcgcgag ttaagcgaca gggaactgat gcacagtttg caaagagctc  11640
tgactggagc tggaaccgag ggtgagaatt acttcgacat gggagctgac ttgcagtggc  11700
agcctagtcg cagggctctg agcgccgcga cggcaggatg tgagcttcct tacatagaag  11760
aggcggatga aggcgaggag gaagagggcg agtacttgga agactgatgg cacaacccgt  11820
gttttttgct agatggaaca gcaagcaccg gatcccgcaa tgcgggcggc gctgcagagc  11880
cagccgtccg gcattaactc ctcggacgat tggacccagg ccatgcaacg tatcatggcg  11940
ttgacgactc gcaaccccga agcctttaga cagcaacccc aggccaaccg tctatcggcc  12000
atcatggaag ctgtagtgcc ttcccgctct aatcccactc atgagaaggt cctggccatc  12060
```

```
gtgaacgcgt tggtggagaa caaagctatt cgtccagatg aggccggact ggtatacaac    12120
gctctcttag aacgcgtggc tcgctacaac agtagcaatg tgcaaaccaa tttggaccgt    12180
atgataacag atgtacgcga agccgtgtct cagcgcgaaa ggttccagcg tgatgccaac    12240
ctgggttcgc tggtggcgtt aaatgctttc ttgagtactc agcctgctaa tgtgccgcgt    12300
ggtcaacagg attatactaa cttttttaagt gctttgagac tgatggtatc agaagtacct   12360
cagagcgaag tgtatcagtc cggtcctgat tacttctttc agactagcag acagggcttg    12420
cagacggtaa atctgagcca agcttttaaa aaccttaaag gtttgtgggg agtgcatgcc    12480
ccggtaggag aaagagcaac cgtgtctagc ttgttaactc cgaactcccg cctattatta    12540
ctgttggtag ctccttttcac cgacagcggt agcatcgacc gtaattccta tttgggttac    12600
ctactaaacc tgtatcgcga agccataggg caaagtcagg tggacgagca gacctatcaa    12660
gaaattaccc aagtcagtcg cgctttggga caggaagaca ctggcagttt ggaagccact    12720
ctgaacttct tgcttaccaa tcggtctcaa aagatccctc tcaatatgc tcttactgcg     12780 gaggaggaga ggatccttag atatgtgcag cagagcgtgg gattgtttct gatgcaagag    12840
ggggcaactc cgactgcagc actggacatg acagcgcgaa atatggagcc cagcatgtat    12900
gccagtaacc gacctttcat taacaaactg ctggactact tgcacagagc tgccgctatg    12960
aactctgatt atttcaccaa tgccatctta aacccgcact ggctgccccc acctggtttc    13020
tacacgggcg aatatgacat gcccgacccl aatgacggat ttctgtggga cgacgtggac    13080
agcgatgttt tttcacctct ttctgatcat cgcacgtgga aaaaggaagg cggcgataga    13140
atgcattctt ctgcatcgct gtccggggtc atgggtgcta ccgcggctga gcccgagtct    13200
gcaagtcctt ttcctagtct accctttcct ctacacagtg tacgtagcag cgaagtgggt    13260
agaataagtc gcccgagttt aatgggcgaa gaggagtatc taaacgattc cttgctcaga    13320
ccggcaagag aaaaaaattt cccaaacaat ggaatagaaa gtttggtgga taaaatgagt    13380
agatggaaga cttatgctca ggatcacaga acgagcctg ggatcatggg gattacaagt     13440
agagcgagcc gtagacgcca gcgccatgac agacagaggg gtcttgtgtg ggacgatgag    13500
gattcggccg atgatagcag cgtgctggac ttgggtggga gaggaagggg caacccgttt    13560
gctcatttgc gccctcgctt gggtggtatg ttgtaaaaaa aaataaaaaa aaaactcacc    13620
aaggccatgg cgacgagcgt acgttcgttc ttctttatta tctgtgtcta gtataatgag    13680
gcgagtcgtg ctaggcggag cggtggtgta tccggagggt cctcctcctt cgtacgagag    13740
cgtgatgcag cagcagcagg cgacggcggt gatgcaatcc ccactggagg ctcccttttgt   13800 gcctccgcga tacctggcac ctacggaggg cagaaacagc attcgttatt cggaactggc    13860
acctcagtac gataccacca ggttgtatct ggtggacaac aagtcggcgg acattgcttc    13920
tctgaactat cagaatgacc acagcaactt cttgaccacg gtggtgcaaa acaatgactt    13980 taccccctacg gaagccagca cccagaccat taactttgat gaacgatcgc ggtgggggcgg   14040 tcagctaaag accatcatgc atactaacat gccaaacgtg aacgagtata tgtttagtaa    14100
caagttcaaa gcgcgtgtga tggtgtccag aaaacctccc gacggtgctg cagttgggga    14160
tacttatgat cacaagcagg atattttgaa atatgagtgg ttcgagttta ctttgccaga    14220
aggcaacttt tcagttacta tgactattga tttgatgaac aatgccatca tagataatta    14280
cttgaaagtg ggtagacaga atggagtgct tgaaagtgac attggtgtta agttcgacac    14340
caggaacttc aagctgggat gggatcccga aaccaagttg atcatgcctg gagtgtatac    14400
gtatgaagcc ttccatcctg acattgtctt actgcctggc tgcggagtgg attttaccga    14460
```

```
gagtcgtttg agcaaccttc ttggtatcag aaaaaaacag ccatttcaag agggttttaa    14520
gattttgtat gaagatttag aaggtggtaa tattccggcc ctcttggatg tagatgccta    14580
tgagaacagt aagaaagaac aaaaagccaa aatagaagct gctacagctg ctgcagaagc    14640
taaggcaaac atagttgcca gcgactctac aagggttgct aacgctggag aggtcagagg    14700
agacaatttt gcgccaacac ctgttccgac tgcagaatca ttattggccg atgtgtctga    14760
aggaacggac gtgaaactca ctattcaacc tgtagaaaaa gatagtaaga atagaagcta    14820
taatgtgttg gaagacaaaa tcaacacagc ctatcgcagt tggtatcttt cgtacaatta    14880
tggcgatccc gaaaaaggag tgcgttcctg gacattgctc accacctcag atgtcacctg    14940
cggagcagag caggtctact ggtcgcttcc agacatgatg aaggatcctg tcactttccg    15000
ctccactaga caagtcagta actaccctgt ggtgggtgca gagcttatgc ccgtcttctc    15060
aaagagcttc tacaacgaac aagctgtgta ctcccagcag ctccgccagt ccacctcgct    15120
tacgcacgtc ttcaaccgct ttcctgagaa ccagatttta atccgtccgc cggcgcccac    15180
cattaccacc gtcagtgaaa acgttcctgc tctcacagat cacgggaccc tgccgttgcg    15240
cagcagtatc cggggagtcc aacgtgtgac cgttactgac gccagacgcc gcacctgtcc    15300
ctacgtgtac aaggcactgg gcatagtcgc accgcgcgtc ctttcaagcc gcactttcta    15360
aaaaaaaaaa aaatgtccat tcttatctcg cccagtaata acaccggttg gggtctgcgc    15420
gctccaagca agatgtacgg aggcgcacgc aaacgttcta cccaacatcc tgtccgtgtt    15480
cgcggacatt ttcgcgctcc atggggcgcc ctcaagggcc gcactcgcgt tcgaaccacc    15540
gtcgatgatg taatcgatca ggtggttgcc gacgcccgta attatactcc tactgcgcct    15600
acatctactg tggatgcagt tattgacagt gtagtggctg acgctcgcaa ctatgctcga    15660
cgtaagagcc ggcgaaggcg cattgccaga cgccaccgag ctaccactgc catgcgagcc    15720
gcaagagctc tgctacgaag agctagacgc gtggggcgaa gagccatgct tagggcggcc    15780
agacgtgcag cttcgggcgc cagcgccggc aggtcccgca ggcaagcagc cgctttcgca    15840
gcggcgacta ttgccgacat ggcccaatcg cgaagaggca atgtatactg ggtgcgtgac    15900
gctgccaccg gtcaacgtgt acccgtgcgc acccgtcccc ctcgcactta gaagatactg    15960
agcagtctcc gatgttgtgt cccagcggcg aggatgtcca agcgcaaata caaggaagaa    16020
atgctgcagg ttatcgcacc tgaagtctac ggccaaccgt tgaaggatga aaaaaaaccc    16080
cgcaaaatca gcgggttaaa aaggacaaaa aagaagagg aagatggcga tgatgggctg    16140
gcggagtttg tgcgcgagtt tgccccacgg cgacgcgtgc aatggcgtgg gcgcaaagtt    16200
cgacatgtgt tgagacctgg aacttcggtg gtctttacac ccggcgagcg ttcaagcgct    16260
acttttaagc gttcctatga tgaggtgtac ggggatgatg atattcttga gcaggcggct    16320
gaccgattag gcgagtttgc ttatggcaag cgtagtagaa taacttccaa ggatgagaca    16380
gtgtcgatac ccttggatca tggaaatccc accctagtc ttaaaccggt cactttgcag    16440
caagtgttac ccgtaactcc gcgaacaggt gttaaacgcg aaggtgaaga tttgtatccc    16500
actatgcaac tgatggtacc caaacgccag aagttggagg acgttttgga gaaagtaaaa    16560
gtggatccga atattcaacc tgaggttaaa gtgagaccca ttaagcaggt agcgcctggt    16620 ctggggggtac aaactgtaga cattaagatt cccactgaaa gtatggaagt gcaaactgaa    16680
cccgcaaagc ctactgccac ctccactgaa gtgcaaacgg atccatggat gcccatgcct    16740
attacaactg acgccgccgg tcccactcga agatcccgac gaaagtacgg tccagcaagt    16800
```

```
ctgttgatgc ccaattatgt tgtacaccca tctattattc ctactcctgg ttaccgaggc   16860
actcgctact atcgcagccg aaacagtacc tcccgccgtc gccgcaagac acctgcaaat   16920
cgcagtcgtc gccgtagacg cacaagcaaa ccgactcccg gcgccctggt gcggcaagtg   16980
taccgcaatg gtagtgcgga acctttgaca ctgccgcgtg cgcgttacca tccgagtatc   17040
atcacttaat caatgttgcc gctgcctcct tgcagatatg gccctcactt gtcgccttcg   17100
cgttcccatc actggttacc gaggaagaaa ctcgcgccgt agaagaggga tgttgggacg   17160
cggaatgcga cgctacaggc gacggcgtgc tatccgcaag caattgcggg gtggtttttt   17220
accagcctta attccaatta tcgctgctgc aattggcgcg ataccaggca tagcttccgt   17280
ggcggttcag gcctcgcaac gacattgaca ttggaaaaaa acgtataaat aaaaaaaaaa   17340
aaatacaatg gactctgaca ctcctggtcc tgtgactatg ttttcttaga gatgaaagac   17400 atcaatttt catccttggc tccgcgacac ggcacgaagc cgtacatggg cacctggagc    17460
gacatcggca cgagccaact gaacgggggc gccttcaatt ggagcagtat ctggagcggg   17520
cttaaaaatt ttggctcaac cataaaaaca tacgggaaca aagcttggaa cagcagtaca   17580
ggacaggcgc ttagaaataa acttaaagac cagaacttcc aacaaaaagt agtcgatggg   17640
atagcttccg gcatcaatgg agtggtagat ttggctaacc aggctgtgca gaaaaagata   17700
aacagtcgtt tggacccgcc gccagcaacc ccaggtgaaa tgcaagtgga ggaagaaatt   17760
cctccgccag aaaaacgagg cgacaagcgt ccgcgtcccg atttggaaga gacgctggtg   17820
acgcgcgtag atgaaccgcc ttcttatgag gaagcaacga agcttggaat gcccaccact   17880
agaccgatag ccccaatggc caccggggtg atgaaacctt ctcagttgca tcgacccgtc   17940
accttggatt tgcccctcc ccctgctgct actgctgtac ccgcttctaa gcctgtcgct    18000
gccccgaaac cagtcgccgt agccaggtca cgtcccgggg gcgctcctcg tccaaatgcg   18060
cactggcaaa atactctgaa cagcatcgtg ggtctaggcg tgcaaagtgt aaaacgccgt   18120
cgctgctttt aattaaatat ggagtagcgc ttaacttgcc tatctgtgta tatgtgtcat   18180
tacacgccgt cacagcagca gaggaaaaaa ggaagaggtc gtgcgtcgac gctgagttac   18240
tttcaagatg gccaccccat cgatgctgcc ccaatgggca tacatgcaca tcgccggaca   18300
ggatgcttcg gagtacctga gtccgggtct ggtgcagttc gcccgcgcca cagacaccta   18360
cttcaatctg ggaaataagt ttagaaatcc caccgtagcg ccgacccacg atgtgaccac   18420
cgaccgtagc cagcggctca tgttgcgctt cgtgcccgtt gaccgggagg acaatacata   18480
ctcttacaaa gtgcggtaca ccctggccgt gggcgacaac agagtgctgg atatggccag   18540
cacgttcttt gacattaggg gtgtgttgga cagaggtccc agtttcaaac cctattctgg   18600
tacggcttac aactccctgg ctcctaaagg cgctccaaat acatctcagt ggattgcaga   18660
aggtgtaaaa aatacaactg gtgaggaaca cgtaacagaa gaggaaacca atactactac   18720
ttacactttt ggcaatgctc ctgtaaaagc tgaagctgaa attacaaaag aaggactccc   18780
agtaggtttg gaagtttcag atgaagaaag taaaccgatt tatgctgata aaacatatca   18840
gccagaacct cagctgggag atgaaacttg gactgacctt gatggaaaaa ccgaaaagta   18900
tggaggcagg gctctcaaac ccgatactaa gatgaaacca tgctacgggt cctttgccaa   18960
acctactaat gtgaaaggcg gtcaggcaaa acaaaaaaca acggagcagc caaatcagaa   19020
agtcgaatat gatatcgaca tggagttttt tgatgcggca tcgcagaaaa caaacttaag   19080
tcctaaaatt gtcatgtatg cagaaaatgt aaatttggaa actccagaca ctcatgtagt   19140
gtacaaacct ggaacagaag acacaagttc cgaagctaat ttgggacaac aatctatgcc   19200
```

```
caacagaccc aactacattg gcttcagaga taactttatt ggactatgt actataacag   19260 tactggtaac atggggggtgc tggctggtca agcgtctcag ttaaatgcag tggttgactt   19320
gcaggacaga aacacagaac tttcttacca actcttgctt gactctctgg gcgacagaac   19380
cagatacttt agcatgtgga atcaggctgt ggacagttat gatcctgatg tacgtgttat   19440
tgaaaatcat ggtgtggaag atgaacttcc caactactgt tttccactgg acggcatagg   19500
tgttccaaca accagttaca aatcaatagt tccaaatgga gacaatgcgc taattggaa    19560 ggaacctgaa gtaaatggaa caagtgagat cggacagggt aatttgtttg ccatggaaat   19620
taaccttcaa gccaatctat ggcgaagttt cctttattcc aatgtggctc tatatctccc   19680
agactcgtac aaatacaccc cgtccaatgt cactcttcca gaaaacaaaa acacctacga   19740
ctacatgaac gggcgggtgg tgccgccatc tctagtagac acctatgtga acattggtgc   19800
caggtggtct ctggatgcca tggacaatgt caacccattc aaccaccacc gtaacgctgg   19860
cttgcgttac cgatccatgc ttctgggtaa cggacgttat gtgccttttcc acatacaagt   19920 gcctcaaaaa ttcttcgctg ttaaaaacct gctgcttctc ccaggctcct acacttatga   19980
gtggaacttt aggaaggatg tgaacatggt tctacagagt cccctcggta acgacctgcg   20040
ggtagatggc gccagcatca gtttcacgag catcaacctc tatgctactt ttttcccat    20100 ggctcacaac accgcttcca cccttgaagc catgctgcgg aatgacacca atgatcagtc   20160
attcaacgac tacctatctg cagctaacat gctctacccc attcctgcca atgcaaccaa   20220
tattcccatt tccattcctt ctcgcaactg ggcggctttc agaggctggt catttaccag   20280
actgaaaacc aaagaaactc cctctttggg gtctggattt gaccctact ttgtctattc     20340 tggttctatt ccctacctgg atggtacctt ctacctgaac cacactttta gaaaggtttc    20400
catcatgttt gactcttcag tgagctggcc tggaaatgac aggttactat ctcctaacga    20460
atttgaaata aagcgcactg tggatggcga aggctacaac gtagcccaat gcaacatgac    20520
caaagactgg ttcttggtac agatgctcgc caactacaac atcggctatc agggcttcta    20580
cattccagaa ggatacaaag atcgcatgta ttcatttttc agaaacttcc agcccatgag    20640
caggcaggtg gttgatgagg tcaattacaa agacttcaag gccgtcgcca taccctacca    20700
acacaacaac tctggctttg tgggttacat ggctccgacc atgcgccaag gtcaaccccta   20760 tcccgctaac tatccctatc cactcattgg aacaactgcc gtaaatagtg ttacgcagaa    20820
aaagttcttg tgtgacagaa ccatgtggcg cataccgttc tcgagcaact tcatgtctat    20880 gggggcccctt acagacttgg gacagaatat gctctatgcc aactcagctc atgctctgga   20940
catgaccttt gaggtggatc ccatggatga gcccacccctg ctttatcttc tcttcgaagt   21000
tttcgacgtg gtcagagtgc atcagccaca ccgcggcatc atcgaggcag tctacctgcg   21060
tacaccgttc tcggccggta acgctaccac gtaagaagct tcttgcttct tgcaaatagc    21120
agctgcaacc atggcctgcg gatcccaaaa cggctccagc gagcaagagc tcagagccat    21180
tgtccaagac ctgggttgcg gaccctattt tttgggaacc tacgataagc gcttcccggg    21240
gttcatggcc cccgataagc tcgcctgtgc cattgtaaat acggccggac gtgagacggg    21300
gggagagcac tggttggctt tcggttggaa cccacgttct aacacctgct accttttga    21360 tccttttgga ttctcggatg atcgtctcaa acagatttac cagtttgaat atgagggtct    21420
cctgcgccgc agcgctcttg ctaccaagga ccgctgtatt acgctggaaa aatctaccca   21480
gaccgtgcag ggtccccgtt ctgccgcctg cggacttttc tgctgcatgt tccttcacgc   21540
```

```
ctttgtgcac tggcctgacc gtcccatgga cggaaacccc accatgaaat tgctaactgg    21600
agtgccaaac aacatgcttc attctcctaa agtccagccc accctgtgtg acaatcaaaa    21660
agcactctac cattttctta atacccattc gccttatttt cgctcccatc gtacacacat    21720
cgaaagggcc actgcgttcg accgtatgga tgttcaataa tgactcatgt aaacaacgtg    21780
ttcaataaac atcactttat ttttttacat gtatcaaggc tctgcattac ttatttattt    21840
acaagtcgaa tgggttctga cgagaatcag aatgacccgc aggcagtgat acgttgcgga    21900
actgatactt gggttgccac ttgaattcgg gaatcaccaa cttgggaacc ggtatatcgg    21960
gcaggatgtc actccacagc tttctggtca gctgcaaagc tccaagcagg tcaggagccg    22020
aaatcttgaa atcacaatta ggaccagtgc tttgagcgcg agagttgcgg tacaccggat    22080
tgcagcactg aaacaccatc agcgacggat gtctcacgct tgccagcacg gtgggatctg    22140
caatcatgcc cacatccaga tcttcagcat tggcaatgct gaacggggtc atcttgcagg    22200
tctgcctacc catggcgggc acccaattag gcttgtggtt gcaatcgcag tgcagggga    22260 tcagtatcat cttggcctga tcctgtctga ttcctggata cacggctctc atgaaagcat    22320
catattgctt gaaagcctgc tgggctttac taccctcggt ataaaacatc ccgcaggacc    22380
tgctcgaaaa ctggttagct gcacagccgg catcattcac acagcagcgg cgtcattgt    22440 tagctatttg caccacactt ctgccccagc ggttttgggt gattttggtt cgctcgggat    22500 tctccttaa ggctcgttgt ccgttctcgc tggccacatc catctcgata atctgctcct    22560
tctgaatcat aatattgcca tgcaggcact tcagcttgcc ctcataatca ttgcagccat    22620
gaggccacaa cgcacagcct gtacattccc aattatggtg ggcgatctga gaaaagaat    22680 gtatcattcc ctgcagaaat cttcccatca tcgtgctcag tgtcttgtga ctagtgaaag    22740
ttaactggat gcctcggtgc tcctcgttta cgtactggtg acagatgcgc ttgtattgtt    22800
cgtgttgctc aggcattagt ttaaaagagg ttctaagttc gttatccagc ctgtacttct    22860
ccatcagcag acacatcact tccatgcctt tctcccaagc agacaccagg ggcaagctaa    22920
tcggattctt aacagtgcag gcagcagctc ctttagccag agggtcatct ttagcgatct    22980
tctcaatgct tcttttgcca tccttctcaa cgatgcgcac gggcgggtag ctgaaaccca    23040
ctgctacaag ttgcgcctct tctctttctt cttcgctgtc ttgactgatg tcttgcatgg    23100
ggatatgttt ggtcttcctt ggcttctttt tgggggtat cggaggagga ggactgtcgc    23160
tccgttccgg agacagggag gattgtgacg tttcgctcac cattaccaac tgactgtcgg    23220
tagaagaacc tgaccccaca cggcgacagg tgtttctctt cggggcaga ggtggaggcg    23280 attgcgaagg gctgcggtcc gacctggaag gcggatgact ggcagaaccc cttccgcgtt    23340
cgggggtgtg ctccctgtgg cggtcgctta actgatttcc ttcgcggctg gccattgtgt    23400
tctcctaggc agagaaacaa cagacatgga aactcagcca ttgctgtcaa catcgccacg    23460
agtgccatca catctcgtcc tcagcgacga ggaaaaggag cagagcttaa gcattccacc    23520
gcccagtcct gccaccacct ctaccctaga agataaggag gtcgacgcat ctcatgacat    23580
gcagaataaa aaagcgaaag agtctgagac agacatcgag caagacccgg gctatgtgac    23640
accggtggaa cacgaggaag agttgaaacg ctttctagag agagaggatg aaaactgccc    23700
aaaacaacga gcagataact atcaccaaga tgctggaaat agggatcaga acaccgacta    23760
cctcataggg cttgacgggg aagacgcgct ccttaaacat ctagcaagac agtcgctcat    23820
agtcaaggat gcattattgg acagaactga agtgccatc agtgtggaag agctcagccg    23880
cgcctacgag cttaacctct tttcacctcg tactccccc aaacgtcagc caaacggcac    23940
```

```
ctgcgagcca aatcctcgct taaacttttta tccagctttt gctgtgccag aagtactggc   24000
tacctatcac atctttttta aaaatcaaaa aattccagtc tcctgccgcg ctaatcgcac   24060
ccgcgccgat gccctactca atctgggacc tggttcacgc ttacctgata tagcttcctt   24120
ggaagaggtt ccaaagatct tcgagggtct gggcaataat gagactcggg ccgcaaatgc   24180
tctgcaaaag ggagaaaatg gcatggatga gcatcacagc gttctggtgg aattggaagg   24240
cgataatgcc agactcgcag tactcaagcg aagcatcgag gtcacacact tcgcatatcc   24300
cgctgtcaac ctgcccccta aagtcatgac ggcggtcatg gaccagttac tcattaagcg   24360
cgcaagtccc ctttcagaag acatgcatga cccagatgcc tgtgatgagg gtaaaccagt   24420
ggtcagtgat gagcagctaa cccgatggct gggcaccgac tctcccaggg atttggaaga   24480
gcgtcgcaag cttatgatgg ccgtggtgct ggttaccgta gaactagagt gtctccgacg   24540
tttctttacc gattcagaaa ccttgcgcaa actcgaagag aatctgcact acacttttag   24600
acacggcttt gtgcggcagg catgcaagat atctaacgtg gaactcacca acctggtttc   24660
ctacatgggt attctgcatg agaatcgcct aggacaaagc gtgctgcaca gcaccctgaa   24720
gggggaagcc cgccgtgatt acatccgcga ttgtgtctat ctgtacctgt gccaaacgtg   24780
gcaaaccggc atgggtgtat ggcagcaatg tttagaagaa cagaacttga aagagcttga   24840
caagctctta cagaaatctc ttaaggttct gtggacaggg ttcgacgagc gcaccgtcgc   24900
ttccgacctg gcagacctca tcttcccaga gcgtctcagg gttactttgc gaaacggatt   24960
gcctgacttt atgagccaga gcatgcttaa caattttcgc tctttcatcc tggaacgctc   25020
cggtatcctg cccgccacct gctgcgcact gccctccgac tttgtgcctc tcacctaccg   25080
cgagtgcccc ccgccgctat ggagtcactg ctacctgttc cgtctggcca actatctctc   25140
ctaccactcg gatgtgatcg aggatgtgag cggagacggc ttgctggagt gtcactgccg   25200
ctgcaatctg tgcacgcccc accggtccct agcttgcaac ccccagttga tgagcgaaac   25260
ccagataata ggcacctttg aattgcaagg ccccagcagc caaggcgatg ggtcttctcc   25320
tgggcaaagt ttaaaactga ccccgggact gtggacctcc gcctacttgc gcaagtttgc   25380
tccggaagat taccacccct atgaaatcaa gttctatgag gaccaatcac agcctccaaa   25440
ggccgaactt tcggcctgcg tcatcaccca gggggcaatt ctggcccaat gcaagccat   25500 ccaaaaatcc cgccaagaat ttctactgaa aaagggtaag gggtctacc ttgaccccca   25560 gaccggcgag gaactcaaca caaggttccc tcaggatgtc ccaacgacga gaaaacaaga   25620
agttgaaggt gcagccgccg cccccagaag atatggagga agattgggac agtcaggcag   25680
aggaggcgga ggaggacagt ctggaggaca gtctggagga agacagtttg gaggaggaaa   25740
acgaggaggc agaggaggtg gaagaagtaa ccgccgacaa acagttatcc tcggctgcgg   25800
agacaagcaa cagcgctacc atctccgctc cgagtcgagg aacccggcgg cgtcccagca   25860
gtagatggga cgagaccgga cgcttcccga acccaaccag cgcttccaag accggtaaga   25920
aggatcggca gggatacaag tcctggcggg ggcataagaa tgccatcatc tcctgcttgc   25980
atgagtgcgg gggcaacata tccttcacgc ggcgctactt gctattccac catggggtga   26040
actttccgcg caatgttttg cattactacc gtcacctcca cagcccctac tatagccagc   26100
aaatcccggc agtctcgaca gataaagaca gcggcggcga cctccaacag aaaaccagca   26160
gcggcagtta gaaaatacac aacaagtgca gcaacaggag gattaaagat tacagccaac   26220
gagccagcgc aaacccgaga gttaagaaat cggatctttc caaccctgta tgccatcttc   26280
```

```
cagcagagtc ggggtcaaga gcaggaactg aaaataaaaa accgatctct gcgttcgctc  26340
accagaagtt gtttgtatca caagagcgaa gatcaacttc agcgcactct cgaggacgcc  26400
gaggctctct tcaacaagta ctgcgcgctg actcttaaag agtaggcagc gaccgcgctt  26460
attcaaaaaa ggcgggaatt acatcatcct cgacatgagt aaagaaattc ccacgcctta  26520
catgtggagt tatcaacccc aaatgggatt ggcggcaggc gcctcccagg actactccac  26580
ccgcatgaat tggctcagcg ccgggccttc tatgatttct cgagttaatg atatacgcgc  26640
ctaccgaaac caaatacttt tggaacagtc agctcttacc accacgcccc gccaacacct  26700
taatcccaga aattgcccg ccgccctagt gtaccaggaa agtcccgctc ccaccactgt  26760
attacttcct cgagacgccc aggccgaagt ccaaatgact aatgcaggtg cgcagttagc  26820
tggcggctcc accctatgtc gtcacaggcc tcggcataat ataaaacgcc tgatgatcag  26880
aggccgaggt atccagctca acgacgagtc ggtgagctct ccgcttggtc tacgaccaga  26940
cggaatcttt cagattgccg gctgcgggag atcttccttc accctcgtc aggctgttct  27000 gactttggaa agttcgtctt cgcaacccg ctcgggcgga atcgggaccg ttcaatttgt  27060
ggaggagttt actccctctg tctacttcaa ccccttctcc ggatctcctg ggcattaccc  27120
ggacgagttc ataccgaact cgacgcgat tagcgagtca gtggacggct acgattgatg  27180
tctggtgacg cggctgagct atctcggctg cgacatctag accactgccg ccgctttcgc  27240
tgctttgccc gggaactcat tgagttcatc tacttcgaac tccccaagga tcaccctcaa  27300
ggtccggccc acggagtgcg gatttctatc gaaggcaaaa tagactctcg cctgcaacga  27360
attttctccc agcggcccgt gctgatcgag cgagaccagg aaacaccac ggtttccatc  27420 tactgcattt gtaatcaccc cggattgcat gaaagccttt gctgtcttat gtgtactgag  27480
tttaataaaa actgaattaa gactctccta cggactgccg cttcttcaac ccggatttta  27540
caaccagaag aacgaaactt ttcctgtcgt ccaggactct gttaacttca cctttcctac  27600
tcacaaacta gaagctcaac gactacaccg cttttccaga agcatttcc ctactaatac  27660 tactttcaaa accggaggtg agctccaagg tcttcctaca gaaaacccct gggtggaagc  27720
gggccttgta gtgctaggaa ttcttgcggg tgggcttgtg attattcttt gctacctata  27780
cacaccttgc ttcactttct tagtggtgtt gtggtattgg tttaaaaaat ggggcccata  27840
ctagtcttgc ttgttttact ttcgcttttg gaacccgggtt ctgccaatta cgatccatgt  27900
ctagacttcg acccagaaaa ctgcacactt acttttgcac ccgacacaag ccgcatctgt  27960
ggagttctta ttaagtgcgg atgggaatgc aggtccgttg aaattacaca caataacaaa  28020
acctggaaca ataccttatc caccacatgg gagccaggag ttcccgagtg gtacactgtc  28080
tctgtccgag gtcctgacgg ttccatccgc attagtaaca cactttcat tttttctgaa  28140 atgtgcgatc tggccatgtt catgagcaaa cagtattctc tatggcctcc tagcaaggac  28200
aacatcgtaa cgttctccat tgcttattgc ttgtgcgctt gccttcttac tgctttactg  28260
tgcgtatgca tacacctgct tgtaaccact cgcatcaaaa acgccaataa caaagaaaaa  28320
atgccttaac ctctttctgt ttacctcttt ctgtttacag acatggcttc tcttacatct  28380
ctcatatttg tcagcattgt cactgccgct catggacaaa cagtcgtctc tatccctcta  28440
ggacataatt acactctcat aggaccccca atcacttcag aggtcatctg gccaaactg  28500 ggaagcgttg attactttga tataatctgc aacaaaacaa aaccaataat agtaacttgc  28560
aacatacaaa atcttacatt gattaatgtt agcaaagttt acagcggtta ctattatggt  28620
tatgacagat acagtagtca atatagaaat tacttggttc gtgttaccca gttgaaaacc  28680
```

```
acgaaaatgc caaatatggc aaagattcga tccgatgaca attctctaga aacttttaca   28740
tctcccacca cacccgacga aaaaaacatc ccagattcaa tgattgcaat tgttgcagcg   28800
gtggcagtgg tgatggcact aataataata tgcatgcttt tatatgcttg tcgctacaaa   28860
aagtttcatc ctaaaaaaca agatctccta ctaaggctta acatttaatt tcttttttata  28920 cagccatggt ttccactacc acattcctta tgcttactag tctcgcaact ctgacttctg   28980
ctcgctcaca cctcactgta actataggct caaactgcac actaaaagga cctcaaggtg   29040
gtcatgtctt ttggtggaga atatatgaca atggatggtt tacaaaacca tgtgaccaac   29100
ctggtagatt tttctgcaac ggcagagacc taaccattat caacgtgaca gcaaatgaca   29160
aaggcttcta ttatggaacc gactataaaa gtagtttaga ttataacatt attgtactgc   29220
catctaccac tccagcaccc cgcacaacta ctttctctag cagcagtgtc gctaacaata   29280
caatttccaa tccaaccttt gccgcgcttt aaaaacgcac tgtgaataat tctacaactt   29340
cacatacaac aatttccact tcaacaatca gcattatcgc tgcagtgaca attggaatat   29400
ctattcttgt ttttaccata acctactacg cctgctgcta tagaaaagac aaacataaag   29460
gtgatccatt acttagattt gatatttaat ttgttctttt tttttttatt tacagtatgg   29520
tgaacaccaa tcatggtacc tagaaatttc ttcttcacca tactcatttg tgcatttaat   29580
gtttgcgcta ctttcacagc agtagccaca gcaaccccag actgtatagg agcatttgct   29640
tcctatgcac ttttttgcttt tgttacttgc atctgcgtat gtagcatagt ctgcctggtt   29700
attaattttt tccaacttat agactggatc cttgtgcgaa ttgcctacct gcgccaccat   29760
cccgaatacc gcaaccaaaa tatcgcggca cttcttagac tcatctaaaa ccatgcaggc   29820
tatactacca atatttttgc ttctattgct tccctacgct gtctcaaccc cagctgccta   29880
tagtactcca ccagaacacc ttagaaaatg caaattccaa caaccgtggt catttcttgc   29940
ttgctatcga gaaaaatcag aaattccccc aaatttaata atgattgctg gaataattaa   30000
tataatctgt tgcaccataa tttcatttttt gatataccccc ctatttgatt ttggctggaa   30060
tgctcccaat gcacatgatc atccacaaga cccagaggaa cacattcccc tacaaaacat   30120
gcaacatcca atagcgctaa tagattacga aagtgaacca caaccccccac tactccctgc   30180 tattagttac ttcaacctaa ccggcggaga tgactgaaac actcaccacc tccaattccg   30240
ccgaggatct gctcgatatg gacggccgcg tctcagaaca gcgactcgcc caactacgca   30300
tccgccagca gcaggaacgc gcggccaaag agctcagaga tgtcatccaa attcaccaat   30360
gcaaaaaagg catattctgt ttggtaaaac aagccaagat atcctacgag atcaccgcta   30420
ctgaccatcg cctctcttac gaacttggcc cccaacgaca aaaatttacc tgcatggtgg   30480
gaatcaaccc catagttatc acccagcaaa gtggagatac taagggttgc attcactgct   30540
cctgcgattc catcgagtgc acctacaccc tgctgaagac cctatgcggc ctaagagacc   30600
tgctaccaat gaattaaaaa atgattaata aaaaatcact tacttgaaat cagcaataag   30660
gtctctgttg aaattttctc ccagcagcac ctcacttccc tcttcccaac tctggtattc   30720
taaaccccgt tcagcggcat actttctcca tactttaaag gggatgtcaa attttagctc   30780
ctctcctgta cccacaatct tcatgtcttt cttcccagat gaccaagaga gtccggctca   30840
gtgactcctt caaccctgtc taccctatg aagatgaaag cacctcccaa caccccttta   30900
taaacccagg gtttatttcc ccaaatggct tcacacaaag cccaaacgga gttcttactt   30960
taaaatgttt aaccccacta acaaccacag gcggatctct acagctaaaa gtgggagggg   31020
```

```
gacttacagt ggatgacacc aacggttttt tgaaagaaaa cataagtgcc accacaccac   31080
tcgttaagac tggtcactct ataggtttac cactaggagc cggattggga acgaatgaaa   31140
ataaactttg tatcaaatta ggacaaggac ttacattcaa ttcaaacaac atttgcattg   31200
atgacaatat taacaccttta tggacaggag tcaaccccac cgaagccaac tgtcaaatca   31260
tgaactccag tgaatctaat gattgcaaat taattctaac actagttaaa actggagcac   31320
tagtcactgc atttgtttat gttataggag tatctaacaa ttttaatatg ctaactacac   31380
acagaaatat aaattttact gcagagctgt ttttcgattc tactggtaat ttactaacta   31440
gactctcatc cctcaaaact ccacttaatc ataaatcagg acaaaacatg gctactggtg   31500
ccattactaa tgctaaaggt ttcatgccca gcacgactgc ctatccttc aatgataatt   31560 ctagagaaaa agaaaactac atttacggaa cttgttacta cacagctagt gatcgcactg   31620
cttttcccat tgacatatct gtcatgctta accgaagagc aataaatgac gagacatcat   31680
attgtattcg tataacttgg tcctggaaca caggagatgc cccagaggtg caaacctctg   31740
ctacaaccct agtcacctcc ccatttacct tttactacat cagagaagac gactgacaaa   31800
taaagtttaa cttgtttatt tgaaaatcaa ttcacaaaat ccgagtagtt attttgcctc   31860 cccccttccca tttaacagaa tacaccaatc tctccccacg cacagcttta aacatttgga   31920
taccattaga tatagacatg gttttagatt ccacattcca aacagtttca gagcgagcca   31980
atctggggtc agtgatagat aaaaatccat cgggatagtc ttttaaagcg ctttcacagt   32040
ccaactgctg cggatggact ccggagtctg gatcacggtc atctggaaga agaacgatgg   32100
gaatcataat ccgaaaacgg tatcggacga ttgtgtctca tcaaacccac aagcagccgc   32160
tgtctgcgtc gctccgtgcg actgctgttt atgggatcag ggtccacagt gtcctgaagc   32220
atgattttaa tagcccttaa catcaacttt ctggtgcgat gcgcgcagca acgcattctg   32280
atttcactca aatctttgca gtaggtacaa cacattatta caatattgtt taataaacca   32340
taattaaaag cgctccagcc aaaactcata tctgatataa tcgcccctgc atgaccatca   32400
taccaaagtt aatataaat taaatgacgt tccctcaaaa acacactacc cacatacatg   32460
atctcttttg gcatgtgcat attaacaatc tgtctgtacc atggacaacg ttggttaatc   32520
atgcaaccca atataacctt ccggaaccac actgccaaca ccgctccccc agccatgcat   32580
tgaagtgaac cctgctgatt acaatgacaa tgaagaaccc aattctctcg accgtgaatc   32640
acttgagaat gaaaaatatc tatagtggca caacatagac ataaatgcat gcatcttctc   32700
ataattttta actcctcagg atttagaaac atatcccagg gaataggaag ctcttgcaga   32760
acagtaaagc tggcagaaca aggaagacca cgaacacaac ttacactatg catagtcata   32820
gtatcacaat ctggcaacag cgggtggtct tcagtcatag aagctcgggt ttcatttcc   32880 tcacaacgtg gtaactgggc tctggtgtaa gggtgatgtc tggcgcatga tgtcgagcgt   32940
gcgcgcaacc ttgtcataat ggagttgctt cctgacattc tcgtattttg tatagcaaaa   33000
cgcggccctg gcagaacaca ctcttcttcg ccttctatcc tgccgcttag cgtgttccgt   33060
gtgatagttc aagtacaacc acactcttaa gttggtcaaa agaatgctgg cttcagttgt   33120
aatcaaaact ccatcgcatc taatcgttct gaggaaatca tccacggtag catatgcaaa   33180
tcccaaccaa gcaatgcaac tggattgtgt ttcaagcagg agaggagagg gaagagacgg   33240
aagaaccatg ttaattttta ttccaaacga tctcgcagta cttcaaattg tagatcgcgc   33300
agatggcatc tctcgccccc actgtgttgg tgaaaaagca cagctagatc aaaagaaatg   33360
cgattttcaa ggtgctcaac ggtggcttcc agcaaagcct ccacgcgcac atccaagaac   33420
```

| | |
|---|---|
| aaaagaatac caaaagaagg agcattttct aactcctcaa tcatcatatt acattcctgc | 33480 |
| accattccca gataatttc agcttttcag ccttgaatta ttcgtgtcag ttcttgtggt | 33540 |
| aaatccaatc cacacattac aaacaggtcc cggagggcgc cctccaccac cattcttaaa | 33600 |
| cacaccctca taatgacaaa atatcttgct cctgtgtcac ctgtagcgaa ttgagaatgg | 33660 |
| caacatcaat tgacatgccc ttggctctaa gttcttcttt aagttctagt tgtaaaaact | 33720 |
| ctctcatatt atcaccaaac tgcttagcca gaagccccc gggaacaaga gcagggacg | 33780 |
| ctacagtgca gtacaagcgc agacctcccc aattggctcc agcaaaaaca agattggaat | 33840 |
| aagcatattg ggaaccgcca gtaatatcat cgaagttgct ggaaatataa tcaggcagag | 33900 |
| tttcttgtaa aaattgaata aagaaaaat ttgccaaaaa aacattcaaa acctctggga | 33960 |
| tgcaaatgca ataggttacc gcgctgcgct ccaacattgt tagttttgaa ttagtctgca | 34020 |
| aaaataaaaa aaaaaacaag cgtcatatca tagtagcctg acgaacagat ggataaatca | 34080 |
| gtctttccat cacaagacaa gccacagggt ctccagctcg accctcgtaa aacctgtcat | 34140 |
| catgattaaa caacagcacc gaaagttcct cgcggtgacc agcatgaata attcttgatg | 34200 |
| aagcatacaa tccagacatg ttagcatcag ttaacgagaa aaaacagcca acatagcctt | 34260 |
| tgggtataat tatgcttaat cgtaagtata gcaaagccac ccctcgcgga tacaaagtaa | 34320 |
| aaggcacagg agaataaaaa atataattat ttctctgctg ctgttcaggc aacgtcgccc | 34380 |
| ccggtccctc taaatacaca tacaaagcct catcagccat ggcttaccag acaaagtaca | 34440 |
| gcgggcacac aaagcacaag ctctaaagtg actctccaac ctctccacaa tatatatata | 34500 |
| cacaagccct aaactgacgt aatgggagta aagtgtaaaa aatcccgcca aacccaacac | 34560 |
| acaccccgaa actgcgtcac cagggaaaag tacagtttca cttccgcaat cccaacaggc | 34620 |
| gtaacttcct ctttctcacg gtacgtgata tcccactaac ttgcaacgtc attttcccac | 34680 |
| ggtcgcaccg ccccttttag ccgttaaccc cacagccaat caccacacga tccacacttt | 34740 |
| ttaaaatcac ctcatttaca tattggcacc attccatcta taaggtatat tattgatgat | 34800 |
| g | 34801 |

<210> SEQ ID NO 8
<211> LENGTH: 873
<212> TYPE: DNA
<213> ORGANISM: Artificial Sequence
<220> FEATURE:
<223> OTHER INFORMATION: Fully synthetic

<400> SEQUENCE: 8

| | |
|---|---|
| atgagagatt tgcgatttct gcctcaggaa ataatctctg ctgagactgg aaatgaaata | 60 |
| ttggagcttg tggtgcacgc cctgatggga gacgatccgg agccacctgt gcagcttttt | 120 |
| gagcctccta cgcttcagga actgtatgat ttagaggtag agggatcgga ggattctaat | 180 |
| gaggaagctg taaatggctt ttttaccgat tctatgcttt tagctgctaa tgaagggtta | 240 |
| gaattagatc cgcctttgga cacttttgat actccagggg taattgtgga aagcggtaca | 300 |
| ggtgtaagaa aattacctga tttgagttcc gtggactgtg atttgcactg ctatgaagac | 360 |
| gggtttcctc cgagtgatga ggaggaccat gaaaaggagc agtccatgca gactgcagcg | 420 |
| ggtgagggag tgaaggctgc caatgttggt tttcagttgg attgcccgga gcttcctgga | 480 |
| catggctgta agtcttgtga atttcacagg aaaaatactg gagtaaagga actgttatgt | 540 |
| tcgctttgtt atatgagaac gcactgccac ctttatttaca gtaagtgtgt ttaagttaaa | 600 |

| | |
|---|---|
| atttaaagga atatgctgtt tttcacatgt atattgagtg tgagttttgt gcttcttatt | 660 |
| ataggtcctg tgtctgatgc tgatgaatca ccatctcctg attctactac ctcacctcct | 720 |
| gagattcaag cacctgttcc tgtggacgtg cgcaagccca ttcctgtgaa gcttaagcct | 780 |
| gggaaacgtc cagcagtgga aaaacttgag gacttgttac agggtgggga cggacctttg | 840 |
| gacttgagta cacggaaacg tccaagacaa taa | 873 |

```
<210> SEQ ID NO 9
<211> LENGTH: 543
<212> TYPE: DNA
<213> ORGANISM: Artificial Sequence
<220> FEATURE:
<223> OTHER INFORMATION: Fully synthetic

<400> SEQUENCE: 9
```

| | |
|---|---|
| atggaggttt gggccatttt ggaagacctt aggaagacta ggcaactgtt agagaacgct | 60 |
| tcggacggag tctccggttt ttggagattc tggttcgcta gtgaattagc tagggtagtt | 120 |
| tttaggataa acaggactg taaacaagaa tttgaaaagt tgttggtaga ttgcccagga | 180 |
| cttttgaag ctcttaattt gggccatcag gttcacttta agaaaaagt tttatcagtt | 240 |
| ttagacttt caaccccagg tagaactgct gctgctgtgg ctttcttac ttttatatta | 300 |
| gataaatgga tcccgcagac tcatttcagc aggggatacg ttttggattt catagccaca | 360 |
| gcattgtgga gaacatggaa ggttcgcaag atgaggacaa tcttaggtta ctggccagtg | 420 |
| cagcctttgg gtgtagcggg aatcctgagg catccaccgg tcatgccagc ggttctggag | 480 |
| gaggaacagc aagaggacaa cccgagagcc ggcctggacc ctccagtgga ggaggcggag | 540 |
| tag | 543 |

```
<210> SEQ ID NO 10
<211> LENGTH: 35541
<212> TYPE: DNA
<213> ORGANISM: Artificial Sequence
<220> FEATURE:
<223> OTHER INFORMATION: Fully synthetic

<400> SEQUENCE: 10
```

| | |
|---|---|
| catcatcaat aatataccct atagatggaa tggtgccaat atgtaaatga ggtgatttta | 60 |
| aaaagtgtgg atcgtgtggt gattggctgt ggggttaacg gctaaaaggg gcggtgcgac | 120 |
| cgtgggaaaa tgacgttttg tgggggtgga gttttttgc aagttgtcgc gggaaatgtg | 180 |
| acgcataaaa aggctacaca ggaagtgaca attttcgcgc ggttttaggc ggatgttgta | 240 |
| gtaaatttgg gcgtaaccga gtaagatttg gccattttcg cgggaaaact gaataagagg | 300 |
| aagtgaaatc tgaataattt tgtgttactc atagcgcgta atatttgtct agggccgcgg | 360 |
| ggactttgac cgtttacgtg tgtcaaggag cccaagtcgc ggggaagtgt tgcagggagg | 420 |
| cactccggga ggtccgcgt gcccgtccag ggagcaatgc gtcctcgggt tcgtccccag | 480 |
| ccgcgtctac gcgcctccgt cctccccttc acgtccggca ttcgtggtgc ccggagcccg | 540 |
| acgccccgcg tcggacctg aggcagccc tgggtctccg gatcaggcca gcggccaaag | 600 |
| ggtcgccgca cgcacctgtt cccagggcct ccacatcatg gcccctccct cgggttaccc | 660 |
| cacagcttag gccgattcga cctctctccg ctggggccct cgctggcgtc cctgcaccct | 720 |
| gggagcgcga gcgcgcgcg gcggggaag cgcggcccag accccgggt ccgcccggag | 780 |
| cagctgcgct gtcggggcca ggccgggctc ccagtggatt cgcgggcaca gacgcccagg | 840 |
| accgcgcttc ccacgtggcg gagggactgg ggacccgggc accgtcctg cccccttcacc | 900 |

```
ttccagctcc gcctcctccg cgcggacccc gccccgtccc gacccctccc gggtccccgg    960
cccagccccc tccgggccct cccagcccct cccttccttt tccgcggccc cgccctctcc   1020
tcgcggcgcg agtttcaggc agcgctgcgt cctgctgcgc acgtgggaag ccctggcccc   1080
ggccaccccc gcgatgagag atttgcgatt tctgcctcag gaaataatct ctgctgagac   1140
tggaaatgaa atattggagc ttgtggtgca cgccctgatg ggagacgatc cggagccacc   1200
tgtgcagctt tttgagcctc ctacgcttca ggaactgtat gatttagagg tagggatc     1260
ggaggattct aatgaggaag ctgtaaatgg ctttttacc gattctatgc ttttagctgc   1320
taatgaaggg ttagaattag atccgccttt ggacactttt gatactccag ggtaattgt    1380
ggaaagcggt acaggtgtaa gaaaattacc tgatttgagt tccgtggact gtgatttgca   1440
ctgctatgaa gacgggtttc ctccgagtga tgaggaggac catgaaaagg agcagtccat   1500
gcagactgca gcgggtgagg gagtgaaggc tgccaatgtt ggttttcagt tggattgccc   1560
ggagcttcct ggacatggct gtaagtcttg tgaatttcac aggaaaaata ctggagtaaa   1620
ggaactgtta tgttcgcttt gttatatgag aacgcactgc cactttattt acagtaagtg   1680
tgtttaagtt aaaatttaaa ggaatatgct gttttttcaca tgtatattga gtgtgagttt   1740
tgtgcttctt attataggtc ctgtgtctga tgctgatgaa tcaccatctc ctgattctac   1800
tacctcacct cctgagattc aagcaccgtgt tcctgtggac gtgcgcaagc ccattcctgt   1860
gaagcttaag cctgggaaac gtccagcagt ggaaaaactt gaggacttgt tacagggtgg   1920
ggacggacct ttggacttga gtacacggaa acgtccaaga caataagtgt tccatatccg   1980
tgtttactta aggtgacgtc aatatttgtg tgacagtgca atgtaataaa aatatgttaa   2040
ctgttcactg gttttattg cttttttgggc ggggactcag gtatataagt agaagcagac   2100
ctgtgtggtt agctcatagg agctggcttt catccatgga ggtttgggcc attttggaag   2160
accttaggaa gactaggcaa ctgttagaga acgcttcgga cggagtctcc ggttttggga   2220
gattctggtt cgctagtgaa ttagctaggg tagttttag gataaaacag gactataaac   2280
aagaatttga aaagttgttg gtagattgcc caggactttt tgaagctctt aatttgggcc   2340
atcaggttca ctttaaagaa aaagttttat cagttttaga ctttcaacc ccaggtagaa   2400
ctgctgctgc tgtggctttt cttacttta tattagataa atggatcccg cagactcatt   2460
tcagcagggg atacgttttg gatttcatag ccacagcatt gtggagaaca tggaaggttc   2520
gcaagatgag gacaatctta ggttactggc cagtgcagcc tttgggtgta gcgggaatcc   2580
tgaggcatcc accggtcatg ccagcggttc tggaggagga acagcaagag gacaacccga   2640
gagccggcct ggaccctcca gtggaggagg cggagtagct gacttgtctc ctgaactgca   2700
acgggtgctt actggatcta cgtccactgg acgggatagg ggcgttaaga gggagaggggc   2760
atctagtggt actgatgcta gatctgagtt ggctttaagt ttaatgagtc gcagacgtcc   2820
tgaaaccatt tggtggcatg aggttcagaa agagggaagg gatgaagttt ctgtattgca   2880
ggagaaatat tcactggaac aggtgaaaac atgttggttg gagcctgagg atgattggga   2940
ggtggccatt aaaaattatg ccaagatagc tttgaggcct gataaacagt ataagattac   3000
tagacggatt aatatccgga atgcttgtta catatctgga atggggctg aggtggtaat   3060
agatactcaa gacaaggcag ttattagatg ctgcatgatg atatgtggc ctggggtagt   3120
cggtatggaa gcagtaactt ttgtaaatgt taagttaggg ggagatggtt ataatggaat   3180
agtgtttatg gccaatacca aacttatatt gcatggttgt agctttttg gtttcaacaa   3240
```

```
tacctgtgta gatgcctggg gacaggttag tgtacgggga tgtagtttct atgcgtgttg    3300
gattgccaca gctggcagaa ccaagagtca attgtctctg aagaaatgca tatttcaaag    3360
atgtaacctg ggcattctga atgaaggcga agcaagggtc cgccactgcg cttctacaga    3420
tactggatgt tttattttga ttaagggaaa tgccagcgta aagcataaca tgatttgcgg    3480
tgcttccgat gagaggcctt atcaaatgct cacttgtgct ggtgggcatt gtaatatgct    3540
ggctactgtg catattgttt cccatcaacg caaaaaatgg cctgttttg atcacaatgt     3600
gatgacgaag tgtaccatgc atgcaggtgg gcgtagagga atgtttatgc cttaccagtg    3660
taacatgaat catgtgaaag tgttgttgga accagatgcc ttttccagaa tgagcctaac    3720
aggaattttt gacatgaaca tgcaaatctg gaagatcctg aggtatgatg atacgagatc    3780
gagggtacgc gcatgcgaat gcggaggcaa gcatgccagg ttccagccgg tgtgtgtaga    3840
tgtgactgaa gatctcagac cggatcattt ggttattgcc cgcactggag cagagttcgg    3900
atccagtgga gaagaaactg actaaggtga gtattgggaa aactttgggg tgggatttc     3960
agatggacag attgagtaaa aatttgtttt ttctgtcttg cagctgtcat gagtggaaac    4020
gcttctttta aggggggagt cttcagccct tatctgacag ggcgtctccc atcctgggca    4080
ggagttcgtc agaatgttat gggatctact gtggatggaa gacccgtcca acccgccaat    4140
tcttcaacgc tgacctatgc tactttaagt tcttcacctt tggacgcagc tgcagctgcc    4200
gccgccgctt ctgttgccgc taacactgtg cttggaatgg gttactatgg aagcatcatg    4260
gctaattcca cttcctctaa taaccttct accctgactc aggacaagtt acttgtcctt     4320
ttggcccagc tggaggcttt gacccaacgt ctgggtgaac tttctcagca ggtggtcgag    4380
ttgcgagtac aaactgagtc tgctgtcggc acggcaaagt ctaaataaaa aaatcccaga    4440
atcaatgaat aaataaacaa gcttgttgtt gatttaaaat caagtgtttt tatttcattt    4500
ttcgcgcacg gtatgcccta gaccaccgat ctctatcatt gagaactcgg tggattttt     4560
ccaggatcct atagaggtgg gattgaatgt ttagatacat gggcattagg ccgtctttgg    4620
ggtggagata gctccattga agggattcat gctccggggt agtgttgtaa atcacccagt    4680
cataacaagg tcgcagtgca tggtgttgca caatatcttt tagaagtagg ctgattgcca    4740
cagataagcc cttggtgtag gtgtttacaa accggttgag ctgggatggg tgcattcggg    4800
gtgaaattat gtgcattttg gattggattt ttaagttggc aatattgccg ccaagatccc    4860
gtcttgggtt catgttatga aggaccacca agacggtgta tccggtacat ttaggaaatt    4920
tatcgtgcag cttggatgga aaagcgtgga aaaatttgga gacacccttg tgtcctccaa    4980
gattttccat gcactcatcc atgataatag caatggggcc gtgggcagcg gcgcgggcaa    5040
acacgttccg tgggtctgac acatcatagt tatgttcctg agttaaatca tcataagcca    5100
ttttaatgaa tttggggcgg agagtaccag attggggtat gaatgttcct tcgggccccg    5160
gagcatagtt ccctcacag atttgcattt cccaagcttt cagttccgag ggtgaaatca    5220
tgtccacctg gggggctatg aaaaacaccg tttctggggc gggggtgatt aattgtgatg    5280
atagcaaatt tctgagcaat tgagatttgc cacatccggt ggggccataa atgattccga    5340
ttacgggttg caggtggtag tttagggaac ggcaactgcc gtcttctcga agcaaggggg    5400
ccacctcgtt catcatttcc cttacatgca tattttcccg caccaaatcc attaggaggc    5460
gctctcctcc tagtgataga agttcttgta gtgaggaaaa gttttcagc ggtttcagac     5520
cgtcagccat gggcatttg gagagagttt gctgcaaaag ttctagtctg ttccacagtt     5580
cagtgatgtg ttctatggca tctcgatcca gcagacctcc tcgtttcgcg ggtttggacg    5640
```

```
gctcctggaa tagggtatga gacgatgggc gtccagcgct gccagggttc ggtccttcca   5700
gggtctcagt gttcgagtca gggttgtttc cgtcacagtg aaggggtgtg cgcctgcttg   5760
ggcgcttgcc agggtgcgct tcagactcat cctgctggtc gaaaacttct gtcgcttggc   5820
gccctgtatg tcggccaagt agcagtttac catgagttcg tagttgagcg cctcggctgc   5880
gtggcctttg gcgcggagct tacctttgga agttttcttg cataccgggc agtataggca   5940
tttcagcgca tacaacttgg gcgcaaggaa aacggattct ggggagtatg catctgcgcc   6000
gcaggaggcg caaacagttt cacattccac cagccaggtt aaatccggtt cattggggtc   6060
aaaaacaagt tttccgccat attttttgat gcgtttctta cctttggtct ccatgagttc   6120
gtgtcctcgt tgagtgacaa acaggctgtc cgtgtccccg tagactgatt ttacaggcct   6180
cttctccagt ggagtgcctc ggtcttcttc gtacaggaac tctgaccact ctgatacaaa   6240
ggcgcgcgtc caggccagca caaggaggc tatgtgggag gggtagcgat cgttgtcaac   6300
cagggggtcc acctttttcca aagtatgcaa acacatgtca ccctcttcaa catccaggaa   6360
tgtgattggc ttgtaggtgt atttcacgtg acctgggtc cccgctgggg gggtataaaa   6420
gggggcggtt ctttgctctt cctcactgtc ttccggatcg ctgtccagga acgtcagctg   6480
ttggggtagg tattccctct cgaaggcggg catgacctct gcactcaggt tgtcagtttc   6540
taagaacgag gaggatttga tattgacagt gccggttgag atgccttttca tgaggttttc   6600
gtccatttgg tcagaaaaca caattttttt attgtcaagt ttggtggcaa atgatccata   6660
cagggcgttg gataaaagtt tggcaatgga tcgcatggtt tggttctttt ccttgtccgc   6720
gcgctctttg gcggcgatgt tgagttggac atactcgcgt gccaggcact tccattcggg   6780
gaagatagtt gttaattcat ctggcacgat tctcacttgc caccctcgat tatgcaaggt   6840
aattaaatcc acactggtgg ccacctcgcc tcgaaggggt tcattggtcc aacagagcct   6900
acctcctttc ctagaacaga aagggggaag tgggtctagc ataagttcat cgggagggtc   6960
tgcatccatg gtaaagattc ccggaagtaa atccttatca aaatagctga tgggagtggg   7020
gtcatctaag gccatttgcc attctcgagc tgccagtgcg cgctcatatg ggttaagggg   7080
actgccccat ggcatgggat gggtgagtgc agaggcatac atgccacaga tgtcatagac   7140
gtagatggga tcctcaaaga tgcctatgta ggttggatag catcgcccc ctctgatact   7200
tgctcgcaca tagtcatata gttcatgtga tggcgctagc agccccggac ccaagttggt   7260
gcgattgggt ttttctgttc tgtagacgat ctggcgaaag atggcgtgag aattggaaga   7320
gatggtgggt ctttgaaaaa tgttgaaatg ggcatgaggt agacctacag agtctctgac   7380
aaagtgggca taagattctt gaagcttggt taccagttcg gcggtgacaa gtacgtctag   7440
ggcgcagtag tcaagtgttt cttgaatgat gtcataacct ggttggtttt tcttttccca   7500
cagttcgcgg ttgagaaggt attcttcgcg atccttccag tactcttcta gcggaaaccc   7560
gtctttgtct gcacggtaag atcctagcat gtagaactga ttaactgcct tgtaagggca   7620
gcagcccttc tctacgggta gagagtatgc ttgagcagct tttcgtagcg aagcgtgagt   7680
aagggcaaag gtgtctctga ccatgacttt gagaaattgg tatttgaagt cgatgtcgtc   7740
acaggctccc tgttcccaga gttggaagtc tacccgtttc ttgtaggcgg ggttgggcaa   7800
agcgaaagta acatcattga agagaatctt accggctctg gcataaaaat tgcgagtgat   7860
gcgaaaaggc tgtggtactt ccgctcgatt gttgatcacc tggcagcta ggacgatctc   7920
gtcgaaaccg ttgatgttgt gtcctacgat gtataattct atgaaacgcg gcgtgcctct   7980
```

```
gacgtgaggt agcttactga gctcatcaaa ggttaggtct gtggggtcag ataaggcgta    8040
gtgttcgaga gcccattcgt gcaggtgagg atttgcatgt aggaatgatg accaaagatc    8100
taccgccagt gctgtttgta actggtcccg atactgacga aaatgccggc caattgccat    8160
tttttctgga gtgacacagt agaaggttct ggggtcttgt tgccatcgat cccacttgag    8220
tttaatggct agatcgtggg ccatgttgac gagacgctct tctcctgaga gtttcatgac    8280
cagcatgaaa ggaactagtt gtttgccaaa ggatcccatc caggtgtaag tttccacatc    8340
gtaggtcagg aagagtcttt ctgtgcgagg atgagagccg atcgggaaga actggatttc    8400
ctgccaccag ttggaggatt ggctgttgat gtgatggaag tagaagtttc tgcggcgcgc    8460
cgagcattcg tgtttgtgct tgtacagacg gccgcagtag tcgcagcgtt gcacgggttg    8520
tatctcgtga atgagttgta cctggcttcc cttgacgaga aatttcagtg ggaagccgag    8580
gcctggcgat tgtatctcgt gctcttctat attcgctgta tcggcctgtt catcttctgt    8640
ttcgatggtg gtcatgctga cgagcccccg cgggaggcaa gtccagacct cggcgcggga    8700
ggggcggagc tgaaggacga gagcgcgcag gctggagctg tccagagtcc tgagacgctg    8760
cggactcagg ttagtaggta gggacagaag attaacttgc atgatctttt ccagggcgtg    8820
cgggaggttc agatggtact tgatttccac aggttcgttt gtagagacgt caatggcttg    8880
cagggttccg tgtcctttgg gcgccactac cgtacctttg ttttttcttt tgatcggtgg    8940
tggctctctt gcttcttgca tgctcagaag cggtgacggg gacgcgcgcc gggcggcagc    9000
ggttgttccg gacccgaggg catggctggt agtggcacgt cggcgccgcg cacgggcagg    9060
ttctggtact gcgctctgag aagacttgcg tgcgccacca cgcgtcgatt gacgtcttgt    9120
atctgacgtc tctgggtgaa agctaccggc cccgtgagct tgaacctgaa agagagttca    9180
acagaatcaa tttcggtatc gttaacggca gcttgtctca gtatttcttg tacgtcacca    9240
gagttgtcct ggtaggcgat ctccgccatg aactgctcga tttcttcctc ctgaagatct    9300
ccgcgacccg ctctttcgac ggtggccgcg aggtcattgg agatacggcc catgagttgg    9360
gagaatgcat tcatgcccgc ctcgttccag acgcggctgt aaaccacggc cccctcggag    9420
tctcttgcgc gcatcaccac ctgagcgagg ttaagctcca cgtgtctggt gaagaccgca    9480
tagttgcata ggcgctgaaa aaggtagttg agtgtggtgg caatgtgttc ggcgacgaag    9540
aaatacatga tccatcgtct cagcggcatt tcgctaacat cgcccagagc ttccaagcgc    9600
tccatggcct cgtagaagtc cacggcaaaa ttaaaaaact gggagtttcg cgcggacacg    9660
gtcaattcct cctcgagaag acggatgagt tcggctatgg tggcccgtac ttcgcgttcg    9720
aaggctcccg ggatctcttc ttcctcttct atctcttctt ccactaacat ctcttcttcg    9780
tcttcaggcg ggggcggagg gggcacgcgc cgacgtcgac ggcgcacggg caaacggtcg    9840
atgaatcgtt caatgacctc tccgcggcgg cggcgcatgg tttcagtgac ggcgcggccg    9900
ttctcgcgcg gtcgcagagt aaaaacaccg ccgcgcatct ccttaaagtg gtgactggga    9960
ggttctccgt ttgggaggga gagggcgctg attatacatt ttattaattg gcccgtaggg    10020
actgcacgca gagatctgat cgtgtcaaga tccacgggat ctgaaaacct ttcgacgaaa    10080
gcgtctaacc agtcacagtc acaaggtagg ctgagtacgg cttcttgtgg gcggggtgg     10140
ttatgtgttc ggtctgggtc ttctgtttct tcttcatctc gggaaggtga gacgatgctg    10200
ctggtgatga aattaaagta ggcagttcta agacggcgga tggtggcgag gagcaccagg    10260
tcttttgggtc cggcttgctg gatacgcagg cgattggcca ttccccaagc attatcctga    10320
catctagcaa gatctttgta gtagtcttgc atgagccgtt ctacgggcac ttcttcctca    10380
```

```
cccgttctgc catgcatacg tgtgagtcca aatccgcgca ttggttgtac cagtgccaag   10440
tcagctacga ctctttcggc gaggatggct tgctgtactt gggtaagggt ggcttgaaag   10500
tcatcaaaat ccacaaagcg gtggtaagct cctgtattaa tggtgtaagc acagttggcc   10560
atgactgacc agttaactgt ctggtgacca gggcgcacga gctcggtgta tttaaggcgc   10620
gaataggcgc gggtgtcaaa gatgtaatcg ttgcaggtgc gcaccagata ctggtaccct   10680
ataagaaaat gcggcggtgg ttggcggtag agaggccatc gttctgtagc tggagcgcca   10740
ggggcgaggt cttccaacat aaggcggtga tagccgtaga tgtacctgga catccaggtg   10800
attcctgcgg cggtagtaga agcccgagga aactcgcgta cgcggttcca aatgttgcgt   10860
agcggcatga agtagttcat tgtaggcacg gtttgaccag tgaggcgcgc gcagtcattg   10920
atgctctata gacacggaga aaatgaaagc gttcagcgac tcgactccgt agcctggagg   10980
aacgtgaacg ggttgggtcg cggtgtaccc cggttcgaga cttgtactcg agccggccgg   11040
agccgcggct aacgtggtat tggcactccc gtctcgaccc agcctacaaa aatccaggat   11100
acggaatcga gtcgttttgc tggtttccga atggcaggga agtgagtcct attttttttt   11160
ttttgccgct cagatgcatc ccgtgctgcg acagatgcgc ccccaacaac agcccccctc   11220
gcagcagcag cagcagcaat cacaaaaggc tgtccctgca actactgcaa ctgccgccgt   11280
gagcggtgcg ggacagcccg cctatgatct ggacttggaa gagggcgaag gactggcacg   11340
tctaggtgcg ccttcacccg agcggcatcc gcgagttcaa ctgaaaaaag attctcgcga   11400
ggcgtatgtg ccccaacaga acctatttag agacagaagc ggcgaggagc cggaggagat   11460
gcgagcttcc cgctttaacg cgggtcgtga gctgcgtcac ggtttggacc gaagacgagt   11520
gttgcgggac gaggatttcg aagttgatga aatgacaggg atcagtcctg ccagggcaca   11580
cgtggctgca gccaaccttg tatcggctta cgagcagaca gtaaaggaag agcgtaactt   11640
ccaaaagtct tttaataatc atgtgcgaac cctgattgcc cgcgaagaag ttacccttgg   11700
tttgatgcat ttgtgggatt tgatggaagc tatcattcag aaccctacta gcaaacctct   11760
gaccgcccag ctgtttctgg tggtgcaaca cagcagagac aatgaggctt tcagagaggc   11820
gctgctgaac atcaccgaac ccgaggggag atggttgtat gatcttatca acattctaca   11880
gagtatcata gtgcaggagc ggagcctggg cctggccgag aaggtggctg ccatcaatta   11940
ctcggttttg agcttgggaa aatattacgc tcgcaaaatc tacaagactc catacgttcc   12000
catagacaag gaggtgaaga tagatggggtt ctacatgcgc atgacgctca aggtcttgac   12060
cctgagcgat gatcttgggg tgtatcgcaa tgacagaatg catcgcgcgg ttagcgccag   12120
caggaggcgc gagttaagcg acagggaact gatgcacagt ttgcaaagag ctctgactgg   12180
agctggaacc gagggtgaga attacttcga catgggagct gacttgcagt ggcagcctag   12240
tcgcagggct ctgagcgccg cgacggcagg atgtgagctt ccttacatag aagaggcgga   12300
tgaaggcgag gaggaagagg gcgagtactt ggaagactga tggcacaacc cgtgtttttt   12360
gctagatgga acagcaagca ccggatcccg caatgcgggc ggcgctgcag agccagccgt   12420
ccggcattaa ctcctcggac gattggaccc aggccatgca acgtatcatg gcgttgacga   12480
ctcgcaaccc cgaagccttt agacagcaac cccaggccaa ccgtctatcg gccatcatgg   12540
aagctgtagt gccttcccgc tctaatccca ctcatgagaa ggtcctggcc atcgtgaacg   12600
cgttggtgga gaacaaagct attcgtccag atgaggccgg actggtatac aacgctctct   12660
tagaacgcgt ggctcgctac aacagtagca atgtgcaaac caatttggac cgtatgataa   12720
```

```
cagatgtacg cgaagccgtg tctcagcgcg aaaggttcca gcgtgatgcc aacctgggtt   12780
cgctggtggc gttaaatgct ttcttgagta ctcagcctgc taatgtgccg cgtggtcaac   12840
aggattatac taacttttta agtgctttga gactgatggt atcagaagta cctcagagcg   12900
aagtgtatca gtccggtcct gattacttct ttcagactag cagacagggc ttgcagacgg   12960
taaatctgag ccaagctttt aaaaaccttaa aaggtttgtg gggagtgcat gccccggtag   13020
gagaaagagc aaccgtgtct agcttgttaa ctccgaactc ccgcctatta ttactgttgg   13080
tagctccttt caccgacagc ggtagcatcg accgtaattc ctatttgggt tacctactaa   13140
acctgtatcg cgaagccata gggcaaagtc aggtggacga gcagacctat caagaaatta   13200
cccaagtcag tcgcgctttg ggacaggaag acactggcag tttggaagcc actctgaact   13260
tcttgcttac caatcggtct caaaagatcc ctcctcaata tgctcttact gcggaggagg   13320
agaggatcct tagatatgtg cagcagagcg tgggattgtt tctgatgcaa gaggggggcaa   13380 ctccgactgc agcactggac atgacagcgc gaaatatgga gcccagcatg tatgccagta   13440
accgaccttt cattaacaaa ctgctggact acttgcacag agctgccgct atgaactctg   13500
attatttcac caatgccatc ttaaacccgc actggctgcc cccacctggt ttctacacgg   13560
gcgaatatga catgcccgac cctaatgacg gatttctgtg ggacgacgtg gacagcgatg   13620
ttttttcacc tctttctgat catcgcacgt ggaaaaagga aggcggcgat agaatgcatt   13680
cttctgcatc gctgtccggg gtcatgggtg ctaccgcggc tgagcccgag tctgcaagtc   13740 ctttttcctag tctacccttt tctctacaca gtgtacgtag cagcgaagtg ggtagaataa   13800
gtcgcccgag tttaatgggc gaagaggagt atctaaacga ttccttgctc agaccggcaa   13860
gagaaaaaaa tttcccaaac aatggaatag aaagtttggt ggataaaatg agtagatgga   13920
agacttatgc tcaggatcac agagacgagc ctgggatcat ggggattaca agtagagcga   13980
gccgtagacg ccagcgccat gacagacaga ggggtcttgt gtgggacgat gaggattcgg   14040
ccgatgatag cagcgtgctg gacttgggtg ggagaggaag gggcaacccg tttgctcatt   14100
tgcgccctcg cttgggtggt atgttgtaaa aaaaaataaa aaaaaaactc accaaggcca   14160
tggcgacgag cgtacgttcg ttcttctta ttatctgtgt ctagtataat gaggcgagtc   14220
gtgctaggcg gagcggtggt gtatccggag ggtcctcctc cttcgtacga gagcgtgatg   14280
cagcagcagc aggcgacggc ggtgatgcaa tccccactgg aggctccctt tgtgcctccg   14340
cgatacctgg cacctacgga gggcagaaac agcattcgtt attcggaact ggcacctcag   14400
tacgatacca ccaggttgta tctggtggac aacaagtcgg cggacattgc ttctctgaac   14460
tatcagaatg accacagcaa cttcttgacc acggtggtgc aaaacaatga ctttaccccct   14520 acggaagcca gcacccagac cattaacttt gatgaacgat cgcggtgggg cggtcagcta   14580
aagaccatca tgcatactaa catgccaaac gtgaacgagt atatgtttag taacaagttc   14640
aaagcgcgtg tgatggtgtc cagaaaacct cccgacggtg ctgcagttgg ggatacttat   14700
gatcacaagc aggatatttt gaaatatgag tggttcgagt ttacttttgcc agaaggcaac   14760 ttttcagtta ctatgactat tgatttgatg aacaatgcca tcatagataa ttacttgaaa   14820
gtgggtagac agaatggagt gcttgaaagt gacattggtg ttaagttcga caccaggaac   14880
ttcaagctgg gatgggatcc cgaaaccaag ttgatcatgc ctggagtgta tacgtatgaa   14940
gccttccatc ctgacattgt cttactgcct ggctgcggag tggattttac cgagagtcgt   15000
ttgagcaacc ttcttggtat cagaaaaaaa cagccatttc aagagggttt taagattttg   15060
tatgaagatt tagaaggtgg taatattccg gccctcttgg atgtagatgc ctatgagaac   15120
```

```
agtaagaaag aacaaaaagc caaaatagaa gctgctacag ctgctgcaga agctaaggca   15180
aacatagttg ccagcgactc tacaagggtt gctaacgctg gagaggtcag aggagacaat   15240
tttgcgccaa cacctgttcc gactgcagaa tcattattgg ccgatgtgtc tgaaggaacg   15300
gacgtgaaac tcactattca acctgtagaa aagatagta agaatagaag ctataatgtg    15360
ttggaagaca aaatcaacac agcctatcgc agttggtatc tttcgtacaa ttatggcgat   15420
cccgaaaaag gagtgcgttc ctggacattg ctcaccacct cagatgtcac ctgcggagca   15480
gagcaggtct actggtcgct tccagacatg atgaaggatc ctgtcacttt ccgctccact   15540
agacaagtca gtaactaccc tgtggtgggt gcagagctta tgcccgtctt ctcaaagagc   15600
ttctacaacg aacaagctgt gtactcccag cagctccgcc agtccacctc gcttacgcac   15660
gtcttcaacc gctttcctga gaaccagatt ttaatccgtc cgccggcgcc caccattacc   15720
accgtcagtg aaaacgttcc tgctctcaca gatcacggga ccctgccgtt gcgcagcagt   15780
atccggggag tccaacgtgt gaccgttact gacgccagac gccgcacctg tccctacgtg   15840
tacaaggcac tgggcatagt cgcaccgcgc gtccttttcaa gccgcacttt ctaaaaaaaa   15900
aaaaaatgtc cattcttatc tcgcccagta ataacaccgg ttggggtctg cgcgctccaa   15960
gcaagatgta cggaggcgca cgcaaacgtt ctacccaaca tcctgtccgt gttcgcggac   16020
attttcgcgc tccatggggc gccctcaagg gccgcactcg cgttcgaacc accgtcgatg   16080
atgtaatcga tcaggtggtt gccgacgccc gtaattatac tcctactgcg cctacatcta   16140
ctgtggatgc agttattgac agtgtagtgg ctgacgctcg caactatgct cgacgtaaga   16200
gccggcgaag gcgcattgcc agacgccacc gagctaccac tgccatgcga gccgcaagag   16260
ctctgctacg aagagctaga cgcgtggggc gaagagccat gcttagggcg ccagacgtg    16320 cagcttcggg cgccagcgcc ggcaggtccc gcaggcaagc agccgctttc gcagcggcga   16380
ctattgccga catggcccaa tcgcgaagag gcaatgtata ctgggtgcgt gacgctgcca   16440
ccggtcaacg tgtacccgtg cgcacccgtc cccctcgcac ttagaagata ctgagcagtc   16500
tccgatgttg tgtcccagcg gcgaggatgt ccaagcgcaa atacaaggaa gaaatgctgc   16560
aggttatcgc acctgaagtc tacggccaac cgttgaagga tgaaaaaaaa ccccgcaaaa   16620
tcaagcgggt taaaaaggac aaaaaagaag aggaagatgg cgatgatggg ctggcggagt   16680
ttgtgcgcga gtttgcccca cggcgacgcg tgcaatggcg tgggcgcaaa gttcgacatg   16740
tgttgagacc tggaacttcg gtggtctttta cacccggcga gcgttcaagc gctacttta   16800 agcgttccta tgatgaggtg tacggggatg atgatattct tgagcaggcg gctgaccgat   16860
taggcgagtt tgcttatggc aagcgtagta gaataacttc caaggatgag acagtgtcga   16920
tacccttgga tcatggaaat cccaccccta gtcttaaacc ggtcactttg cagcaagtgt   16980
tacccgtaac tccgcgaaca ggtgttaaac gcgaaggtga agatttgtat cccactatgc   17040
aactgatggt acccaaacgc cagaagttgg aggacgtttt ggagaaagta aagtggatc    17100 cagatattca acctgaggtt aaagtgagac ccattaagca ggtagcgcct ggtctggggg   17160
tacaaactgt agacattaag attcccactg aaagtatgga agtgcaaact gaacccgcaa   17220
agcctactgc cacctccact gaagtgcaaa cggatccatg gatgcccatg cctattacaa   17280
ctgacgccgc cggtcccact cgaagatccc gacgaaagta cggtccagca agtctgttga   17340
tgcccaatta tgttgtacac ccatctatta ttcctactcc tggttaccga ggcactcgct   17400
actatcgcag ccgaaacagt acctcccgcc gtcgccgcaa gacacctgca aatcgcagtc   17460
```

```
gtcgccgtag acgcacaagc aaaccgactc ccggcgccct ggtgcggcaa gtgtaccgca    17520
atggtagtgc ggaacctttg acactgccgc gtgcgcgtta ccatccgagt atcatcactt    17580
aatcaatgtt gccgctgcct ccttgcagat atggccctca cttgtcgcct tcgcgttccc    17640
atcactggtt accgaggaag aaactcgcgc cgtagaagag ggatgttggg acgcggaatg    17700
cgacgctaca ggcgacggcg tgctatccgc aagcaattgc ggggtggttt tttaccagcc    17760
ttaattccaa ttatcgctgc tgcaattggc gcgataccag gcatagcttc cgtgcggtt    17820
caggcctcgc aacgacattg acattggaaa aaaacgtata aataaaaaaa aaaaaataca    17880
atggactctg acactcctgg tcctgtgact atgttttctt agagatggaa gacatcaatt    17940
tttcatcctt ggctccgcga cacggcacga agccgtacat gggcacctgg agcgacatcg    18000
gcacgagcca actgaacggg ggcgccttca attggagcag tatctggagc gggcttaaaa    18060
attttggctc aaccataaaa acatacggga acaaagcttg gaacagcagt acaggacagg    18120
cgcttagaaa taaacttaaa gaccagaact tccaacaaaa agtagtcgat gggatagctt    18180
ccggcatcaa tggagtggta gatttggcta accaggctgt gcagaaaaag ataaacagtc    18240
gtttggaccc gccgccagca accccaggtg aaatgcaagt ggaggaagaa attcctccgc    18300
cagaaaaacg aggcgacaag cgtccgcgtc ccgatttgga agagacgctg gtgacgcgcg    18360
tagatgaacc gccttcttat gaggaagcaa cgaagcttgg aatgcccacc actagaccga    18420
tagccccaat ggccaccggg gtgatgaaac cttctcagtt gcatcgaccc gtcaccttgg    18480
atttgccccc tccccctgct gctactgctg tacccgcttc taagcctgtc gctgccccga    18540
aaccagtcgc cgtagccagg tcacgtcccg ggggcgctcc tcgtccaaat gcgcactggc    18600
aaaatactct gaacagcatc gtgggtctag gcgtgcaaag tgtaaaacgc cgtcgctgct    18660
tttaattaaa tatggagtag cgcttaactt gccatctgt gtatatgtgt cattacacgc    18720
cgtcacagca gcagaggaaa aaaggaagag gtcgtgcgtc gacgctgagt tactttcaag    18780
atggccaccc catcgatgct gccccaatgg gcatacatgc acatcgccgg acaggatgct    18840
tcggagtacc tgagtccggg tctggtgcag ttcgcccgcg ccacagacac ctacttcaat    18900
ctgggaaata agtttagaaa tcccaccgta gcgccgaccc acgatgtgac caccgaccgt    18960
agccagcggc tcatgttgcg cttcgtgccc gttgaccggg aggacaatac atactcttac    19020
aaagtgcggt cacccctggc cgtgggcgac aacagagtgc tggatatggc cagcacgttc    19080
tttgacatta ggggtgtgtt ggacagaggt cccagtttca acccctattc tggtacggct    19140
tacaactccc tggctcctaa aggcgctcca aatacatctc agtggattgc agaaggtgta    19200
aaaaatacaa ctggtgagga acacgtaaca gaagaggaaa ccaatactac tacttacact    19260
tttggcaatg ctcctgtaaa agctgaagct gaaattacaa agaaggact cccagtaggt    19320
ttggaagttt cagatgaaga agtaaaccg atttatgctg ataaaacata tcagccagaa    19380
cctcagctgg gagatgaaac ttggactgac cttgatggaa aaaccgaaaa gtatggaggc    19440
agggctctca aacccgatac taagatgaaa ccatgctacg ggtcctttgc caaacctact    19500
aatgtgaaag gcggtcaggc aaaacaaaaa acaacggagc agccaaatca gaaagtcgaa    19560
tatgatatcg acatggagtt ttttgatgcg gcatcgcaga aaacaaactt aagtcctaaa    19620
attgtcatgt atgcagaaaa tgtaaatttg gaaactccag acactcatgt agtgtacaaa    19680
cctggaacag aagacacaag ttccgaagct aatttgggac aacaatctat gccaacaga    19740
cccaactaca ttggcttcag agataacttt attggactta tgtactataa cagtactggt    19800
aacatggggg tgctggctgg tcaagcgtct cagttaaatg cagtggttga cttgcaggac    19860
```

```
agaaacacag aactttctta ccaactcttg cttgactctc tgggcgacag aaccagatac   19920
tttagcatgt ggaatcaggc tgtggacagt tatgatcctg atgtacgtgt tattgaaaat   19980
catggtgtgg aagatgaact tcccaactac tgttttccac tggacggcat aggtgttcca   20040
acaaccagtt acaaatcaat agttccaaat ggagacaatg cgcctaattg gaaggaacct   20100
gaagtaaatg gaacaagtga gatcggacag ggtaatttgt ttgccatgga aattaacctt   20160
caagccaatc tatggcgaag tttcctttat tccaatgtgg ctctatatct cccagactcg   20220
tacaaataca ccccgtccaa tgtcactctt ccagaaaaca aaacaccta cgactacatg   20280 aacgggcggg tggtgccgcc atctctagta gacacctatg tgaacattgg tgccaggtgg   20340
tctctggatg ccatggacaa tgtcaaccca ttcaaccacc accgtaacgc tggcttgcgt   20400
taccgatcca tgcttctggg taacggacgt tatgtgcctt tccacataca agtgcctcaa   20460
aaattcttcg ctgttaaaaa cctgctgctt ctcccaggct cctacactta tgagtggaac   20520
tttaggaagg atgtgaacat ggttctacag agttccctcg gtaacgacct gcgggtagat   20580
ggcgccagca tcagtttcac gagcatcaac ctctatgcta cttttttccc catggctcac   20640
aacaccgctt ccaccttga agccatgctg cggaatgaca ccaatgatca gtcattcaac   20700
gactacctat ctgcagctaa catgctctac cccattcctg ccaatgcaac caatattccc   20760
atttccattc cttctcgcaa ctgggcggct ttcagaggct ggtcatttac cagactgaaa   20820
accaaagaaa ctccctcttt ggggtctgga tttgacccct actttgtcta ttctggttct   20880
attccctacc tggatggtac cttctacctg aaccacactt ttaagaaggt ttccatcatg   20940
tttgactctt cagtgagctg gcctggaaat gacaggttac tatctcctaa cgaatttgaa   21000
ataaagcgca ctgtggatgg cgaaggctac aacgtagccc aatgcaacat gaccaaagac   21060
tggttcttgg tacagatgct cgccaactac aacatcggct atcagggctt ctacattcca   21120
gaaggataca aagatcgcat gtattcattt ttcagaaact tccagcccat gagcaggcag   21180
gtggttgatg aggtcaatta caaagacttc aaggccgtcg ccatacccta ccaacacaac   21240
aactctggct ttgtgggtta catggctccg accatgcgcc aaggtcaacc ctatcccgct   21300
aactatccct atccactcat ggaacaact gccgtaaata tgttacgca gaaaaagttc   21360 ttgtgtgaca gaaccatgtg gcgcataccg ttctcgagca acttcatgtc tatggggcc   21420 cttacagact tgggacagaa tatgctctat gccaactcag ctcatgctct ggacatgacc   21480
tttgaggtgg atcccatgga tgagcccacc ctgctttatc ttctcttcga agttttcgac   21540
gtggtcagag tgcatcagcc acaccgcggc atcatcgagg cagtctacct gcgtacaccg   21600
ttctcggccg gtaacgctac cacgtaagaa gcttcttgct tcttgcaaat agcagctgca   21660
accatggcct gcggatccca aaacggctcc agcgagcaag agctcagagc cattgtccaa   21720
gacctgggtt gcggacccta ttttttggga acctacgata gcgcttccc ggggttcatg   21780 gcccccgata agctcgcctg tgccattgta aatacggccg gacgtgagac gggggggagag   21840 cactggttgg ctttcggttg gaacccacgt tctaacacct gctacctttt tgatccttt   21900 ggattctcgg atgatcgtct caaacagatt taccagtttg aatatgaggg tctcctgcgc   21960
cgcagcgctc ttgctaccaa ggaccgctgt attacgctgg aaaaatctac ccagaccgtg   22020
cagggtcccc gttctgccgc ctgcggactt ttctgctgca tgttccttca cgcctttgtg   22080
cactggcctg accgtcccat ggacggaaac cccaccatga aattgctaac tggagtgcca   22140
aacaacatgc ttcattctcc taaagtccag cccaccctgt gtgacaatca aaaagcactc   22200
```

```
taccattttc ttaatacccca ttcgccttat tttcgctccc atcgtacaca catcgaaagg    22260
gccactgcgt tcgaccgtat ggatgttcaa taatgactca tgtaaacaac gtgttcaata    22320
aacatcactt tatttttta catgtatcaa ggctctgcat tacttattta tttacaagtc    22380
gaatgggttc tgacgagaat cagaatgacc cgcaggcagt gatacgttgc ggaactgata    22440
cttgggttgc cacttgaatt cgggaatcac caacttggga accggtatat cgggcaggat    22500
gtcactccac agctttctgg tcagctgcaa agctccaagc aggtcaggag ccgaaatctt    22560
gaaatcacaa ttaggaccag tgctttgagc gcgagagttg cggtacaccg gattgcagca    22620
ctgaaacacc atcagcgacg gatgtctcac gcttgccagc acggtgggat ctgcaatcat    22680
gcccacatcc agatcttcag cattggcaat gctgaacggg gtcatcttgc aggtctgcct    22740
acccatggcg ggcacccaat taggcttgtg gttgcaatcg cagtgcaggg ggatcagtat    22800
catcttggcc tgatcctgtc tgattcctgg atacacggct ctcatgaaag catcatattg    22860
cttgaaagcc tgctgggctt tactaccctc ggtataaaac atcccgcagg acctgctcga    22920
aaactggtta gctgcacagc cggcatcatt cacacagcag cgggcgtcat tgttagctat    22980
ttgcaccaca cttctgcccc agcggttttg ggtgattttg gttcgctcgg gattctcctt    23040
taaggctcgt tgtccgttct cgctggccac atccatctcg ataatctgct ccttctgaat    23100
cataatattg ccatgcaggc acttcagctt gccctcataa tcattgcagc catgaggcca    23160
caacgcacag cctgtacatt cccaattatg gtgggcgatc tgagaaaaag aatgtatcat    23220
tccctgcaga aatcttccca tcatcgtgct cagtgtcttg tgactagtga aagttaactg    23280
gatgcctcgg tgctcctcgt ttacgtactg gtgacagatg cgcttgtatt gttcgtgttg    23340
ctcaggcatt agtttaaaag aggttctaag ttcgttatcc agcctgtact tctccatcag    23400
cagacacatc acttccatgc ctttctccca agcagacacc aggggcaagc taatcggatt    23460
cttaacagtg caggcagcag ctcctttagc cagagggtca tctttagcga tcttctcaat    23520
gcttcttttg ccatccttct caacgatgcg cacgggcggg tagctgaaac ccactgctac    23580
aagttgcgcc tcttctcttt cttcttcgct gtcttgactg atgtcttgca tggggatatg    23640
tttggtcttc cttggcttct tttgggggg tatcggagga ggaggactgt cgctccgttc    23700
cggagacagg gaggattgtg acgtttcgct caccattacc aactgactgt cggtagaaga    23760
acctgacccc acacggcgac aggtgtttct cttcggggc agaggtggag gcgattgcga    23820
agggctgcgg tccgacctgg aaggcggatg actggcagaa ccccttccgc gttcggggt    23880 gtgctccctg tggcggtcgc ttaactgatt tccttgcgg ctggccattg tgttctccta    23940
ggcagagaaa caacagacat ggaaactcag ccattgctgt caacatcgcc acgagtgcca    24000
tcacatctcg tcctcagcga cgaggaaaag gagcagagct taagcattcc accgcccagt    24060
cctgccacca cctctaccct agaagataag gaggtcgacg catctcatga catgcagaat    24120 aaaaagcga aagagtctga gacagacatc gagcaagacc cgggctatgt gacaccggtg    24180
gaacacgagg aagagttgaa acgctttcta gagagagagg atgaaaactg cccaaaacaa    24240
cgagcagata actatcacca agatgctgga ataggatc agaacaccga ctacctcata    24300
gggcttgacg gggaagacgc gctccttaaa catctagcaa gacagtcgct catagtcaag    24360
gatgcattat tggacagaac tgaagtgccc atcagtgtgg aagagctcag ccgcgcctac    24420
gagcttaacc tcttttcacc tcgtactccc cccaaacgtc agccaaacgg cacctgcgag    24480
ccaaatcctc gcttaaactt ttatccagct tttgctgtgc cagaagtact ggctaccat    24540 cacatctttt ttaaaaatca aaaaattcca gtctcctgcc gcgctaatcg cacccgcgcc    24600
```

```
gatgccctac tcaatctggg acctggttca cgcttacctg atatagcttc cttggaagag  24660
gttccaaaga tcttcgaggg tctgggcaat aatgagactc gggccgcaaa tgctctgcaa  24720
aagggagaaa atggcatgga tgagcatcac agcgttctgg tggaattgga aggcgataat  24780
gccagactcg cagtactcaa gcgaagcatc gaggtcacac acttcgcata tcccgctgtc  24840
aacctgcccc ctaaagtcat gacggcggtc atggaccagt tactcattaa gcgcgcaagt  24900
cccctttcag aagacatgca tgacccagat gcctgtgatg agggtaaacc agtggtcagt  24960
gatgagcagc taacccgatg gctgggcacc gactctccca gggatttgga agagcgtcgc  25020
aagcttatga tggccgtggt gctggttacc gtagaactag agtgtctccg acgtttcttt  25080
accgattcag aaaccttgcg caaactcgaa gagaatctgc actacacttt tagacacggc  25140
tttgtgcggc aggcatgcaa gatatctaac gtggaactca ccaacctggt ttcctacatg  25200
ggtattctgc atgagaatcg cctaggacaa agcgtgctgc acagcaccct gaagggggaa  25260
gcccgccgtg attacatccg cgattgtgtc tatctgtacc tgtgccaaac gtggcaaacc  25320
ggcatgggtg tatggcagca atgtttagaa gaacagaact gaaagagct tgacaagctc  25380 ttacagaaat ctcttaaggt tctgtggaca gggttcgacg agcgcaccgt cgcttccgac  25440
ctggcagacc tcatcttccc agagcgtctc agggttactt tgcgaaacgg attgcctgac  25500
tttatgagcc agagcatgct taacaatttt cgctctttca tcctggaacg ctccggtatc  25560
ctgcccgcca cctgctgcgc actgccctcc gactttgtgc ctctcaccta ccgcgagtgc  25620
cccccgccgc tatggagtca ctgctacctg ttccgtctgg ccaactatct ctcctaccac  25680
tcggatgtga tcgaggatgt gagcggagac ggcttgctgg agtgtcactg ccgctgcaat  25740
ctgtgcacgc cccaccggtc cctagcttgc aaccccagt tgatgagcga aacccagata  25800
ataggcacct ttgaattgca aggccccagc agccaaggcg atgggtcttc tcctgggcaa  25860
agtttaaaac tgaccccggg actgtggacc tccgcctact tgcgcaagtt tgctccggaa  25920
gattaccacc cctatgaaat caagttctat gaggaccaat cacagcctcc aaaggccgaa  25980
ctttcggcct cgtcatcac ccaggggca attctggccc aattgcaagc catccaaaaa  26040
tcccgccaag aatttctact gaaaaagggt aaggggtct accttgaccc ccagaccggc  26100
gaggaactca acacaaggtt ccctcaggat gtcccaacga cgagaaaaca agaagttgaa  26160
ggtgcagccg ccgcccccag aagatatgga ggaagattgg gacagtcagg cagaggaggc  26220
ggaggaggac agtctggagg acagtctgga ggaagacagt ttggaggagg aaaacgagga  26280
ggcagaggag gtgaagaag taaccgccga caaacagtta tcctcggctg cggagacaag  26340
caacagcgct accatctccg ctccgagtcg aggaacccgg cggcgtccca gcagtagatg  26400
ggacgagacc ggacgcttcc cgaacccaac cagcgcttcc aagaccggta agaaggatcg  26460
gcagggatac aagtcctggc gggggcataa gaatgccatc atctcctgct tgcatgagtg  26520
cgggggcaac atatccttca cgcggcgcta cttgctattc caccatgggg tgaactttcc  26580
gcgcaatgtt ttgcattact accgtcacct ccacagcccc tactatagcc agcaaatccc  26640
ggcagtctcg acagataaag acagcggcgg cgacctccaa cagaaaacca gcagcggcag  26700
ttagaaaata cacaacaagt gcagcaacag gaggattaaa gattacagcc aacgagccag  26760
cgcaaacccg agagttaaga aatcggatct ttccaaccct gtatgccatc ttccagcaga  26820 gtcgggtca agagcaggaa ctgaaaataa aaaaccgatc tctgcgttcg ctcaccagaa  26880
gttgtttgta tcacaagagc gaagatcaac ttcagcgcac tctcgaggac gccgaggctc  26940
```

```
tcttcaacaa gtactgcgcg ctgactctta aagagtaggc agcgaccgcg cttattcaaa   27000
aaaggcggga attacatcat cctcgacatg agtaaagaaa ttcccacgcc ttacatgtgg   27060
agttatcaac cccaaatggg attggcggca ggcgcctccc aggactactc cacccgcatg   27120
aattggctca gcgccgggcc ttctatgatt tctcgagtta atgatatacg cgcctaccga   27180
aaccaaatac ttttggaaca gtcagctctt accaccacgc cccgccaaca ccttaatccc   27240
agaaattggc ccgccgccct agtgtaccag gaaagtcccg ctcccaccac tgtattactt   27300
cctcgagacg cccaggccga agtccaaatg actaatgcag gtgcgcagtt agctggcggc   27360 tccacccctat gtcgtcacag gcctcggcat aatataaaac gcctgatgat cagaggccga   27420
ggtatccagc tcaacgacga gtcggtgagc tctccgcttg gtctacgacc agacggaatc   27480
tttcagattg ccggctgcgg gagatcttcc ttcacccctc gtcaggctgt tctgactttg   27540
gaaagttcgt cttcgcaacc ccgctcgggc ggaatcggga ccgttcaatt tgtggaggag   27600
tttactccct ctgtctactt caaccccttc tccggatctc ctgggcatta cccggacgag   27660
ttcataccga acttcgacgc gattagcgag tcagtggacg gctacgattg atgtctggtg   27720
acgcggctga gctatctcgg ctgcgacatc tagaccactg ccgccgcttt cgctgctttg   27780
cccgggaact cattgagttc atctacttcg aactccccaa ggatcaccct caaggtccgg   27840
cccacggagt gcggatttct atcgaaggca aaatagactc tcgcctgcaa cgaattttct   27900
cccagcggcc cgtgctgatc gagcgagacc agggaaacac cacggttttcc atctactgca   27960 tttgtaatca ccccggattg catgaaagcc tttgctgtct tatgtgtact gagtttaata   28020
aaaactgaat taagactctc ctacggactg ccgcttcttc aacccggatt ttacaaccag   28080
aagaacgaaa cttttcctgt cgtccaggac tctgttaact tcaccttttcc tactcacaaa   28140 ctagaagctc aacgactaca ccgcttttcc agaagcattt tccctactaa tactactttc   28200
aaaaccggag gtgagctcca aggtcttcct acagaaaacc cttgggtgga agcgggcctt   28260
gtagtgctag gaattcttgc gggtgggctt gtgattattc tttgctacct atacacacct   28320
tgcttcactt tcttagtggt gttgtggtat tggtttaaaa aatatggtga gcaagggcga   28380
ggagctgttc accggggtgg tgcccatcct ggtcgagctg gacggcgacg taaacggcca   28440
caagttcagc gtgtccggcg agggcgaggg cgatgccacc tacggcaagc tgaccctgaa   28500
gttcatctgc accaccggca agctgcccgt gccctggccc accctcgtga ccaccctgac   28560
ctacggcgtg cagtgcttca gccgctaccc cgaccacatg aagcagcacg acttcttcaa   28620
gtccgccatg cccgaaggct acgtccagga gcgcaccatc ttcttcaagg acgacggcaa   28680
ctacaagacc cgcgccgagg tgaagttcga gggcgacacc ctggtgaacc gcatcgagct   28740
gaagggcatc gacttcaagg aggacggcaa catcctgggg cacaagctgg agtacaacta   28800
caacagccac aacgtctata tcatggccga caagcagaag aacggcatca aggtgaactt   28860
caagatccgc cacaacatcg aggacggcag cgtgcagctc gccgaccact accagcagaa   28920
caccccatcg gcgacggcc ccgtgctgct gcccgacaac cactacctga gcacccagtc   28980
cgccctgagc aaagacccca acgagaagcg cgatcacatg gtcctgctgg agttcgtgac   29040
cgccgccggg atcactctcg gcatggacga gctgtacaag taacctcttt ctgtttacag   29100
acatggcttc tcttacatct ctcatatttg tcagcattgt cactgccgct catggacaaa   29160
cagtcgtctc tatccctcta ggacataatt acactctcat aggaccccca atcacttcag   29220
aggtcatctg ggccaaactg ggaagcgttg attactttga tataatcgc aacaaaacaa   29280 aaccaataat agtaacttgc aacatacaaa atcttacatt gattaatgtt agcaaagttt   29340
```

```
acagcggtta ctattatggt tatgacagat acagtagtca atatagaaat tacttggttc   29400
gtgttaccca gttgaaaacc acgaaaatgc caaatatggc aaagattcga tccgatgaca   29460
attctctaga aacttttaca tctcccacca cacccgacga aaaaaacatc ccagattcaa   29520
tgattgcaat tgttgcagcg gtggcagtgg tgatggcact aataataata tgcatgcttt   29580
tatatgcttg tcgctacaaa aagtttcatc ctaaaaaaca agatctccta ctaaggctta   29640
acatttaatt tcttttata cagccatggt ttccactacc acattcctta tgcttactag   29700
tctcgcaact ctgacttctg ctcgctcaca cctcactgta actataggct caaactgcac   29760
actaaaagga cctcaaggtg gtcatgtctt tggtggaga atatatgaca atggatggtt   29820
tacaaaacca tgtgaccaac ctggtagatt tttctgcaac ggcagagacc taaccattat   29880
caacgtgaca gcaaatgaca aaggcttcta ttatggaacc gactataaaa gtagtttaga   29940
ttataacatt attgtactgc catctaccac tccagcaccc cgcacaacta ctttctctag   30000
cagcagtgtc gctaacaata caattccaa tccaaccttt gccgcgcttt taaaacgcac   30060
tgtgaataat tctacaactt cacatacaac aatttccact caacaatca gcattatcgc   30120
tgcagtgaca attggaatat ctattcttgt ttttaccata acctactacg cctgctgcta   30180
tagaaaagac aaacataaag gtgatccatt acttagattt gatatttaat tgttcttttt   30240
tttttttatt tacagtatgg tgaacaccaa tcatggtacc tagaaatttc ttcttcacca   30300
tactcatttg tgcattaat gtttgcgcta ctttcacagc agtagccaca gcaaccccag   30360
actgtatagg agcattgct tcctatgcac ttttgcttt tgttacttgc atctgcgtat   30420
gtagcatagt ctgcctggtt attaattttt tccaacttat agactggatc cttgtgcgaa   30480
ttgcctacct gcgccaccat cccgaatacc gcaaccaaaa tatcgcggca cttcttagac   30540
tcatctaaaa ccatgcaggc tatactacca atattttgc ttctattgct tccctacgct   30600
gtctcaaccc cagctgccta tagtactcca ccagaacacc ttagaaaatg caaattccaa   30660
caaccgtggt catttcttgc ttgctatcga gaaaaatcag aaattccccc aaatttaata   30720
atgattgctg gaataattaa tataatctgt tgcaccataa tttcatttt gatataccc   30780
ctatttgatt ttggctggaa tgctcccaat gcacatgatc atccacaaga cccagaggaa   30840
cacattcccc tacaaaacat gcaacatcca atagcgctaa tagattacga aagtgaacca   30900
caacccccac tactccctgc tattagttac ttcaacctaa ccggcggaga tgactgaaac   30960
actcaccacc tccaattccg ccgaggatct gctcgatatg gacggccgcg tctcagaaca   31020
gcgactcgcc caactacgca tccgccagca gcaggaacgc gcggcaaag agctcagaga   31080
tgtcatccaa attcaccaat gcaaaaagg catattctgt ttggtaaaac aagccaagat   31140
atcctacgag atcaccgcta ctgaccatcg cctctcttac gaacttggcc cccaacgaca   31200
aaaatttacc tgcatggtgg gaatcaaccc catagttatc acccagcaaa gtggagatac   31260
taagggttgc attcactgct cctgcgattc catcgagtgc acctcacccc tgctgaagac   31320
cctatgcggc ctaagagacc tgctaccaat gaattaaaaa atgattaata aaaaatcact   31380
tacttgaaat cagcaataag gtctctgttg aaattttctc ccagcagcac ctcacttccc   31440
tcttcccaac tctggtattc taaacccccgt tcagcggcat actttctcca tactttaaag   31500
gggatgtcaa attttagctc ctctcctgta cccacaatct tcatgtcttt cttcccagat   31560
gaccaagaga gtccggctca gtgactcctt caacctgtc tacccctatg aagatgaaag   31620
cacctcccaa caccccttta taaacccagg gtttatttcc ccaaatggct tcacacaaag   31680
```

```
cccaaacgga gttcttactt taaaatgttt aaccccacta acaaccacag gcggatctct   31740
acagctaaaa gtgggagggg gacttacagt ggatgacacc aacggttttt tgaaagaaaa   31800
cataagtgcc accacaccac tcgttaagac tggtcactct ataggtttac cactaggagc   31860
cggattggga acgaatgaaa ataaactttg tatcaaatta ggacaaggac ttacattcaa   31920
ttcaaacaac atttgcattg atgacaatat taacaccttca tggacaggag tcaaccccac   31980
cgaagccaac tgtcaaatca tgaactccag tgaatctaat gattgcaaat taattctaac   32040
actagttaaa actggagcac tagtcactgc atttgtttat gttataggag tatctaacaa   32100
ttttaatatg ctaactacac acagaaatat aaatttttact gcagagctgt ttttcgattc   32160
tactggtaat ttactaacta gactctcatc cctcaaaact ccacttaatc ataaatcagg   32220
acaaaacatg gctactggtg ccattactaa tgctaaaggt ttcatgccca gcacgactgc   32280
ctatcctttc aatgataatt ctagagaaaa agaaaactac atttacggaa cttgttacta   32340
cacagctagt gatcgcactg cttttcccat tgacatatct gtcatgctta accgaagagc   32400
aataaatgac gagacatcat attgtattcg tataacttgg tcctggaaca caggagatgc   32460
cccagaggtg caaacctctg ctacaaccct agtcacctcc ccatttacct tttactacat   32520
cagagaagac gactgacaaa taaagtttaa cttgtttatt tgaaaatcaa ttcacaaaat   32580
ccgagtagtt attttgcctc ccccttccca tttaacagaa tacaccaatc tctccccacg   32640
cacagcttta acatttggga taccattaga tatagacatg gttttagatt ccacattcca   32700
aacagtttca gagcgagcca atctggggtc agtgatagat aaaaatccat cgggatagtc   32760
tttaaagcg ctttcacagt ccaactgctg cggatggact ccggagtctg gatcacggtc    32820
atctggaaga agaacgatgg gaatcataat ccgaaacgg tatcggacga ttgtgtctca    32880
tcaaacccac aagcagccgc tgtctgcgtc gctccgtgcg actgctgttt atgggatcag   32940
ggtccacagt gtcctgaagc atgatttaaa tagcccttaa catcaacttt ctggtgcgat   33000
gcgcgcagca acgcattctg atttcactca aatctttgca gtaggtacaa cacattatta   33060
caatattgtt taataaacca taattaaaag cgctccagcc aaaactcata tctgatataa   33120
tcgcccctgc atgaccatca taccaaagtt taatataaat taaatgacgt tccctcaaaa   33180
acacactacc cacatacatg atctcttttg gcatgtgcat attaacaatc tgtctgtacc   33240
atggacaacg ttggttaatc atgcaaccca atataaccttt ccggaaccac actgccaaca   33300
ccgctccccc agccatgcat tgaagtgaac cctgctgatt acaatgacaa tgaagaaccc   33360
aattctctcg accgtgaatc acttgagaat gaaaaatatc tatagtggca caacatagac   33420
ataaatgcat gcatcttctc ataattttta actcctcagg atttagaaac atatcccagg   33480
gaataggaag ctcttgcaga acagtaaagc tggcagaaca aggaagacca cgaacacaac   33540
ttacactatg catagtcata gtatcacaat ctggcaacag cgggtggtct tcagtcatag   33600
aagctcgggt ttcatttcc tcacaacgtg taactgggc tctggtgtaa gggtgatgtc     33660
tggcgcatga tgtcgagcgt gcgcgcaacc ttgtcataat ggagttgctt cctgacattc   33720
tcgtattttg tatagcaaaa cgcggccctg gcagaacaca ctcttcttcg ccttctatcc   33780
tgccgcttag cgtgttccgt gtgatagttc aagtacaacc acactcttaa gttggtcaaa   33840
agaatgctgg cttcagttgt aatcaaaact ccatcgcatc taatcgttct gaggaaatca   33900
tccacggtag catatgcaaa tcccaaccaa gcaatgcaac tggattgtgt ttcaagcagg   33960
agaggagagg gaagagacgg aagaaccatg ttaattttta ttccaaacga tctcgcagta   34020
cttcaaattg tagatcgcgc agatggcatc tctcgccccc actgtgttgg tgaaaaagca   34080
```

```
cagctagatc aaaagaaatg cgattttcaa ggtgctcaac ggtggcttcc agcaaagcct    34140
ccacgcgcac atccaagaac aaaagaatac caaaagaagg agcatttct aactcctcaa     34200 tcatcatatt acattcctgc accattccca gataatttc agctttcag ccttgaatta      34260 ttcgtgtcag ttcttgtggt aaatccaatc cacacattac aaacaggtcc cggagggcgc    34320
cctccaccac cattcttaaa cacaccctca taatgacaaa atatcttgct cctgtgtcac    34380
ctgtagcgaa ttgagaatgg caacatcaat tgacatgccc ttggctctaa gttcttcttt    34440
aagttctagt tgtaaaaact ctctcatatt atcaccaaac tgcttagcca gaagccccc    34500 gggaacaaga gcaggggacg ctacagtgca gtacaagcgc agacctcccc aattggctcc    34560
agcaaaaaca agattggaat aagcatattg gaaccgcca gtaatatcat cgaagttgct     34620
ggaaatataa tcaggcagag tttcttgtaa aaattgaata aagaaaaat ttgccaaaaa     34680 aacattcaaa acctctggga tgcaaatgca ataggttacc gcgctgcgct ccaacattgt    34740
tagttttgaa ttagtctgca aaataaaaa aaaaaacaag cgtcatatca tagtagcctg     34800
acgaacagat ggataaatca gtctttccat cacaagacaa gccacagggt ctccagctcg    34860
accctcgtaa aacctgtcat catgattaaa caacagcacc gaaagttcct cgcggtgacc    34920
agcatgaata attcttgatg aagcatacaa tccagacatg ttagcatcag ttaacgagaa    34980
aaaacagcca acatagcctt tgggtataat tatgcttaat cgtaagtata gcaaagccac    35040
ccctcgcgga tacaaagtaa aaggcacagg agaataaaaa atataattat ttctctgctg    35100
ctgttcaggc aacgtcgccc ccggtccctc taaatacaca tacaaagcct catcagccat    35160
ggcttaccag acaaagtaca gcgggcacac aaagcacaag ctctaaagtg actctccaac    35220
ctctccacaa tatatatata cacaagccct aaactgacgt aatgggagta aagtgtaaaa    35280
aatcccgcca aacccaacac acaccccgaa actgcgtcac cagggaaaag tacagtttca    35340
cttccgcaat cccaacaggc gtaacttcct ctttctcacg gtacgtgata tcccactaac    35400
ttgcaacgtc attttcccac ggtcgcaccg cccccttttag ccgttaaccc cacagccaat    35460
caccacacga tccacacttt ttaaaatcac ctcatttaca tattggcacc attccatcta    35520
taaggtatat tattgatgat g                                              35541
```

<210> SEQ ID NO 11
<211> LENGTH: 35541
<212> TYPE: DNA
<213> ORGANISM: Artificial Sequence
<220> FEATURE:
<223> OTHER INFORMATION: Fully synthetic

<400> SEQUENCE: 11

```
catcatcaat aatataccttt atagatggaa tggtgccaat atgtaaatga ggtgattttta     60 aaaagtgtgg atcgtgtggt gattggctgt ggggttaacg gctaaagggg gcggtgcgac    120
cgtgggaaaa tgacgttttg tgggggtgga gttttttttgc aagttgtcgc gggaaatgtg    180
acgcataaaa aggctacaca ggaagtgaca attttcgcgc ggttttaggc ggatgttgta    240
gtaaatttgg gcgtaaccga gtaagatttg gccattttcg cgggaaaact gaataagagg    300
aagtgaaatc tgaataattt tgtgttactc atagcgcgta atatttgtct agggccgcgg    360
ggactttgac cgtttacgtg tgtcaaggag cccaagtcgc ggggaagtgt tgcagggagg    420
cactccggga ggtcccgcgt gcccgtccag ggagcaatgc gtcctcgggt tcgtccccag    480
ccgcgtctac gcgcctccgt cctccccttc acgtccggca ttcgtggtgc ccggagcccg    540
```

```
acgccccgcg tccggacctg gaggcagccc tgggtctccg gatcaggcca gcggccaaag    600
ggtcgccgca cgcacctgtt cccagggcct ccacatcatg gcccctccct cgggttaccc    660
cacagcttag gccgattcga cctctctccg ctggggccct cgctggcgtc cctgcaccct    720
gggagcgcga gcgcgcgcg ggcggggaag cgcggcccag accccgggt ccgcccggag    780
cagctgcgct gtcggggcca ggccgggctc ccagtggatt cgcgggcaca gacgcccagg    840
accgcgcttc ccacgtggcg gagggactgg ggacccgggc accgtcctg cccttcacc    900
ttccagctcc gcctcctccg cgcggacccc gccccgtccc gaccctccc gggtccccgg    960
cccagccccc tccgggccct cccagcccct ccccttcctt tccgcggccc cgccctctcc   1020
tcgcggcgcg agtttcaggc agcgctgcgt cctgctgcgc acgtgggaag ccctggcccc   1080
ggccacccc gcgatgagag atttgcgatt tctgcctcag gaaataatct ctgctgagac   1140
tggaaatgaa atattggagc ttgtggtgca cgccctgatg ggagacgatc cggagccacc   1200
tgtgcagctt tttgagcctc ctacgcttca ggaactgtat gatttagagg tagagggatc   1260
ggaggattct aatgaggaag ctgtaaatgg ctttttttacc gattctatgc ttttagctgc   1320
taatgaaggg ttagaattag atccgccttt ggacactttt gatactccag gggtaattgt   1380
ggaaagcggt acaggtgtaa gaaaattacc tgatttgagt tccgtggact gtgatttgca   1440
ctgctatgaa gacgggtttc ctccgagtga tgaggaggac catgaaaagg agcagtccat   1500
gcagactgca gcgggtgagg gagtgaaggc tgccaatgtt ggttttcagt tggattgccc   1560
ggagcttcct ggacatggct gtaagtcttg tgaatttcac aggaaaaata ctggagtaaa   1620
ggaactgtta tgttcgcttt gttatatgag aacgcactgc cactttattt acagtaagtg   1680
tgtttaagtt aaaatttaaa ggaatatgct gttttcaca tgtatattga gtgtgagttt   1740
tgtgcttctt attataggtc ctgtgtctga tgctgatgaa tcaccatctc ctgattctac   1800
tacctcacct cctgagattc aagcacctgt tcctgtggac gtgcgcaagc ccattcctgt   1860
gaagcttaag cctgggaaac gtccagcagt ggaaaaactt gaggacttgt tacagggtgg   1920
ggacggacct ttggacttga gtacacggaa acgtccaaga caataagtgt tccatatccg   1980
tgtttactta aggtgacgtc aatatttgtg tgacagtgca atgtaataaa atatgttaa   2040
ctgttcactg gtttttattg cttttgggc ggggactcag gtatataagt agaagcagac   2100
ctgtgtggtt agctcatagg agctggcttt catccatgga ggtttgggcc attttggaag   2160
accttaggaa gactaggcaa ctgttagaga acgcttcgga cggagtctcc ggttttgga   2220
gattctggtt cgctagtgaa ttagctaggg tagtttttag gataaaacag gactataaac   2280
aagaatttga aaagttgttg gtagattgcc caggactttt tgaagctctt aatttgggcc   2340
atcaggttca ctttaaagaa aaagttttat cagttttaga cttttcaacc ccaggtagaa   2400
ctgctgctgc tgtggctttt cttactttta tattagataa atggatcccg cagactcatt   2460
tcagcagggg atacgttttg gatttcatag ccacagcatt gtggaaaca tggaaggttc   2520
gcaagatgag gacaatctta ggttactggc cagtgcagcc tttgggtgta gcggaatcc   2580
tgaggcatcc accggtcatg ccagcggttc tggaggagga acagcaagag gacaacccga   2640
gagccggcct ggaccctcca gtggaggagg cggagtagcc gacttgtctc ctgaactgca   2700
acgggtgctt actggatcta cgtccactgg acgggatagg ggcgttaaga gggagagggc   2760
atctagtggt actgatgcta gatctgagtt ggctttaagt ttaatgagtc gcagacgtcc   2820
tgaaaccatt tggtggcatg aggttcagaa agagggaagg gatgaagttt ctgtattgca   2880
ggagaaatat tcactggaac aggtgaaaac atgttggttg gagcctgagg atgattggga   2940
```

```
ggtggccatt aaaaattatg ccaagatagc tttgaggcct gataaacagt ataagattac    3000
tagacggatt aatatccgga atgcttgtta catatctgga atggggctg aggtggtaat    3060 agatactcaa gacaaggcag ttattagatg ctgcatgatg gatatgtggc ctggggtagt    3120
cggtatggaa gcagtaactt ttgtaaatgt taagtttagg ggagatggtt ataatggaat    3180
agtgtttatg gccaatacca aacttatatt gcatggttgt agcttttttg gtttcaacaa    3240
tacctgtgta gatgcctggg gacaggttag tgtacgggga tgtagtttct atgcgtgttg    3300
gattgccaca gctggcagaa ccaagagtca attgtctctg aagaaatgca tatttcaaag    3360
atgtaacctg gcattctga atgaaggcga agcaagggtc cgccactgcg cttctacaga    3420
tactggatgt tttattttga ttaagggaaa tgccagcgta aagcataaca tgatttgcgg    3480
tgcttccgat gagaggcctt atcaaatgct cacttgtgct ggtgggcatt gtaatatgct    3540
ggctactgtg catattgttt cccatcaacg caaaaaatgg cctgttttg atcacaatgt    3600 gatgacgaag tgtaccatgc atgcaggtgg gcgtagagga atgtttatgc cttaccagtg    3660
taacatgaat catgtgaaag tgttgttgga accagatgcc ttttccagaa tgagcctaac    3720
aggaattttt gacatgaaca tgcaaatctg gaagatcctg aggtatgatg atacgagatc    3780
gagggtacgc gcatgcgaat gcggaggcaa gcatgccagg ttccagccgg tgtgtgtaga    3840
tgtgactgaa gatctcagac cggatcattt ggttattgcc cgcactggag cagagttcgg    3900
atccagtgga gaagaaactg actaaggtga gtattgggaa actttgggg tgggattttc    3960 agatggacag attgagtaaa aatttgtttt ttctgtcttg cagctgtcat gagtggaaac    4020
gcttctttta agggggagt cttcagccct tatctgacag ggcgtctccc atcctgggca    4080
ggagttcgtc agaatgttat gggatctact gtggatggaa gacccgtcca acccgccaat    4140
tcttcaacgc tgacctatgc tactttaagt tcttcacctt tggacgcagc tgcagctgcc    4200
gccgccgctt ctgttgccgc taacactgtg cttggaatgg gttactatgg aagcatcatg    4260
gctaattcca cttcctctaa taacccttct accctgactc aggacaagtt acttgtcctt    4320
ttggcccagc tggaggcttt gacccaacgt ctgggtgaac tttctcagca ggtggtcgag    4380
ttgcgagtac aaactgagtc tgctgtcggc acggcaaagt ctaaataaaa aaatcccaga    4440
atcaatgaat aaataaacaa gcttgttgtt gatttaaaat caagtgtttt tatttcattt    4500
ttcgcgcacg gtatgcccta gaccaccgat ctctatcatt gagaactcgg tggattttt    4560 ccaggatcct atagaggtgg gattgaatgt ttagatacat gggcattagg ccgtctttgg    4620
ggtggagata gctccattga agggattcat gctccggggt agtgttgtaa atcacccagt    4680
cataacaagg tcgcagtgca tggtgttgca caatatcttt tagaagtagg ctgattgcca    4740
cagataagcc cttggtgtag gtgtttacaa accggttgag ctgggatggg tgcattcggg    4800
gtgaaattat gtgcattttg gattggattt ttaagttggc aatattgccg ccaagatccc    4860
gtcttgggtt catgttatga aggaccacca agacggtgta tccggtacat ttaggaaatt    4920
tatcgtgcag cttggatgga aaagcgtgga aaaatttgga gacacccttg tgtcctccaa    4980
gattttccat gcactcatcc atgataatag caatggggcc gtgggcagcg gcgcgggcaa    5040
acacgttccg tgggtctgac acatcatagt tatgttcctg agttaaatca tcataagcca    5100
ttttaatgaa tttggggcgg agagtaccag attggggtat gaatgttcct tcgggccccg    5160
gagcatagtt cccctcacag atttgcattt cccaagcttt cagttccgag ggtggaatca    5220
tgtccacctg gggggctatg aaaaacaccg tttctggggc ggggtgatt aattgtgatg    5280
```

```
atagcaaatt tctgagcaat tgagatttgc cacatccggt ggggccataa atgattccga    5340
ttacggggttg caggtggtag tttagggaac ggcaactgcc gtcttctcga agcaaggggg    5400
ccacctcgtt catcatttcc cttacatgca tattttcccg caccaaatcc attaggaggc    5460
gctctcctcc tagtgataga agttcttgta gtgaggaaaa gttttttcagc ggtttcagac    5520
cgtcagccat gggcattttg gagagagttt gctgcaaaag ttctagtctg ttccacagtt    5580
cagtgatgtg ttctatggca tctcgatcca gcagacctcc tcgtttcgcg ggtttggacg    5640
gctcctggaa tagggtatga gacgatgggc gtccagcgct gccagggttc ggtccttcca    5700
gggtctcagt gttcgagtca gggttgtttc cgtcacagtg aagggggtgtg cgcctgcttg    5760
ggcgcttgcc agggtgcgct tcagactcat cctgctggtc gaaaacttct gtcgcttggc    5820
gccctgtatg tcggccaagt agcagtttac catgagttcg tagttgagcg cctcggctgc    5880
gtggcctttg gcgcggagct taccttttgga agttttcttg cataccgggc agtataggca    5940
tttcagcgca tacaacttgg gcgcaaggaa aacggattct ggggagtatg catctgcgcc    6000
gcaggaggcg caaacagttt cacattccac cagccaggtt aaatccggtt cattggggtc    6060
aaaaacaagt tttccgccat atttttttgat gcgtttctta cctttggtct ccatgagttc    6120
gtgtcctcgt tgagtgacaa acaggctgtc cgtgtccccg tagactgatt ttacaggcct    6180
cttctccagt ggagtgcctc ggtcttcttc gtacaggaac tctgaccact ctgatacaaa    6240
ggcgcgcgtc caggccagca caaaggaggc tatgtgggag gggtagcgat cgttgtcaac    6300
caggggggtcc accttttcca agtatgcaa acacatgtca ccctcttcaa catccaggaa    6360
tgtgattggc ttgtaggtgt atttcacgtg acctggggtc cccgctgggg gggtataaaa    6420
gggggcggtt ctttgctctt cctcactgtc ttccggatcg ctgtccagga acgtcagctg    6480
ttggggtagg tattccctct cgaaggcggg catgacctct gcactcaggt tgtcagtttc    6540
taagaacgag gaggattttga tattgacagt gccggttgag atgccttttca tgaggttttc    6600
gtccatttgg tcagaaaaca caattttttt attgtcaagt ttggtggcaa atgatccata    6660
cagggcgttg gataaaagtt tggcaatgga tcgcatggtt tggttctttt ccttgtccgc    6720
gcgctctttg gcggcgatgt tgagttggac atactcgcgt gccaggcact tccattcggg    6780
gaagatagtt gttaattcat ctggcacgat tctcacttgc caccctcgat tatgcaaggt    6840
aattaaatcc acactggtgg ccacctcgcc tcgaagggggt tcattggtcc aacagagcct    6900
acctcctttc ctagaacaga aagggggaag tgggtctagc ataagttcat cgggagggtc    6960
tgcatccatg gtaaagattc ccggaagtaa atccttatca aaatagctga tgggagtggg    7020
gtcatctaag gccatttgcc attctcgagc tgccagtgcg cgctcatatg ggttaagggg    7080
actgccccat ggcatgggat gggtgagtgc agaggcatac atgccacaga tgtcatagac    7140
gtagatggga tcctcaaaga tgcctatgta ggttggatag catcgccccc ctctgatact    7200
tgctcgcaca tagtcatata gttcatgtga tggcgctagc agccccggac ccaagttggt    7260
gcgattgggt ttttctgttc tgtagacgat ctggcgaaag atggcgtgag aattggaaga    7320
gatggtgggt cttttgaaaaa tgttgaaatg ggcatgaggt agacctacag agtctctgac    7380
aaagtgggca taagattctt gaagcttggt taccagttcg gcggtgacaa gtacgtctag    7440
ggcgcagtag tcaagtgttt cttgaatgat gtcataacct ggttggtttt tcttttccca    7500
cagttcgcgg ttgagaaggt attcttcgcg atccttccag tactcttcta gcggaaaccc    7560
gtctttgtct gcacggtaag atcctagcat gtagaactga ttaactgcct tgtaagggca    7620
gcagcccttc tctacgggta gagagtatgc ttgagcagct tttcgtagcg aagcgtgagt    7680
```

```
aagggcaaag gtgtctctga ccatgacttt gagaaattgg tatttgaagt cgatgtcgtc   7740
acaggctccc tgttcccaga gttggaagtc tacccgtttc ttgtaggcgg ggttgggcaa   7800
agcgaaagta acatcattga agagaatctt accggctctg gcataaaat tgcgagtgat    7860 gcgaaaaggc tgtggtactt ccgctcgatt gttgatcacc tgggcagcta ggacgatctc   7920
gtcgaaaccg ttgatgttgt gtcctacgat gtataattct atgaaacgcg gcgtgcctct   7980
gacgtgaggt agcttactga gctcatcaaa ggttaggtct gtggggtcag ataaggcgta   8040
gtgttcgaga gcccattcgt gcaggtgagg atttgcatgt aggaatgatg accaaagatc   8100
taccgccagt gctgtttgta actggtcccg atactgacga aaatgccggc caattgccat   8160 ttttctgga gtgacacagt agaaggttct ggggtcttgt tgccatcgat cccacttgag     8220
tttaatggct agatcgtggg ccatgttgac gagacgctct tctcctgaga gtttcatgac   8280
cagcatgaaa ggaactagtt gtttgccaaa ggatcccatc caggtgtaag tttccacatc   8340
gtaggtcagg aagagtcttt ctgtgcgagg atgagagccg atcgggaaga actggatttc   8400
ctgccaccag ttggaggatt ggctgttgat gtgatggaag tagaagtttc tgcggcgcgc   8460
cgagcattcg tgtttgtgct tgtacagacg gccgcagtag tcgcagcgtt gcacgggttg    8520
tatctcgtga atgagttgta cctggcttcc cttgacgaga aatttcagtg ggaagccgag   8580
gcctggcgat tgtatctcgt gctcttctat attcgctgta tcggcctgtt catcttctgt    8640
ttcgatggtg gtcatgctga cgagcccccg cgggaggcaa gtccagacct cggcgcggga   8700
ggggcggagc tgaaggacga gagcgcgcag gctggagctg tccagagtcc tgagacgctg   8760
cggactcagg ttagtaggta gggacagaag attaacttgc atgatctttt ccagggcgtg   8820
cgggaggttc agatggtact tgatttccac aggttcgttt gtagagacgt caatggcttg   8880
cagggttccg tgtcctttgg gcgccactac cgtacctttg ttttttcttt tgatcggtgg    8940
tggctctctt gcttcttgca tgctcagaag cggtgacggg gacgcgcgcc gggcggcagc   9000
ggttgttccg gacccgaggg catggctggt agtggcacgt cggcgccgcg cacgggcagg   9060
ttctggtact gcgctctgag aagacttgcg tgcgccacca cgcgtcgatt gacgtcttgt     9120
atctgacgtc tctgggtgaa agctaccggc cccgtgagct tgaacctgaa agagagttca   9180
acagaatcaa tttcggtatc gttaacggca gcttgtctca gtatttcttg tacgtcacca   9240
gagttgtcct ggtaggcgat ctccgccatg aactgctcga tttcttcctc ctgaagatct    9300
ccgcgacccg ctcttcgac ggtggccgcg aggtcattgg agatacggcc catgagttgg   9360
gagaatgcat tcatgcccgc ctcgttccag acgcggctgt aaaccacggc ccctcggag     9420 tctcttgcgc gcatcaccac ctgagcgagg ttaagctcca cgtgtctggt gaagaccgca   9480
tagttgcata ggcgctgaaa aaggtagttg agtgtggtgg caatgtgttc ggcgacgaag   9540
aaatacatga tccatcgtct cagcggcatt tcgctaacat cgcccagagc ttccaagcgc   9600
tccatggcct cgtagaagtc cacggcaaaa ttaaaaaact gggagtttcg cgcggacacg   9660
gtcaattcct cctcgagaag acggatgagt tcggctatgg tggcccgtac ttcgcgttcg   9720
aaggctcccg ggatctcttc ttcctcttct atctcttctt ccactaacat ctcttcttcg   9780
tcttcaggcg ggggcggagg gggcacgcgg cgacgtcgac ggcgcacggg caaacggtcg   9840
atgaatcgtt caatgacctc tccgcggcgg cggcgcatgg tttcagtgac ggcgcggccg   9900
ttctcgcgcg gtcgcagagt aaaaacaccg ccgcgcatcc ccttaaagtg gtgactggga   9960
ggttctccgt ttgggaggga gagggcgctg attatacatt ttattaattg gcccgtaggg   10020
```

```
actgcacgca gagatctgat cgtgtcaaga tccacgggat ctgaaaacct ttcgacgaaa   10080
gcgtctaacc agtcacagtc acaaggtagg ctgagtacgg cttcttgtgg gcggggggtgg  10140 ttatgtgttc ggtctgggtc ttctgtttct tcttcatctc gggaaggtga gacgatgctg   10200
ctggtgatga aattaaagta ggcagttcta agacggcgga tggtggcgag gagcaccagg   10260
tctttgggtc cggcttgctg gatacgcagg cgattggcca ttccccaagc attatcctga   10320
catctagcaa gatctttgta gtagtcttgc atgagccgtt ctacgggcac ttcttcctca   10380
cccgttctgc catgcatacg tgtgagtcca aatccgcgca ttggttgtac cagtgccaag   10440
tcagctacga ctctttcggc gaggatggct tgctgtactt gggtaagggt ggcttgaaag   10500
tcatcaaaat ccacaaagcg gtggtaagct cctgtattaa tggtgtaagc acagttggcc   10560
atgactgacc agttaactgt ctggtgacca gggcgcacga gctcggtgta tttaaggcgc   10620
gaataggcgc gggtgtcaaa gatgtaatcg ttgcaggtgc gcaccagata ctggtaccct   10680
ataagaaaat gcggcggtgg ttggcggtag agaggccatc gttctgtagc tggagcgcca   10740
ggggcgaggt cttccaacat aaggcggtga tagccgtaga tgtacctgga catccaggtg   10800
attcctgcgg cggtagtaga agcccgagga aactcgcgta cgcggttcca aatgttgcgt   10860
agcggcatga agtagttcat tgtaggcacg gtttgaccag tgaggcgcgc gcagtcattg   10920
atgctctata gacacggaga aaatgaaagc gttcagcgac tcgactccgt agcctggagg   10980
aacgtgaacg ggttgggtcg cggtgtaccc cggttcgaga cttgtactcg agccggccgg   11040
agccgcggct aacgtggtat tggcactccc gtctcgaccc agcctacaaa aatccaggat   11100
acggaatcga gtcgttttgc tggtttccga atggcaggga agtgagtcct atttttttt   11160 ttttgccgct cagatgcatc ccgtgctgcg acagatgcgc ccccaacaac agccccctc   11220 gcagcagcag cagcagcaat cacaaaaggc tgtccctgca actactgcaa ctgccgccgt   11280
gagcggtgcg ggacagcccg cctatgatct ggacttggaa gagggcgaag gactggcacg   11340
tctaggtgcg ccttcacccg agcggcatcc gcgagttcaa ctgaaaaaag attctcgcga   11400
ggcgtatgtg ccccaacaga acctatttag agacagaagc ggcgaggagc cggaggagat   11460
gcgagcttcc cgctttaacg cgggtcgtga gctgcgtcac ggtttggacc gaagacgagt   11520
gttgcgggac gaggatttcg aagttgatga aatgacaggg atcagtcctg ccagggcaca   11580
cgtggctgca gccaaccttg tatcggctta cgagcagaca gtaaaggaag agcgtaactt   11640
ccaaaagtct tttaataatc atgtgcgaac cctgattgcc cgcgaagaag ttacccttgg   11700
tttgatgcat ttgtgggatt tgatggaagc tatcattcag aaccctacta gcaaacctct   11760
gaccgcccag ctgtttctgg tggtgcaaca cagcagagac aatgaggctt tcagagaggc   11820
gctgctgaac atcaccgaac ccgaggggag atggttgtat gatcttatca acattctaca   11880
gagtatcata gtgcaggagc ggagcctggg cctggccgag aaggtggctg ccatcaatta   11940
ctcggttttg agcttgggaa aatattacgc tcgcaaaatc tacaagactc catacgttcc   12000
catagacaag gaggtgaaga tagatgggtt ctacatgcgc atgacgctca aggtcttgac   12060
cctgagcgat gatcttgggg tgtatcgcaa tgacagaatg catcgcgcgg ttagcgccag   12120
caggaggcgc gagttaagcg acagggaact gatgcacagt ttgcaaagag ctctgactgg   12180
agctggaacc gagggtgaga attacttcga catgggagct gacttgcagt ggcagcctag   12240
tcgcagggct ctgagcgccg cgacggcagg atgtgagctt ccttacatag aagaggcgga   12300
tgaaggcgag gaggaagagg gcgagtactt ggaagactga tggcacaacc cgtgttttt   12360 gctagatgga acagcaagca ccggatcccg caatgcgggc ggcgctgcag agccagccgt   12420
```

```
ccggcattaa ctcctcggac gattggaccc aggccatgca acgtatcatg gcgttgacga   12480
ctcgcaaccc cgaagccttt agacagcaac cccaggccaa ccgtctatcg gccatcatgg   12540
aagctgtagt gccttcccgc tctaatccca ctcatgagaa ggtcctggcc atcgtgaacg   12600
cgttggtgga gaacaaagct attcgtccag atgaggccgg actggtatac aacgctctct   12660
tagaacgcgt ggctcgctac aacagtagca atgtgcaaac caatttggac cgtatgataa   12720
cagatgtacg cgaagccgtg tctcagcgcg aaaggttcca gcgtgatgcc aacctgggtt   12780
cgctggtggc gttaaatgct ttcttgagta ctcagcctgc taatgtgccg cgtggtcaac   12840
aggattatac taacttttta agtgctttga gactgatggt atcagaagta cctcagagcg   12900
aagtgtatca gtccggtcct gattacttct ttcagactag cagacagggc ttgcagacgg   12960
taaatctgag ccaagctttt aaaaacctta aaggtttgtg gggagtgcat gccccggtag   13020
gagaaagagc aaccgtgtct agcttgttaa ctccgaactc ccgcctatta ttactgttgg   13080
tagctccttt caccgacagc ggtagcatcg accgtaattc ctatttgggt tacctactaa   13140
acctgtatcg cgaagccata gggcaaagtc aggtggacga gcagacctat caagaaatta   13200
cccaagtcag tcgcgctttg ggacaggaag acactggcag tttggaagcc actctgaact   13260
tcttgcttac caatcggtct caaaagatcc ctcctcaata tgctcttact gcggaggagg   13320
agaggatcct tagatatgtg cagcagagcg tgggattgtt tctgatgcaa gagggggcaa   13380
ctccgactgc agcactggac atgacagcgc gaaatatgga gcccagcatg tatgccagta   13440
accgaccttt cattaacaaa ctgctggact acttgcacag agctgccgct atgaactctg   13500
attatttcac caatgccatc ttaaacccgc actggctgcc cccacctggt ttctacacgg   13560
gcgaatatga catgcccgac cctaatgacg gatttctgtg ggacgacgtg gacagcgatg   13620
ttttttcacc tctttctgat catcgcacgt ggaaaaagga aggcggcgat agaatgcatt   13680
cttctgcatc gctgtccggg gtcatgggtg ctaccgcggc tgagcccgag tctgcaagtc   13740
cttttcctag tctacccttt tctctacaca gtgtacgtag cagcgaagtg ggtagaataa   13800
gtcgcccgag tttaatgggc gaagaggagt atctaaacga ttccttgctc agaccggcaa   13860
gagaaaaaaa tttcccaaac aatggaatag aaagtttggt ggataaaatg agtagatgga   13920
agacttatgc tcaggatcac agagacgagc ctgggatcat gggggattaca agtagagcga   13980 gccgtagacg ccagcgccat gacagacaga gggtcttgt gtgggacgat gaggattcgg   14040
ccgatgatag cagcgtgctg gacttgggtg ggagaggaag gggcaacccg tttgctcatt   14100
tgcgccctcg cttgggtggt atgttgtaaa aaaaataaa aaaaaactc accaaggcca   14160 tggcgacgag cgtacgttcg ttcttcttta ttatctgtgt ctagtataat gaggcgagtc   14220
gtgctaggcg gagcggtggt gtatccgag ggtcctcctc cttcgtacga gagcgtgatg   14280
cagcagcagc aggcgacggc ggtgatgcaa tccccactgg aggctcccttt tgtgcctccg   14340 cgatacctgg cacctacgga gggcagaaac agcattcgtt attcggaact ggcacctcag   14400
tacgatacca ccaggttgta tctggtggac aacaagtcgg cggacattgc ttctctgaac   14460
tatcagaatg accacagcaa cttcttgacc acggtggtgc aaaacaatga ctttaccccct   14520 acggaagcca gcacccagac cattaacttt gatgaacgat cgcggtgggg cggtcagcta   14580
aagaccatca tgcatactaa catgccaaac gtgaacgagt atatgtttag taacaagttc   14640
aaagcgcgtg tgatggtgtc cagaaaacct cccgacggtg ctgcagttgg ggatacttat   14700
gatcacaagc aggatatttt gaaatatgag tggttcgagt ttactttgcc agaaggcaac   14760
```

-continued

| | |
|---|---|
| ttttcagtta ctatgactat tgatttgatg aacaatgcca tcatagataa ttacttgaaa | 14820 |
| gtgggtagac agaatggagt gcttgaaagt gacattggtg ttaagttcga caccaggaac | 14880 |
| ttcaagctgg gatgggatcc cgaaaccaag ttgatcatgc ctggagtgta tacgtatgaa | 14940 |
| gccttccatc ctgacattgt cttactgcct ggctgcggag tggattttac cgagagtcgt | 15000 |
| ttgagcaacc ttcttggtat cagaaaaaaa cagccatttc aagagggttt taagattttg | 15060 |
| tatgaagatt tagaaggtgg taatattccg gccctcttgg atgtagatgc ctatgagaac | 15120 |
| agtaagaaag aacaaaaagc caaatagaa gctgctacag ctgctgcaga agctaaggca | 15180 |
| aacatagttg ccagcgactc tacaagggtt gctaacgctg gagaggtcag aggagacaat | 15240 |
| tttgcgccaa cacctgttcc gactgcagaa tcattattgg ccgatgtgtc tgaaggaacg | 15300 |
| gacgtgaaac tcactattca acctgtagaa aaagatagta agaatagaag ctataatgtg | 15360 |
| ttggaagaca aaatcaacac agcctatcgc agttggtatc tttcgtacaa ttatggcgat | 15420 |
| cccgaaaaag gagtgcgttc ctggacattg ctcaccacct cagatgtcac ctgcggagca | 15480 |
| gagcaggtct actggtcgct tccagacatg atgaaggatc ctgtcacttt ccgctccact | 15540 |
| agacaagtca gtaactaccc tgtggtgggt gcagagctta tgcccgtctt ctcaaagagc | 15600 |
| ttctacaacg aacaagctgt gtactcccag cagctccgcc agtccacctc gcttacgcac | 15660 |
| gtcttcaacc gctttcctga gaaccagatt ttaatccgtc cgccggcgcc caccattacc | 15720 |
| accgtcagtg aaaacgttcc tgctctcaca gatcacggga ccctgccgtt gcgcagcagt | 15780 |
| atccggggag tccaacgtgt gaccgttact gacgccagac gccgcacctg tccctacgtg | 15840 |
| tacaaggcac tgggcatagt cgcaccgcgc gtcctttcaa gccgcacttt ctaaaaaaaa | 15900 |
| aaaaaatgtc cattcttatc tcgcccagta ataacaccgg ttggggtctg cgcgctccaa | 15960 |
| gcaagatgta cggaggcgca cgcaaacgtt ctacccaaca tcctgtccgt gttcgcggac | 16020 |
| attttcgcgc tccatggggc gccctcaagg gccgcactcg cgttcgaacc accgtcgatg | 16080 |
| atgtaatcga tcaggtggtt gccgacgccc gtaattatac tcctactgcg cctacatcta | 16140 |
| ctgtggatgc agttattgac agtgtagtgg ctgacgctcg caactatgct cgacgtaaga | 16200 |
| gccggcgaag gcgcattgcc agacgccacc gagctaccac tgccatgcga gccgcaagag | 16260 |
| ctctgctacg aagagctaga cgcgtggggc gaagagccat gcttagggcg ccagacgtg | 16320 |
| cagcttcggg cgccagcgcc ggcaggtccc gcaggcaagc agccgctttc gcagcggcga | 16380 |
| ctattgccga catggcccaa tcgcgaagag gcaatgtata ctgggtgcgt gacgctgcca | 16440 |
| ccggtcaacg tgtacccgtg cgcacccgtc ccctcgcac ttagaagata ctgagcagtc | 16500 |
| tccgatgttg tgtcccagcg gcgaggatgt ccaagcgcaa atacaaggaa gaaatgctgc | 16560 |
| aggttatcgc acctgaagtc tacgccaac cgttgaagga tgaaaaaaaa ccccgcaaaa | 16620 |
| tcaagcgggt taaaaaggac aaaaaagaag aggaagatgg cgatgatggg ctggcggagt | 16680 |
| ttgtgcgcga gtttgcccca cggcgacgcg tgcaatggcg tgggcgcaaa gttcgacatg | 16740 |
| tgttgagacc tggaacttcg gtggtctta cacccggcga gcgttcaagc gctactttta | 16800 |
| agcgttccta tgatgaggtg tacggggatg atgatattct tgagcaggcg gctgaccgat | 16860 |
| taggcgagtt tgcttatggc aagcgtagta gaataacttc caaggatgag acagtgtcga | 16920 |
| tacccttgga tcatggaaat cccaccccta gtcttaaacc ggtcactttg cagcaagtgt | 16980 |
| tacccgtaac tccgcgaaca ggtgttaaac gcgaaggtga agatttgtat cccactatgc | 17040 |
| aactgatggt acccaaacgc cagaagttgg aggacgtttt ggagaaagta aaagtggatc | 17100 |
| cagatattca acctgaggtt aaagtgagac ccattaagca ggtagcgcct ggtctggggg | 17160 |

```
tacaaactgt agacattaag attcccactg aaagtatgga agtgcaaact gaacccgcaa   17220
agcctactgc cacctccact gaagtgcaaa cggatccatg gatgcccatg cctattacaa   17280
ctgacgccgc cggtcccact cgaagatccc gacgaaagta cggtccagca agtctgttga   17340
tgcccaatta tgttgtacac ccatctatta ttcctactcc tggttaccga ggcactcgct   17400
actatcgcag ccgaaacagt acctcccgcc gtcgccgcaa gacacctgca aatcgcagtc   17460
gtcgccgtag acgcacaagc aaaccgactc ccggcgccct ggtgcggcaa gtgtaccgca   17520
atggtagtgc ggaacctttg acactgccgc gtgcgcgtta ccatccgagt atcatcactt   17580
aatcaatgtt gccgctgcct ccttgcagat atggccctca cttgtcgcct tcgcgttccc   17640
atcactggtt accgaggaag aaactcgcgc cgtagaagag ggatgttggg acgcggaatg   17700
cgacgctaca ggcgacggcg tgctatccgc aagcaattgc ggggtggttt tttaccagcc   17760
ttaattccaa ttatcgctgc tgcaattggc gcgataccag gcatagcttc cgtggcggtt   17820
caggcctcgc aacgacattg acattggaaa aaaacgtata aataaaaaaa aaaaaataca   17880
atggactctg acactcctgg tcctgtgact atgttttctt agagatggaa gacatcaatt   17940
tttcatcctt ggctccgcga cacggcacga agccgtacat gggcacctgg agcgacatcg   18000
gcacgagcca actgaacggg ggcgccttca attggagcag tatctggagc gggcttaaaa   18060
attttggctc aaccataaaa acatacggga acaaagcttg gaacagcagt acaggacagg   18120
cgcttagaaa taaacttaaa gaccagaact tccaacaaaa agtagtcgat gggatagctt   18180
ccggcatcaa tggagtggta gatttggcta accaggctgt gcagaaaaag ataaacagtc   18240
gtttggaccc gccgccagca accccaggtg aaatgcaagt ggaggaagaa attcctccgc   18300
cagaaaaacg aggcgacaag cgtccgcgtc ccgatttgga agagacgctg gtgacgcgcg   18360
tagatgaacc gccttcttat gaggaagcaa cgaagcttgg aatgcccacc actagaccga   18420
tagccccaat ggccaccggg gtgatgaaac cttctcagtt gcatcgaccc gtcaccttgg   18480
atttgccccc tcccctgct gctactgctg tacccgcttc taagcctgtc gctgcccga    18540 aaccagtcgc cgtagccagg tcacgtcccg ggggcgctcc tcgtccaaat gcgcactggc   18600
aaaatactct gaacagcatc gtgggtctag gcgtgcaaag tgtaaaacgc cgtcgctgct   18660
tttaattaaa tatggagtag cgcttaactt gcctatctgt gtatatgtgt cattacacgc   18720
cgtcacagca gcagaggaaa aaaggaagag gtcgtgcgtc gacgctgagt tactttcaag   18780
atggccaccc catcgatgct gccccaatgg gcatacatgc acatcgccgg acaggatgct   18840
tcggagtacc tgagtccggg tctggtgcag ttcgcccgcg ccacagacac ctacttcaat   18900
ctgggaaata agtttagaaa tcccaccgta gcgccgaccc acgatgtgac caccgaccgt   18960
agccagcggc tcatgttgcg cttcgtgccc gttgaccggg aggacaatac atactcttac   19020
aaagtgcggt acaccctggc cgtgggcgac aacagagtgc tggatatggc cagcacgttc   19080
tttgacatta ggggtgtgtt ggacagaggt cccagtttca aaccctattc tggtacggct   19140
tacaactccc tggctcctaa aggcgctcca aatacatctc agtggattgc agaaggtgta   19200
aaaaatacaa ctggtgagga acacgtaaca gaagaggaaa ccaatactac tacttacact   19260
tttggcaatg ctcctgtaaa agctgaagct gaaattacaa agaaggact cccagtaggt    19320 ttggaagttt cagatgaaga aagtaaaccg atttatgctg ataaaacata tcagccagaa   19380
cctcagctgg gagatgaaac ttggactgac cttgatggaa aaaccgaaaa gtatggaggc   19440
agggctctca aacccgatac taagatgaaa ccatgctacg ggtcctttgc caaacctact   19500
```

```
aatgtgaaag gcggtcaggc aaaacaaaaa acaacggagc agccaaatca gaaagtcgaa    19560
tatgatatcg acatggagtt ttttgatgcg gcatcgcaga aaacaaactt aagtcctaaa    19620
attgtcatgt atgcagaaaa tgtaaatttg gaaactccag acactcatgt agtgtacaaa    19680
cctggaacag aagacacaag ttccgaagct aatttgggac aacaatctat gcccaacaga    19740
cccaactaca ttggcttcag agataacttt attggactta tgtactataa cagtactggt    19800
aacatggggg tgctggctgg tcaagcgtct cagttaaatg cagtggttga cttgcaggac    19860
agaaacacag aactttctta ccaactcttg cttgactctc tgggcgacag aaccagatac    19920
tttagcatgt ggaatcaggc tgtggacagt tatgatcctg atgtacgtgt tattgaaaat    19980
catggtgtgg aagatgaact tcccaactac tgttttccac tggacggcat aggtgttcca    20040
acaaccagtt acaaatcaat agttccaaat ggagacaatg cgcctaattg aaggaacct     20100 gaagtaaatg gaacaagtga gatcggacag ggtaatttgt ttgccatgga aattaacctt    20160
caagccaatc tatggcgaag tttcctttat tccaatgtgg ctctatatct cccagactcg    20220
tacaaataca ccccgtccaa tgtcactctt ccagaaaaca aaaacaccta cgactacatg    20280
aacgggcggg tggtgccgcc atctctagta gacacctatg tgaacattgg tgccaggtgg    20340
tctctggatg ccatggacaa tgtcaaccca ttcaaccacc accgtaacgc tggcttgcgt    20400
taccgatcca tgcttctggg taacggacgt tatgtgcctt tccacataca agtgcctcaa    20460
aaattcttcg ctgttaaaaa cctgctgctt ctcccaggct cctacactta tgagtggaac    20520
tttaggaagg atgtgaacat ggttctacag agttccctcg gtaacgacct gcgggtagat    20580
ggcgccagca tcagtttcac gagcatcaac ctctatgcta ctttttttccc catggctcac    20640 aacaccgctt ccaccccttga agccatgctg cggaatgaca ccaatgatca gtcattcaac    20700
gactacctat ctgcagctaa catgctctac cccattcctg ccaatgcaac caatattccc    20760
atttccattc cttctcgcaa ctgggcggct ttcagaggct ggtcatttac cagactgaaa    20820
accaaagaaa ctccctcttt ggggtctgga tttgacccct actttgtcta ttctggttct    20880
attccctacc tggatggtac cttctacctg aaccacactt ttaagaaggt ttccatcatg    20940
tttgactctt cagtgagctg gcctggaaat gacaggttac tatctcctaa cgaatttgaa    21000
ataaagcgca ctgtggatgg cgaaggctac aacgtagccc aatgcaacat gaccaaagac    21060
tggttcttgg tacagatgct cgccaactac aacatcggct atcagggctt ctacattcca    21120
gaaggataca aagatcgcat gtattcattt ttcagaaact tccagcccat gagcaggcag    21180
gtggttgatg aggtcaatta caaagacttc aaggccgtcg ccataccctca ccaacacaac    21240 aactctggct ttgtgggtta catggctccg accatgcgcc aaggtcaacc ctatcccgct    21300
aactatccct atccactcat tggaacaact gccgtaaata gtgttacgca gaaaaagttc    21360
ttgtgtgaca gaaccatgtg gcgcataccg ttctcgagca acttcatgtc tatggggcc    21420 cttacagact tgggacagaa tatgctctat gccaactcag ctcatgctct ggacatgacc    21480
tttgaggtgg atcccatgga tgagcccacc ctgctttatc ttctcttcga agttttcgac    21540
gtggtcagag tgcatcagcc acaccgcggc atcatcgagg cagtctacct gcgtacaccg    21600
ttctcggccg gtaacgctac cacgtaagaa gcttcttgct tcttgcaaat agcagctgca    21660
accatggcct gcggatccca aaacggctcc agcgagcaag agctcagagc cattgtccaa    21720
gacctggggt tcgggaccctta ttttttggga acctacgata gcgcttccc ggggttcatg     21780 gcccccgata agctcgcctg tgccattgta aatacggccg gacgtgagac ggggggagag    21840
cactggttgg cttttcggttg gaacccacgt tctaacacct gctacctttt tgatccttttt   21900
```

-continued

```
ggattctcgg atgatcgtct caaacagatt taccagtttg aatatgaggg tctcctgcgc  21960
cgcagcgctc ttgctaccaa ggaccgctgt attacgctgg aaaaatctac ccagaccgtg  22020
cagggtcccc gttctgccgc ctgcggactt ttctgctgca tgttccttca cgcctttgtg  22080
cactggcctg accgtcccat ggacggaaac cccaccatga aattgctaac tggagtgcca  22140
aacaacatgc ttcattctcc taaagtccag cccaccctgt gtgacaatca aaaagcactc  22200
taccattttc ttaatacccca ttcgcctttat tttcgctccc atcgtacaca catcgaaagg  22260
gccactgcgt tcgaccgtat ggatgttcaa taatgactca tgtaaacaac gtgttcaata  22320
aacatcactt tattttttta catgtatcaa ggctctgcat tacttattta tttacaagtc  22380
gaatgggttc tgacgagaat cagaatgacc cgcaggcagt gatacgttgc ggaactgata  22440
cttgggttgc cacttgaatt cgggaatcac caacttggga accggtatat cgggcaggat  22500
gtcactccac agctttctgg tcagctgcaa agctccaagc aggtcaggag ccgaaatctt  22560
gaaatcacaa ttaggaccag tgctttgagc gcgagagttg cggtacaccg gattgcagca  22620
ctgaaacacc atcagcgacg gatgtctcac gcttgccagc acggtgggat ctgcaatcat  22680
gcccacatcc agatcttcag cattggcaat gctgaacggg gtcatcttgc aggtctgcct  22740
acccatggcg ggcacccaat taggcttgtg gttgcaatcg cagtgcaggg ggatcagtat  22800
catcttggcc tgatcctgtc tgattcctgg atacacggct ctcatgaaag catcatattg  22860
cttgaaagcc tgctgggctt tactaccctc ggtataaaac atcccgcagg acctgctcga  22920
aaactggtta gctgcacagc cggcatcatt cacacagcag cgggcgtcat tgttagctat  22980
ttgcaccaca cttctgcccc agcggttttg ggtgattttg gttcgctcgg gattctcctt  23040
taaggctcgt tgtccgttct cgctggccac atccatctcg ataatctgct ccttctgaat  23100
cataatattg ccatgcaggc acttcagctt gccctcataa tcattgcagc catgaggcca  23160
caacgcacag cctgtacatt cccaattatg gtgggcgatc tgagaaaaag aatgtatcat  23220
tccctgcaga aatcttccca tcatcgtgct cagtgtcttg tgactagtga aagttaactg  23280
gatgcctcgg tgctcctcgt ttacgtactg gtgacagatg cgcttgtatt gttcgtgttg  23340
ctcaggcatt agtttaaaag aggttctaag ttcgttatcc agcctgtact tctccatcag  23400
cagacacatc acttccatgc cttttctccca agcagacacc aggggcaagc taatcggatt  23460
cttaacagtg caggcagcag ctcctttagc cagagggtca tctttagcga tcttctcaat  23520
gcttcttttg ccatccttct caacgatgcg cacgggcggg tagctgaaac ccactgctac  23580
aagttgcgcc tcttctcttt cttcttcgct gtcttgactg atgtcttgca tggggatatg  23640
tttggtcttc cttggcttct ttttgggggg tatcggagga ggaggactgt cgctccgttc  23700
cggagacagg gaggattgtg acgtttcgct caccattacc aactgactgt cggtagaaga  23760
acctgaccccc acacggcgac aggtgtttct cttcggggc agaggtggag gcgattgcga  23820
agggctgcgg tccgacctgg aaggcggatg actggcagaa ccccttccgc gttcgggggt  23880
gtgctccctg tggcggtcgc ttaactgatt tccttcgcgg ctggccattg tgttctccta  23940
ggcagagaaa caacagacat ggaaactcag ccattgctgt caacatcgcc acgagtgcca  24000
tcacatctcg tcctcagcga cgaggaaaag gagcagagct taagcattcc accgcccagt  24060
cctgccacca cctctacccct agaagataag gaggtcgacg catctcatga catgcagaat  24120
aaaaaagcga aagagtctga gacagacatc gagcaagacc cgggctatgt gacaccggtg  24180
gaacacgagg aagagttgaa acgctttcta gagagagagg atgaaaactg cccaaaacaa  24240
```

```
cgagcagata actatcacca agatgctgga aatagggatc agaacaccga ctacctcata    24300
gggcttgacg gggaagacgc gctccttaaa catctagcaa gacagtcgct catagtcaag    24360
gatgcattat tggacagaac tgaagtgccc atcagtgtgg aagagctcag ccgcgcctac    24420
gagcttaacc tcttttcacc tcgtactccc cccaaacgtc agccaaacgg cacctgcgag    24480
ccaaatcctc gcttaaactt ttatccagct tttgctgtgc cagaagtact ggctacctat    24540
cacatctttt ttaaaaatca aaaaattcca gtctcctgcc gcgctaatcg cacccgcgcc    24600
gatgccctac tcaatctggg acctggttca cgcttacctg atatagcttc cttggaagag    24660
gttccaaaga tcttcgaggg tctgggcaat aatgagactc gggccgcaaa tgctctgcaa    24720
aagggagaaa atggcatgga tgagcatcac agcgttctgg tggaattgga aggcgataat    24780
gccagactcg cagtactcaa gcgaagcatc gaggtcacac acttcgcata tcccgctgtc    24840
aacctgcccc ctaaagtcat gacggcggtc atggaccagt tactcattaa gcgcgcaagt    24900 ccccttttcag aagacatgca tgacccagat gcctgtgatg agggtaaacc agtggtcagt    24960
gatgagcagc taacccgatg gctgggcacc gactctccca gggatttgga agagcgtcgc    25020
aagcttatga tggccgtggt gctggttacc gtagaactag agtgtctccg acgtttcttt    25080
accgattcag aaaccttgcg caaactcgaa gagaatctgc actacacttt tagacacggc    25140
tttgtgcggc aggcatgcaa gatatctaac gtggaactca ccaacctggt ttcctacatg    25200
ggtattctgc atgagaatcg cctaggacaa agcgtgctgc acagcaccct gaaggtggaa    25260
gcccgccgtg attacatccg cgattgtgtc tatctgtacc tgtgccaaac gtggcaaacc    25320
ggcatgggtg tatggcagca atgtttagaa gaacagaact tgaaagagct tgacaagctc    25380
ttacagaaat ctcttaaggt tctgtggaca gggttcgacg agcgcaccgt cgcttccgac    25440
ctggcagacc tcatcttccc agagcgtctc agggttactt tgcgaaacgg attgcctgac    25500
tttatgagcc agagcatgct taacaatttt cgctctttca tcctggaacg ctccggtatc    25560
ctgcccgcca cctgctgcgc actgccctcc gactttgtgc ctctcaccta ccgcgagtgc    25620 ccccgccgc tatggagtca ctgctacctg ttccgtctgg ccaactatct ctcctaccac    25680
tcggatgtga tcgaggatgt gagcggagac ggcttgctgg agtgtcactg ccgctgcaat    25740
ctgtgcacgc cccaccggtc cctagcttgc aaccccagt tgatgagcga accccagata    25800
ataggcacct ttgaattgca aggccccagc agccaaggcg atgggtcttc tcctgggcaa    25860
agtttaaaac tgaccccggg actgtggacc tccgcctact gcgcaagtt tgctccggaa    25920 gattaccacc cctatgaaat caagttctat gaggaccaat cacagcctcc aaaggccgaa    25980
ctttcggcct gcgtcatcac ccaggggggca attctggccc aattgcaagc catccaaaaa    26040
tcccgccaag aatttctact gaaaaagggt aaggggtct accttgaccc ccagaccggc    26100
gaggaactca acacaaggtt ccctcaggat gtcccaacga cgagaaaaca agaagttgaa    26160
ggtgcagccg ccgcccccag aagatatgga ggaagattgg gacagtcagg cagaggaggc    26220
ggaggaggac agtctggagg acagtctgga ggaagacagt ttggaggagg aaaacgagga    26280
ggcagaggag gtggaagaag taaccgccga caaacagtta tcctcggctg cggagacaag    26340
caacagcgct accatctccg ctccgagtcg aggaacccgg cggcgtccca gcagtagatg    26400
ggacgagacc ggacgcttcc cgaacccaac cagcgcttcc aagaccggta agaaggatcg    26460
gcagggatac aagtcctggc gggggcataa gaatgccatc atctcctgct tgcatgagtg    26520 cggggggcaac atatccttca cgcggcgcta cttgctattc caccatgggg tgaactttcc    26580
gcgcaatgtt ttgcattact accgtcacct ccacagcccc tactatagcc agcaaatccc    26640
```

```
ggcagtctcg acagataaag acagcggcgg cgacctccaa cagaaaacca gcagcggcag   26700
ttagaaaata cacaacaagt gcagcaacag gaggattaaa gattacagcc aacgagccag   26760
cgcaaacccg agagttaaga aatcggatct ttccaaccct gtatgccatc ttccagcaga   26820
gtcggggtca agagcaggaa ctgaaaataa aaaaccgatc tctgcgttcg ctcaccagaa   26880
gttgtttgta tcacaagagc gaagatcaac ttcagcgcac tctcgaggac gccgaggctc   26940
tcttcaacaa gtactgcgcg ctgactctta aagagtaggc agcgaccgcg cttattcaaa   27000
aaaggcggga attacatcat cctcgacatg agtaaagaaa ttcccacgcc ttacatgtgg   27060
agttatcaac cccaaatggg attggcggca ggcgcctccc aggactactc cacccgcatg   27120
aattggctca gcgccgggcc ttctatgatt tctcgagtta atgatatacg cgcctaccga   27180
aaccaaatac ttttggaaca gtcagctctt accaccacgc cccgccaaca ccttaatccc   27240
agaaattggc ccgccgccct agtgtaccag gaaagtcccg ctcccaccac tgtattactt   27300
cctcgagacg cccaggccga agtccaaatg actaatgcag gtgcgcagtt agctggcggc   27360
tccaccctat gtcgtcacag gcctcggcat aatataaaac gcctgatgat cagaggccga   27420
ggtatccagc tcaacgacga gtcggtgagc tctccgcttg gtctacgacc agacggaatc   27480
tttcagattg ccggctgcgg gagatcttcc ttcacccctc gtcaggctgt tctgactttg   27540
gaaagttcgt cttcgcaacc ccgctcgggc ggaatcggga ccgttcaatt tgtggaggag   27600
tttactccct ctgtctactt caacccct tc tccggatctc ctgggcatta cccggacgag   27660
ttcataccga acttcgacgc gattagcgag tcagtggacg gctacgattg atgtctggtg   27720
acgcggctga gctatctcgg ctgcgacatc tagaccactg ccgccgcttt cgctgctttg   27780
cccgggaact cattgagttc atctacttcg aactccccaa ggatcaccct caaggtccgg   27840
cccacggagt gcggatttct atcgaaggca aaatagactc tcgcctgcaa cgaattttct   27900
cccagcggcc cgtgctgatc gagcgagacc agggaaacac cacggtttcc atctactgca   27960
tttgtaatca ccccggattg catgaaagcc tttgctgtct tatgtgtact gagtttaata   28020
aaaactgaat taagactctc ctacggactg ccgcttcttc aacccggatt ttacaaccag   28080
aagaacgaaa cttttcctgt cgtccaggac tctgttaact tcacctttcc tactcacaaa   28140
ctagaagctc aacgactaca ccgcttttcc agaagcattt tccctactaa tactactttc   28200
aaaaccggag gtgagctcca aggtcttcct acagaaaacc cttgggtgga agcgggcctt   28260
gtagtgctag gaattcttgc gggtgggctt gtgattattc tttgctacct atacacacct   28320
tgcttcactt tcttagtggt gttgtggtat tggtttaaaa aatatggtga gcaagggcga   28380
ggagctgttc accggggtgg tgcccatcct ggtcgagctg gacggcgacg taaacggcca   28440
caagttcagc gtgtccggcg agggcgaggg cgatgccacc tacggcaagc tgaccctgaa   28500
gttcatctgc accaccggca agctgcccgt gccctggccc accctcgtga ccaccctgac   28560
ctacggcgtg cagtgcttca gccgctaccc cgaccacatg aagcagcacg acttcttcaa   28620
gtccgccatg cccgaaggct acgtccagga gcgcaccatc ttcttcaagg acgacggcaa   28680
ctacaagacc cgcgccgagg tgaagttcga gggcgacacc ctggtgaacc gcatcgagct   28740
gaagggcatc gacttcaagg aggacggcaa catcctgggg cacaagctgg agtacaacta   28800
caacagccac aacgtctata tcatggccga caagcagaag aacggcatca aggtgaactt   28860
caagatccgc cacaacatcg aggacggcag cgtgcagctc gccgaccact accagcagaa   28920
cacccccatc ggcgacggcc ccgtgctgct gcccgacaac cactacctga gcacccagtc   28980
```

```
cgccctgagc aaagacccca acgagaagcg cgatcacatg gtcctgctgg agttcgtgac    29040
cgccgccggg atcactctcg gcatggacga gctgtacaag taacctcttt ctgtttacag    29100
acatggcttc tcttacatct ctcatatttg tcagcattgt cactgccgct catggacaaa    29160
cagtcgtctc tatccctcta ggacataatt acactctcat aggaccccca atcacttcag    29220
aggtcatctg gccaaactg ggaagcgttg attactttga tataatctgc aacaaaacaa    29280
aaccaataat agtaacttgc aacatacaaa atcttacatt gattaatgtt agcaaagttt    29340
acagcggtta ctattatggt tatgacagat acagtagtca atatagaaat tacttggttc    29400
gtgttaccca gttgaaaacc acgaaaatgc caaatatggc aaagattcga tccgatgaca    29460
attctctaga aactttttaca tctcccacca cacccgacga aaaaaacatc ccagattcaa    29520
tgattgcaat tgttgcagcg gtggcagtgg tgatggcact aataataata tgcatgcttt    29580
tatatgcttg tcgctacaaa aagtttcatc ctaaaaaaca agatctccta ctaaggctta    29640
acatttaatt tcttttttata cagccatggt ttccactacc acattcctta tgcttactag    29700
tctcgcaact ctgacttctg ctcgctcaca cctcactgta actataggct caaactgcac    29760
actaaaagga cctcaaggtg gtcatgtctt ttggtggaga atatatgaca atggatggtt    29820
tacaaaacca tgtgaccaac ctggtagatt tttctgcaac ggcagagacc taaccattat    29880
caacgtgaca gcaaatgaca aaggcttcta ttatggaacc gactataaaa gtagtttaga    29940
ttataacatt attgtactgc catctaccac tccagcaccc cgcacaacta ctttctctag    30000
cagcagtgtc gctaacaata caatttccaa tccaaccttt gccgcgcttt taaaacgcac    30060
tgtgaataat tctacaactt cacatacaac aatttccact tcaacaatca gcattatcgc    30120
tgcagtgaca attggaatat ctattcttgt ttttaccata acctactacg cctgctgcta    30180
tagaaaagac aaacataaag gtgatccatt acttagattt gatatttaat ttgttctttt    30240 ttttttttatt tacagtatgg tgaacaccaa tcatggtacc tagaaatttc ttcttcacca    30300
tactcatttg tgcatttaat gtttgcgcta cttttcacagc agtagccaca gcaaccccag    30360
actgtatagg agcatttgct tcctatgcac ttttttgcttt tgttacttgc atctgcgtat    30420
gtagcatagt ctgcctggtt attaattttt tccaacttat agactggatc cttgtgcgaa    30480
ttgcctacct gcgccaccat cccgaatacc gcaaccaaaa tatcgcggca cttcttagac    30540
tcatctaaaa cctgcaggc tatactacca atatttttgc ttctattgct tccctacgct    30600
gtctcaaccc cagctgccta gtactccca ccagaacacc ttagaaaatg caaattccaa    30660
caaccgtggt catttcttgc ttgctatcga gaaaaatcag aaattccccc aaatttaata    30720
atgattgctg gaataattaa tataatctgt tgcaccataa tttcattttt gatataccc    30780 ctatttgatt ttggctggaa tgctcccaat gcacatgatc atccacaaga cccagaggaa    30840
cacattcccc tacaaaacat gcaacatcca atagcgctaa tagattacga aagtgaacca    30900 caaccccac tactccctgc tattagttac ttcaacctaa ccggcggaga tgactgaaac    30960
actcaccacc tccaattccg ccgaggatct gctcgatatg gacggccgcg tctcagaaca    31020
gcgactcgcc caactacgca tccgccagca gcaggaacgc gcggccaaag agctcagaga    31080
tgtcatccaa attcaccaat gcaaaaaagg catattctgt ttggtaaaac aagccaagat    31140
atcctacgag atcaccgcta ctgaccatcg cctctcttac gaacttggcc cccaacgaca    31200
aaaatttacc tgcatggtgg gaatcaaccc catagttatc acccagcaaa gtggagatac    31260
taagggttgc attcactgct cctgcgattc catcgagtgc acctacaccc tgctgaagac    31320
cctatgcggc ctaagagacc tgctaccaat gaattaaaaa atgattaata aaaaatcact    31380
```

```
tacttgaaat cagcaataag gtctctgttg aaattttctc ccagcagcac ctcacttccc   31440
tcttcccaac tctggtattc taaaccccgt tcagcggcat actttctcca tactttaaag   31500
gggatgtcaa attttagctc ctctcctgta cccacaatct tcatgtcttt cttcccagat   31560
gaccaagaga gtccggctca gtgactcctt caaccctgtc taccccatg aagatgaaag    31620 cacctcccaa caccccttta taaacccagg gtttatttcc ccaaatggct tcacacaaag   31680
cccaaacgga gttcttactt taaaatgttt aaccccacta acaaccacag gcggatctct   31740
acagctaaaa gtgggagggg gacttacagt ggatgacacc aacggttttt tgaaagaaaa   31800
cataagtgcc accacaccac tcgttaagac tggtcactct ataggtttac cactaggagc   31860
cggattggga acgaatgaaa ataaactttg tatcaaatta ggacaaggac ttacattcaa   31920
ttcaaacaac atttgcattg atgacaatat taacaccta tggacaggag tcaaccccac   31980
cgaagccaac tgtcaaatca tgaactccag tgaatctaat gattgcaaat taattctaac   32040
actagttaaa actggagcac tagtcactgc atttgtttat gttataggag tatctaacaa   32100
ttttaatatg ctaactacac acagaaatat aaattttact gcagagctgt ttttcgattc   32160
tactggtaat ttactaacta gactctcatc cctcaaaact ccacttaatc ataaatcagg   32220
acaaaacatg gctactggtg ccattactaa tgctaaaggt ttcatgccca gcacgactgc   32280
ctatcctttc aatgataatt ctagagaaaa agaaaactac atttacgaa cttgttacta    32340 cacagctagt gatcgcactg cttttcccat tgacatatct gtcatgctta accgaagagc   32400
aataaatgac gagacatcat attgtattcg tataacttgg tcctggaaca caggagatgc   32460
cccagaggtg caaacctctg ctacaaccct agtcacctcc ccatttacct tttactacat   32520
cagagaagac gactgacaaa taaagtttaa cttgtttatt tgaaaatcaa ttcacaaaat   32580
ccgagtagtt attttgcctc cccttccca tttaacagaa tacaccaatc tctccccacg    32640
cacagcttta aacatttgga taccattaga tatagacatg gttttagatt ccacattcca   32700
aacagtttca gagcgagcca atctggggtc agtgatagat aaaaatccat cgggatagtc   32760
ttttaaagcg ctttcacagt ccaactgctg cggatggact ccggagtctg gatcacggtc   32820
atctggaaga agaacgatgg gaatcataat ccgaaaacgg tatcggacga ttgtgtctca   32880
tcaaacccac aagcagccgc tgtctgcgtc gctccgtgcg actgctgttt atgggatcag   32940
ggtccacagt gtcctgaagc atgatttaa tagcccttaa catcaacttt ctggtgcgat    33000
gcgcgcagca acgcattctg atttcactca aatctttgca gtaggtacaa cacattatta   33060
caatattgtt taataaacca taattaaaag cgctccagcc aaaactcata tctgatataa   33120
tcgcccctgc atgaccatca taccaaagtt taatataaat taaatgacgt tccctcaaaa   33180
acacactacc cacatacatg atctcttttg gcatgtgcat attaacaatc tgtctgtacc   33240
atggacaacg ttggttaatc atgcaaccca atataacctt ccggaaccac actgccaaca   33300
ccgctccccc agccatgcat tgaagtgaac cctgctgatt acaatgacaa tgaagaaccc   33360
aattctctcg accgtgaatc acttgagaat gaaaaatatc tatagtggca caacatagac   33420
ataaatgcat gcatcttctc ataattttta actcctcagg atttagaaac atatcccagg   33480
gaataggaag ctcttgcaga acagtaaagc tggcagaaca aggaagacca cgaacacaac   33540
ttacactatg catagtcata gtatcacaat ctggcaacag cgggtggtct tcagtcatag   33600
aagctcgggt ttcattttcc tcacaacgtg gtaactgggc tctggtgtaa gggtgatgtc   33660
tggcgcatga tgtcgagcgt gcgcgcaacc ttgtcataat ggagttgctt cctgacattc   33720
```

| | |
|---|---:|
| tcgtattttg tatagcaaaa cgcggccctg gcagaacaca ctcttcttcg ccttctatcc | 33780 |
| tgccgcttag cgtgttccgt gtgatagttc aagtacaacc acactcttaa gttggtcaaa | 33840 |
| agaatgctgg cttcagttgt aatcaaaact ccatcgcatc taatcgttct gaggaaatca | 33900 |
| tccacggtag catatgcaaa tcccaaccaa gcaatgcaac tggattgtgt ttcaagcagg | 33960 |
| agaggagagg gaagagacgg aagaaccatg ttaatttta ttccaaacga tctcgcagta | 34020 |
| cttcaaattg tagatcgcgc agatggcatc tctcgccccc actgtgttgg tgaaaaagca | 34080 |
| cagctagatc aaaagaaatg cgattttcaa ggtgctcaac ggtggcttcc agcaaagcct | 34140 |
| ccacgcgcac atccaagaac aaaagaatac caaagaagg agcattttct aactcctcaa | 34200 |
| tcatcatatt acattcctgc accattccca gataattttc agctttccag ccttgaatta | 34260 |
| ttcgtgtcag ttcttgtggt aaatccaatc cacacattac aaacaggtcc cggagggcgc | 34320 |
| cctccaccac cattcttaaa cacaccctca taatgacaaa atatcttgct cctgtgtcac | 34380 |
| ctgtagcgaa ttgagaatgg caacatcaat tgacatgccc ttggctctaa gttcttcttt | 34440 |
| aagttctagt tgtaaaaact ctctcatatt atcaccaaac tgcttagcca gaagccccc | 34500 |
| gggaacaaga gcagggggacg ctacagtgca gtacaagcgc agacctcccc aattggctcc | 34560 |
| agcaaaaaca agattggaat aagcatattg ggaaccgcca gtaatatcat cgaagttgct | 34620 |
| ggaaatataa tcaggcagag tttcttgtaa aaattgaata aagaaaaat ttgccaaaaa | 34680 |
| aacattcaaa acctctggga tgcaaatgca ataggttacc cgcgctgcgct ccaacattgt | 34740 |
| tagttttgaa ttagtctgca aaaataaaaa aaaaaacaag cgtcatatca tagtagcctg | 34800 |
| acgaacagat ggataaatca gtcttttccat cacaagacaa gccacagggt ctccagctcg | 34860 |
| accctcgtaa aacctgtcat catgattaaa caacagcacc gaaagttcct cgcggtgacc | 34920 |
| agcatgaata attcttgatg aagcatacaa tccagacatg ttagcatcag ttaacgagaa | 34980 |
| aaaacagcca acatagcctt tgggtataat tatgcttaat cgtaagtata gcaaagccac | 35040 |
| ccctcgcgga tacaaagtaa aaggcacagg agaataaaaa atataattat ttctctgctg | 35100 |
| ctgttcaggc aacgtcgccc ccggtccctc taaatacaca tacaaagcct catcagccat | 35160 |
| ggcttaccag acaaagtaca gcgggcacac aaagcacaag ctctaaagtg actctccaac | 35220 |
| ctctccacaa tatatatata cacaagccct aaactgacgt aatgggagta aagtgtaaaa | 35280 |
| aatcccgcca aacccaacac acaccccgaa actgcgtcac cagggaaaag tacagtttca | 35340 |
| cttccgcaat cccaacaggc gtaacttcct cttttctcacg gtacgtgata tcccactaac | 35400 |
| ttgcaacgtc attttcccac ggtcgcaccg cccctttag ccgttaaccc cacagccaat | 35460 |
| caccacacga tccacacttt ttaaaatcac ctcatttaca tattggcacc attccatcta | 35520 |
| taaggtatat tattgatgat g | 35541 |

<210> SEQ ID NO 12
<211> LENGTH: 1900
<212> TYPE: DNA
<213> ORGANISM: Artificial Sequence
<220> FEATURE:
<223> OTHER INFORMATION: Fully synthetic

<400> SEQUENCE: 12

| | |
|---|---:|
| atacctgtga cggaagatca cttcgcagaa taaataaatc ctggtgtccc tgttgatacc | 60 |
| gggaagccct gggccaactt ttggcgaaaa tgagacgttg atcggcacgt aagaggttcc | 120 |
| aactttcacc ataatgaaat aagatcacta ccgggcgtat ttttgagtt atcgagattt | 180 |
| tcaggagcta aggaagctaa aatggagaaa aaaatcactg gatataccac cgttgatata | 240 |

```
tcccaatggc atcgtaaaga acatttttgag gcatttcagt cagttgctca atgtacctat    300
aaccagaccg ttcagctgga tattacggcc tttttaaaga ccgtaaagaa aaataagcac    360 aagtttttatc cggcctttat tcacattctt gcccgcctga tgaatgctca tccggaattc    420
cgtatggcaa tgaaagacgg tgagctggtg atatgggata tgttcaccc ttgttacacc     480 gttttccatg agcaaactga aacgttttca tcgctctgga gtgaatacca cgacgatttc    540
cggcagtttc tacacatata ttcgcaagat gtggcgtgtt acggtgaaaa cctggcctat    600
ttccctaaag ggtttattga atatgtttt tcgtctcag ccaatccctg ggtgagtttc       660
accagttttg atttaaacgt ggccaatatg acaacttct tcgcccccgt tttcaccatg      720
ggcaaatatt atacgcaagg cgacaaggtg ctgatgccgc tggcgattca ggttcatcat    780
gccgtctgtg atggcttcca tgtcggcaga atgcttaatg aattacaaca gtactgcgat    840
gagtggcagg gcggggcgta attttttttaa ggcagttatt ggtggcctta aacgcctatt   900
taaattacgt agcgatcgct tagactcgag cggccgcggt ccgtttaaac tgtcagacca    960
agtttactca tatatacttt agattgattt aaaacttcat ttttaattta aaaggatcta   1020
ggtgaagatc cttttttgata atctcatgac caaaatccct taacgtgagt tttcgttcca   1080
ctgagcgtca gaccccgtag aaaagaccaa aggatcttct tgagatcctt ttttttctgcg  1140 cgtaatctgc tgcttgcaaa caaaaaaacc accgctacca gcggtggttt gtttgccgga   1200
tcaagagcta ccaactcttt ttccgaaggt aactggcttc agcagagcgc agataccaaa   1260
tactgtcctt ctagtgtagc cgtagttggg ccaccacttc aagaactctg tagcaccgcc   1320 tacataccctc gctctgctaa tcctgttacc agtggctgct gccagtggcg ataagtcgtg   1380
tcttaccggg ttggactcaa gacgatagtt accggataag cgcagcggt cgggctgaac     1440 gggggggttcg tgcacacagc ccagcttgga gcgaacgacc tacaccgaac tgagatacct   1500
acagcgtgag ctatgagaaa gcgccacgct tcccgaaggg agaaaggcgg acaggtatcc    1560
ggtaagcggc agggtcggaa caggagagcg cacgaaggag cttccagggg gaaacgcctg    1620
gtatctttat agtcctgtcg ggtttcgcca cctctgactt gagcgtcgat ttttgtgatg    1680
ctcgtcaggg gggcggagcc tatggaaaaa cgccagcaac gcggcctttt tacggttcct   1740
ggccttttgc tggccttttg ctcacatgtt ccttcctgcg ttatcccctg attctgtgga    1800
taaccgtatt accgcctttg agtgagctga taccgctcgc cgcaggttta acagatctg     1860 tcgacgcccg ggcaagctgg ccggccgata tcatttaaat                           1900
```

<210> SEQ ID NO 13
<211> LENGTH: 2056
<212> TYPE: DNA
<213> ORGANISM: Artificial Sequence
<220> FEATURE:
<223> OTHER INFORMATION: Fully synthetic

<400> SEQUENCE: 13

```
atacctgtga cggaagatca cttcgcagaa taaataaatc ctggtgtccc tgttgatacc      60
gggaagccct gggccaactt ttggcgaaaa tgagacgttg atcggcacgt aagaggttcc     120
aactttcacc ataatgaaat aagatcacta ccgggcgtat tttttgagtt atcgagattt     180
tcaggagcta aggaagctaa aatgagccat attcaacggg aaacgtcttg ctctaggccg    240
cgattaaatt ccaacatgga tgctgattta tatgggtata atgggctcg cgataatgtc      300 gggcaatcag gtgcgacaat ctatcgattg tatgggaagc ccgatgcgcc agagttgttt    360
```

| | |
|---|---:|
| ctgaaacatg gcaaaggtag cgttgccaat gatgttacag atgagatggt cagactaaac | 420 |
| tggctgacgg aatttatgcc tcttccgacc atcaagcatt ttatccgtac tcctgatgat | 480 |
| gcatggttac tcaccactgc gatccccggg aaaacagcat tccaggtatt agaagaatat | 540 |
| cctgattcag gtgaaaacat tgttgatgcg ctggcagtgt tcctgcgccg gttgcattcg | 600 |
| attcctgttt gtaattgtcc ttttaacagc gatcgcgtat ttcgtctcgc tcaggcgcaa | 660 |
| tcacgaatga ataacggttt ggttgatgcg agtgattttg atgacgagcg taatggctgg | 720 |
| cctgttgaac aagtctggaa agaaatgcat aaacttttgc cattctcacc ggattcagtc | 780 |
| gtcactcatg gtgatttctc acttgataac cttattttg acgaggggaa attaataggt | 840 |
| tgtattgatg ttggacgagt cggaatcgca gaccgatacc aggatcttgc catcctatgg | 900 |
| aactgcctcg gtgagttttc tccttcatta cagaaacggc ttttcaaaa atatggtatt | 960 |
| gataatcctg atatgaataa attgcagttt catttgatgc tcgatgagtt tttctaattt | 1020 |
| ttttaaggca gttattggtg gccttaaacg cctatttaaa ttacgtagcg atcgcttaga | 1080 |
| ctcgagcggc cgcggtccgt ttaaactgtc agaccaagtt tactcatata cttttagat | 1140 |
| tgatttaaaa cttcattttt aatttaaaag gatctaggtg aagatccttt ttgataatct | 1200 |
| catgaccaaa atcccttaac gtgagttttc gttccactga gcgtcagacc ccgtagaaaa | 1260 |
| gaccaaagga tcttcttgag atcctttttt tctgcgcgta atctgctgct tgcaaacaaa | 1320 |
| aaaaccaccg ctaccagcgg tggtttgttt gccggatcaa gagctaccaa ctcttttcc | 1380 |
| gaaggtaact ggcttcagca gagcgcagat accaaatact gtccttctag tgtagccgta | 1440 |
| gttgggccac cacttcaaga actctgtagc accgcctaca tacctcgctc tgctaatcct | 1500 |
| gttaccagtg gctgctgcca gtggcgataa gtcgtgtctt accgggttgg actcaagacg | 1560 |
| atagttaccg gataaggcgc agcggtcggg ctgaacgggg ggttcgtgca cacagcccag | 1620 |
| cttggagcga acgacctaca ccgaactgag atacctacag cgtgagctat gagaaagcgc | 1680 |
| cacgcttccc gaagggagaa aggcggacag gtatccggta agcggcaggg tcggaacagg | 1740 |
| agagcgcacg aaggagcttc caggggggaaa cgcctggtat ctttatagtc ctgtcgggtt | 1800 |
| tcgccacctc tgacttgagc gtcgattttt gtgatgctcg tcaggggggc ggagcctatg | 1860 |
| gaaaaacgcc agcaacgcgg cctttttacg gttcctggcc ttttgctggc cttttgctca | 1920 |
| catgttcctt cctgcgttat cccctgattc tgtggataac cgtattaccg cctttgagtg | 1980 |
| agctgatacc gctcgccgca gtttaaaca gatctgtcga cgcccgggca agctggccgg | 2040 |
| ccgatatcat ttaaat | 2056 |

<210> SEQ ID NO 14
<211> LENGTH: 4361
<212> TYPE: DNA
<213> ORGANISM: Artificial Sequence
<220> FEATURE:
<223> OTHER INFORMATION: Fully synthetic

<400> SEQUENCE: 14

| | |
|---|---:|
| ttctcatgtt tgacagctta tcatcgataa gctttaatgc ggtagtttat cacagttaaa | 60 |
| ttgctaacgc agtcaggcac cgtgtatgaa atctaacaat gcgctcatcg tcatcctcgg | 120 |
| caccgtcacc ctggatgctg taggcatagg cttggttatg ccggtactgc cgggcctctt | 180 |
| gcgggatatc gtccattccg acagcatcgc cagtcactat ggcgtgctgc tagcgctata | 240 |
| tgcgttgatg caatttctat gcgcacccgt tctcggagca ctgtccgacc gctttggccg | 300 |
| ccgcccagtc ctgctcgctt cgctacttgg agccactatc gactacgcga tcatggcgac | 360 |

```
cacacccgtc ctgtggatcc tctacgccgg acgcatcgtg gccggcatca ccggcgccac      420
aggtgcggtt gctggcgcct atatcgccga catcaccgat ggggaagatc gggctcgcca      480
cttcgggctc atgagcgctt gtttcggcgt gggtatggtg gcaggcccg tggccggggg       540 actgttgggc gccatctcct tgcatgcacc attccttgcg gcggcggtgc tcaacggcct      600
caacctacta ctgggctgct tcctaatgca ggagtcgcat aagggagagc gtcgaccgat      660
gcccttgaga gccttcaacc cagtcagctc cttccggtgg gcgcggggca tgactatcgt      720
cgccgcactt atgactgtct tctttatcat gcaactcgta ggacaggtgc cggcagcgct      780
ctgggtcatt ttcggcgagg accgctttcg ctggagcgcg acgatgatcg gcctgtcgct      840
tgcggtattc ggaatcttgc acgccctcgc tcaagccttc gtcactggtc ccgccaccaa      900
acgtttcggc gagaagcagg ccattatcgc cggcatggcg gccgacgcgc tgggctacgt      960
cttgctggcg ttcgcgacgc gaggctggat ggccttcccc attatgattc ttctcgcttc     1020
cggcggcatc gggatgcccg cgttgcaggc catgctgtcc aggcaggtag atgacgacca     1080
tcagggacag cttcaaggat cgctcgcggc tcttaccagc ctaacttcga tcactggacc     1140
gctgatcgtc acggcgattt atgccgcctc ggcgagcaca tggaacgggt tggcatggat     1200
tgtaggcgcc gccctatacc ttgtctgcct ccccgcgttg cgtcgcggtg catggagccg     1260
ggccacctcg acctgaatgg aagcggcgg cacctcgcta acggattcac cactccaaga     1320
attggagcca atcaattctt gcggagaact gtgaatgcgc aaaccaaccc ttggcagaac     1380
atatccatcg cgtccgccat ctccagcagc cgcacgcggc gcatctcggg cagcgttggg     1440
tcctggccac gggtgcgcat gatcgtgctc ctgtcgttga ggacccggct aggctggcgg     1500
ggttgcctta ctggttagca gaatgaatca ccgatacgcg agcgaacgtg aagcgactgc     1560
tgctgcaaaa cgtctgcgac ctgagcaaca acatgaatgg tcttcggttt ccgtgtttcg     1620
taaagtctgg aaacgcggaa gtcagcgccc tgcaccatta tgttccggat ctgcatcgca     1680
ggatgctgct ggctaccctg tggaacacct acatctgtat aacgaagcg ctggcattga      1740 ccctgagtga ttttctctg gtcccgccgc atccataccg ccagttgttt accctcacaa      1800
cgttccagta accgggcatg ttcatcatca gtaacccgta tcgtgagcat cctctctcgt     1860
ttcatcggta tcattacccc catgaacaga atccccctt acacggaggc atcagtgacc      1920
aaacaggaaa aaaccgccct taacatggcc cgctttatca gaagccagac attaacgctt     1980
ctggagaaac tcaacgagct ggacgcggat gaacaggcag acatctgtga atcgcttcac     2040
gaccacgctg atgagcttta ccgcagctgc ctcgcgcgtt tcggtgatga cggtgaaaac     2100
ctctgacaca tgcagctccc ggagacggtc acagcttgtc tgtaagcgga tgccgggagc     2160
agacaagccc gtcagggcgc gtcagcgggt gttggcgggt gtcggggcgc agccatgacc     2220
cagtcacgta gcgatagcgg agtgtatact ggcttaacta tgcggcatca gagcagattg     2280
tactgagagt gcaccatatg cggtgtgaaa taccgcacag atgcgtaagg agaaaatacc     2340
gcatcaggcg ctcttccgct tcctcgctca ctgactcgct gcgctcggtc gttcggctgc     2400
ggcgagcggt atcagctcac tcaaaggcgg taatacggtt atccacagaa tcaggggata     2460
acgcaggaaa gaacatgtga gcaaaaggcc agcaaaaggc caggaaccgt aaaaaggccg     2520
cgttgctggc gttttcccat aggctccgcc cccctgacga gcatcacaaa aatcgacgct     2580
caagtcagag gtggcgaaac ccgacaggac tataaagata ccaggcgttt ccccctggaa     2640
gctccctcgt gcgctctcct gttccgaccc tgccgcttac cggatacctg tccgcctttc     2700
```

| | |
|---|---:|
| tcccttcggg aagcgtggcg ctttctcata gctcacgctg taggtatctc agttcggtgt | 2760 |
| aggtcgttcg ctccaagctg ggctgtgtgc acgaaccccc cgttcagccc gaccgctgcg | 2820 |
| ccttatccgg taactatcgt cttgagtcca acccggtaag acacgactta tcgccactgg | 2880 |
| cagcagccac tggtaacagg attagcagag cgaggtatgt aggcggtgct acagagttct | 2940 |
| tgaagtggtg gcctaactac ggctacacta aaggacagt atttggtatc tgcgctctgc | 3000 |
| tgaagccagt taccttcgga aaagagttg gtagctcttg atccggcaaa caaaccaccg | 3060 |
| ctggtagcgg tggtttttttt gtttgcaagc agcagattac gcgcagaaaa aaaggatctc | 3120 |
| aagaagatcc tttgatcttt tctacggggt ctgacgctca gtggaacgaa aactcacgtt | 3180 |
| aagggatttt ggtcatgaga ttatcaaaaa ggatcttcac ctagatcctt ttaaattaaa | 3240 |
| aatgaagttt taaatcaatc taaagtatat atgagtaaac ttggtctgac agttaccaat | 3300 |
| gcttaatcag tgaggcacct atctcagcga tctgtctatt tcgttcatcc atagttgcct | 3360 |
| gactccccgt cgtgtagata actacgatac gggagggctt accatctggc cccagtgctg | 3420 |
| caatgatacc gcgagaccca cgctcaccgg ctccagattt atcagcaata aaccagccag | 3480 |
| ccggaagggc cgagcgcaga agtggtcctg caactttatc cgcctccatc cagtctatta | 3540 |
| attgttgccg ggaagctaga gtaagtagtt cgccagttaa tagtttgcgc aacgttgttg | 3600 |
| ccattgctgc aggcatcgtg gtgtcacgct cgtcgtttgg tatggcttca ttcagctccg | 3660 |
| gttcccaacg atcaaggcga gttacatgat cccccatgtt gtgcaaaaaa gcggttagct | 3720 |
| ccttcggtcc tccgatcgtt gtcagaagta agttggccgc agtgttatca ctcatggtta | 3780 |
| tggcagcact gcataattct cttactgtca tgccatccgt aagatgcttt tctgtgactg | 3840 |
| gtgagtactc aaccaagtca ttctgagaat agtgtatgcg gcgaccgagt tgctcttgcc | 3900 |
| cggcgtcaac acgggataat accgcgccac atagcagaac tttaaaagtg ctcatcattg | 3960 |
| gaaaacgttc ttcggggcga aaactctcaa ggatcttacc gctgttgaga tccagttcga | 4020 |
| tgtaacccac tcgtgcaccc aactgatctt cagcatcttt tactttcacc agcgtttctg | 4080 |
| ggtgagcaaa acaggaagg caaaatgccg caaaaaggg aataagggcg acacggaaat | 4140 |
| gttgaatact catactcttc ctttttcaat attattgaag catttatcag ggttattgtc | 4200 |
| tcatgagcgg atacatattt gaatgtattt agaaaaataa acaaataggg gttccgcgca | 4260 |
| catttccccg aaaagtgcca cctgacgtct aagaaaccat tattatcatg acattaacct | 4320 |
| ataaaaatag gcgtatcacg aggccctttc gtcttcaaga a | 4361 |

<210> SEQ ID NO 15
<211> LENGTH: 2686
<212> TYPE: DNA
<213> ORGANISM: Artificial Sequence
<220> FEATURE:
<223> OTHER INFORMATION: Fully synthetic

<400> SEQUENCE: 15

| | |
|---|---:|
| gcgcccaata cgcaaaccgc ctctccccgc gcgttggccg attcattaat gcagctggca | 60 |
| cgacaggttt cccgactgga aagcgggcag tgagcgcaac gcaattaatg tgagttagct | 120 |
| cactcattag gcaccccagg ctttacactt tatgcttccg gctcgtatgt tgtgtggaat | 180 |
| tgtgagcgga taacaatttc acacaggaaa cagctatgac catgattacg aattcgagct | 240 |
| cggtacccgg ggatcctcta gagtcgacct gcaggcatgc aagcttggca ctggccgtcg | 300 |
| ttttacaacg tcgtgactgg gaaaaccctg gcgttaccca acttaatcgc cttgcagcac | 360 |
| atccccctttt cgccagctgg cgtaatagcg aagaggcccg caccgatcgc ccttcccaac | 420 |

-continued

```
agttgcgcag cctgaatggc gaatggcgcc tgatgcggta ttttctcctt acgcatctgt    480
gcggtatttc acaccgcata tggtgcactc tcagtacaat ctgctctgat gccgcatagt    540
taagccagcc ccgacacccg ccaacacccg ctgacgcgcc ctgacgggct tgtctgctcc    600
cggcatccgc ttacagacaa gctgtgaccg tctccgggag ctgcatgtgt cagaggtttt    660
caccgtcatc accgaaacgc gcgagacgaa agggcctcgt gatacgccta tttttatagg    720
ttaatgtcat gataataatg gtttcttaga cgtcaggtgg cacttttcgg ggaaatgtgc    780
gcggaacccc tatttgttta tttttctaaa tacattcaaa tatgtatccg ctcatgagac    840
aataaccctg ataaatgctt caataatatt gaaaaaggaa gagtatgagt attcaacatt    900
tccgtgtcgc ccttattccc ttttttgcgg cattttgcct tcctgttttt gctcacccag    960
aaacgctggt gaaagtaaaa gatgctgaag atcagttggg tgcacgagtg ggttacatcg   1020
aactggatct caacagcggt aagatccttg agagttttcg ccccgaagaa cgttttccaa   1080
tgatgagcac ttttaaagtt ctgctatgtg gcgcggtatt atcccgtatt gacgccgggc   1140
aagagcaact cggtcgccgc atacactatt ctcagaatga cttggttgag tactcaccag   1200
tcacagaaaa gcatcttacg gatggcatga cagtaagaga attatgcagt gctgccataa   1260
ccatgagtga taacactgcg gccaacttac ttctgacaac gatcggagga ccgaaggagc   1320
taaccgcttt tttgcacaac atgggggatc atgtaactcg ccttgatcgt tgggaaccgg   1380
agctgaatga agccatacca aacgacgagc gtgacaccac gatgcctgta gcaatggcaa   1440
caacgttgcg caaactatta actggcgaac tacttactct agcttcccgg caacaattaa   1500
tagactggat ggaggcggat aaagttgcag gaccacttct gcgctcggcc cttccggctg   1560
gctggtttat tgctgataaa tctggagccg gtgagcgtgg gtctcgcggt atcattgcag   1620
cactggggcc agatggtaag ccctcccgta tcgtagttat ctacacgacg gggagtcagg   1680
caactatgga tgaacgaaat agacagatcg ctgagatagg tgcctcactg attaagcatt   1740
ggtaactgtc agaccaagtt tactcatata ctttagat tgatttaaaa cttcattttt    1800
aatttaaaag gatctaggtg aagatccttt ttgataatct catgaccaaa atcccttaac   1860
gtgagttttc gttccactga gcgtcagacc ccgtagaaaa gatcaaagga tcttcttgag   1920
atccttttt tctgcgcgta atctgctgct tgcaaacaaa aaaaccaccg ctaccagcgg   1980
tggtttgttt gccggatcaa gagctaccaa ctctttttcc gaaggtaact ggcttcagca   2040
gagcgcagat accaaatact gtccttctag tgtagccgta gttaggccac cacttcaaga   2100
actctgtagc accgcctaca tacctcgctc tgctaatcct gttaccagtg gctgctgcca   2160
gtggcgataa gtcgtgtctt accgggttgg actcaagacg atagttaccg gataaggcgc   2220
agcggtcggg ctgaacgggg ggttcgtgca cacagcccag cttggagcga acgacctaca   2280
ccgaactgag atacctacag cgtgagctat gagaaagcgc cacgcttccc gaagggagaa   2340
aggcggacag gtatccggta agcggcaggg tcggaacagg agagcgcacg agggagcttc   2400
caggggaaa cgcctggtat ctttatagtc ctgtcgggtt tcgccacctc tgacttgagc   2460
gtcgatttt gtgatgctcg tcagggggc ggagcctatg gaaaaacgcc agcaacgcgg   2520
cctttttacg gttcctggcc ttttgctgg cttttgctca catgttcttt cctgcgttat   2580
cccctgattc tgtggataac cgtattaccg cctttgagtg agctgatacc gctcgccgca   2640
gccgaacgac cgagcgcagc gagtcagtga gcgaggaagc ggaaga              2686
```

<210> SEQ ID NO 16

<211> LENGTH: 3697
<212> TYPE: DNA
<213> ORGANISM: Artificial Sequence
<220> FEATURE:
<223> OTHER INFORMATION: Fully synthetic

<400> SEQUENCE: 16

| | | | | | | |
|---|---|---|---|---|---|---|
| atacctgtga | cggaagatca | cttcgcagaa | taaataaatc | ctggtgtccc | tgttgatacc | 60 |
| gggaagccct | gggccaactt | ttggcgaaaa | tgagacgttg | atcggcacgt | aagaggttcc | 120 |
| aactttcacc | ataatgaaat | aagatcacta | ccgggcgtat | tttttgagtt | atcgagattt | 180 |
| tcaggagcta | aggaagctaa | aatggagaaa | aaaatcactg | gatataccac | cgttgatata | 240 |
| tcccaatggc | atcgtaaaga | acattttgag | gcatttcagt | cagttgctca | atgtacctat | 300 |
| aaccagaccg | ttcagctgga | tattacggcc | ttttttaaaga | ccgtaaagaa | aaataagcac | 360 |
| aagttttatc | cggcctttat | tcacattctt | gcccgcctga | tgaatgctca | tccggaattc | 420 |
| cgtatggcaa | tgaaagacgg | tgagctggtg | atatgggata | gtgttcaccc | ttgttacacc | 480 |
| gttttccatg | agcaaactga | aacgttttca | tcgctctgga | gtgaatacca | cgacgatttc | 540 |
| cggcagtttc | tacacatata | ttcgcaagat | gtggcgtgtt | acggtgaaaa | cctggcctat | 600 |
| ttccctaaag | ggtttattga | gaatatgttt | ttcgtctcag | ccaatccctg | ggtgagtttc | 660 |
| accagttttg | atttaaacgt | ggccaatatg | gacaacttct | tcgcccccgt | tttcaccatg | 720 |
| ggcaaatatt | atacgcaagg | cgacaaggtg | ctgatgccgc | tggcgattca | ggttcatcat | 780 |
| gccgtctgtg | atggcttcca | tgtcggcaga | atgcttaatg | aattacaaca | gtactgcgat | 840 |
| gagtggcagg | gcggggcgta | atttttttaa | ggcagttatt | ggtggcctta | aacgcctatt | 900 |
| taaattacgt | catttttccca | cggtcgcacc | gccccttttta | gccgttaacc | ccacagccaa | 960 |
| tcaccacacg | atccacactt | tttaaaatca | cctcatttac | atattggcac | cattccatct | 1020 |
| ataaggtata | ttattgatga | tgcatcatca | ataatatacc | ttatagatgg | aatggtgcca | 1080 |
| atatgtaaat | gaggtgattt | taaaaagtgt | ggatcgtgtg | gtgattggct | gtggggttaa | 1140 |
| cggctaaaag | gggcggtgcg | accgtgggaa | aatgacgttt | tgtgggggtg | gagttttttt | 1200 |
| gcaagttgtc | gcgggaaatg | tgacgcataa | aaaggctgta | gcgatcgctt | agactcgagc | 1260 |
| ggccgcggtc | cgtttaaact | gtcagaccaa | gtttactcat | atatacttta | gattgattta | 1320 |
| aaacttcatt | tttaatttaa | aaggatctag | gtgaagatcc | ttttttgataa | tctcatgacc | 1380 |
| aaaatccctt | aacgtgagtt | ttcgttccac | tgagcgtcag | accccgtaga | aaagaccaaa | 1440 |
| ggatcttctt | gagatccttt | tttttctgcgc | gtaatctgct | gcttgcaaac | aaaaaaacca | 1500 |
| ccgctaccag | cggtggtttg | tttgccggat | caagagctac | caactctttt | tccgaaggta | 1560 |
| actggcttca | gcagagcgca | gataccaaat | actgtccttc | tagtgtagcc | gtagttgggc | 1620 |
| caccacttca | agaactctgt | agcaccgcct | acatacctcg | ctctgctaat | cctgttacca | 1680 |
| gtggctgctg | ccagtggcga | taagtcgtgt | cttaccgggt | tggactcaag | acgatagtta | 1740 |
| ccggataagg | cgcagcggtc | gggctgaacg | gggggttcgt | gcacacagcc | cagcttggag | 1800 |
| cgaacgacct | acaccgaact | gagataccta | cagcgtgagc | tatgagaaag | cgccacgctt | 1860 |
| cccgaaggga | gaaaggcgga | caggtatccg | gtaagcggca | gggtcggaac | aggagagcgc | 1920 |
| acgaaggagc | ttccagggg | aaacgcctgg | tatctttata | gtcctgtcgg | gtttcgccac | 1980 |
| ctctgacttg | agcgtcgatt | tttgtgatgc | tcgtcagggg | ggcggagcct | atggaaaaac | 2040 |
| gccagcaacg | cggcctttttt | acggttcctg | gccttttgct | ggccttttgc | tcacatgttc | 2100 |
| cttcctgcgt | tatcccctga | ttctgtggat | aaccgtatta | ccgcctttga | gtgagctgat | 2160 |

| | |
|---|---|
| accgctcgcc gcaggtttaa acagatctgt cgacgcccgg gcaagctggc cggccgatac | 2220 |
| acaggaagtg acaattttcg cgcggtttta ggcggatgtt gtagtaaatt tgggcgtaac | 2280 |
| cgagtaagat ttggccattt tcgcgggaaa actgaataag aggaagtgaa atctgaataa | 2340 |
| ttttgtgtta ctcatagcgc gtaatatttg tctaggccg cggggacttt gaccgtttac | 2400 |
| gttctagagt gtcaaggagc ccaagtcgcg gggaagtgtt gcagggaggc actccgggag | 2460 |
| gtcccgcgtg cccgtccagg gagcaatgcg tcctcgggtt cgtccccagc cgcgtctacg | 2520 |
| cgcctccgtc ctccccttca cgtccggcat tcgtggtgcc cggagcccga cgccccgcgt | 2580 |
| ccggacctgg aggcagccct gggtctccgg atcaggccag cggccaaagg gtcgccgcac | 2640 |
| gcacctgttc ccagggcctc cacatcatgg cccctccctc gggttacccc acagcttagg | 2700 |
| ccgattcgac ctctctccgc tggggccctc gctggcgtcc ctgcaccctg ggagcgcgag | 2760 |
| cggcgcgcgg gcggggaagc gcggcccaga cccccgggtc cgcccggagc agctgcgctg | 2820 |
| tcggggccag gccgggctcc cagtggattc gcggcacag acgccagga ccgcgcttcc | 2880 |
| cacgtggcgg agggactggg gacccgggca cccgtcctgc cccttcacct tccagctccg | 2940 |
| cctcctccgc gcggaccccg ccccgtcccg acccctcccg gtccccggc ccagccccct | 3000 |
| ccgggccctc ccagcccctc cccttccttt ccgcggcccc gccctctcct cgcggcgcga | 3060 |
| gtttcaggca gcgctgcgtc ctgctgcgca cgtgggaagc cctggccccg gccacccccg | 3120 |
| cgccatggat gagagatttg cgatttctgc ctcaggaaat aatctctgct gagactggaa | 3180 |
| atgaaatatt ggagcttgtg gtgcacgccc tgatgggaga cgatccggag ccacctgtgc | 3240 |
| agcttttga gcctcctacg cttcaggaac tgtatgattt agaggtagag ggatcggagg | 3300 |
| attctaatga ggaagctgta aatggctttt ttaccgattc tatgcttta gctgctaatg | 3360 |
| aagggttaga attagatccg cctttggaca cttttgatac tccagggta attgtggaaa | 3420 |
| gcggtacagg tgtaagaaaa ttacctgatt tgagttccgt ggactgtgat ttgcactgct | 3480 |
| atgaagacgg gtttcctccg agtgatgagg aggaccatga aaaggagcag tccatgcaga | 3540 |
| ctgcagcggg tgagggagtg aaggctgcca atgttggttt tcagttggat tgcccggagc | 3600 |
| ttcctggaca tggctgtaag tcttgtgaat ttcacaggaa aaatactgga gtaaaggaac | 3660 |
| tgttatgttc gctttgttat atgagaatca tttaaat | 3697 |

<210> SEQ ID NO 17
<211> LENGTH: 3903
<212> TYPE: DNA
<213> ORGANISM: Artificial Sequence
<220> FEATURE:
<223> OTHER INFORMATION: Fully synthetic

<400> SEQUENCE: 17

| | |
|---|---|
| atacctgtga cggaagatca cttcgcagaa taaataaatc ctggtgtccc tgttgatacc | 60 |
| gggaagccct gggccaactt ttggcgaaaa tgagacgttg atcggcacgt aagaggttcc | 120 |
| aactttcacc ataatgaaat aagatcacta ccggcgtat tttttgagtt atcgagattt | 180 |
| tcaggagcta aggaagctaa aatgagccat attcaacggg aaacgtcttg ctctaggccg | 240 |
| cgattaaatt ccaacatgga tgctgattta tatgggtata aatgggctcg cgataatgtc | 300 |
| gggcaatcag gtgcgacaat ctatcgattg tatgggaagc ccgatgcgcc agagttgttt | 360 |
| ctgaaacatg gcaaaggtag cgttgccaat gatgttacag atgagatggt cagactaaac | 420 |
| tggctgacgg aatttatgcc tcttccgacc atcaagcatt ttatccgtac tcctgatgat | 480 |

```
gcatggttac tcaccactgc gatccccggg aaaacagcat tccaggtatt agaagaatat    540
cctgattcag gtgaaaacat tgttgatgcg ctggcagtgt tcctgcgccg gttgcattcg    600
attcctgttt gtaattgtcc ttttaacagc gatcgcgtat ttcgtctcgc tcaggcgcaa    660
tcacgaatga ataacggttt ggttgatgcg agtgattttg atgacgagcg taatggctgg    720
cctgttgaac aagtctggaa agaaatgcat aaacttttgc cattctcacc ggattcagtc    780
gtcactcatg gtgatttctc acttgataac cttattttg  acgagggaa  attaataggt    840
tgtattgatg ttggacgagt cggaatcgca gaccgatacc aggatcttgc catcctatgg    900
aactgcctcg gtgagttttc tccttcatta cagaaacggc ttttcaaaa  atatggtatt    960
gataatcctg atatgaataa attgcagttt catttgatgc tcgatgagtt tttctaattt   1020
ttttaaggca gttattggtg gccttaaacg cctatttaaa ttacccctca aggtccggcc   1080
cacggagtgc ggatttctat cgaaggcaaa atagactctc gcctgcaacg aattttctcc   1140
cagcggcccg tgctgatcga gcgagaccag ggaaacacca cggtttccat ctactgcatt   1200
tgtaatcacc ccggattgca tgaaagcctt tgctgtctta tgtgtactga gtttaataaa   1260
aactgaatta agactctcct acggactgcc gcttcttcaa cccggatttt acaaccagaa   1320
gaacgaaact tttcctgtcg tccaggactc tgttaacttc acctttccta ctcacaaact   1380
agaagctcaa cgactacacc gcttttccag aagcattttc cctactaata ctactttcaa   1440
aaccggaggt gagctccaag gtcttcctac agaaaaccct tgggtggaag cgggccttgt   1500
agtgctagga attcttgcgg gtgggcttgt gattattctt tgctacctat acacaccttg   1560
cttcactttc ttagtggtgt tgtggtattg gtttaaaaaa tccatggatg gtgagcaagg   1620
gcgaggagct gttcaccggg gtggtgccca tcctggtcga gctggacggc gacgtaaacg   1680
gccacaagtt cagcgtgtcc ggcgagggcg agggcgatgc cacctacggc aagctgaccc   1740
tgaagttcat ctgcaccacc ggcaagctgc ccgtgccctg gcccaccctc gtgaccaccc   1800
tgacctacgg cgtgcagtgc ttcagccgct accccgacca catgaagcag cacgacttct   1860
tcaagtccgc catgcccgaa ggctacgtcc aggagcgcac catcttcttc aaggacgacg   1920
gcaactacaa gacccgcgcc gaggtgaagt tcgagggcga caccctggtg aaccgcatcg   1980
agctgaaggg catcgacttc aaggaggacg gcaacatcct ggggcacaag ctggagtaca   2040
actacaacag ccacaacgtc tatatcatgg ccgacaagca gaagaacggc atcaaggtga   2100
acttcaagat ccgccacaac atcgaggacg gcagcgtgca gctcgccgac cactaccagc   2160
agaacacccc catcggcgac ggccccgtgc tgctgcccga caaccactac ctgagcaccc   2220
agtccgccct gagcaaagac cccaacgaga gcgcgatca  catggtcctg ctggagttcg   2280
tgaccgccgc cgggatcact ctcggcatgg acgagctgta caagtaagta gcgatcgctt   2340
agactcgagc ggccgcggtc cgtttaaact gtcagaccaa gtttactcat atatacttta   2400
gattgattta aaacttcatt tttaatttaa aaggatctag gtgaagatcc ttttgataa    2460
tctcatgacc aaaatccctt aacgtgagtt ttcgttccac tgagcgtcag accccgtaga   2520
aaagaccaaa ggatcttctt gagatccttt ttttctgcgc gtaatctgct gcttgcaaac   2580
aaaaaaacca ccgctaccag cggtggtttg tttgccggat caagagctac caactctttt   2640
tccgaaggta actggcttca gcagagcgca gataccaaat actgtccttc tagtgtagcc   2700
gtagttgggc caccacttca agaactctgt agcaccgcct acatacctcg ctctgctaat   2760
cctgttacca gtggctgctg ccagtggcga taagtcgtgt cttaccgggt tggactcaag   2820
acgatagtta ccggataagg cgcagcggtc gggctgaacg gggggttcgt gcacacagcc   2880
```

```
cagcttggag cgaacgacct acaccgaact gagataccta cagcgtgagc tatgagaaag    2940
cgccacgctt cccgaaggga gaaaggcgga caggtatccg gtaagcggca gggtcggaac    3000
aggagagcgc acgaaggagc ttccaggggg aaacgcctgg tatctttata gtcctgtcgg    3060
gtttcgccac ctctgacttg agcgtcgatt tttgtgatgc tcgtcagggg ggcggagcct    3120
atggaaaaac gccagcaacg cggccttttt acggttcctg gccttttgct ggccttttgc    3180
tcacatgttc cttcctgcgt tatcccctga ttctgtggat aaccgtatta ccgcctttga    3240
gtgagctgat accgctcgcc gcaggtttaa acagatctgt cgacgcccgg gcaagctggc    3300
cggccgatcc tctttctgtt tacagacatg gcttctctta catctctcat atttgtcagc    3360
attgtcactg ccgctcatgg acaaacagtc gtctctatcc ctctaggaca taattacact    3420
ctcataggac ccccaatcac ttcagaggtc atctgggcca aactgggaag cgttgattac    3480
tttgatataa tctgcaacaa aacaaaacca ataatagtaa cttgcaacat acaaaatctt    3540
acattgatta atgttagcaa agtttacagc ggttactatt atggttatga cagatacagt    3600
agtcaatata gaaattactt ggttcgtgtt acccagttga aaaccacgaa aatgccaaat    3660
atggcaaaga ttcgatccga tgacaattct ctagaaactt ttacatctcc caccacaccc    3720
gacgaaaaaa acatcccaga ttcaatgatt gcaattgttg cagcggtggc agtggtgatg    3780
gcactaataa taatatgcat gcttttatat gcttgtcgct acaaaaagtt tcatcctaaa    3840
aaacaagatc tcctactaag gcttaacatt taatttcttt ttatacagcc atatcattta    3900
aat                                                                  3903
```